US007572455B2

(12) United States Patent
Meyers et al.

(10) Patent No.: US 7,572,455 B2
(45) Date of Patent: Aug. 11, 2009

(54) VACCINE COMPRISING AN ATTENUATED PESTIVIRUS

(75) Inventors: Gregor Meyers, Walddorfhaeslach (DE); Andreas Ege, Teubingen (DE); Christiane Fetzer, Meunster (DE); Martina von Freyburg, Heilbronn (DE)

(73) Assignee: Boehringer Ingelheim Vetmedica GmbH, Ingelheim (DE)

( * ) Notice: Subject to any disclaimer, the term of this patent is extended or adjusted under 35 U.S.C. 154(b) by 403 days.

(21) Appl. No.: 11/132,686

(22) Filed: May 19, 2005

(65) Prior Publication Data

US 2005/0287171 A1 Dec. 29, 2005

Related U.S. Application Data

(60) Provisional application No. 60/589,361, filed on Jul. 20, 2004.

(30) Foreign Application Priority Data

May 19, 2004 (DE) ...................... 10 2004 025 452

(51) Int. Cl.

*A61K 39/12* (2006.01)
*A61K 39/00* (2006.01)
*A61K 49/00* (2006.01)
*C12N 15/86* (2006.01)
*C12N 7/04* (2006.01)
*C12P 13/04* (2006.01)
*C12Q 1/70* (2006.01)

(52) U.S. Cl. .................. 424/218.1; 424/9.2; 424/185.1; 424/204.1; 435/5; 435/106; 435/236; 435/456

(58) Field of Classification Search ...................... None
See application file for complete search history.

(56) References Cited

U.S. PATENT DOCUMENTS

| | | | | |
|---|---|---|---|---|
| 6,610,305 | B1 | 8/2003 | Elbers | |
| 2003/0044426 | A1 * | 3/2003 | Meyers | 424/204.1 |
| 2003/0165520 | A1 * | 9/2003 | Cao et al. | 424/186.1 |
| 2004/0038198 | A1 * | 2/2004 | Elbers et al. | 435/5 |

FOREIGN PATENT DOCUMENTS

| | | | |
|---|---|---|---|
| CA | 2 363 493 | | 5/2002 |
| EP | 1 013 757 | A2 | 6/2000 |
| WO | WO 03/023041 | A2 | 3/2003 |

OTHER PUBLICATIONS

Mayer, Daniel, et al; Attenuation of classical swine fever virus by deletion of the viral Npro gene; Vaccine, 22 (2004); 317,328.
Bolin, Steven R.; Control of Bovine Viral Diarrrhea Infection by Use of Vaccination; Verterinary Clinics of North America: Food Animal Practice, vol. II No. 3, Nov. 1995 pp. 615-625.
van Gennip, H.G.P., et al; Experimental non-transmissible marker vaccines for classical swine fever (CSF) by trans-complementation of Erns or E2 of CSFV; Vaccine 20 (2002) 1544-1556.

* cited by examiner

*Primary Examiner*—Bruce Campell
*Assistant Examiner*—Sharon Hurt
(74) *Attorney, Agent, or Firm*—Michael P. Morris; Mary-Ellen M. Devlin

(57) ABSTRACT

Attenuated pestiviruses, in particular attenuated BVDV, wherein at least one mutation is in the coding sequence for glycoprotein $E^{rns}$ and at least another mutation in the coding sequence for $N^{pro}$ which preferably leads to combined inactivation of the RNase activity residing in glycoprotein $E^{rns}$ in addition to the inactivation of the (hypothesized) immunomodulating activity residing in $N^{pro}$. Methods for attenuating pestiviruses such as BVDV, nucleic acids encoding the pestiviruses, in particular BVDV, compositions and vaccines comprising the attenuated pestiviruses, in particular BVDV, of the invention.

42 Claims, 3 Drawing Sheets

Figure 3

VACCINE COMPRISING AN ATTENUATED PESTIVIRUS

RELATED APPLICATIONS

This application claims benefit of U.S. Ser. No. 60/589,361, filed Jul. 20, 2004, and claims priority to German Application No. 10 2004 025 452.4, filed May 19, 2004, each of which is hereby incorporated by reference in its entirety.

FIELD OF THE INVENTION

The present invention relates to the field of animal health and in particular to attenuated pestiviruses such as bovine viral diarrhea virus (BVDV).

BACKGROUND OF THE INVENTION

Pestiviruses are causative agents of economically important diseases of animals in many countries worldwide. Presently known virus isolates have been grouped into four different species which together form one genus within the family Flaviviridae.

I./II. Bovine viral diarrhea virus (BVDV) type 1 (BVDV-1) and type 2 (BVDV-2) cause bovine viral diarrhea (BVD) and mucosal disease (MD) in cattle (Baker, 1987; Moennig and Plagemann, 1992; Thiel et al., 1996). The division of BVDV into 2 species is based on significant differences at the level of genomic sequences (summarized in Heinz et al., 2000) which are also obvious from limited cross neutralizing antibody reactions (Ridpath et al. 1994).

III. Classical swine fever virus (CSFV), formerly named hog cholera virus, is responsible for classical swine fever (CSF) or hog cholera (HC) (Moennig and Plagemann, 1992; Thiel et al., 1996).

IV. Border disease virus (BDV) is typically found in sheep and causes border disease (BD). After intrauterine infection of lambs with BDV persistently infected lambs can be born that are weak and show different abnormalities among which the "hairy shaker" syndrome is best known (Moennig and Plagemann, 1992; Thiel et al., 1996).

Pestiviruses are small enveloped viruses with a single stranded RNA genome of positive polarity lacking both 5' cap and 3' poly(A) sequences. The viral genome codes for a polyprotein of about 4000 amino acids giving rise to final cleavage products by co- and post-translational processing involving cellular and viral proteases. The viral proteins are arranged in the polyprotein in the order $NH_2$-$N^{pro}$-C-$E^{rns}$-E1-E2-p7-NS2-NS3-NS4A-NS4B-NS5A-NS5B-COOH (Lindenbach and Rice, 2001). Protein C (=core- or capsidprotein) and the glycoproteins $E^{rns}$, E1, and E2 represent structural components of the pestivirus virion as demonstrated for CSFV (Thiel et al., 1991). This also holds true for BVDV. E2 and, to a lesser extent, $E^{rns}$ were found to be targets for antibody neutralization (Donis et al., 1988; Paton et al., 1992; van Rijn et al., 1993; Weiland et al., 1990, 1992). $E^{rns}$ lacks a typical membrane anchor and is secreted in considerable amounts from the infected cells; this protein has been reported to exhibit RNase activity (Hulst et al., 1994; Schneider et al., 1993; Windisch et al., 1996). The function of this enzymatic activity for the viral life cycle is presently unknown. The enzymatic activity depends on the presence of two stretches of amino acids conserved between the pestivirus $E^{rns}$ and different known RNases of plant and fungal origin. Both of these conserved sequences contain a histidine residue (Schneider et al., 1993). Exchange of each of these residues against lysine in the $E^{rns}$ protein of a CSFV vaccine strain resulted in the destruction of RNase activity (Hulst et al., 1998). Introduction of these mutations into the genome of the CSFV vaccine strain did not influence viral viability or growth properties but led to a virus exhibiting a cytopathogenic phenotype (Hulst et al., 1998). Similarly, Meyers et al. showed that an RNase negative variant of the virulent CSFV strain Alfort/Tübingen was fully viable. However, the respective virus mutant showed no cytopathogenic phenotype (Meyers et al., 1999).

$N^{pro}$ represents the first protein encoded by the long open reading frame in the pestivirus RNA. $N^{pro}$ represents a nonstructural protein that has protease activity and cleaves itself of the nascent polyprotein (Stark et al., 1993; Wiskerchen et al., 1991) presumably already during translation. $N^{pro}$ is a cysteine protease (Rümenapf et al., 1998) that is not essential for virus replication (Tratschin et al., 1998). Recently, it was shown that $N^{pro}$ somehow interferes with the cellular antiviral defense so that it can be hypothesized to modulate the immune system within an infected host (Rüggli et al., 2003). Mayer and coworkers presented indications for an attenuation of CSFV in consequence of a deletion of the $N^{pro}$ gene (Mayer et al., 2004).

Present BVDV vaccines for the prevention and treatment of BVDV infections still have drawbacks (Oirschot et al., 1999). Vaccines against the classical BVDV-1 provide only partial protection from BVDV-2 infection, and vaccinated dams may produce calves that are persistently infected with virulent BVDV-2 (Bolin et al., 1991; Ridpath et al., 1994). This problem is probably due to the great antigenic diversity between type 1 and type 2 strains which is most pronounced in the glycoprotein E2, the major antigen for virus neutralization (Tijssen et al., 1996). Most monoclonal antibodies against type 1 strains fail to bind to type 2 viruses (Ridpath et al., 1994).

Vaccines comprising attenuated or killed viruses or viral proteins expressed in heterologous expression systems have been generated for CSFV and BVDV and are presently used. Killed vaccines (inactivated whole virus) or subunit vaccines (conventionally purified or heterologously expressed viral proteins) are most often inferior to live vaccines in their efficacy to produce a full protective immune response even in the presence of adjuvants.

The structural basis of the attenuation of BVDV used as live vaccines is not known. These vaccines, although attenuated, are most often associated with safety problems. The vaccine viruses may cross the placenta of pregnant animals, e.g., cows, and lead to clinical manifestations in the fetus and/or the induction of persistently infected calves. Therefore, they cannot be applied to breeding herds that contain pregnant cows. Pregnant cows have to be kept separate from vaccinated cattle to protect fetuses and must not be vaccinated themselves. Furthermore, revertants of attenuated live BVDV pose a serious threat to animals. For conventionally derived attenuated viruses wherein the attenuation is achieved by conventional multiple passaging, the molecular origin as well as the genetic stability of the attenuation remains unknown and reversion to the virulent wild-type is unpredictable.

Because of the importance of an effective and safe as well as detectable prophylaxis and treatment of pestiviral infections, there is a strong need for improved attenuated pestiviruses, such as BVDV, with a high potential for induction of immunity as well as a defined basis of attenuation which can also be distinguished from pathogenic pestiviruses, such as BVDV, as well as compositions and vaccines comprising the attenuated pestiviruses, such as BVDV.

Therefore, the technical problem underlying the present invention is to provide improved attenuated pestivirus, preferably an attenuated BVDV for use as live attenuated vaccines. Such improved attenuated pestivirus, preferably BVDV, should especially (i) not cross the placenta themselves, and (ii) induce an immunity that prevents viral transmission across the placenta and thereby prevents pregnancy problems like abortion of the fetus or birth of persistently infected host such calves in the case of BVDV infection.

BRIEF DESCRIPTION OF THE DRAWINGS

FIG. 3 shows the serum neutralization assay against NY93/C (BVDV type II).

Figure 1:
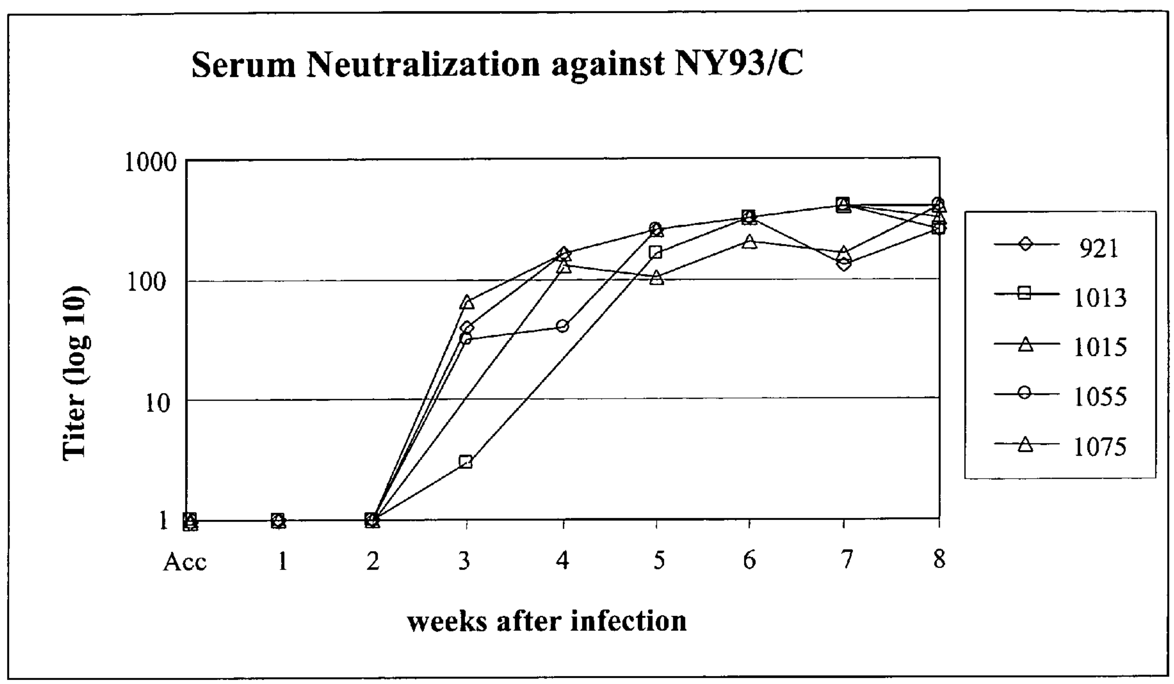
FIG. 1 shows the serum neutralization against NY93/C (BVDV type II)

All subsequent sequences show the deleted regions indicated with dashes (–), which are also numbered, whereas the sequences in the sequence listing attached hereto are continuously numbered without the deleted regions or amino acid codons.

| | |
|---|---|
| SEQ ID NO: 1 | XIKE-A-cDNA sequence |
| SEQ ID NO: 2 | XIKE-A-NdN-cDNA sequence |
| SEQ ID NO: 3 | XIKE-B-cDNA sequence |
| SEQ ID NO: 4 | XIKE-B-NdN-cDNA |
| SEQ ID NO: 5 | XIKE-A amino acid sequence |
| SEQ ID NO: 6 | XIKE-A-NdN amino acid sequence |
| SEQ ID NO: 7 | XIKE-B amino acid sequence |
| SEQ ID NO: 8 | XIKE-B-NdN amino acid sequence |
| SEQ ID NO: 9 | XIKE-C-NdN amino acid sequence |
| SEQ ID NO: 10 | XIKE-C-NdN-cDNA sequence |
| SEQ ID NO: 11 | XIKE-C-cDNA sequence |
| SEQ ID NO: 12 | XIKE-C amino acid sequence |

SUMMARY OF THE INVENTION

The present invention relates to attenuated pestivirus, preferably to attenuated BVDV, wherein at least one mutation is in the coding sequence for glycoprotein $E^{rns}$ and at least another mutation in the coding sequence for $N^{pro}$ which preferably leads to combined inactivation of the RNase activity residing in glycoprotein $E^{rns}$ in addition to the inactivation of the (hypothesized) immunomodulating activity residing in $N^{pro}$. The invention also relates to methods for attenuating pestivirus in such that the attenuation results in an attenuated pestivirus, preferably in an attenuated BVDV, as described above. The present invention furthermore relates to nucleic acid molecules encoding the attenuated pestiviruses, preferably encoding attenuated BVDV, compositions and vaccines comprising the attenuated pestivirus, preferably BVDV as disclosed herein.

DETAILED DESCRIPTION OF THE INVENTION

Definitions of Terms Used in the Description

Before the embodiments of the present invention it must be noted that as used herein and in the appended claims, the singular forms "a", "an", and "the" include plural reference unless the context clearly dictates otherwise. Thus, for example, reference to "a BVDV" includes a plurality of such BVDV, reference to the "cell" is a reference to one or more cells and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

The term "pestivirus" as used herein refers to all members of the genus *Pestivirus*, including BVDV, CSFV, and BDV, within the family Flaviviridae.

The term "CSFV" as used herein refers to all viruses belonging to species of classical swine fever virus (CSFV) in the genus *Pestivirus* within the family Flaviviridae.

The term "BVDV" as used herein refers to all viruses belonging to species bovine viral diarrhea virus (BVDV) type 1 (BVDV-1) and BVDV type 2 (BVDV-2) in the genus *Pestivirus* within the family Flaviviridae (Heinz et al., 2000). The more classical BVDV type 1 strains and the more recently recognized BVDV type 2 strains display some limited but distinctive differences in nucleotide and amino acid sequences.

The term "$N^{pro}$" as understood herein relates to the first protein encoded by the viral open reading frame and cleaves itself from the rest of the synthesized polyprotein (Stark et al., J. Virol. 67:7088-7093 (1993); Wiskerchen et al., Virol. 65:4508-4514 (1991)). The term, depending on the context, may also relate to the remaining "$N^{pro}$" amino acids after mutation of the encoding nucleotide sequence or to the coding nucleotide sequence for the protein itself. "Protease activity residing in $N^{pro}$" relates to the polypeptide cleavage activity of the "$N^{pro}$".

"$E^{rns}$" as used herein relates to the glycoprotein $E^{rns}$ which represents a structural component of the pestivirus virion (Thiel et al., 1991). $E^{rns}$ lacks a typical membrane anchor and is secreted in considerable amounts from the infected cells; this protein has been reported to exhibit RNase activity (Hulst et al., 1994; Schneider et al., 1993; Windisch et al., 1996). It should be noted that the term glycoprotein E0 is often used synonymously to glycoprotein $E^{rns}$ in publications. The term, depending on the context, may also relate to the mutated "$E^{rns}$" protein after mutation of the encoding nucleotide sequence or to the coding nucleotide sequence for the protein itself. "RNase activity residing in glycoprotein $E^{rns}$" relates to the RNA cleavage activity of the glycoprotein, i.e., the ability of the glycoprotein $E^{rns}$ to hydrolyze RNA. The term "inactivation of the RNase activity residing in the glycoprotein" refers to the inability or reduced capability of a modified glycoprotein $E^{rns}$ to hydrolyze RNA as compared to the unmodified wild-type of the glycoprotein $E^{rns}$.

"An attenuated pestivirus or BVDV particle" as used herein means that there is a statistically significant difference between the virulence of attenuated pestivirus or BVDV particles of the present invention, wherein the attenuated viral particles being attenuated by a method described herein, and wild-type pestivirus or BVDV isolates from which the attenuated pestivirus or BVDV particles have been derived, for the predominant clinical parameters, in case of BVDV for diarrhea, pyrexia, and lethality in animals infected with the same dose, preferably $6 \times 10^6$ $TCID_{50}$. Thus, the attenuated BVDV particles do not cause diarrhea, pyrexia, and lethality and thus may be used in a vaccine.

"Inactivation of $E^{rns}$" as used herein means RNase activity not significantly above the level measured for noninfected control cells in an RNase assay as described in Meyers et al., 1999. "Not significantly above the level measured for noninfected control cells in an RNase assay as described in Meyers et al., 1999," means for example, that the RNase activity is less than 150% compared to the noninfected control cells.

"Inactivation of $N^{pro}$" as used herein means the prevention or considerable reduction of the probable immunomodulating activity of $N^{pro}$ by mutation. In a preferred embodiment, this mutation prevents or considerably reduces the interference of $N^{pro}$ with the induction of an interferon response by the infected cells as described by Rüggli et al., 2003. In this case, the inactivation of $N^{pro}$ would allow the cell to mount a normal interferon response.

"Processing signal" as used herein relates to a substance that ensures the generation of a functional N-terminal of the C protein of the pestivirus, preferably of BVDV, in particular a substance selected from the group of ubiquitin, LC3, SUMO-1, NEDD8, GATE-16, and GABA(A)RAP. Also proteases selected from the group of intein, picornavirus 3C, caridovirus 2A, and p15 of rabbit hemorrhagic disease virus are understood as "processing signals" as used herein. Any other similar processing signal known to the skilled person that ensures the generation of a functional N-terminal of the C protein shall also be comprised in the term "processing signal".

"Protein C" or "C protein" or "C-protein" as used herein relates to a structural component of the pestivirus virion (Thiel et al., 1991). "Protein C" is the capsid or core protein of pestiviruses. The term, depending on the context, may also relate to the "Protein C" with one or several amino acids exchanges resulting from mutation of the encoding nucleotide sequence.

A "fragment" according to the invention is any subunit of a polynucleotide molecule according to the invention, i.e., any subset. For DNA, the fragment is characterized in that it is shorter than the DNA covering the full length viral genome.

A "functional variant" of the nucleotide molecule according to the invention is a nucleotide molecule which possesses a biological activity (either functional or structural) that is substantially similar to the nucleotide molecule according to the invention. The term "functional variant" also includes "a fragment", "a functional variant", "variant based on the degenerative nucleic acid code", or "chemical derivative". Such a "functional variant", e.g., may carry one or several nucleotide exchanges, deletions, or insertions. The functional variant at least partially retains its biological activity, e.g., function as an infectious clone or a vaccine strain, or even exhibits improved biological activity. "Possess a biological activity that is substantially similar" means with respect to the pestiviruses provided herewith, for example, that the pestivirus is attenuated in a manner described herein and result in an non-pathogenic virus suitable for the production of live attenuated virus, which loss ability to pass the placenta but mediates an immune response after vaccination.

A "variant based on the degenerative nature of the genetic code" is a variant resulting from the fact that a certain amino acid may be encoded by several different nucleotide triplets. The variant at least partially retains its biological activity, or even exhibits improved biological activity.

A molecule is "substantially similar" to another molecule if both molecules have substantially similar nucleotide sequences or biological activity. Thus, provided that two molecules possess a similar activity, they are considered variants as that term is used herein if the nucleotide sequence is not identical, and two molecules which have a similar nucleotide sequence are considered variants as that term is used herein even if their biological activity is not identical.

A mutation as used herein relates to modifications in the nucleic acid molecules encoding the proteins/amino acids according to the invention. The mutations relate to, but are not limited to, substitutions (replacement of one or several nucleotides/base pairs), deletions (removal of one or several nucleotides/base pairs), and/or insertions (addition of one or several nucleotides/base pairs). As used herein, mutation may be a single mutation or several mutations, therefore, often the term "mutation(s)" is used and relates to both a single mutation and several mutations. The mutations include, but are not limited to point mutations (single nucleotide mutations) or larger mutations wherein, e.g., parts of the encoding nucleic acid molecules are deleted, substituted, and/or additional coding nucleic acid is inserted. The mutations may result in a modified expressed polypeptide due to the change in the coding sequence. Such modified polypeptides are desired, as set out in the disclosure of the invention as set out below.

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. The immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. The term "vaccine" as understood herein is a vaccine for veterinary use comprising antigenic substances and is administered for the purpose of inducing a specific and active immunity against a disease provoked by a pestivirus infection, preferably by a BVDV infection. The attenuated pestivirus, in particular the attenuated BVDV as described herein, confer active immunity that may be transferred passively via maternal antibodies against the immunogens it contains and sometimes also against antigenically related organisms. A vaccine of the invention refers to a vaccine as defined above, wherein one immunologically active component is a BVDV or of pestiviral origin or derived from a nucleotide sequence that is more than 70% homologous to any known pestivirus sequence (sense or antisense).

The term "live vaccine" refers to a vaccine comprising a living, in particular, a living viral active component.

Additional components to enhance the immune response are constituents commonly referred to as "adjuvants", e.g., aluminum hydroxide, mineral or other oils, or ancillary molecules added to the vaccine or generated by the body after the respective induction by such additional components, like but not restricted to interferons, interleukins, or growth factors.

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA)) and the mixture is subsequently lyophilized or dehydrated by other methods. Prior to vaccination, the mixture is then rehydrated in aqueous (e.g., saline, phosphate buffered saline (PBS)) or non-aqueous solutions (e.g., oil emulsion, aluminum-based adjuvant).

The solution to the above technical problem is achieved by the description and the embodiments characterized in the claims.

It has surprisingly been found that pestiviruses, in particular BVDV, can be more effectively attenuated by introducing at least one mutation in the coding sequence for glycoprotein $E^{rns}$ and at least another mutation in the coding sequence for $N^{pro}$ which preferably leads to combined inactivation of the RNase activity residing in glycoprotein $E^{rns}$ in addition to the inactivation of the immunomodulating activity residing in $N^{pro}$. An immunomodulating effect in one aspect is indicated but not limited to the indicated function for one pestivirus in an exemplary manner by Rüggli et al., 2003.

A pestivirus, in particular BVDV, attenuated in accordance with the present invention may be advantageously used in vaccines. The attenuated pestivirus, in particular the attenuated BVDV, now provide live vaccines of high immunogenicity. Surprisingly, the pestivirus, in particular the BVDV, according to the invention furthermore are safe for use in pregnant animals as they do not cross the placenta. This is exemplified in a non-limiting manner for BVDV in Example 3.

Furthermore, live vaccines with defined mutations as a basis for attenuation will allow to avoid the disadvantages of the present generation of vaccines, e.g., the risk of reversion to an more pathogenic strain. A further advantage of the attenuating mutations lies in their molecular uniqueness which allows to use them as distinctive labels for an attenuated pestivirus, in particular BVDV, and to distinguish them from pestivirus, in particular BVDV, from the field. Therefore, in one aspect the present invention provides an attenuated pestivirus, in particular an attenuated BVDV, having at least one mutation in the coding sequence for glycoprotein $E^{rns}$ and at least another mutation in the coding sequence for $N^{pro}$. Preferably, in such attenuated pestivirus, preferably in such attenuated BVDV, the mutation in the coding sequence for glycoprotein $E^{rns}$ leads to inactivation of the RNase activity residing in $E^{rns}$ and/or the mutation in the coding sequence for $N^{pro}$ leads to inactivation of the $N^{pro}$. The inactivation may take place by any mutation known to the person skilled in the art of the $E^{rns}$- and the $N^{pro}$-coding sequence, wherein the mutations are any mutation as defined in the Definitions of Terms Used in the Description section above, such as deletions, insertion mutations, and/or substitution mutations. Most preferably, the mutation(s) are deletions, as the likelihood for revertation to the wild-type is the lowest for deletions.

It has been shown that the glycoprotein $E^{rns}$ forms a disulfide-bonded homodimer of about 97 kD, wherein each monomer consists of 227 amino acids corresponding to the amino acids 268 to 494 of the CSFV polyprotein as described by Rümenapf et al., 1993. The genome sequence of the Alfort/Tübingen strain of CSFV is available in the GenBank/EMBL data library under accession number J04358; alternatively, the amino acid sequence for the BVDV strain CP7 can be accessed in the GenBank/EMBL data library (accession number U63479); in the BVDV CP7 polyprotein, the $E^{rns}$ protein corresponds to residues 271 to 497. Two regions of amino acids are highly conserved in glycoprotein $E^{rns}$ as well as in some plant and fungal RNase-active proteins (Schneider et al., 1993). These two regions are of particular importance to the RNase enzymatic activity. The first region consists of the region at the amino acids at position 295 to 307 (298 to 310 for BVDV strain CP7) and the second region consists of the amino acids at position 338 to 357 (341 to 360 for BVDV strain CP7) of the viral polyprotein as exemplified for the Alfort strain of CSFV in Meyers et al., 1999 (numbering according to the published deduced amino acid sequence of CSFV strain Alfort/Tübingen (Meyers et al., 1989). The amino acids of particular importance to the RNase activity as mentioned above are by no means limited to the exact position as defined for the Alfort/Tübingen strain of CSFV but are simply used in an exemplary manner to point out the preferred amino acids being at that position or corresponding to that position in other strains such as found in BVDV, BDV, and pestiviruses in general since they are highly conserved. For pestiviruses other than the CSFV Alfort/Tübingen strain, the numbering of the positions of the preferred amino acids can be different but an expert in the field of the molecular biology of pestiviruses will easily identify these preferred amino acids by the high degree of conservation of this amino acid sequence and the position of these motifs in the sequence context. In one particular non-limiting example, the position of CSFV Alfort/Tübingen 346 is identical to position 349 of BVDV strain CP7.

As a consequence, the present invention preferably relates to a BVDV according to the invention, wherein the mutation(s) in the coding sequence for glycoprotein $E^{rns}$ are located in the encoding nucleotide sequence corresponding to amino acids at position 298 to 310 and/or position 341 to 360. Preferably, such mutations are (where amino acids are given in the one letter symbols; the amino acid before the position number indicates the amino acid to be substituted, the amino acid after the position number the substituting amino acid (del indicates deletion): for example, H300L means histidine 300 was substituted by leucine):

Suitable modification of the glycoprotein $E^{rns}$ are for example, the single substitutions/deletions: S298G, H300K, H300L, H300R, H300del, W303G, P304del, E305A, C308G, R343G, E345del, W346G, K348A, H349K, H349L, H349del, H349Q, H349SV (mutation H349S and insertion of V), K348R, W351P, W351G, W351L, W351K, W351H; the double substitutions/deletions: H300L/H349L, K348del/H349del, H349del/G350del, E345del/H349del, W303G/E305A, H300K/H349K, H300K/H349L and the triple deletions: L299del/H300del/G300del, K348del/H349del/G350del. Numbering is according to the published amino acid sequence of BVDV CP7 for all the mutants listed above (the given numbers minus 3 would correspond to the equivalent residues of the CSFV Alfort/Tübingen amino acid sequence). All the above-listed mutants were at least tested as respective CSFV or BVDV mutants without mutations in the $N^{pro}$ region. Suitable mutants of the pestiviral glycoprotein $E^{rns}$ are provided, for example, by WO 99/64604, which is incorporated herein in its entirety. It should be noted, however, that according to the present invention, at least one additional mutation in the $N^{pro}$ region, as disclosed in further detail below, must be present.

It was particularly found that deletion or substitution of the histidine residue at position 346 (CSFV) or 349 (BVDV) leads to effective inactivation of $E^{rns}$ and therefore leads to particularly useful pestiviral live vaccines. The present invention demonstrates that pestiviruses are viable and code for an $E^{rns}$ protein without RNase activity when the histidine residue at position 346 of the viral polyprotein (numbering according to the published sequence of CSFV Alfort/Tübingen (Meyers et al., 1989)), or at position 349 (numbering according to the published sequence of BVDV CP7 (Meyers et al., 1996b)) if the pestivirus is BVDV, which represents one of the conserved putative active site residues of the $E^{rns}$ RNase, is deleted. Thus, preferably, the invention also relates to a BVDV according to the invention, wherein the mutation in the coding sequence for glycoprotein $E^{rns}$ is a deletion or substitution of the histidine residue at position 349. Even more specifically, the putative active site of the RNase is represented by the conserved $E^{rns}$ sequences SLHGIWPEKICTG and/or LQRHEWNKHGWCNWFHIEPW (sequence of the BVDV-2 NewYork93 protein given here in an exemplary manner; minor changes can possibly be found in other pestivirus sequences but the identity of the motif will always be obvious for an expert in the field. As an example, the corresponding amino acid sequences of BVDV-1 CP7 would be SLHGIWPEKICTG and/or LQRHEWNKHGWCNWYNIEPW and that of CSFV Alfort/Tübingen SLHGIWPEKICKG and/or LQRHEWNKHGWCNWYNIDPW). Thus, preferably, the invention further relates to a BVDV according to the invention, wherein the mutation(s) in the coding sequence for glycoprotein $E^{rns}$ are located in the nucleotide sequence coding for the conserved $E^{rns}$ sequence SLHGIWPEKICTG and/or LQRHEWNKHGWCNWFHIEPW. These sequences are representing the putative active site of the RNase. The sequences SLHGIWPEKIC and RHEWNKHGWCNW of the putative $E^{rns}$ active site are even more conserved across pestiviruses. Thus, preferably, the invention also relates to a pestivirus, in particular to BVDV, having at least one mutation in the coding sequence of the $N^{pro}$ protein and the glycoprotein $E^{rns}$, wherein the mutation(s) in the coding sequence for glycoprotein $E^{rns}$ are located in the nucleotide sequence coding for the conserved $E^{rns}$ sequence SLHGIWPEKIC and/or RHEWNKHGWCNW. Preferably, the mutation is located in only one of the sequences. Thus the invention also relates to a pestivirus, in particular to BVDV, having at least one mutation in the coding sequence of the $N^{pro}$ protein and the glycoprotein $E^{rns}$, wherein the mutation(s) in the coding sequence for glycoprotein $E^{rns}$ are located in the nucleotide sequence coding for the conserved $E^{rns}$ sequence SLHGIWPEKIC or RHEWNKHGWCNW. Preferably, such mutations concern two different amino acids, i.e., are double mutations. Thus, the mutations may be 1 to 3 nucleotide mutations in two different triplets encoding two amino acids. Thus, the invention also relates to a pestivirus, in particular to BVDV having at least one mutation in the coding sequence of the $N^{pro}$ protein and the glycoprotein $E^{rns}$, wherein the mutation(s) in the coding sequence for glycoprotein $E^{rns}$ are two mutations located in the nucleotide sequence coding for the conserved $E^{rns}$ sequence SLHGIWPEKIC and/or RHEWNKHGWCNW. Preferably, such mutations concern a single amino acid. Thus, the mutation may be 1 to 3 nucleotide mutations in one triplet encoding one amino acid. Thus, the invention also relates to a pestivirus, in particular to BVDV, having at least one mutation in the coding sequence of the $N^{pro}$ protein and the glycoprotein $E^{rns}$, wherein a single mutation is located in the conserved $E^{rns}$ sequence SLHGIWPEKIC or RHEWNKHGWCNW.

As mentioned above, the attenuated pestiviruses provided by the present invention, having at least on mutation in the coding sequence of the glycoprotein $E^{rns}$ and in the coding sequence of the $N^{pro}$ protein, wherein the mutation preferably result in inactivation of the RNase activity residing in the glycoprotein $E^{rns}$ and of the immunomodulating activity residing in $N^{pro}$. Inactivation of the $N^{pro}$ is achieved in pestiviruses, in particular BVDV, of the specified formula described more in detail below, wherein between 0 and all amino acids of $N^{pro}$ are present; ubiquitin or LC3 or another sequence serving as processing signal (e.g., SUMO-1, NEDD8, GATE-16, GABA(A)RAP, or proteases, e.g., intein, picornavirus 3C, caridovirus 2A, or p15 of rabbit hemorrhagic disease virus) is present or absent. In case a processing signal is present, the coding sequence of the processing signal is inserted at or close to the C-terminal end of the (remaining part of the) $N^{pro}$-protein. Only in the case that a processing signal is present, any number of amino acids coding for $N^{pro}$ (=$N^{pro}$ amino acids) may be present. In case no processing signal sequence is inserted, a maximum of 12 amino acids, preferably aminoterminal amino acids, of $N^{pro}$ may be present, the remaining amino acids have to be deleted. Furthermore, other than the $E^{rns}$ mutations as disclosed above (at least one of which has to be present in the pestivirus, in particular in BVDV according to the invention), the remaining sequences of the pestivirus, in particular BVDV may remain unchanged, i.e., are not mutated, or may also have mutations close to the N-terminal end of the C-protein. A number of more specific embodiments as disclosed below exemplify this.

Thus, the invention relates to a pestivirus, in particular to BVDV according to the invention, wherein the mutation(s) in the coding sequence for $N^{pro}$ lead to an encoded polyprotein as characterized by the following formula:

$$[N^{pro}]_x\text{-}[PS]_y\text{-}[C\text{-term}],$$

wherein:

[$N^{pro}$] relates to the $N^{pro}$ portion of the polyprotein, wherein x represents the number of amino acids of the $N^{pro}$ present in the polyprotein;

[PS] relates to a processing signal selected from: ubiquitin, LC3, SUMO-1, NEDD8, GATE-16 or GABA(A)RAP) or proteases, e.g., intein, picornavirus 3C, caridovirus 2A, or p15 of rabbit hemorrhagic disease virus, or the like, or any processing signal known to the skilled person that ensures the generation of a functional N-terminal of the C-protein and y may be 0, which means that no processing signal is present (i.e., that PS is absent), or y may be 1, which means that a processing signal is present (i.e., that PS is present);

[C-term] relates to the complete pestivirus, in particular the complete BVDV polyprotein except for $N^{pro}$, but including the capsid (C)-protein and any other protein present in the pestivirus polyprotein, in particular in the BVDV polyprotein including the carboxyterminal NS5B. Preferably, the glycoprotein $E^{rns}$ in the [C-term] is mutated, in such that the RNase activity residing in the glycoprotein $E^{rns}$ is inactivated. The term "any other protein present in the pestivirus polyprotein/BVDV polyprotein" relates to $E^{rns}$, E1, E2, p7, NS2, NS3, NS4A, NS4B, and NS5A, wherein glycoprotein $E^{rns}$ is mutated, preferably as disclosed herein (see above), in such that the RNase activity residing in the glycoprotein $E^{rns}$ is inactivated. Preferably, the pestivirus, in particular the BVDV, according to the invention has a C-protein which is not mutated except for the amino acid at position 2 which is changed from D to N. Therefore, [C-term*] is the same as [C-term] but with a mutation at position 2 of the C-protein (N instead of D);

if y is 0 (which means that no [PS] is present) then x is 0 to 12, (which means no $N^{pro}$ specific amino acid or 1 to 12 amino acids of $N^{pro}$, preferably of the N-terminus of $N^{pro}$, are present); and if y is 1 (which means that [PS] is present) then x is 0 to 168; (which means no $N^{pro}$ specific amino acid or 1 to all 168 amino acids of $N^{pro}$, preferably of the N-terminus of $N^{pro}$, are present).

Also more preferably, the invention relates to a pestivirus, in particular to BVDV according to the invention, wherein the mutation(s) in the coding sequence for $N^{pro}$ lead to an encoded polyprotein as characterized by the following formula:

$[N^{pro}]_1$-$[PS]_0$-[C-term], wherein the definitions are as defined above.

A specific example thereof is disclosed below, wherein the N-terminal methionine is followed by the C-protein and any other protein present in the polyprotein including the carboxyterminal NS5B. Hence, most preferably, the invention relates to a pestivirus, in particular BVDV, according to the invention, wherein the mutation(s) in the coding sequence for $N^{pro}$ lead to an encoded polyprotein as characterized by the following formula:

M[C-term], wherein the definitions are as defined above.

Also more preferably, the invention relates to a pestivirus, in particular to BVDV, according to the invention, wherein the mutation(s) in the coding sequence for $N^{pro}$ lead to an encoded polyprotein as characterized by the following formula:

$[N^{pro}]_3$-$[PS]_0$-[C-term], wherein the definitions are as defined above.

A specific example of BVDV is disclosed below, wherein the N-terminal methionine is followed by the $N^{pro}$ sequence EL and the C-protein and any other protein present in the polyprotein including the carboxyterminal NS5B. Hence, most preferably, the invention relates to a BVDV according to the invention, wherein the mutation(s) in the coding sequence for $N^{pro}$ lead to an encoded polyprotein as characterized by the following formula:

MEL-[C-term], wherein the definitions are as defined above.

Also more preferably, the invention relates to a pestivirus, in particular to BVDV according to the invention, wherein the mutation(s) in the coding sequence for $N^{pro}$ lead to an encoded polyprotein as characterized by the following formula:

$[N^{pro}]_4$-$[PS]_0$-[C-term], wherein the definitions are as defined above.

A specific example of BVDV is disclosed below, wherein the N-terminal methionine is followed by the $N^{pro}$ sequence ELF and the C-protein and any other protein present in the polyprotein including the carboxyterminal NS5B. Hence, most preferably, the invention relates to a BVDV according to the invention, wherein the mutation(s) in the coding sequence for $N^{pro}$ lead to an encoded polyprotein as characterized by the following formula:

MELF-[C-term], wherein the definitions are as defined above.

Also more preferably, the invention relates to a pestivirus, in particular to BVDV, according to the invention, wherein the mutation(s) in the coding sequence for $N^{pro}$ lead to an encoded polyprotein as characterized by the following formula:

$[N^{pro}]_6$-$[PS]_0$-[C-term], wherein the definitions are as defined above.

A specific example of BVDV is disclosed below, wherein the N-terminal methionine is followed by the $N^{pro}$ sequence ELFSN and the C-protein and any other protein present in the polyprotein including the carboxyterminal NS5B. Hence, most preferably, the invention relates to a BVDV according to the invention, wherein the mutation(s) in the coding sequence for $N^{pro}$ lead to an encoded polyprotein as characterized by the following formula:

MELFSN-[C-term], wherein the definitions are as defined above.

Also more preferably, the invention relates to a pestivirus, in particular to BVDV, according to the invention, wherein the mutation(s) in the coding sequence for $N^{pro}$ lead to an encoded polyprotein as characterized by the following formula:

$[N^{pro}]_4$-$[PS]_0$-[C-term*], wherein the definitions are as defined above except for the fact that the aminoterminal part of the C-protein is changed.

A specific example of BVDV is disclosed below, wherein the N-terminal methionine is followed by the $N^{pro}$ sequence ELF and in the C-protein sequence, the amino acid at position 2 is changed from D to N. Therefore, the aminoterminal C-protein sequence is SNEGSK . . . instead of SDEGSK. Hence, most preferably, the invention relates to a BVDV according to the invention, wherein the mutation(s) in the coding sequence for $N^{pro}$ lead to an encoded polyprotein as characterized by the following formula:

MELF-[C-term*], wherein in the C-protein the amino acid at position 2 is changed from D to N, and the definitions are as defined above.

Also more preferably, the invention relates to a pestivirus, in particular BVDV, according to the invention, wherein the mutation(s) in the coding sequence for $N^{pro}$ lead to an encoded polyprotein as characterized by the following formula:

$[N^{pro}]_x$-$[PS]_1$-[C-term], wherein the definitions are as defined as above, and PS is any of the PS disclosed above, preferably selected from the group of ubiquitin or LC3.

A specific example of BVDV is disclosed below, wherein the N-terminal methionine is followed by any 21 or 28 $N^{pro}$ amino acids, ubiquitin, or LC3 and the C-protein. Hence most preferably, the invention relates to a BVDV according to the invention, wherein the mutation(s) in the coding sequence for $N^{pro}$ lead to an encoded polyprotein as characterized by the following formula:

$[N^{pro}]_{22}$-$[PS]_1$-[C-term], wherein preferably the PS is ubiquitin or LC3, or $[N^{pro}]_{29}$-$[PS]_1$-[C-term], wherein preferably the PS is ubiquitin or LC3.

Ubiquitin is a well known highly conserved cellular protein of 76 amino acids. Among other functions, ubiquitin is a key player in protein catabolism since conjugation with ubiquitin can mark a protein for degradation via the proteasome. Ubiquitin conjugated with or fused to other proteins via the carboxyterminal glycine can be cleaved off by cellular ubiquitin-specific proteases. Thus, fusion of a protein to the carboxyterminus of ubiquitin will usually result in defined proteolytic cleavage of the fusion protein into its components when expressed within a cell.

LC3 (light chain 3 of microtubule associated proteins) represents a cellular protein of 125 amino acids that serves a variety of functions (length given for bovine LC3). Recently, a fundamental role of the protein in autophagy has been defined. During this process, LC3 is activated by carboxyterminal cleavage. Thereby, a new carboxyterminus is generated that consists of glycine. LC3 is then conjugated via the carboxyterminal glycine to phosphatidylethanolamine present in the membranes of autophagic vesicles. Because of this process, a protein fused to the carboxyterminus of LC3 will be cleaved off by a cellular protease at a defined position.

Also more preferably, the invention relates to a pestivirus, preferably to BVDV according to the invention, wherein the mutation(s) in the coding sequence for $N^{pro}$ lead to an encoded polyprotein as characterized by the following formula selected from the group of:

$[N^{pro}]_2$-$[PS]_y$-[C-term] and preferably ME-$[PS]_y$-[C-term];

$[N^{pro}]_5$-$[PS]_y$-[C-term] and preferably MELFS-$[PS]_y$-[C-term];

$[N^{pro}]_7$-$[PS]_y$-[C-term] and preferably MELFSNE-$[PS]_y$-[C-term];

$[N^{pro}]_8$-$[PS]_y$-[C-term] and preferably MELFSNEL-$[PS]_y$-[C-term];

$[N^{pro}]_9$-$[PS]_y$-[C-term] and preferably MELFSNELL-$[PS]_y$-[C-term];

$[N^{pro}]_{10}$-$[PS]_y$-[C-term] and preferably MELFSNELLY-$[PS]_y$-[C-term];

$[N^{pro}]_{11}$-$[PS]_y$-[C-term] and preferably MELFSNELLYK-$[PS]_y$-[C-term]; and $[N^{pro}]_{12}$-$[PS]_y$-[C-term] and preferably MELFSNELLYKT-$[PS]_y$-[C-term], wherein the definitions are as defined as above. The preferably disclosed embodiments refers to BVDV. Most preferably, y is 0 (i.e., no PS is present).

Also more preferably, the BVDV according to the invention as described supra is a BVDV type 1 BVDV. Most preferably, the BVDV according to the invention as described supra is a BVDV type 2 BVDV. BVDV-1 and BVDV-2 are differentiated according to features of their genomic sequences (Heinz et al., 2000 and references therein). BVDV-1 as disclosed herein may be used in the manufacture of a composition for use in the prevention and/or treatment of BVDV type 1 infections in breeding stocks of cattle, in pregnant cows and in the induction of fetal protection against BVDV type 1 infection is pregnant cows. Surprisingly, a BVDV-2 as disclosed herein may be used in the manufacture of a composition for use in the prevention and/or treatment of BVDV type 1 infections in breeding stocks of cattle. In particular, the invention relates to the use of a BVDV type 2 according to the invention in the manufacture of a composition for use in the prevention and/or treatment of BVDV type 1 infections in pregnant cows. Preferably, the BVDV type 2 according to the invention may be used in the manufacture of a composition for use in the induction of fetal protection against BVDV type 1 infections in pregnant cows. Surprisingly also, a BVDV-1 as disclosed herein may be used in the manufacture of a composition for use in the prevention and/or treatment of BVDV type 2 infections in breeding stocks of cattle. In particular, the invention relates to the use of a BVDV type 1 according to the invention in the manufacture of a composition for use in the prevention and/or treatment of BVDV type 2 infections in pregnant cows. Preferably, the BVDV type 1 according to the invention may be used in the manufacture of a composition for use in the induction of fetal protection against BVDV type 2 infections in pregnant cows. Most preferred is the use of BVDV type 1 and type 2 in combination for the manufacture of a composition for use in the prevention and/or treatment of BVDV type 1 and or type 2 infections in breeding stocks of cattle, in pregnant cows and in the induction of fetal protection against BVDV type 1 and/or type 2 infections is pregnant cows.

Most preferably, the wild-type BVDV according to the invention which is to be mutated as disclosed herein corresponds to amino acid sequence SEQ ID NO:5 (termed XIKE-A) or is a functional variant thereof. Most preferably also, the BVDV according to the invention has a $N^{pro}$ mutation according to the invention and corresponds to amino acid sequence SEQ ID NO:6 (termed XIKE-A-NdN) or is a functional variant thereof. Preferably, such a functional variant is at least 65% homologous to the amino acid sequence disclosed herein. On the amino acid level, homologies are very roughly: BVDV-1/-BVDV-1: 93%; BVDV-1/-BVDV-2: 84%; BVDV-2/-BVDV-2: 98%. Therefore, more preferable, such a functional variant is at least 70%, 71%, 72%, 73%, 74%, 75%, 76%, 77%, 78%, 79%, 80%, 81%, 82%, 83%, 84%, 85%, 86%, 87%, 88%, 89%, or 90% homologous to the amino acid sequence disclosed herein. More preferably also, such functional variant is at least 91%, 92%, 93%, 94%, 95%, 96%, 97%, or 98% homologous to the amino acid sequence disclosed herein. Most preferably, such functional variant is at least 99% or 99.9% homologous to the amino acid sequence disclosed herein.

Most preferably also, the BVDV according to the invention has a $E^{rns}$ mutation according to the invention which has a deletion of the codon coding for histidine 349, and corresponds to amino acid sequence SEQ ID NO:7 (termed XIKE-B) or is a functional variant thereof. Most preferably also, the BVDV according to the invention has both a $E^{rns}$ mutation and a $N^{pro}$ mutation according to the invention, wherein the codon coding for histidine 349 of $E^{rns}$ is deleted and also the complete $N^{pro}$ coding region is deleted, except for codons 1 to 4, thus amino acids MELF of $N^{pro}$ remain. The mutant corresponds to amino acid sequence SEQ ID NO:8 (termed XIKE-B-NdN) or is a functional variant thereof. Preferably, such a functional variant is at least 65% homologous to the amino acid sequence disclosed herein. More preferable, such a functional variant is at least 70%, 71%, 72%, 73%, 74%, 75%, 76%, 77%, 78%, 79%, 80%, 81%, 82%, 83%, 84%, 85%, 86%, 87%, 88%, 89%, or 90% homologous to the amino acid sequence disclosed herein. More preferably also, such functional variant is at least 91%, 92%, 93%, 94%, 95%, 96%, 97%, or 98% homologous to the amino acid sequence disclosed herein. Most preferably, such functional variant is at least 99% or 99.9% homologous to the amino acid sequence disclosed herein.

Most preferably also, the BVDV according to the invention has a $E^{rns}$ mutation according to the invention which has a substitution of the codon coding for histidine 300 by the codon coding for leucine and corresponds to amino acid sequence SEQ ID NO:9 (termed XIKE-C) or is a functional variant thereof. Most preferably also, the BVDV according to the invention has both a $E^{rns}$ mutation and a $N^{pro}$ mutation according to the invention, wherein the codon coding for histidine 300 is substituted by the codon coding for leucine and also the complete $N^{pro}$ coding region is deleted, except for codons 1 to 4, thus amino acids MELF of $N^{pro}$ remain. The mutant corresponds to amino acid sequence SEQ ID NO:10 (termed XIKE-C NdN) or is a functional variant thereof. Preferably, such a functional variant is at least 65% homologous to the amino acid sequence disclosed herein. More preferable, such a functional variant is at least 70%, 71%, 72%, 73%, 74%, 75%, 76%, 77%, 78%, 79%, 80%, 81%, 82%, 83%, 84%, 85%, 86%, 87%, 88%, 89%, or 90% homologous to the amino acid sequence disclosed herein. More preferably also, such functional variant is at least 91%, 92%, 93%, 94%, 95%, 96%, 97%, or 98% homologous to the amino acid sequence disclosed herein. Most preferably, such functional variant is at least 99% or 99.9% homologous to the amino acid sequence disclosed herein.

Another important embodiment of the invention described herein is a composition comprising a pestivirus, in particular a BVDV according to the invention and a solution. The skilled person knows additional components which may be comprised in the composition (see also Remington's Pharmaceutical Sciences, 18th ed. Mack Publ., Easton (1990)). The expert may use known injectable, physiologically acceptable sterile solutions. For preparing a ready-to-use solution for parenteral injection or infusion, aqueous isotonic solutions, such as, e.g., saline or corresponding plasma protein solutions, are readily available. The pharmaceutical compositions may be present as lyophylisates or dry preparations, which can be reconstituted with a known injectable solution directly before use under sterile conditions, e.g., as a kit of parts.

The final preparation of the compositions of the present invention are prepared for, e.g., injection by mixing the pestivirus, preferably BVDV according to the invention with a sterile physiologically acceptable solution, that may be supplemented with known carrier substances or/and additives (e.g., serum albumin, dextrose, sodium bisulfite, EDTA). The solution may be based on a physiologically acceptable solvent, e.g., an aqueous solution between pH 7 and 8. The pH may be stabilized by a pharmaceutically acceptable buffer. The solution may also contain further stabilizing agents like a detergent like Tween 20, serum albumin such as bovine serum albumin (BSA), ascorbic acid, and/or spermidine. The composition may also comprise adjuvants, e.g., aluminum hydroxide, mineral or other oils or ancillary molecules added to the vaccine or generated by the body after the respective induction by such additional components, like but not restricted to interferons, interleukins, or growth factors.

For example, in a composition according to the invention, the pestivirus, in particular BVDV may be solved in:

| | |
|---|---|
| Pestivirus (preferably BVDV) | $10^2$-$10^8$ $TCID_{50}$ |
| SGS* | 25% v/v |
| Cell culture medium | qsp 1 dose |
| *SGS: | Composition per 2 mL |

-continued

| | |
|---|---|
| Sucrose | 75 mg |
| Gelatin | 20 mg |
| Potassium hydroxide | 0.274 mg |
| L-glutamic acid | 0.72 mg |
| Potassium dihydrogen phosphate | 0.516 mg |
| Dipotassium phosphate | 1.254 mg |
| Water for injection | qsp 2 mL |

If the composition is first lyophilized or dehydrated by other methods, then, prior to vaccination, the composition is rehydrated in aqueous (e.g., saline, phosphate buffered saline (PBS)) or non-aqueous solutions (e.g., oil emulsion (mineral oil, or vegetable/metabolizable oil based/single or double emulsion based), aluminum-based, carbomer based adjuvant).

Preferably, the composition according to the invention induces an immunological response in an animal. More preferred, the composition according to the invention is a vaccine. A vaccine as understood herein comprises a pestivirus, in particular BVDV according to the invention and is defined above in the Definitions of Terms Used in the Description section.

Most preferred, the composition according to the invention further comprises a pharmaceutically acceptable carrier or excipient. Several carriers or excipients are disclosed above. The composition may comprise, if aimed at injections or infusion, substances for preparing isotonic solutions, preservatives such as p-hydroxybenzoates, stabilizers such as alkali salts of ethylendiamintetracetic acid, possibly also containing emulsifying and/or dispersing agents.

The composition according to the invention may be applied intradermally, intratracheally, or intravaginally. The composition preferably may be applied intramuscularly or intranasally. In an animal body, it can prove advantageous to apply the pharmaceutical compositions as described above via an intravenous or by direct injection into target tissues. For systemic application, the intravenous, intravascular, intramuscular, intranasal, intraarterial, intraperitoneal, oral, or intrathecal routes are preferred. A more local application can be effected subcutaneously, intradermally, intracutaneously, intracardially, intralobally, intramedullarly, intrapulmonarily, or directly in or near the tissue to be treated (connective-, bone-, muscle-, nerve-, or epithelial tissue). Depending on the desired duration and effectiveness of the treatment, the compositions according to the invention may be administered once or several times, also intermittently, for instance on a daily basis for several days, weeks, or months and in different dosages.

The invention also relates to the use of a pestivirus, in particular BVDV, according to the invention in the manufacture of a vaccine for the prophylaxis and treatment of pestiviral infections, in particular of BVDV infections.

Another important part of the invention is a polynucleotide molecule comprising the nucleic acid coding for a pestivirus, in particular for a BVDV, according to the invention, or a fragment, functional variant, variant based on the degenerative nucleic acid code, fusion molecule, or a chemical derivative thereof. Preferably, the polynucleotide molecule is DNA. Also preferably, the polynucleotide molecule is RNA. In a more preferred embodiment, the polynucleotide molecule also comprises the nucleotide sequence of a functional 5'- and/or 3'-non-translated region of a pestivirus, in particular of BVDV.

There are several nucleotide sequences known in the art, which represents the basis for the production of a polynucleotide molecule coding for a pestivirus attenuated according to the present invention, having at least one mutation in the coding sequence of $N^{pro}$ and at least one in the coding sequence of glycoprotein $E^{rns}$, wherein the mutations result in an combined inactivation of the RNase activity residing in glycoprotein $E^{rns}$ and in the inactivation of the immunomodulating activity residing in $N^{pro}$. Examples of nucleic acid sequences of wild-type sequences of several members of pestiviruses are listed below:

| | |
|---|---|
| Border disease virus | |
| Strain BD31 | NCBI GenBank Accession No. [U70263] |
| Strain X818 | NCBI GenBank Accession No. [AF037405] |
| Bovine viral diarrhea virus 1 | |
| Strain NADL | NCBI GenBank Accession No. [M31182] |
| Strain Osloss | NCBI GenBank Accession No. [M96687] |
| Strain SD-1 | NCBI GenBank Accession No. [M96751] |
| Strain CP7 | NCBI GenBank Accession No. [U63479] |
| Bovine viral diarrhea virus 2 | |
| Strain 890 | NCBI GenBank Accession No. [U18059] |
| Strain C413 | NCBI GenBank Accession No. [AF002227] |
| Classical swine fever virus | |
| Strain Alfort/187 | NCBI GenBank Accession No. [X87939] |
| Strain Alfort-Tubingen | NCBI GenBank Accession No. [J04358] |
| Strain Brescia | NCBI GenBank Accession No. [M31768] |
| Strain C strain | NCBI GenBank Accession No. [Z46258] |

The mutations/modifications according to the invention relating to the coding sequence of $N^{pro}$ and $E^{rns}$ are described above more in detail. Having this information, a person skilled in the art is able to realize the manufacture of any polynucleotide/polynucleic acid coding for a pestivirus according to the present invention. Furthermore, this person is able to manufacture an attenuated pestivirus according to the invention. Molecular method for introducing a mutation into a polynucleotide sequence, cloning, and amplification of the mutated polynucleotide are for example provided by Sambrook et al., 1989 or Ausubel et al., 1994.

Most preferably, the wild-type BVDV according to the invention which is to be mutated as disclosed herein is encoded by the nucleic acid sequence SEQ ID NO:1 (termed XIKE-A) or a functional variant thereof. Most preferably also, the BVDV according to the invention has a $N^{pro}$ mutation according to the invention and is encoded by nucleic acid sequence SEQ ID NO:2 (termed XIKE-A-NdN) or a functional variant thereof. Preferably, such a functional variant is at least 65% homologous to the nucleic acid sequence disclosed herein. On the nucleic acid level, homologies are very roughly: BVDV-1/-BVDV-1: 80%; BVDV-1/-BVDV-2: 70%; BVDV-2/-BVDV-2: 96%. Therefore, more preferable, such a functional variant is at least 70%, 71%, 72%, 73%, 74%, 75%, 76%, 77%, 78%, 79%, 80%, 81%, 82%, 83%, 84%, 85%, 86%, 87%, 88%, 89%, or 90% homologous to the nucleic acid sequence disclosed herein. More preferably also, such functional variant is at least 91%, 92%, 93%, 94%, 95%, 96%, 97%, or 98% homologous to the nucleic acid sequence disclosed herein. Most preferably, such functional variant is at least 99% or 99.9% homologous to the nucleic acid sequence disclosed herein.

Most preferably also, the BVDV according to the invention has a $E^{rns}$ mutation according to the invention which has a deletion of codon H349 and is encoded by nucleic acid sequence SEQ ID NO:7 (termed XIKE-B) or by a functional variant thereof. Most preferably also, the BVDV according to the invention has both a $E^{rns}$ mutation and a $N^{pro}$ mutation according to the invention, wherein the codon coding for histidine 349 of $E^{rns}$ is deleted and also the complete $N^{pro}$ coding region is deleted, except for codons 1 to 4, thus amino acids MELF of $N^{pro}$ remain. The mutant is encoded by nucleic acid sequence SEQ ID NO:8 (termed XIKE-B-NdN) or by a functional variant thereof. Preferably, such a functional variant is at least 65% homologous to the nucleic acid sequence disclosed herein. More preferable, such a functional variant is at least 70%, 71%, 72%, 73%, 74%, 75%, 76%, 77%, 78%, 79%, 80%, 81%, 82%, 83%, 84%, 85%, 86%, 87%, 88%, 89%, or 90% homologous to the nucleic acid sequence disclosed herein. More preferably also, such functional variant is at least 91%, 92%, 93%, 94%, 95%, 96%, 97%, or 98% homologous to the nucleic acid sequence disclosed herein. Most preferably, such functional variant is at least 99% or 99.9% homologous to the nucleic acid sequence disclosed herein.

Most preferably also, the BVDV according to the invention has a $E^{rns}$ mutation according to the invention which is a substitution of codon “H300” by a leucine codon, and is encoded by nucleic acid sequence SEQ ID NO:11 (termed XIKE-C) or a functional variant thereof. Most preferably also, the BVDV according to the invention has both a $E^{rns}$ mutation and a $N^{pro}$ mutation according to the invention, wherein the codon coding for histidine 300 is substituted by the codon coding for leucine and also the complete $N^{pro}$ coding region is deleted, except for codons 1 to 4, thus amino acids MELF of $N^{pro}$ remain. The mutant is encoded by nucleic acid sequence SEQ ID NO:12 (termed XIKE-C-NdN) or by a functional variant thereof. Preferably, such a functional variant is at least 65% homologous to the nucleic acid sequence disclosed herein. More preferable, such a functional variant is at least 70%, 71%, 72%, 73%, 74%, 75%, 76%, 77%, 78%, 79%, 80%, 81%, 82%, 83%, 84%, 85%, 86%, 87%, 88%, 89%, or 90% homologous to the nucleic acid sequence disclosed herein. More preferably also, such functional variant is at least 91%, 92%, 93%, 94%, 95%, 96%, 97%, or 98% homologous to the nucleic acid sequence disclosed herein. Most preferably, such functional variant is at least 99% or 99.9% homologous to the nucleic acid sequence disclosed herein.

Another important aspect of the invention is a method for attenuating a pestivirus, characterized in that at least one mutation in the coding sequence for glycoprotein $E^{rns}$ and at least another mutation in the coding sequence for $N^{pro}$ is generated in a pestivirus genome. According to a preferred embodiment, the pestivirus is BVDV.

According to a more preferred embodiment, the method comprises the steps:

a) reverse transcription of a wild-type pestivirus nucleotide sequence into a cDNA;
b) cloning the cDNA;
c) introducing mutations selected from the group of deletions, insertion mutations, and/or substitution mutations into the cDNA, wherein the mutations are located in the coding sequence encoding glycoprotein $E^{rns}$ and the protease $N^{pro}$; and
d) incorporating the cDNA into a plasmid or into a DNA virus capable of directing the transcription of pestivirus cDNA into RNA in vitro or upon infection of suitable cells.

Regarding the method for attenuating a BVDV according to the invention, the preferred methods comprises the steps:

a) reverse transcription of a wild-type BVDV nucleotide sequence into a cDNA;

b) cloning the cDNA;

c) introducing mutations selected from the group of deletions, insertion mutations, and/or substitution mutations into the cDNA, wherein the mutations are located in the coding sequence encoding glycoprotein $E^{rns}$ and the protease $N^{pro}$; and d) incorporating the cDNA into a plasmid or into a DNA virus capable of directing the transcription of pestivirus cDNA into RNA in vitro or upon infection of suitable cells.

Yet another important embodiment of the invention is a method of treatment of disease caused by a pestivirus, wherein a pestivirus according to the invention or a composition according to the invention, wherein the pestivirus or the composition is administered to an animal in need thereof at a suitable doses as known to the skilled person and the reduction of symptoms of the pestivirus infection.

Yet another important embodiment of the invention is a method of treatment of disease caused by BVDV, wherein a BVDV according to the invention or a composition according to the invention, wherein the BVDV or the composition is administered to an animal in need thereof at a suitable doses as known to the skilled person and the reduction of symptoms of BVDV infection such as viremia and leukopenia and/or pyrexia and/or diarrhea is monitored.

EXAMPLES

The following examples serve to further illustrate the present invention; but the same should not be construed as limiting the scope of the invention disclosed herein.

Example 1

BVDV XIKE-B: Fetopathogenicity Assessment in Pregnant Heifers

BVDV XIKE-B, an RNase negative mutant of the highly pathogenic BVDV type 2 isolate NewYork93/C was recovered from the infectious cDNA clone pKANE40B and showed wild-type-like (wt-like) growth characteristics in tissue culture. In animal experiments the mutant virus was found to be considerably attenuated so that it represented a promising candidate for development of a live attenuated vaccine virus (Meyer et al., 2002). To test whether this attenuated virus is still able to cross the placenta and infect the fetus, pregnant heifers were infected with XIKE-B. As a control, wild-type BVDV recovered from cDNA clone pKANE40A was used. The respective virus named XIKE-A expresses an active $E^{rns}$ RNase in the infected cell. The study aimed to assess the safety of XIKE-A and XIKE-B in pregnant animals.

Experimental Design

Ten pregnant heifers were selected from a BVDV negative herd. The following groups of 5 heifers were included in the trial:

| | No. | Inoculation | Virus |
|---|---|---|---|
| Group 1: | 5 | One i.n. administration, 3 mL in each nostril | XIKE-A |
| Group 2: | 5 | One i.n. administration, 3 mL in each nostril | XIKE-B |

Heifers were moved to the experimental facilities 8 days before inoculations. Pregnancy status was confirmed after transport into the experimental facility. Heifers were between days 60 and 90 of gestation on the day of inoculation. Inoculation took place for all animals at one point of time.

Heifers were monitored for the presence of clinical signs of BVDV infection including abortions during the observation period. Blood samples were collected from the animals for serology, antigen detection, and white blood cells were counted. The experiment was terminated 9 weeks after infection. Non-aborted cows were slaughtered, the uterus examined, and collected. Fetal organ samples were collected during routine necropsy and examined for BVDV infection.

The presence of fetal infection was the main evaluation parameter, composed from the number of BVDV-related cow mortality, the number of BVDV-related abortions, and the number of BVDV positive fetuses at termination. In addition to the main parameter, clinical signs characteristic for BVDV infection, viremia, and white blood cell counts in cows and rectal temperature after challenge were evaluated.

Animals

Heifers were purchased from a farm free of BVDV. Only animals which met the following inclusion criteria were used.

Inclusion Criteria

Free of BVD antibodies; each individual was tested in the serum antibody test prior to transport and at the initiation of the study (at the animal test facility).

Free of BVDV; plasma and/or buffy-coat preparation from each individual was tested by a suitable test.

Clinically healthy at the initiation of the study judged upon physical examination. The health examination of the animals was accomplished in accordance with the current, generally accepted veterinary practice.

Pregnancy confirmed by physical examination before inoculation. Pregnancy was between 60-90 days at the time of inoculation, proven by insemination records.

| Test Strain A | |
|---|---|
| Description: | XIKE-A, live virus BVDV strain |
| Composition: | Experimental material comprising of cell culture supernatant of low passaged XIKE-A |
| BVD components: | BVDV type II strain: XIKE-A |
| Supplied by: | Dr. Gregor Meyers, "Bundesforschungsanstalt für Viruskrankheiten der Tiere" (BFAV), Paul-Ehrlich-Straβe 28, 72076 Tübingen, Germany |
| Applied BVD virus dose: | Type 1 strain: $10^5$ $TCID_{50}$/6 mL (TCID = Tissue Culture Infective Dose) |
| Applied vaccine volume: | 3 mL per nostril |
| Application route: | Intranasal |
| Preparation of dosage form: | The inoculum was sent in a pre-diluted frozen form in a 50 mL vial on dry ice and was to be stored at −70° C. before inoculation. Immediately before inoculation of Group 1 heifers, the material was thawed avoiding local temperatures above 37° C. After no ice was visible in the fluid, material was gently stirred and immediately used for inoculation of the animals. |
| Unused inoculum: | The volume of the unused material was be measured and split on two aliquots before immediate freezing in dry ice or liquid nitrogen and stored for re-titration purposes. Virus and contaminated plastic or glassware were incubated with an appropriate volume of an 8-10% formaldehyde solution for at least 24 hours at room temperature before discarding in order to inactivate viruses. |

-continued

| Test Strain B | |
|---|---|
| Description: | XIKE-B, live virus BVDV strain |
| Composition: | Experimental material comprising of cell culture supernatant of low passaged XIKE-B |
| BVD components: | BVDV type II strain: XIKE-B |
| Supplied by: | Dr. Gregor Meyers, "Bundesforschungsanstalt für Viruskrankheiten der Tiere" (BFAV), Paul-Ehrlich-Straβe 28, 72076 Tübingen, Germany |
| Applied BVD virus dose: | Type 1 strain: $10^5$ $TCID_{50}$/6 mL (TCID = Tissue Culture Infective Dose) |
| Applied vaccine volume: | 3 mL per nostril |
| Application route: | Intranasal |
| Preparation of dosage form: | The inoculum was sent in a pre-diluted frozen form in a 50 mL vial on dry ice and was stored at −70° C. before inoculation. Immediately before inoculation of Group 2 heifers, the material was thawed avoiding local temperatures above 37° C. After no ice was visible in the fluid, material was gently stirred and immediately used for inoculation of the animals. |
| Unused vaccine: | The volume of the unused material was measured and split on two aliquots before immediate freezing in dry ice or liquid nitrogen and stored for retitration purposes. Virus and contaminated plastic or glassware was incubated with an appropriate volume of an 8-10% formaldehyde solution for at least 24 hours at room temperature before discarding in order to inactivate viruses. |

Pregnancy Control

Pregnancy was confirmed immediately before inoculation.

Inoculation of Heifers

The inoculation is Day 0 of the experiment.

In each nostril, 3 mL of the test material was administered intranasally by syringe without needle. Each time a new sterile syringe was taken. Administration was performed during the aspiration phase in order to minimize loss of fluid via expiration of material.

Post-Inoculation Observations

Collection and Examination of Blood Samples

Blood was collected following standard, aseptic procedures (disinfecting the bleeding site). A new sterile syringe and needle was used for each animal.

Blood Collection to Prepare Serum

At least 10 mL blood was collected from the heifers immediately before inoculation, then weekly after infection and at the termination of the study. Serum was stored at −20° C. until required.

Blood Collection for Leukocyte Counts and Buffy Coat Preparations

For leukocyte counting, 3 mL blood was transferred immediately after collection to suitable sterile vessels (Venoject, Terumo Europe N.V., Leuven, Belgium), pre-filled with 0.06 mL EDTA (0.235 MOL/L).

For buffy coat preparations, at least 15 mL blood was transferred immediately after collection to suitable sterile vessels, pre-filled with 0.1 mL Heparin solution (Na-heparin for inj., 5000 IU/mL lot A7B163A, exp. date: 11/2000: Gedeon Richter RT, Budapest, Hungary) yielding at least 20 IU Heparin per mL blood in the blood sample. The content was carefully mixed thereafter.

For preparation of buffy coats and leukocyte counting, blood was collected from the heifers on every day, between Day 0 and Day 14 after infection; and on every second day, between Day 15 and Day 40, or until all animals were negative for virus isolation for three consecutive sampling time points.

Preparation of Serum

Blood was allowed to clot at room temperature, and separated by centrifugation. Each serum sample was divided into two aliquots of at least 2 mL each. One set of aliquots was assayed for BVDV specific antibodies by ELISA. The rest of the sera was frozen and stored at −20° C. until required.

Leukocyte Counts

Leukocyte counts was determined with a coulter-counter semi-automated electronic device (Diatron Minicell-16, Messtechnik GmbH, Wien, Austria) with a claimed accuracy of $0.1\times10^9$/l, 100 µL. The instrument was used (calibration and leukocyte-counts) according to the manufacturer's recommendations.

Preparation of Buffy Coats

Heparin blood samples was transported to the laboratory as soon as possible. Buffy coat preparation procedure, following a standard laboratory procedure, was performed under aseptic conditions (sterile pipettes, handling, clean bench, etc.).

The obtained buffy coats were re-suspended in a small volume (2 mL) of RPMI 1640 and frozen at −70° C. in two aliquots of 0.5 mL. The residual 1 mL buffy coats was immediately used for determination of blood cell associated BVDV by co-cultivation in a permissive cell culture.

BVD Serum Antibody ELISA-Test

Each serum sample was tested for the presence of BVDV-antibodies using a suitable and validated ELISA test (Svanovir™ BVDV antibody test Cat# 10-2200-10). Test was validated and performed according to the manufacturer's recommendations. Positive samples were diluted according to the $\log_2$ scale to determine BVDV antibody titers.

BVD Antigen Assay(s)

Each buffy coat sample was assayed for the presence of BVDV by co-cultivation of the freshly prepared buffy-coats with susceptible cells or a cell-line. No freezing was allowed before co-cultivation. Plasma was collected and provided to Man-Gene from each sample.

Clinical Observations

Observation of Heifers

Animals were examined daily from Day 0-42 post-inoculation for the presence of clinical symptoms by a sufficiently trained veterinarian.

All clinical signs were recorded and described by its nature, consistence/touch, severity (mild, medium or severe) location, size of the area affected, and they will be scored according to agreed and standard definitions. Special attention was paid to respiratory signs (respiration, its rate; nasal or ocular discharge; conjunctivitis, sneezing, coughing, etc.) and diarrhea.

Rectal Temperatures

Rectal temperatures were measured daily in each heifer, at the same hour of the day (preferably in the morning) from 5 days prior to the inoculation till 21 days post-infection. Daily measurement of rectal temperature was continued until each animal had rectal temperatures below or equal to 39° C. for at least 3 consecutive days.

Detection of Interrupted Pregnancy

Pregnancy was confirmed and suspicion for abortion or resorption of the fetus was established by rectal examination. A trained veterinarian examined all animals at inoculation, 1 and 2 months post-inoculation. The examination was carried out according to the generally accepted veterinary practice. Heifers were examined daily for any sign of abortion until termination of the study (8-12 weeks post-challenge).

Termination of the Study

The study was terminated by slaughtering the heifers and extracting the fetuses. Fetuses and fetal material were transferred into closed transport containers marked with the number of the cow and the date/time. Containers were transported to a selected necropsy room. Necropsy of the heifers was not required. Necropsy was performed on fetuses, findings recorded, and a panel of samples collected as described below.

Post-Mortem Examination

A detailed necropsy of the experimental animals was done in each case of death. Post-mortem examinations were carried out by an experienced veterinary surgeon and the data were recorded on appropriate data sheets. Further laboratory tests were performed according to the clinical signs and lesions observed. If the diagnosis of the necropsy referred to a disease caused by microbial agent the diagnosis was verified by an appropriate test, specific for the agent. Each tissue sample was collected in at least 2 separate, labeled containers and snap-frozen in liquid nitrogen. Samples were stored at −70° C. until required.

Aborted Fetuses and Study Termination

At least the following tissue samples were collected from the fetuses: exudate from the peritoneal cavity or thorax, if present; mesenteric lymph nodes; spleen; thymus; cerebellum; kidney; bone marrow from the sternum; and sample from the placenta, if available.

Dead or Sacrificed Heifers

At least the following tissue samples were collected: blood for buffy coat, if available; blood for serum, if available; Peyer's patches; mesenteric lymph nodes; spleen; kidney; uterus, including a sample from the placenta, if available.

Storage and Transport of Samples

| Samples: | Storage: |
|---|---|
| Serum | −20° C. |
| Buffy coat | −70° C. |
| Virus | −70° C. |
| Tissue from heifers | −70° C. |
| Tissue from fetuses | −70° C. |

Samples were sent for laboratory analysis as required by the sponsor. The choice of samples and the timing of transport were agreed with the study monitor or the project manager. As a matter of general principle, samples coming from aborted material or from new-born calves were investigated as soon as possible.

Results

Mortality

Heifer No. 626 (Group 1) died on Day 13 PI (post-inoculation). The following table summarizes the observed clinical signs and lesions revealed during necropsy:

| Heifer | In-life observations | Post-mortem findings |
|---|---|---|
| No. 626 | signs of disease from 7 DPI<br>lachrymation, nasal discharge on 7-12 DPI<br>loss of appetite from 8-12 DPI<br>diarrhea on 11-12 DPI<br>elevated respiratory rate on 9-10 and 12 DPI<br>coughing on 9 DPI<br>abnormal breathing on 12 DPI | dehydration<br>hemorrhages on the serous membranes<br>hyperemia of the Peyer's patches<br>edema of the lung |

These clinical and gross-pathological findings are consistent with BVDV induced lesions, therefore it may be concluded that the reason of death was the BVDV infection.

Abortions after Infection

One heifer had clinical abortion in each group. Heifer No. 615 (Group 1) aborted on Day 38 PI, Heifer No. 469 (Group 2) aborted on Day 39 PI. Both fetuses showed the signs of autolysis, and they were estimated to die at least 3-7 days before the abortion (around 32-35 DPI). In Group 1, no fetus was found in Heifer No. 526 during the slaughter examination at termination. Gross-pathology of the uterus revealed the following: the right uterine horn was slightly enlarged, and the remains of placenta with progressed autolysis was retained in the lumen. The findings on the uterus of Heifer No. 526 is consistent with a “silent” abortion, most likely due to the BVD infection.

Clinical Observation of Heifers

A summary of the clinical observation data and duration of clinical signs in the groups are presented below.

Clinical Signs and the Days Post-Inoculation (DPI) when they were Observed

| | Group 1 (XIKE-A) | | | | |
|---|---|---|---|---|---|
| | Animal ID | | | | |
| Clinical sign | 526 | 598 | 615<br>DPI | 618 | 626* |
| Loss of appetite | 8-13 | 8-18 | 8-18 | 8-16 | 8-12 |
| Lachrymation | 7-10 | 7-8, 10-12 | 8-10 | 8-10 | 7-8 |
| Conjunctivitis | 9-10 | 9-12 | 9-11 | 9-11 | — |
| Nasal discharge | 7-13 | 7-9, 11-12 | 8-13 | 8-12 | 7-12 |
| Oral erosion | — | — | — | — | — |
| Oral hemorrhage | — | — | — | — | — |
| Diarrhea | — | 11-16 | 10-15 | 11-15 | 11-12 |
| Coughing | 9 | 10, 15 | 9 | 8-9, 13 | 9 |
| Abnormal breathing | — | 11-14 | 12-14 | 12-14 | 12 |
| Elevated respiratory rate | — | 10-13 | 9-13 | 8-13 | 9-10, 12 |
| Hoof erosion | — | — | — | — | — |

*Heifer No. 626 died on Day 13 PI

| | Group 2 (XIKE-B) | | | | |
|---|---|---|---|---|---|
| | Animal ID | | | | |
| Clinical sign | 469 | 588 | 565 | 608 | 619 |
| Loss of appetite | — | — | — | — | — |
| Lachrymation | — | — | — | — | — |
| Conjunctivitis | — | — | — | — | — |
| Nasal discharge | — | — | — | — | — |

-continued

| | Group 2 (XIKE-B) | | | | |
|---|---|---|---|---|---|
| | Animal ID | | | | |
| Clinical sign | 469 | 588 | 565 | 608 | 619 |
| Oral erosion | — | — | — | — | — |
| Oral hemorrhage | — | — | — | — | — |
| Diarrhea | — | — | — | — | — |
| Coughing | — | — | — | — | — |
| Abnormal breathing | — | — | — | — | — |
| Elevated respiratory rate | — | — | — | — | — |
| Hoof erosion | — | — | — | — | — |

All Group 1 animals infected with XIKE-A exhibited a broad spectrum of clinical signs. Respiratory signs appeared first accompanied by loss of appetite, and a few days later heifers developed diarrhea with the exception of Heifer No. 526. One heifer died and another one aborted (see before) after infection. All these signs are consistent with the symptoms expected after infection with a virulent BVDV strain.

All Group 2 animals infected with XIKE-B were free of clinical signs. At the same time, one heifer had abortion during the observation period.

Rectal Temperatures

No abnormal temperature changes were detected before the infection of the animals. In Group 2, all temperature values remained within the physiological range from Day 0 to Day 21 after infection. All Group 1 animals showed elevated rectal temperature after infection that were detected between Days 7-11 PI.

Finding at Study Termination

At study termination, fetuses were examined at slaughter. No fetus was recovered from Heifer No. 526 (see section 10.2 "Abortions after Infection"). The following findings were observed at the necropsy of the fetuses:

| Animal No. | Findings | Conclusion |
|---|---|---|
| | Group 1 | |
| 598 | Ascites, general edema, autolysis | Died at least 2 weeks earlier |
| 618 | Ascites, general edema, autolysis | Died at least 3 weeks earlier |
| | Group 2 | |
| 565 | Ascites, general edema, liver degeneration | Fetus considered non-viable |
| 588 | Normal | — |
| 608 | Normal, perirenal edema | — |
| 619 | General autolysis | Died 3-6 weeks earlier |

The findings suggest that 2 Group 1 animals (Heifers No. 598 and No. 618) and one Group 2 animal (Heifer No. 619) died several weeks before extraction, and so they can be considered abortions.

Abortions Modified by Post-Mortem Findings

After the post-mortem examination it was not clear why some of the heifers had not had abortions. Dead fetuses should be considered as abortions, therefore the clinical picture was modified after the termination of the study as follows:

| Animal No. | Conclusion |
|---|---|
| | Group 1 |
| 526 | BVD abortion (uterus with placenta post-mortem) |
| 598 | BVD abortion (fetus post-mortem) |
| 615 | Clinical BVD abortion |
| 618 | BVD abortion (fetus post-mortem) |
| 626 | Died due to BVD |
| | Group 2 |
| 469 | Clinical BVD abortion |
| 565 | Expected BVD abortion; non-viable fetus |
| 588 | Normal |
| 608 | Normal |
| 619 | BVD abortion (fetus post-mortem) |

Examination of Blood Samples

Leukocyte Count

WBC counting was interrupted on Day 26 PI, as all animals became negative for virus isolation for this time point. 0 DPI values were considered as individual baseline for comparison. In Group 2, the leukocyte counts never went to 40% or more below the baseline value until the end of the observation period (26 DPI). In Group 1, one animal (Heifer No. 598) had WBC count below the 40% baseline for one day.

Serology

None of the selected animals had BVDV specific antibody in their sera before the infection. After infection, all surviving Group 1 heifers developed BVDV specific antibodies detected from 3 weeks PI and lasted until the end of the observation period in all study animals. In Group 2, 4 out of the 5 heifers had BVDV specific antibodies detected from 4 weeks PI. Measurable antibody response lasted only in 3 animals until the end of the observation period. Titers were lower in Group 2 than in Group 1.

Virus Detection by Co-Cultivation

Buffy Coats

BVDV was detected in both groups. The duration of virus detection is summarized below. All samples were co-cultivated immediately after collection, i.e., without freezing.

| Animal No. | DPI when BVDV was detected |
|---|---|
| | Group 1 |
| 615 | 5-12 |
| 526 | 5-9 |
| 626 | 5-12 |
| 618 | 5-11, 14 |
| 598 | 5-11, 13 |
| | Group 2 |
| 565 | 7-9 |
| 588 | 8 |
| 608 | 6-9 |
| 469 | 8 |
| 619 | 5-11 |

Tissue Samples

The presence of BVD virus in the dead heifer and the fetuses is summarized below:

Heifer:

| Animal No. | BVDV in tissue samples |
|---|---|
| Group 1 | |
| 626 | Present# |

Fetuses:

| Animal No. | BVDV in tissue samples |
|---|---|
| Group 1 | |
| 615 | Not present# |
| 526 | NT |
| 626 | Present# |
| 618 | Not present |
| 598 | Present |
| Group 2 | |
| 565 | Present |
| 588 | Not present |
| 608 | Present |
| 469 | Not present# |
| 619 | Not present |

NT = Not tested

Samples were co-cultivated immediately after collection (i.e., without freezing), except "#" marked ones, from which only frozen samples were available.

Summary of BVD Related Clinical and Laboratory Data

| Group 1 | | |
|---|---|---|
| Animal No. | Conclusion | BVD |
| 526 | BVD abortion (uterus with placenta post-mortem) | NT (no sample found) |
| 598 | BVD abortion (fetus post-mortem) | +(fetus)* |
| 615 | Clinical BVD abortion | −(fetus)* |
| 618 | BVD abortion (fetus post-mortem) | −(fetus)* |
| 626 | Died due to BVD | +(fetus)/+(heifer) |

NT = not tested

| Group 2 | | |
|---|---|---|
| Animal No. | Conclusion | BVD |
| 469 | Clinical BVD abortion | −(fetus)* |
| 565 | Expected BVD abortion; non-viable fetus | +(fetus) |
| 588 | Normal | −(fetus) |
| 608 | Normal | +(fetus) |
| 619 | BVD abortion (fetus post-mortem) | −(fetus)* |

*Fetuses were autolyzed at the time of sampling

Conclusion

The study aimed to assess the safety of XIKE-A and XIKE-B in pregnant animals. Ten pregnant heifers were selected from a BVDV negative herd. Two groups of 5 heifers were included in the trial: one was inoculated with XIKE-A the other with XIKE-B virus strain. Heifers were between days 60 and 90 of gestation on the day of inoculation. Heifers were monitored for the presence of clinical signs of BVDV infection including abortions during the observation period. Blood samples were collected from the animals for serology, antigen detection and white blood cells were counted. The experiment was terminated 9 weeks after infection. Non-aborted cows were slaughtered and the uterus examined and collected. Fetal organ samples were collected during routine necropsy and examined for BVDV infection.

The presence of fetal infection was the main evaluation parameter, composed from the number of BVDV-related cow mortality, the number of BVDV-related abortions and the number of BVD positive fetuses at termination. In addition to the main parameter, clinical signs characteristic for BVDV infection, viremia, and white blood cell count in cows and rectal temperature after challenge were evaluated. The XIKE-B virus proved to be less pathogenic than XIKE-A, nevertheless BVD-related abortion and infection of the fetus was observed in the XIKE-B group, too. Therefore it can be concluded that the inactivation of the $E^{rns}$ RNase does not prevent fetal infection.

Example 2

BVDV XIKE-A-NdN: Fetopathogenicity Assessment in Pregnant Heifers

The $N^{pro}$ gene has been shown to be nonessential for growth of CSFV in tissue culture (Tratschin et al., 1998). Even though a proof for BVDV attenuation in consequence of $N^{pro}$ deletion is still missing, a role of this protein in the interaction between virus and host seemed to be possible and was actually indicated by recent experiments for CSFV (Mayer et al., 2004; Rüggli et al., 2003). We therefore investigated whether the deletion of the major part of the $N^{pro}$ coding sequence leads to a virus that no longer infects the fetus in pregnant heifers. The $N^{pro}$ gene except for the 5' terminal 4 codons was deleted from the full length cDNA clone pKANE40A according to standard procedures. The resulting mutant full length clone was used as template for in vitro transcription and the resulting cRNA was transfected into MDBK cells as described (Meyer et al., 2002). The recovered virus was amplified in tissue culture and then used in the animal experiment described below. BVDV XIKE-B served as a control since it was shown before that it is able to cross the placenta (Example 1).

Objective(s)/Purpose of the Study

The study aims to assess the safety of a live attenuated BVDV with a genomic deletion of most of the $N^{pro}$ coding region in pregnant animals.

Materials and Methods applied are as described in Example 1

Study Design

Eight pregnant heifers were assigned at random to two groups. They were treated and observed according to the following schedule:

| | Group 1 | Group 2 |
|---|---|---|
| N | 5 | 3 |
| Treatments | XIKE-A-NdN | XIKE-B/control |
| Route | Intramuscular | |
| Vaccination time | between days 60 and 90 of pregnancy (day 0 of the study) | |
| Observations | Clinical signs | |
| Post-vaccination (in life) | Serum at days 0, 14, 28, 42 and at termination<br>WBC at day 0 and then daily for 14 days<br>Buffy coat at day 0 and then daily for 14 days | |

-continued

| | Group 1 | Group 2 |
|---|---|---|
| Post-mortem (day 60) | Gross-pathology<br>Organ panel for virus isolation | |
| Type of study: | open controlled clinical study | |
| Experimental unit: | Individual animal | |
| Method of blinding: | Partial blinding. No detailed procedures for blinding and access to treatment schedule were applied. The observing veterinarian at the study location and the pathologist were not be aware of the treatment; they only received a protocol extract relevant to their tasks. Vaccination was performed by the investigator or his assignee. Samples for virus isolation were coded by the investigator until all results are available. | |

Results

All heifers were healthy and pregnant at study start. All animals proved to be free of BVDV and BVDV antibodies before the initiation of the study.

Preparation and Control of the Virus Used for the Infection

Samples were collected throughout the dilution steps and assayed on the day of preparation, i.e., without freezing by co-cultivation on suitable tissue culture. The results of virus titration are shown in the following table.

| Sample ID | Virus strain | Dilution/description | $Log_{10}$ titer/mL |
|---|---|---|---|
| VT1a | XIKE-A/NdN (S) | 1:2 (at 4° C.) | 4.4 |
| VT1b | | #2a on ice without opening | 4.0 |
| VT1c | | Return of #2b | 2.8 |
| VT2a | XIKE-B | 1:2.2 (at 4° C.) | 2.3 |
| VT2b | | #3a on ice without opening | 2.8 |
| VT2c | | Return of #3b | Negative |

Clinical Symptoms of BVDV Infection

The table below gives a summary about the animals that had clinical signs during the observation period.

Clinical Signs and the Days Post-Inoculation (DPI) when they were Observed

| | Group 1 (XIKE-A NdN) | Group 2 (XIKE-B) | |
|---|---|---|---|
| | Animal ID | Animal ID | |
| Clinical sign | 1583 | 1438 | 1585 |
| Loss of appetite | 8 | — | 10 |
| Lachrymation | — | — | — |
| Conjunctivitis | — | — | — |
| Nasal discharge | — | — | — |
| Oral erosion | — | — | — |
| Oral hemorrhage | — | — | — |
| Diarrhea | — | — | — |
| Coughing | — | 12 | 10-13 |
| Abnormal breathing | — | — | — |
| Elevated respiratory rate | — | — | — |
| Hoof erosion | — | — | — |

Only mild and transient clinical signs were observed in some of the animals in each group. In Group 1, one out of the 5 heifers had loss of appetite on day 8 PI. In Group 2, two out of the 3 animals had clinical signs. Both heifers experienced coughing around day 21 PI that was accompanied with loss of appetite in one of the animals.

Rectal Temperatures

No abnormal temperature changes were detected before the inoculation of the animals. The few cases of elevated temperatures measured after the inoculation are summarized in the table below.

| Group | Animal ID | Temperature (° C.) | PI day |
|---|---|---|---|
| 1 | 1583 | 39.9 | 8 |
| | 1621 | 39.0 | 5 |
| 2 | 1438 | 39.0 | 2 |
| | 1585 | 40.8 | 9 |

One animal had slightly elevated temperature in each group, and also one animal had fever in each group. Fever was detected on day 8 or 9 PI. Temperature values always returned to normal value on the following day.

Leukocyte Counts

Some leukopenia was observed in all groups between PI days 3-8. The number of animals with at least 40% reduction in white blood cell count was the following:

| Group | Number of animals having leukopenia/total |
|---|---|
| 1 | 3/5 (60%) |
| 2 | 1/3 (33%) |

Serology (BVDV Antibodies)

In compliance with the study protocol, all heifers were free of BVDV antibodies before vaccination. In Group I (inoculated with XIKE-A NdN) and Group 2 (inoculated with XIKE-B), complete seroconversion was detected only at study termination (2 months after inoculation).

BVD Virus Isolation from Buffy Coats

No viremia was detected

BVD Virus Isolation from Fetal Tissue Samples

| | Group 1 | Group 2 |
|---|---|---|
| N | 5 | 3 |
| Treatments | XIKE-A-NdN | XIKE-B/control |
| Route | Intramuscular | Intramuscular |
| Number of fetuses in which fetal transmission was detected: | 4 out of 5 fetuses infected | 2 out of 3 fetuses infected |
| Conclusion of the virus used for treatment has the potential to be transmitted over the placenta: | Fetal transmission for XIKE-A-NdN observed | Fetal transmission for XIKE-B observed |

Conclusion

The $N^{pro}$ deletion resulted in a considerable attenuation of the BVDV in comparison to the parental virus XIKE-A that was shown to be highly pathogenic (Meyer et al., 2002).

However, the $N^{pro}$ deletion alone is not preventing transmission of a NY93-based virus recombinant to the fetus after inoculation of pregnant cows.

Example 3

BVDV XIKE-B-NdN: Fetopathogenicity Assessment in Pregnant Heifers

To be able to test the potential of a combination of RNase inactivation and $N^{pro}$ deletion with regard to BVDV attenuation and fetal transmission, different BVDV-2 mutants with deletions within the $N^{pro}$ coding region were established based on the infectious cDNA clone pKANE40B, the RNase negative mutant of pKANE40A with a deletion of codon 349. The recovered viruses were analyzed with regard to presence of the desired mutations, the absence of second site mutations in the regions flanking the introduced changes, and their growth characteristics in tissue culture. XIKE-B-NdN (V-pK88C), a variant containing a deletion of the complete $N^{pro}$ coding region except for codons 1 to 4 in addition to the RNase inactivating deletion of codon 349 was chosen for an animal experiment since it combined the desired mutations with acceptable growth characteristics. The aim of the study was to assess the safety of a live attenuated BVDV isolate in pregnant animals.

Five BVDV-negative, pregnant heifers were inoculated intranasally with an infective dose of 105 $TCID_{50}$/animal XIKE-B-NdN (back titration data are depicted in Table 3.1). Clinical data were recorded daily. Blood samples were collected for white blood cell counting, for buffy-coat preparation and serology. After termination of the study, fetal tissues were collected for virus isolation.

Materials and Methods

As detailed for Example 1.

Results

No clinical data were observed (data not shown). Leukocyte counts remained virtually unchanged except for a significant decrease by approximately 40% below the baseline value (day 0) in heifer No. 1015 on a single day (day 6 PI) (data not shown).

Analysis of Buffy Coat Preparations

Approximately $10^6$ leukocytes were cultured in duplicates with MDBK-cells in 24-well tissue culture plates for 5 days. Samples were freeze-thawed twice. 100 μL aliquots of thawed samples were inoculated onto freshly seeded 24-well tissue culture plates and tested for virus by indirect immunofluorescence staining (mAb Code 4, directed against a conserved epitope in nonstructural protein NS3). No BVDV could be isolated from the buffy coat preparations of animals # 921, 1013, 1015, 1055 and 1075 (Table 3.2) whereas positive controls clearly showed the correct conduction of the test.

Post-Mortem Examination of Fetal Tissues

After termination of the study the following fetal tissues were collected for virus isolation: spleen, kidney, thymus, sternum, cerebellum, placenta, intestine, and abdominal fluid. Briefly, tissue suspensions were made in a mortar using sterile sea sand and ice-cold PBS without $Ca^{2+}$ and $Mg^{2+}$. Mortars were rinsed with 1 mL ice-cold PBS without $Ca^{2+}$ and $Mg^{2+}$ and suspensions were centrifuged for 10 minutes at 2000×g (4° C.). The supernatant was first passed through a disposable 0.45 μm filter holder, followed by a second filter passage (0.2 μm pore size). Virus isolation was carried out in duplicates (400 μL of fetal tissue suspension or 100 μL of fetal abdominal fluid) on a monolayer of MDBK-cells in a 24 wells tissue culture plate (37° C., 7% $CO_2$). Tissue samples were controlled daily for cytopathic effects or bacterial contamination, and after an incubation time of 5 days plates were frozen and thawed twice. 100 μL of samples were passaged to freshly seeded MDBK-cells. Virus was detected by indirect immunofluorescence staining (mAb Code 4). No BVDV could be detected in the tissue samples or fetal abdominal fluid (Table 3.3).

Serological Findings

Serum neutralization titers were determined before inoculation, 1 month post-inoculation and at termination of the study. Sera from all animals were tested in triplicates for neutralizing antibodies against NY93/C, and the endpoint dilution was read by indirect immunofluorescence staining. Results were expressed as the endpoint dilution, which neutralized approximately 100 $TCID_{50}$ and calculated by the method of Kaerber. No definite data could be obtained for day 0, and 1 and 2 weeks post-infection as the sera were toxic for MBDK-cells in dilutions up to 1:16 and no neutralization could be detected at higher dilutions. Starting with the third week post-vaccination all animals developed neutralizing antibodies against the homologous BVDV-2 virus NY93/C lasting till the end of the experiment (Table 3.4 and FIG. 1).

Conclusions

The data obtained during the animal study clearly show that BVDV XIKE-B-NdN represents a highly attenuated virus. In contrast to wild-type virus or the single mutants XIKE-B or XIKE-A-NdN that show fetal transmission in pregnant heifers at high rates, the double mutant did not cross the placenta. BVDV XIKE-B-NdN as well as similar double mutants are extremely suitable for the use in a live attenuated vaccine.

TABLE 3.1

Study No.: B01 BIVI020 and B01 BIVI022
Back Titration of Viruses

| Sample ID | Virus Strain | Dilution | Titer |
| --- | --- | --- | --- |
| 1a | XIKE-B-NdN | concentrated virus | $10^{5.44}$ $TCID_{50}$/mL |
| 1 | | 1:4 | $10^{4.86}$ $TCID_{50}$/mL |
| 6 | | residues of infection (#1) | $10^{4.27}$ $TCID_{50}$/mL |

TABLE 3.2

Detection of Viremia

| Animal | Days after vaccination | | | | | | | | | | | | | | |
| --- | --- | --- | --- | --- | --- | --- | --- | --- | --- | --- | --- | --- | --- | --- | --- |
| ID No. | 0 | 1 | 2 | 3 | 4 | 5 | 6 | 7 | 8 | 9 | 10 | 11 | 12 | 13 | 14 | |
| 0921 | – | – | – | – | – | – | – | – | – | – | – | – | – | – | – | 1. isolation |
| | – | – | – | – | – | – | – | – | – | – | – | – | – | – | – | 2. isolation |

TABLE 3.2-continued

| Animal | Detection of Viremia Days after vaccination | | | | | | | | | | | | | | | |
|---|---|---|---|---|---|---|---|---|---|---|---|---|---|---|---|---|
| ID No. | 0 | 1 | 2 | 3 | 4 | 5 | 6 | 7 | 8 | 9 | 10 | 11 | 12 | 13 | 14 | |
| 1013 | – | – | – | – | – | – | – | – | – | – | – | – | – | – | – | 1. isolation |
| | – | – | – | – | – | – | – | – | – | – | – | – | – | – | – | 2. isolation |
| 1015 | – | – | – | – | – | – | – | – | – | – | – | – | – | – | – | 1. isolation |
| | – | – | – | – | – | – | – | – | – | – | – | – | – | – | – | 2. isolation |
| 1055 | – | – | – | – | – | – | – | – | – | – | – | – | – | – | – | 1. isolation |
| | – | – | – | – | – | – | – | – | – | – | – | – | – | – | – | 2. isolation |
| 1075 | – | – | – | – | – | – | – | – | – | – | – | – | – | – | – | 1. isolation |
| | – | – | – | – | – | – | – | – | – | – | – | – | – | – | – | 2. isolation |
| Date | 13, Dec. 2001 | 14, Dec. 2001 | 15, Dec. 2001 | 16, Dec. 2001 | 17, Dec. 2001 | 18, Dec. 2001 | 19, Dec. 2001 | 20, Dec. 2001 | 21, Dec. 2001 | 22, Dec. 2001 | 23, Dec. 2001 | 24, Dec. 2001 | 25, Dec. 2001 | 26, Dec. 2001 | 27, Dec. 2001 | |

– = sample negative

TABLE 3.3

| Analysis of fetus tissue samples for the presence of BVDV | | | | | | | | | | | | |
|---|---|---|---|---|---|---|---|---|---|---|---|---|
| Animal No. | Abdominal fluid | Thoracic Fluid | Mesenteric lymph nodes | Spleen | Kidney | Thymus | Bone marrow (sternum) | Cere-bellum | Placenta | Intestine | Date of tissue collection | Isolation |
| 0921 | – | NC | NC | – | – | – | – | – | – | – | 12 Feb. | 1. isolation |
| | – | | | – | – | – | – | – | – | – | 2002 | 2. isolation |
| 1013 | – | NC | NC | – | – | – | – | – | – | – | 12 Feb. | 1. isolation |
| | – | | | – | – | – | – | – | – | – | 2002 | 2. isolation |
| 1015 | – | NC | NC | – | – | – | – | – | – | – | 12 Feb. | 1. isolation |
| | – | | | – | – | – | – | – | – | – | 2002 | 2. isolation |
| 1055 | – | NC | NC | – | – | – | – | – | – | – | 12 Feb. | 1. isolation |
| | – | | | – | – | – | – | – | – | – | 2002 | 2. isolation |
| 1075 | – | NC | NC | – | – | – | – | – | – | – | 12 Feb. | 1. isolation |
| | – | | | – | – | – | – | – | – | – | 2002 | 2. isolation |

– = sample negative
NC = not collected

TABLE 3.4

B01 BIVI022/BVDV XIKE-B-NdN; fetal protection study
Serum Neutralization Assay

| Animal ID No. | From the heifers at selection | during ACC | 1 wPV | 2 wPV | 3 wPV | 4 wPV | 5 wPV | 6 wPV | 7 wPV | 8 wPV |
|---|---|---|---|---|---|---|---|---|---|---|
| 0921 | | * | * | * | 1:40(2) | 1:161(1) | 1:256(1) | 1:323(1) | 1:128(1) | 1:256(1) |
| 1013 | | * | * | * | 1:3(2) | NA | 1:161(1) | 1:323(1) | 1:406(1) | 1:256(1) |
| 1015 | | * | * | * | 1:64(2) | 1:161(1) | 1:256(1) | 1:323(1) | 1:406(1) | 1:323(1) |
| 1055 | | * | * | * | 1:32(2) | 1:40(2) | 1:256(1) | 1:323(1) | 1:406(1) | 1:406(1) |
| 1075 | | * | * | * | NA | 1:128(2) | 1:102(1) | 1:203(1) | 1:161(1) | 1:406(1) |
| Date | | 06 Dec. 2001 | 20 Dec. 2001 | 27 Dec. 2001 | 03 Jan. 2002 | 10 Jan. 2002 | 17 Jan. 2002 | 24 Jan. 2002 | 31 Jan. 2002 | 07 Feb. 2002 |

(1)SNT against 1456 Nase (=NY93/C) $10^{2,03}$ $TCID_{50}$/50 μL
(2)SNT against 1456 Nase (=NY93/C) $10^{1,57}$ $TCID_{50}$/50 μL
* Serum toxic for MBDK-cells in dilutions up to 1:16 ⇒ no data available
NA data not available The Serum Neutralization Assay against NY93/C is illustrated in FIG. 1.

Efficacy and Crossprotection Study

Two possible problems have to be faced with regard to vaccination with attenuated virus mutants BVDV XIKE-B or BVDV XIKE-B-NdN. First, there is a general problem concerning crossprotection between BVDV-1 and BVDV-2. At least vaccination with inactivated BVDV-1 vaccines did not prevent the transmission of BVDV-2 to the fetus in pregnant animals. Since protection against fetal infection represents the major aim of anti-BVDV vaccination, such vaccines cannot be regarded to induce a protective immunity on a broad range. The question therefore was, whether vaccination with live attenuated BVDV-2 can prevent virus transmission to the fetus. Second, the reduced growth rates of BVDV XIKE-B-NdN might result in only a low level of protection not able to prevent transplacental infection of the fetus in pregnant heifers. To address these problems, an animal study was started.

The animals (2 groups of 10 animals each) were vaccinated either with BVDV XIKE-B or XIKE-B-NdN (intended dosage: 1 mL of supernatant with $10^5$ $TCID_{50}$ of virus; backtitration is shown in Table 3.5). None of the animals showed significant clinical signs after the vaccination except for one animal of the nonvaccinated control group with mild coughing for one day. Rectal temperature values were below 39° C. except for one animal of the nonvaccinated control group that had 39.1° C. for one day. Buffy coat samples prepared after vaccination were analyzed for the presence of virus as described above. The experiments showed that only 5 of the 20 animals contained virus in the blood for 1 or 2 days at 4 to 8 days post-infection (Table 3.6).

TABLE 3.5

Back Titration of Viruses used for vaccination

| Sample ID | Virus Strain | Dilution | Titer |
|---|---|---|---|
| 1a | XIKE-B-NdN | concentrated virus | $10^{5.44}$ $TCID_{50}$/mL |
| 1 | | 1:4 | $10^{4.86}$ $TCID_{50}$/mL |
| 6 | | residues of infection (#1) | $10^{4.27}$ $TCID_{50}$/mL |
| 3 | XIKE-B | 1:11 | $10^{5.76}$ $TCID_{50}$/mL |
| 4 | | 1:110 | $10^{4.92}$ $TCID_{50}$/mL |
| 5 | | residues of infection (#4) | $10^{4.27}$ $TCID_{50}$/mL |

TABLE 3.6

Study No./Id.: B01 BIVI020/BVDV Tü XIKE-B-NdN; fetal protection study
Inoculation with white blood cell (buffy coat) preparations collected after vaccination

| Animal | Days After Vaccination | | | | | | | | | | | | | | | |
|---|---|---|---|---|---|---|---|---|---|---|---|---|---|---|---|---|
| ID No. | 0 | 1 | 2 | 3 | 4 | 5 | 6 | 7 | 8 | 9 | 10 | 11 | 12 | 13 | 14 | |
| 1134[(2)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1141[(1)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1142[(1)] | ØØ | ØØ | ØØ | ØØ | ØØ | ØØ | ØØ | +Ø | ØØ | ØØ | ØØ | ØØ | ØØ | ØØ | ØØ | 1. isolation |
| | ØØ | ØØ | ØØ | ØØ | Ø+ | ØØ | ØØ | ØØ | ØØ | ØØ | ØØ | ØØ | ØØ | ØØ | ØØ | 2. isolation |
| 1145[(2)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1149[(1)] | ØØ | ØØ | ØØ | ØØ | +Ø | ØØ | ØØ | ØØ | Ø+ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1151[(2)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1152[(2)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1156[(2)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1158[(1)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1160[(2)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| Date | 13 Dec. 2001 | 14 Dec. 2001 | 15 Dec. 2001 | 16 Dec. 2001 | 17 Dec. 2001 | 18 Dec. 2001 | 19 Dec. 2001 | 20 Dec. 2001 | 21 Dec. 2001 | 22 Dec. 2001 | 23 Dec. 2001 | 24 Dec. 2001 | 25 Dec. 2001 | 26 Dec. 2001 | 27 Dec. 2001 | |
| 1197[(1)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1200[(1)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1206[(2)] | ØØ | ØØ | ØØ | ØØ | ØØ | ØØ | ØØ | Ø+ | ØØ | ØØ | ØØ | ØØ | ØØ | ØØ | ØØ | 1. isolation |
| | ØØ | ØØ | ØØ | ØØ | ØØ | ØØ | Ø+ | ØØ | ØØ | ØØ | ØØ | ØØ | ØØ | ØØ | ØØ | 2. isolation |
| 1210[(2)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1212[(1)] | ØØ | ØØ | ØØ | ØØ | ØØ | ØØ | Ø+ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1214[(1)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1216[(2)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1217[(1)] | ØØ | ØØ | ØØ | ØØ | ØØ | ØØ | Ø+ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1218[(1)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| 1225[(2)] | ØØ | ØØ | ØØ | ØØ | ØØ | ØØ | ØØ | ØØ | ØØ | ØØ | ØØ | ØØ | ØØ | ØØ | ØØ | 1. isolation |
| | ØØ | ØØ | ØØ | ØØ | ØØ | ØØ | ØØ | ØØ | ØØ | ØØ | ØØ | ØØ | ØØ | ØØ | ØØ | 2. isolation |
| Date | 13 Dec. 2001 | 14 Dec. 2001 | 15 Dec. 2001 | 16 Dec. 2001 | 17 Dec. 2001 | 18 Dec. 2001 | 19 Dec. 2001 | 20 Dec. 2001 | 21 Dec. 2001 | 22 Dec. 2001 | 23 Dec. 2001 | 24 Dec. 2001 | 25 Dec. 2001 | 26 Dec. 2001 | 27 Dec. 2001 | |

Immunofluorescence staining: Code 4
Ø sample negative
+ sample positive
B bacterial contamination in well
Code of animal numbers:
[(1)]vaccination with BVDV XIKE-B (RNase mutant)
[(2)]vaccination with BVDV XIKE-B-NdN (RNase and $N^{pro}$ double mutant)

Four weeks after vaccination, insemination of the animals was carried out. Challenge infections were performed 60 to 90 days later using either a BVDV-1 strain (BVDV KE-9, heterologous challenge, animals vaccinated with XIKE-B) or a heterologous BVDV-2 strain (BVDV KE-13, homologous challenge, animals vaccinated with XIKE-B-NdN) (intended dosage: $10^5$ $TCID_{50}$ in 6 mL; backtitration is shown in Table 3.7). From each group of vaccinated animals 5 pregnant heifers were randomly selected for the challenge infection. Animals vaccinated with BVDV XIKE-B were challenged with the BVDV-1 strain KE-9, whereas heifers vaccinated with BVDV XIKE-B/NdN were challenged with BVDV-2 KE-13. In addition, two nonvaccinated control animals were infected with each of the challenge viruses.

TABLE 3.7

Study No./Id.: B01 BIVI020/BVDV Të XIKE-B-NdN; fetal protection study
Back titration of challenge viruses

| Virus Strain | Sample ID | Titer ($TCID_{50}$/mL) | Mean Titer ($TCID_{50}$/mL) |
|---|---|---|---|
| KE 9 | 1 | $10^{4.44}$ | $10^{4.94}$ |
| | | $10^{5.10}$ | |
| | 2 | $10^{4.69}$* | $10^{4.44}$ |
| | 3 | ** | |

TABLE 3.7-continued

Study No./Id.: B01 BIVI020/BVDV Të XIKE-B-NdN; fetal protection study
Back titration of challenge viruses

| Virus Strain | Sample ID | Titer ($TCID_{50}$/mL) | Mean Titer ($TCID_{50}$/mL) |
|---|---|---|---|
| KE13 | 1 | $10^{4.69}$ | $10^{4.76}$ |
| | | $10^{4.82}$ | |
| | 2 | $10^{4.57}$ | $10^{4.63}$ |
| | | $10^{4.69}$ | |
| | 3*** | $10^{3.5}$ | $10^{3.5}$ |

Sample 1: stock of inoculate
Sample 2: stock of inoculate returned from the stable
Sample 3: excess inoculate
*Second inoculation of KE9, sample 2 wasn't interpretable because of cell death.
** KE9, sample 3 wasn't interpretable because of cell death or bacterial contamination.
***First inoculation of KE13, sample 3 wasn't interpretable because of bacterial contamination.

The vaccinated animals did not show viremia or clinical symptoms upon challenge infection. The challenge was successful as all non-vaccinated controls were BVDV positive (Table 3.8). Only mild signs of disease were observed in the control groups. The white blood cell counts were nearly normal (not shown).

TABLE 3.8

Study No./Id.: B01 BIVI020/BVDV Tü XIKE-B/XIKE-B-NdN; fetal protection study
Inoculation with white blood cell (buffy coat) preparations collected after challenge

| Animal | Days After Challenge | | | | | | | | |
|---|---|---|---|---|---|---|---|---|---|
| ID No. | 0 | 2 | 4 | 6 | 8 | 10 | 12 | 14 | 16 |
| 1104[(3)] | ØØ | ØØ | ØØ | Ø+ | ++ | ++ | Ø+ | ØØ | ØØ |
| | ØØ | ØØ | ØØ | +Ø | ++ | ØØ | ØØ | ØØ | ØØ |
| 1108[(3)] | ØØ | ØØ | ØØ | ØØ | ++ | +Ø | ØØ | ØØ | ØØ |
| | ØØ | ØØ | ØØ | ØØ | ØØ | ØØ | ØØ | ØØ | ØØ |
| 1126[(3)] | ØØ | ØØ | ++ | +Ø | ++ | Ø+ | ØØ | Ø+ | Ø+ |
| | ØØ | | | | | | | ØØ | |
| 1145[(2)] | ØØ | ØØ | ØØ | ØØ | ØØ | ØØ | | ØØ | ØØ |
| | | | | | | | ØØ | | |
| 1151[(2)] | ØØ | ØØ | ØØ | ØØ | | ØØ | ØØ | ØØ | |
| | | | | | | | | ØØ | ØØ |
| | ØØ | ØØ | ØØ | ØØ | ØØ | ØØ | ØØ | ØØ | ØØ |
| 1152[(2)] | ØØ | ØØ | ØØ | ØØ | ØØ | ØØ | ØØ | ØØ | ØØ |
| 1156[(2)] | ØØ | ØØ | ØØ | ØØ | ØØ | | ØØ | ØØ | |
| | | | | | | | | | ØØ |
| | ØØ | ØØ | ØØ | ØØ | ØØ | ØØ | ØØ | ØØ | ØØ |
| Date | Apr. 22, 2002 | Apr. 25, 2002 | Apr. 27, 2002 | Apr. 29, 2002 | May 01, 2002 | May 03, 2002 | May 05, 2002 | May 07, 2002 | May 09, 2002 |
| 1197[(1)] | ØØ | ØØ | ØØ | Ø+ | ++ | ++ | Ø+ | ØØ | ØØ |
| | ØØ | ØØ | ØØ | +Ø | ++ | ØØ | ØØ | ØØ | ØØ |
| 1200[(1)] | ØØ | ØØ | ØØ | ØØ | ++ | +Ø | ØØ | ØØ | ØØ |
| | ØØ | ØØ | ØØ | ØØ | ØØ | ØØ | ØØ | ØØ | ØØ |
| 1214[(1)] | ØØ | ØØ | ++ | +Ø | ++ | Ø+ | ØØ | Ø+ | Ø+ |
| | ØØ | | | | | | | ØØ | |
| 1216[(2)] | ØØ | ØØ | ØØ | ØØ | ØØ | ØØ | | ØØ | ØØ |
| | | | | | | | ØØ | | |
| 1217[(1)] | ØØ | ØØ | ØØ | ØØ | | ØØ | ØØ | ØØ | |
| | | | | | | | | ØØ | ØØ |
| | ØØ | ØØ | ØØ | ØØ | ØØ | ØØ | ØØ | ØØ | ØØ |
| 1218[(1)] | ØØ | ØØ | ØØ | ØØ | ØØ | ØØ | ØØ | ØØ | ØØ |
| 1249[(3)] | ØØ | ØØ | ØØ | ØØ | ØØ | | ØØ | ØØ | |
| | | | | | | | | | ØØ |
| | ØØ | ØØ | ØØ | ØØ | ØØ | ØØ | ØØ | ØØ | ØØ |
| Date | Apr. 22, 2002 | Apr. 25, 2002 | Apr. 27, 2002 | Apr. 29, 2002 | May 01, 2002 | May 03, 2002 | May 05, 2002 | May 07, 2002 | May 09, 2002 |

TABLE 3.8-continued

Study No./Id.: B01 BIVI020/BVDV Tü XIKE-B/XIKE-B-NdN; fetal protection study
Inoculation with white blood cell (buffy coat) preparations collected after challenge

| Animal | Days After Challenge | | | | | | | |
|---|---|---|---|---|---|---|---|---|
| ID No. | 18 | 20 | 22 | 24 | 26 | 28 | 30 | Isolation |
| 1104[3] | ØØ | ØØ | ØØ | ØØ | ØØ | ØØ | ØØ | 1. isolation |
| | ØØ | ØØ | ØØ | ØØ | ØØ | ØØ | ØØ | 2. isolation |
| 1108[3] | ØØ | ØØ | ØØ | ØØ | ØØ | ØØ | ØØ | 1. isolation |
| | ØØ | ØØ | ØØ | ØØ | ØØ | ØØ | ØØ | 2. isolation |
| 1126[3] | ØØ | ØØ | ØØ | ØØ | ØØ | ØØ | ØØ | 1. isolation |
| | | | | | | | | 2. isolation |
| 1145[2] | ØØ | ØØ | ØØ | ØØ | ØØ | ØØ | ØØ | 1. isolation |
| | | | | | | | | 2. isolation |
| 1151[2] | ØØ | ØØ | ØØ | ØØ | ØØ | ØØ | ØØ | 1. isolation |
| | | | | | | | | 2. isolation |
| | ØØ | ØØ | ØØ | | | | | 3. isolation |
| 1152[2] | ØØ | ØØ | ØØ | ØØ | ØØ | ØØ | | 1. isolation |
| | | | | | | | ØØ | 2. isolation |
| | | | | | ØØ | ØØ | ØØ | 3. isolation |
| 1156[2] | | ØØ | ØØ | ØØ | ØØ | ØØ | ØØ | 1. isolation |
| | | | | | | | | 2. isolation |
| | ØØ | ØØ | ØØ | | | | | 3. isolation |
| Date | May 11, 2002 | May 13, 2002 | May 15, 2002 | May 17, 2002 | May 19, 2002 | May 21, 2002 | May 23, 2002 | |
| 1197[1] | | | | | | | | 1. isolation |
| | ØØ | ØØ | ØØ | ØØ | ØØ | ØØ | ØØ | 2. isolation |
| | ØØ | ØØ | ØØ | ØØ | ØØ | ØØ | ØØ | 3. isolation |
| 1200[1] | ØØ | ØØ | ØØ | ØØ | ØØ | ØØ | ØØ | 1. isolation |
| | ØØ | ØØ | ØØ | ØØ | ØØ | ØØ | ØØ | 2. isolation |
| 1214[1] | | | | | | | | 1. isolation |
| | ØØ | ØØ | ØØ | ØØ | ØØ | ØØ | ØØ | 2. isolation |
| | | | | | | | | 3. isolation |
| 1216[2] | | | | | | | | 1. isolation |
| | ØØ | ØØ | ØØ | ØØ | ØØ | ØØ | ØØ | 2. isolation |
| | | | | | | | | 3. isolation |
| 1217[1] | ØØ | ØØ | ØØ | ØØ | ØØ | ØØ | ØØ | 1. isolation |
| | | | | | | | | 2. isolation |
| | ØØ | ØØ | ØØ | | | | | 3. isolation |
| 1218[1] | ØØ | ØØ | ØØ | ØØ | ØØ | ØØ | | 1. isolation |
| | | | | | | | ØØ | 2. isolation |
| | | | | | ØØ | ØØ | ØØ | |
| 1249[3] | | ØØ | ØØ | ØØ | ØØ | ØØ | ØØ | 1. isolation |
| | | | | | | | | 2. isolation |
| | ØØ | ØØ | ØØ | | | | | |
| Date | May 11, 2002 | May 13, 2002 | May 15, 2002 | May 17, 2002 | May 19, 2002 | May 21, 2002 | May 23, 2002 | |

Figure 2:
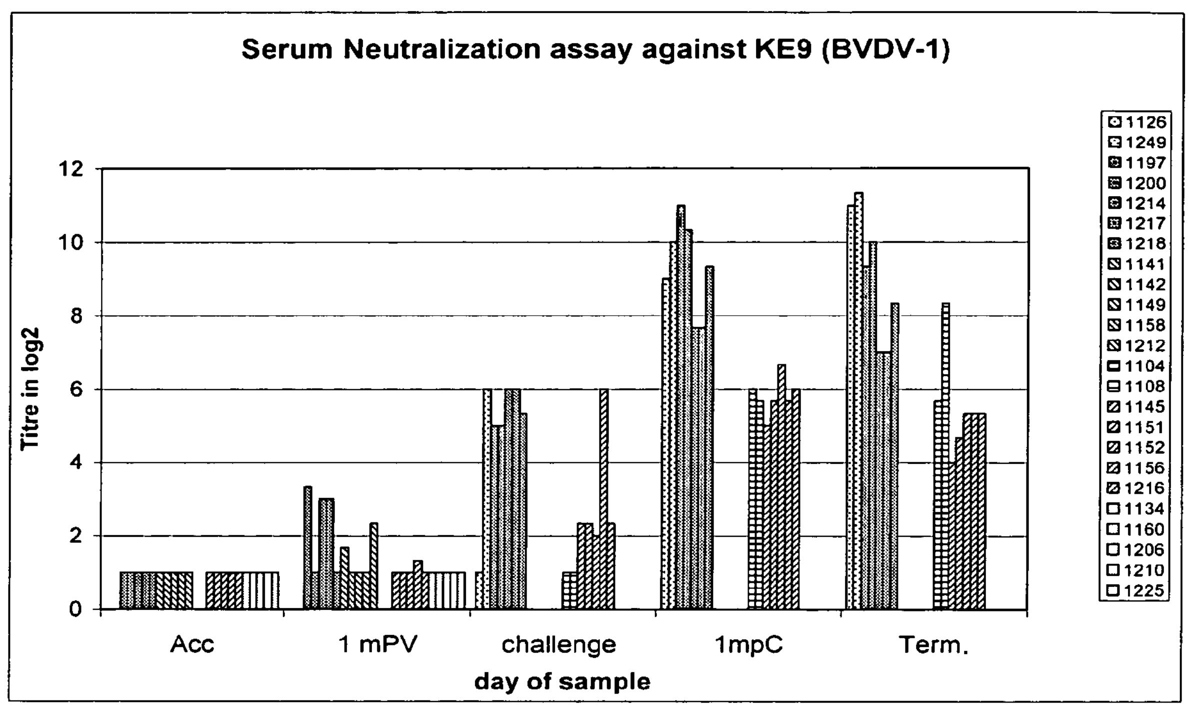
FIG. 2 shows the serum neutralization assay against KE9 (BVDV type I)
Figure 3:
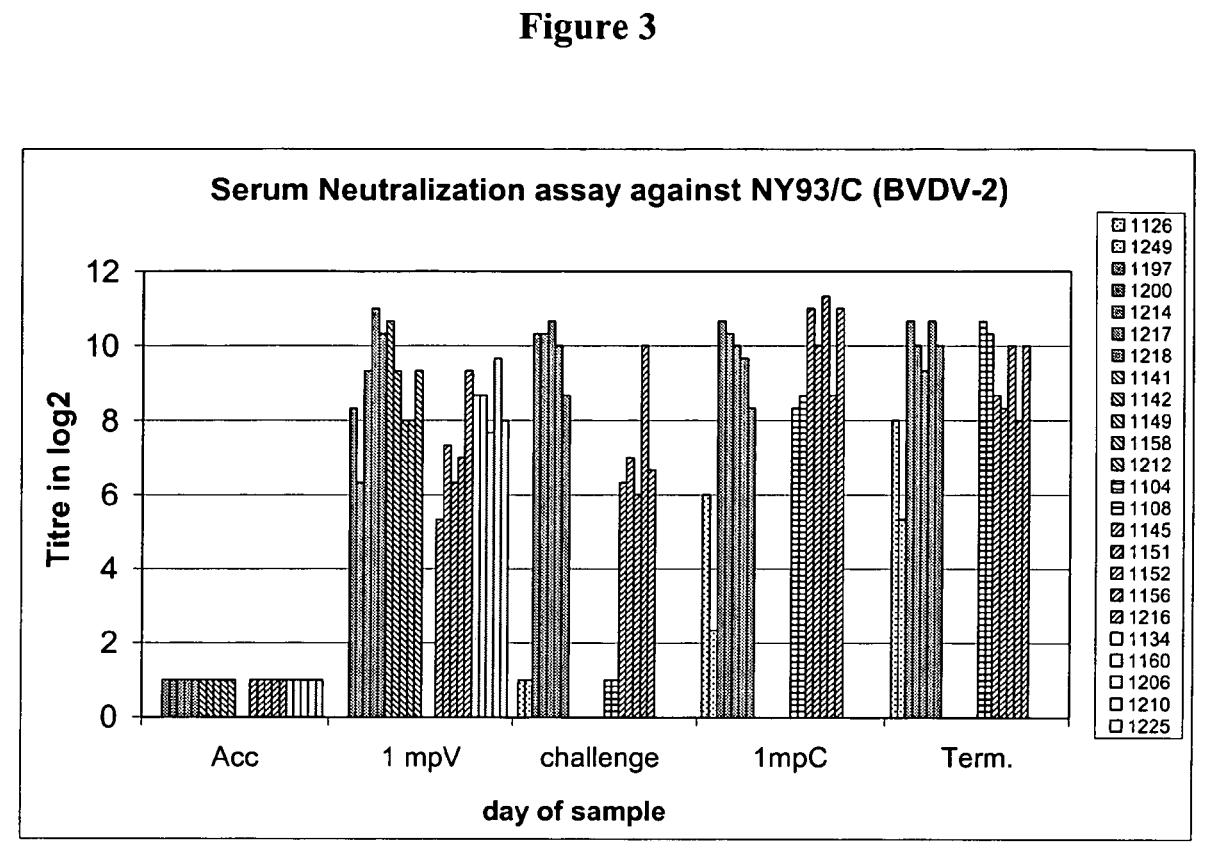

Immunofluorescence staining: Code 4
Ø sample negative
+ sample positive
B bacterial contamination in well
Code of animal numbers:
(1)vaccination with BVDV XIKE-B (RNase mutant)
(2)vaccination with BVDV XIKE-B-NdN (RNase and $N^{pro}$ double mutant)
(3)nonvaccinated controls Serum neutralization titers were determined before inoculation, 1 month post-inoculation, before challenge, 1 month after challenge and at termination of the study. Sera from all animals were tested in triplicates for neutralizing antibodies against KE9 and NY93/C (1456 Nase), and the endpoint dilution was read by indirect immunofluorescence staining. Results were expressed as the endpoint dilution, which neutralized approximately 100 $TCID_{50}$ and calculated by the method of Kaerber. At some of the higher antibody titers, the used endpoint dilution was not high enough. Against KE9, only animals vaccinated with XIKE-B developed low antibody titers starting about week 4. At challenge, all animals had antibody titers, which increased considerably starting around week 4 post-challenge. XIKE-B vaccinated animals had higher antibody titers then those vaccinated with XIKE-B-NdN vaccinated. All animals developed about the same neutralization titer against NY93/C four weeks post-vaccination, with marginally lower titers in XIKE-B-NdN vaccinated animals. After challenge all animals had high antibody titers. FIG. 2 shows the serum neutralization assay against KE9 (BVDV-1) and FIG. 3 shows the serum neutralization assay against NY93/C (BVDV-2).

Analysis of tissue samples obtained after termination of the study from the fetuses revealed that the material obtained from the vaccinated animals gave negative results whereas transmission had occurred in all 4 control animals (Table 3.9). Thus, it is clear that the established BVDV-2 mutants are well suited as efficient cross protective vaccine viruses.

TABLE 3.9

Study No./Id.: B01 BIVI020/BVDV Tü XIKE-B/XIKE-B-NdN; fetal protection study
Analysis of fetus tissue samples for the presence of BVDV

| Animal No. | Abdominal Fluid | Thoracic fluid | Mesenteric lymph notes | Small intestine | Spleen | Thymus | Kidney | Bone marrow (sternum) | Cerebellum | Placenta | Date |
|---|---|---|---|---|---|---|---|---|---|---|---|
| 1214(1) | NA | NA | ØØ | ØØ | ØØ | ØØ | ØØ | ØØ | ØØ | ØØ | 17 Jun. 2002 |
| 1126(3) | ++ | *** | ++ | ++ | ++ | ++ | ++ | ++ | ++ | ++ | 17 Jun. 2002 |
| 1249(3) | ++ | NA | ++ | ++ | ++ | ++ | ++ | ++ | ++ | Ø+ | 17 Jun. 2002 |
| 1218*(1) | NA | NA | NA | NA | NA | NA | NA | NA | NA | ØØ** | 17 Jun. 2002 |
| 1197(1) | ØØ | NA | ØØ | ØØ | ØØ | ØØ | ØØ | ØØ | ØØ | ØØ | 17 Jun. 2002 |
| 1217(1) | ØØ | NA | ØØ | ØØ | ØØ | ØØ | ØØ | ØØ | ØØ | ØØ | 17 Jun. 2002 |
| 1200(1) | ØØ | NA | ØØ | ØØ | ØØ | ØØ | ØØ | ØØ | ØØ | ØØ | 17 Jun. 2002 |
| 1145(2) | ØØ | NA | ØØ | ØØ | ØØ | ØØ | ØØ | ØØ | ØØ | ØØ | 21 Jun. 2002 |
| 1108(3) | +Ø | NA | ++ | ++ | ++ | ++ | ++ | ++ | ++ | ØØ | 21 Jun. 2002 |
| 1156(2) | ØØ | NA | ØØ | ØØ | ØØ | ØØ | ØØ | ØØ | ØØ | ØØ | 21 Jun. 2002 |
| 1104(3) | ++ | NA | ++ | ++ | ++ | ++ | ++ | ++ | ++ | ++ | 21 Jun. 2002 |
| 1216(2) | ØØ | NA | ØØ | ØØ | ØØ | ØØ | ØØ | ØØ | ØØ | ØØ | 21 Jun. 2002 |
| 1151(2) | NA | NA | ØØ | ØØ | ØØ | ØØ | ØØ | ØØ | ØØ | ØØ | 21 Jun. 2002 |
| 1152(2) | ØØ | NA | ØØ | ØØ | ØØ | ØØ | ØØ | ØØ | ØØ | ØØ | 21 Jun. 2002 |

NA = not available
*No fetus was found in the uterus of heifer #1218
**Endometrium (also collected for histology)
***Sample was not sent to BFA Tubingen
Code of animal numbers:
(1)vaccination with BVDV XIKE-B (RNase mutant)
(2)vaccination with BVDV XIKE-B-NdN (RNase and $N^{pro}$ double mutant)
(3)nonvaccinated controls Conclusion The challenge was successful as all non-vaccinated controls were BVDV viremic and fetuses of all non-vaccinated controls were BVDV positive.

Both isolates gave full protection under the present test and assay conditions. Isolate XIKE-B, with the single genetic marker was shown to cross-protect against type 1 BVDV challenge in terms of BVD viremia and transmission to the fetus after challenge. Isolate XIKE-B-NdN with the double genetic marker was able to fully protect against a heterologue type 2 BVDV challenge strain in terms of BVD viremia and transmission to the fetus after challenge.

Isolate XIKE-B (type 2 isolate) was shown to cross-protect against type 1 BVDV challenge in terms of BVD viremia and transmission to the fetus after challenge under the present test and assay conditions (n=4).

Isolate XIKE-B-NdN (type 2 isolate) fully protected against a heterologues type 2 BVDV challenge strain in terms of BVD viremia and transmission to the fetus after challenge under the present test and assay conditions (n=5).

Example 4

Establishment of $N^{pro}$ Mutants

Further analyses of BVDV-2 mutants with $N^{pro}$ deletions. Different mutants with deletions in the $N^{pro}$-coding region of the genome were established. Initially, only true deletions or a deletion accompanied by a point mutation were introduced.

A: $[N^{pro}]_1$-[C-term];

B: $[N^{pro}]_3$-[C-term];

C: $[N^{pro}]_4$-[C-term];

D: $[N^{pro}]_6$-[C-term];

E: $[N^{pro}]_4$-[C-term*]

In the formulas, $[N^{pro}]_x$ represents the number of residues of the aminoterminus of $N^{pro}$ that are left in the mutated polyprotein amino acids, [C-term] is the complete polyprotein except for $N^{pro}$ (starting with the C protein and ending with NS5B), and [C-term*] is the same as [C-term] but with a mutation at position 2 of the C protein (N instead of D).

The growth rates of the recovered viruses were considerably lower than those of wild-type XIKE-A or the RNase negative mutant XIKE-B. There are two possible explanations for this finding: (i) dependent on the virus strain, sequences of variable length of the $N^{pro}$-coding region are necessary for efficient translation initiation (Myers et al., 2001; Tautz et al., 1999), and (ii) the fusion of additional sequences to the aminoterminus of the capsid protein interferes with capsid protein function.

To obtain better growing $N^{pro}$ deletion mutants, a second set of mutants was generated with either a bovine ubiquitin gene or a fragment of the bovine LC3-coding sequence replacing the major part of the N$^{pro}$ gene. These constructs allow efficient translation and generate a capsid protein with the correct amino terminus.

[N$^{pro}$]$_{22}$-[PS]-[C-term]

wherein PS is ubiquitin or LC3 and C-term is the complete polyprotein except for N$^{pro}$ (starting with the C protein and ending with NS5B).

The growth rates of these mutants were more similar to what was determined for XIKE-A. It even seemed that the two RNase positive viruses according to the formula [N$^{pro}$]$_{22}$-[PS]-[C-term] named V-pK87F and V-pK87G showed no significant growth retardation at all, whereas the RNase negative counterpart V-pK88G once again was somewhat hampered in propagation but to a lesser extend than the formerly described mutants.

Further examples of N$^{pro}$ deletion mutants may be:

MESDEGSK...
MELFSSDEGSK...
MELFSNESDEGSK...
MELFSNELSDEGSK...
MELFSNELLSDEGSK...
MELFSNELLYSDEGSK...
MELFSNELLYKSDEGSK...
MELFSNELLYKTSDEGSK...

MELFSNELLYKT represents the aminoterminal sequence of N$^{pro}$ of the BVDV isolate NewYork93/C.

It may also be possible to use variants of this sequence with one or several mutations. Especially the naturally occurring variations as found in other pestiviruses can be expected to be functional. Therefore, the complete list of the tested or proposed variants with the different parts of the aminoterminal end of N$^{pro}$ can be enlarged by equivalent sets with amino acid exchanges. Below, typical examples of the respective sequences are given for several pestiviruses but the possible variations are not limited to these examples.

BVDV NewYork93/C: MELFSNELLYKT
BVDV CP13: MELISNELLYKT
BVDV SD1: MELITNELLYKT
CSFV Brescia: MELNHFELLYKT
BDV X818: MELNKFELLYKT Thus, these variants for example may include: MELI-[PS]$_0$-[C-term];

MELIS-[PS]$_0$-[C-term];

MELISN-[PS]$_0$-[C-term];

MELISNE-[PS]$_0$-[C-term];

MELISNEL-[PS]$_0$-[C-term];

MELISNELL-[PS]$_0$-[C-term];

MELISNELLY-[PS]$_0$-[C-term];

MELISNELLYK-[PS]$_0$-[C-term];

MELISNELLYKT-[PS]$_0$-[C-term];

MELIT-[PS]$_0$-[C-term];

MELITN-[PS]$_0$-[C-term];

MELITNE-[PS]$_0$-[C-term];

MELITNEL-[PS]$_0$-[C-term];

MELITNELL-[PS]$_0$-[C-term];

MELITNELLY-[PS]$_0$-[C-term];

MELITNELLYK-[PS]$_0$-[C-term];

MELITNELLYKT-[PS]$_0$-[C-term];

These formulas may also have [PS]$_1$, i.e., PS may also be one of the PS as described herein. Sequences belonging to the N$^{pro}$ protein are in italics. Amino acid exchanges with regard to the sequence of BVDV NewYork93/C are in bold.

Further examples can be found, e.g., by using the GenBank accession numbers given in Becher et al., 2003, Virology 311, 96-104) or by standard sequence data searches.

A further possibility could be the use of a processing signal (PS) inserted between the (residual) N$^{pro}$ sequence and the aminoterminus of the capsid protein. The PS leads to a cleavage that generates a functional capsid protein. The configuration of such constructs could be as follows:

[N$^{pro}$]$_{22}$-PS-[C-term]

where PS is a processing signal and can either be a target for a protease (e.g., ubiquitin, LC3 as defined herein or a protease or an unstable peptide leading to processing at its own carboxyterminus like e.g., intein (Chong et al. 1998 and references therein) or 3C of picornaviruses, 2A of cardioviruses or aphtoviruses, p15 of rabbit hemorrhagic disease virus, or the corresponding protease of other caliciviruses (Proter, 1993, and references therein; Meyers et al., 2000 and references therein).

When using a PS, a large number of different variants are possible since the PS ensures the generation of the correct amino terminus of the capsid protein C. Thus, when using a PS construct, all kinds of deletions or mutations of the N$^{pro}$ sequence are expected to result in viable mutants as long as the reading frame is not shifted or translation stopped by an in frame stop codon. As an example we established a viable CSFV N$^{pro}$ deletion mutant according to the formula

[N$^{pro}$]$_{29}$-PS-[C-term]

Especially interesting could be N$^{pro}$ mutations blocking the proteolytic activity of the protein. Rümenapf et al., 1998, have published the identification of the active site residues of the protease for CSFV Alfort Tübingen. The respective amino acids (glutamic acid at position 22, histidine at position 49 and cysteine at position 69) are conserved for other pestiviruses. Thus, exchanges of any amino acid expect for serine or threonine for the cysteine at position 69 will result in destruction of the protease activity. Similarly, changing the glutamic acid at position 22 will most likely result in inactivation of the protease unless the new amino acid is aspartic acid. Similarly most if not all exchanges at position 49 will lead to an inactive protease).

REFERENCES

F. M. Ausubel, et al., 1994 (updated), Current Protocols in Molecular Biology, New York: Greene Publishing Associates and Wiley-Interscience.

J. C. Baker, 1987, Bovine Viral Diarrhea Virus: A Review, J. Am. Vet. Med. Assoc. 190: 1449-1458.

P. Becher, M. König, D. J. Paton, and H.-J. Thiel, 1995, Further Characterization of Border Disease Virus Isolates: Evidence for the Presence of More than Three Species within the Genus Pestivirus, Virology 209 (1): 200-206.

S. Chong, K. S. Williams, C. Wotkowicz, and M. Q. Xu, 1998, Modulation of Protein Splicing of the *Saccharomyces cerevisiae* Vacuolar Membrane ATPase Intein, J. Biol. Chem. 273: 10567-10577.

R. O. Donis, W. Corapi, and E. J. Dubovi, 1988, Neutralizing Monoclonal Antibodies to Bovine Viral Diarrhea Virus Bind to the 56K to 58K Glycoprotein, J. Gen. Virol. 69: 77-86.

T. R. Fuerst, et al., 1986, Eukaryotic Transient Expression System Based on Recombinant Vaccinia Virus that Synthesizes Bacteriophage T7 RNA Polymerase, Proc. Natl. Acad. Sci. 83: 8122-8126.

F. X. Heinz, M. S. Collett, R. H. Purcell, E. A. Cold, C. R. Howard, M. Houghton, R. J. M. Moormann, C. M. Rice, and H.-J. Thiel, 2000, Family Flaviviridae, pp. 859-878, in: Virus Taxonomy (H. H. V. van Regenmortel, C. M. Fauquet, and D. H. L. Bishop (eds.)), Academic Press, San Diego.

M. M. Hulst, G. Himes, E. Newbigin, and R. J. M Moormann, 1994, Glycoprotein E2 of Classical Swine Fever Virus: Expression in Insect Cells and Identification as a Ribonuclease, Virology 200: 558-565.

M. M. Hulst, F. E. Panoto, A. Hooekmann, H. G. P. van Gennip, and R. J. M Moormann, 1998, Inactivation of the RNase Activity of Glycoprotein $E^{rns}$ of Classical Swine Fever Virus Results in a Cytopathogenic Virus, J. Virol. 72: 151-157.

M. Kit and S. Kit, 1991, Sensitive Glycoprotein gIII Blocking ELISA to Distinguish Between Pseudorabies (Aujeszky's disease)-infected and Vaccinated Pigs, Veterinary Microbiology 28: 141-155.

T. A. Kunkel, J. D. Roberts, and R. A. Zakour, 1987, Rapid and Efficient Site-Specific Mutagenesis without Phenotypic Selection, Methods Enzymol. 154: 367-392.

M. König, 1994, Virus der klassischen Schweinepest: Untersuchungen zur Pathogenese und zur Induktion einer protektiven Immunantwort, Dissertation, Tierärztliche Hochschule Hanover, Germany.

B. D. Lindenbach and C. M. Rice, 2001, The Pestiviruses, in: Fields Virology, D. M. Knipe and P. M. Howley (eds.), Lippincott-Raven, Philadelphia, pp. 991-1042.

D. Mayer, M. A. Hofmann, and J. D. Tratschin, 2004, Attenuation of Classical Swine Fever Virus by Deletion of the Viral N(pro) Gene, Vaccine 22: 317-328.

G. Meyers, T. Rümenapf, and H.-J. Thiel, 1989, Molecular Cloning and Nucleotide Sequence of the Genome of Hog Cholera Virus, Virology 171: 555-567.

G. Meyers, A. Saalmüller, and M. Büttner, 1999, Mutations Abrogating the RNase Activity in Glycoprotein e(rns) of the Pestivirus Classical Swine Fever Virus Lead to Virus Attenuation, J Virol 73: 10224-10235.

G. Meyers, N. Tautz, P. Becher, H.-J. Thiel, and B. M Kümmerer, 1996b, Recovery of Cytopathogenic and Noncytopathogenic Bovine Viral Diarrhea Viruses from cDNA Constructs, J. Virol., 70: 8606-8613.

G. Meyers, G., H.-J. Theil, and T. Rümenapf, 1996a, Classical Swine Fever Virus: Recovery of Infectious Viruses from cDNA Constructs and Generation of Recombinant Cytopathogenic Swine Fever Virus, J. Virol. 67: 7088-709526.

G. Meyers, C. Wirblich, H.-J. Thiel, and J. O. Thumfart, 2000, Rabbit Hemorrhagic Disease Virus: Genome Organization and Polyprotein Processing of a Calicivirus Studied after Transient Expression of cDNA Constructs, Virology 276: 349-363.

V. Moennig and J. Plagemann, 1992, The Pestiviruses, Adv. Virus Res. 41: 53-91.

D. J. Paton, J. P. Lowings, and A. D. Barrett, 1992, Epitope Mapping of the gp53 Envelope Protein of Bovine Viral Diarrhea Virus, Virology 190: 763-772.

C. Pellerin, et al., 1994, Identification of a New Group of Bovine Viral Diarrhea Virus Strains Associated with Severe Outbreaks and High Mortalities, Virology 203: 260-268.

A. G. Porter, 1993, Picornavirus Nonstructural Proteins: Emerging Roles in Virus Replication and Inhibition of Host Cell Functions, J. Virol. 67: 6917-6921.

N. Rüggli, J. D. Tratschin, M. Schweizer, K. C. McCullough, M. A. Hofmann, A. Summerfield, 2003, Classical Swine Fever Virus Interferes with Cellular Antiviral Defense: Evidence for a Novel Function of N(pro), J. Virol. 77: 7645-7654.

T. Rümenapf, R. Stark, M. Heimann, and H.-J. Theil, 1998, N-terminal Protease of Pestiviruses: Identification of Putative Catalytic Residues by Site Directed Mutagenesis, J. Virol. 72: 2544-2547.

T. Rümenapf, G. Unger, J. H. Strauss, and H.-J. Theil, 1993, Processing of the Envelope Glycoproteins of Pestiviruses. J. Virol. 67: 3288-3294.

R. Schneider, G. Unger, R. Stark, E. Schneider-Scherzer, and H.-J. Thiel, 1993, Identification of a Structural Glycoprotein of an RNA Virus as a Ribonuclease, Science 261: 1169-1171.

J. Sambrook, E. F. Fritsch, and T. Maniatis, Molecular Cloning: A Laboratory Manual Cold Spring Harbor Laboratory, Cold Spring Harbor, N.Y., 1989

R. Stark, G. Meyers, T. Rümenapf, and H.-J. Theil, 1993, Processing of Pestivirus Polyprotein: Cleavage Site between Autoprotease and Nucleocapsid Protein of Classical Swine Fever Virus, J. Virol., 67: 7088-7095.

H.-J. Theil, G. W. Plagemann, and V. Moennig, 1996, The Pestiviruses, in: Fields Virology, B. N. Fields, D. M. Knipe, and P. M. Howley (eds.), Lippincott-Raven, Philadelphia, pp. 1059-1073.

H.-J. Theil, R. Stark, E. Weiland, T. Rümenapf, and G. Meyers, 1991, Hog Cholera Virus: Molecular Composition of Virions from a Pestivirus, J. Virol. 65: 4705-4712.

J.-D. Tratschin, C. Moser, N. Ruggli, and M. A. Hofmann, 1998, Classical Swine Fever Virus Leader Proteinase Npro is Not Required for Viral Replication in Cell Culture, J. Virol. 72: 7681-7684.

P. A. van Rijn, H. G. van Gennip, E. J. de Meijer, and R. J. Moormann, 1993, Epitope Mapping of Envelope Glycoprotein E1 of Hog Cholera Virus Strain Brescia, J. Gen. Virol. 74: 2053-2060.

E. Weiland, H.-J. Theil, G. Hess, and F. Weiland, 1989, Development of Monoclonal Neutralizing Antibodies against Bovine Viral Diarrhea Virus after Pretreatment of Mice with Normal Bovine Cells and Cyclophosphamide, J. Virol. Methods 24: 237-244.

E. Weiland, R. Stark, B. Haas, T. Rümenapf, G. Meyers, and H.-J. Theil, 1990, Pestivirus Glycoprotein which Induces Neutralizing Antibodies Forms Part of a Disulfide-Linked Heterodimer, J. Virology 64: 3563-3569.

E. Weiland, R. Ahl, R. Stark, F. Weiland, and H.-J. Theil, 1992, A Second Envelope Glycoprotein Mediates Neutralization of a Pestivirus, Hog Cholera Virus, J. Virology 66: 3677-3682.

J. M. Windisch, R. Schneider, R. Stark, E. Weiland, G. Meyers, and H.-J. Theil, 1996, RNase of Classical Swine Fever Virus: Biochemical Characterization and Inhibition by Virus-Neutralizing Monoclonal Antibodies. J. Virol. 70: 352-358.

M. Wiskerchen, S. K. Belzer, and M. S. Collett, 1991, Pestivirus Gene Expression: the First Protein Product of the Bovine Viral Diarrhea Virus Large Open Reading Frame, p20, Possesses Proteolytic Activity, J. Virol. 65: 4508-4514.

We claim:

1. An attenuated bovine viral diarrhea virus having at least one mutation in the coding sequence for glycoprotein $E^{rns}$ and at least another mutation in the coding sequence for $N^{pro}$.

2. The bovine viral diarrhea virus according to claim 1, wherein the mutation in the coding sequence for glycoprotein $E^{rns}$ leads to inactivation of RNase activity residing in $E^{rns}$ and/or the mutation in the coding sequence for $N^{pro}$ leads to inactivation of the $N^{pro}$.

3. The bovine viral diarrhea virus according to claim 1, wherein the mutations are selected from the group of deletions, insertion mutations, and substitution mutations.

4. The bovine viral diarrhea virus according to claim 2, wherein the mutations are selected from the group of deletions, insertion mutations, and substitution mutations.

5. The bovine viral diarrhea virus according to claim 1, wherein the mutation(s) are deletions.

6. The bovine viral diarrhea virus according to claim 2, wherein the mutation(s) are deletions.

7. The bovine viral diarrhea virus according to claim 1, wherein the mutation(s) in the coding sequence for glycoprotein $E^{rns}$ is located in the encoding nucleotide sequence corresponding to amino acids at position 298 to 310 and/or position 341 to 360.

8. The bovine viral diarrhea virus according to claim 1, wherein the mutation in the coding sequence for glycoprotein $E^{rns}$ is a deletion or substitution of the histidine at position 349.

9. The bovine viral diarrhea virus according to claim 1, wherein the mutation(s) in the coding sequence for glycoprotein $E^{rns}$ are located in the nucleotide sequence coding for the conserved $E^{rns}$ sequence Sequence ID No. 13, SLHGIWPEKICTG and/or Sequence ID No. 14, LQRHEWNKHGWCNWFHIEPW.

10. The bovine viral diarrhea virus according to claim 1, wherein the mutation(s) in the coding sequence for glycoprotein $E^{rns}$ are located in the nucleotide sequence coding for the conserved $E^{rns}$ sequence Sequence ID No. 15, SLHGIWPEKIC and/or Sequence ID No. 16, RHEWNKHGWCNW.

11. The bovine viral diarrhea virus according to claim 1, wherein the mutation(s) in the coding sequence for glycoprotein $E^{rns}$ are two mutations located in the nucleotide sequence coding for the conserved $E^{rns}$ sequence Sequence ID No. 15, SLHGIWPEKIC and/or Sequence ID No. 16, RHEWNKHGWCNW.

12. The bovine viral diarrhea virus according to claim 1, wherein the mutation in the coding sequence for glycoprotein $E^{rns}$ is a single mutation located in the conserved $E^{rns}$ sequence Sequence ID No. 15, SLHGIWPEKIC and/or Sequence ID No. 16, RHEWNKHGWCNW.

13. The bovine viral diarrhea virus according to claim 1, wherein the mutation(s) in the coding sequence for $N^{pro}$ leads to an encoded polyprotein as characterized by the following formula:

$$[N^{pro}]_x\text{-}[PS]_y\text{-}[C\text{-term}]$$

wherein:

$[N^{pro}]$ is the $N^{pro}$ portion of the polyprotein, wherein x is the number of amino acids of the $N^{pro}$ present in the polyprotein;

[PS] is a processing signal selected from the group consisting of: ubiquitin, LC3, SUMO-1, NEDD8, GATE-16 or GABA(A)RAP), Intein, picornavirus 3C, caridovirus 2A, or p15 of rabbit hemorrhagic disease virus;

[C-term] is the complete virus polyprotein except for $N^{pro}$, but including the capsid (C)-protein and any other protein present in the virus polyprotein including the carboxyterminal NS5B;

y is 0 or 1, where 0 means [PS] is absent and 1 means [PS] is present; and x is 0 to 12 amino acids if y is 0, or G to 168 amino acids if y is 1.

14. The bovine viral diarrhea virus according to claim 13, wherein the mutation(s) in the coding sequence for $N^{pro}$ leads to an encoded polyprotein as characterized by the following formula: $[N^{pro}]_1$-$[PS]_0$-[C-term].

15. The bovine viral diarrhea virus according to claim 13, wherein the mutation(s) in the coding sequence for $N^{pro}$ leads to an encoded polyprotein as characterized by the following formula: $[N^{pro}]_3$-$[PS]_0$-[C-term].

16. The bovine viral diarrhea virus according to claim 13, wherein the mutation(s) in the coding sequence for $N^{pro}$ leads to an encoded polyprotein as characterized by the following formula: $[N^{pro}]_3$-$[PS]_0$-[C-term] and the mutation in the coding sequence for glycoprotein $E^{rns}$ is a single mutation located in the conserved $E^{rns}$ sequence Sequence ID No. 15, SLHGIWPEKIC or Sequence ID No. 16, RHEWNKHG-WCNW.

17. The bovine viral diarrhea virus according to claim 13, wherein the mutation(s) in the coding sequence for $N^{pro}$ leads to an encoded polyprotein as characterized by the following formula: $[N^{pro}]_4$-$[PS]_0$-[C-term].

18. The bovine viral diarrhea virus according to claim 13, wherein the mutation(s) in the coding sequence for $N^{pro}$ leads to an encoded polyprotein as characterized by the following formula: $[N^{pro}]_6$-$[PS]_0$-[C-term].

19. The bovine viral diarrhea virus according to claim 13, wherein the mutation(s) in the coding sequence for $N^{pro}$ leads to an encoded polyprotein as characterized by the following formula:

$[N^{pro}]_4$-$[PS]_0$-[C-term*], wherein [C-term*] is [C-term] wherein in the C-protein the amino acid at position 2 is changed from D to N.

20. The bovine viral diarrhea virus according to claim 13, wherein the mutation(s) in the coding sequence for $N^{pro}$ leads to an encoded polyprotein is characterized by the following formula:

$[N^{pro}]_x$-$[PS]_1$-[C-term], wherein PS is ubiquitin or LC3.

21. The bovine viral diarrhea virus according to claim 13, wherein mutation(s) in the coding sequence for $N^{pro}$ leads to an encoded polyprotein as characterized by a formula selected from the group consisting of:

M-$[PS]_0$-[C-term];

MEL-$[PS]_0$-[C-term];

MELF-$[PS]_0$-[C-term];

MELFS-$[PS]_0$-[C-term];

MELFSN-$[PS]_0$-[C-term];

MELFSNE-$[PS]_0$-[C-term];

MELFSNEL-$[PS]_0$-[C-term];

MELFSNELL-$[PS]_0$-[C-term];

MELFSNELLY-$[PS]_0$-[C-term];

MELFSNELLYK-$[PS]_0$-[C-term]; and

MELFSNELLYKT-$[PS]_0$-[C-term].

22. The bovine viral diarrhea virus according to claim 13, wherein the mutation(s) in the coding sequence for $N^{pro}$ leads to an encoded polyprotein as characterized by a formula selected from the group consisting of:

MELI-$[PS]_0$-[C-term];

MELIS-$[PS]_0$-[C-term];

MELISN-$[PS]_0$-[C-term];

MELISNE-$[PS]_0$-[C-term];

MELISNEL-$[PS]_0$-[C-term];

MELISNELL-$[PS]_0$-[C-term];

MELISNELLY-$[PS]_0$-[C-term];

MELISNELLYK-$[PS]_0$-[C-term]; and

MELISNELLYKT-$[PS]_0$-[C-term].

23. The bovine viral diarrhea virus according to claim 13, wherein the mutation(s) in the coding sequence for $N^{pro}$ leads to an encoded polyprotein as characterized by a formula selected from the group consisting of:

MELIT-$[PS]_0$-[C-term];

MELITN-$[PS]_0$-[C-term];

MELITNE-$[PS]_0$-[C-term];

MELITNEL-$[PS]_0$-[C-term];

MELITNELL-$[PS]_0$-[C-term];

MELITNELLY-$[PS]_0$-[C-term];

MELITNELLYK-$[PS]_0$-[C-term]; and

MELITNELLYKT-$[PS]_0$-[C-term].

24. The bovine viral diarrhea virus according to claim 13, wherein the mutation(s) in the coding sequence for $N^{pro}$ leads to an encoded polyprotein as characterized by the following formula:

$[N^{pro}]_x$-$[PS]_0$-MELF-$[PS]_0$-[C-term*], wherein [C-term*] is [C-term] wherein in the C-protein the amino acid at position 2 is changed from D to N.

25. The bovine viral diarrhea virus according to claim 13, wherein the mutation(s) in the coding sequence for $N^{pro}$ leads to an encoded polyprotein as characterized by the following formula:

$[N^{pro}]_{22}$-$[PS]_1$-[C-term], wherein PS is ubiquitin or LC3.

26. The bovine viral diarrhea virus according to any one of claims 14, 15, 16, 17, 19, and 19, wherein the $[PS]_0$ is replaced by $[PS]_1$, and wherein the PS is selected from the group of consisting of: ubiquitin, LC3, SUMO-1, NEDD8, GATE-16, GABA(A)RAP, intein, picornavirus 3C, caridovirus 2A, and p15 of rabbit hemorrhagic disease virus.

27. The bovine viral diarrhea virus according to any one of claims 1, 13, 14, 15, 16, 17, 18, and 19, wherein the bovine viral diarrhea virus is BVDV type 1 or BVDV type 2.

28. A bovine viral diarrhea virus having a sequence corresponding to SEQ ID NO:8 or a functional variant thereof.

29. A composition comprising the bovine viral diarrhea virus according to claim 1 or 2 and a solution.

30. A composition comprising the bovine viral diarrhea virus according to claim 13, and a solution.

31. The composition according to claim 29, which induces an immunological response in an animal.

32. The composition according to claim 30, which induces an immunological response in an animal.

33. The composition according to claim 29, which is a vaccine.

34. The composition according to claim 30, which is a vaccine.

35. The composition according to claim 33, further comprising a pharmaceutically acceptable carrier or excipient.

36. The composition according to claim 34, further comprising a pharmaceutically acceptable carrier or excipient.

37. A nucleic acid molecule comprising the nucleic acid encoding a live attenuated bovine viral diarrhea virus according to one of claim 1 or 13, or a variant based on the degenerative nucleic acid code that encodes the same protein.

38. The nucleic acid molecule according to claim 37, wherein the nucleotide molecule is DNA.

39. The nucleic acid molecule according to claim 38, wherein the nucleotide molecule is RNA.

40. A method for attenuating a bovine viral diarrhea virus, wherein at least one mutation in the coding sequence for glycoprotein $E^{rns}$ and at least another mutation in the coding sequence for $N^{pro}$ is generated in a bovine viral diarrhea virus and wherein the attenuated virus does not cross the placenta in animals infected with the virus.

41. The method according to claim 40, the method comprising:

(a) reversely transcribing a wild type bovine viral diarrhea virus to obtain a cDNA;

(b) cloning the cDNA;

(c) introducing mutations selected from deletions, insertion mutations, and/or substitution mutations into the cDNA, wherein the mutations are located in the coding sequence encoding glycoprotein $E^{rns}$ and the protease $N^{pro}$; and (d) incorporating the cDNA into a plasmid or into a DNA virus capable of directing the transcription of bovine viral diarrhea virus cDNA into RNA in vitro or upon infection of suitable cells.

42. A method of treatment of disease caused by bovine viral diarrhea virus, the method comprising administering to an animal in need thereof an effective amount of the attenuated bovine viral diarrhea virus according to one of claim 1 or 13.

* * * * *

SEQUENCE LISTING

<160> NUMBER OF SEQ ID NOS: 12

<210> SEQ ID NO 1
<211> LENGTH: 12332
<212> TYPE: DNA
<213> ORGANISM: Wildtyp BVDV: XIKE-A

<400> SEQUENCE: 1

```
gtatacgaga ttagctaaag aactcgtata tggattggac gtcaacaaat ttttaattgg     60

caacgtaggg aaccttcccc tcagcgaagg ccgaaaagag gctagccatg cccttagtag    120

gactagcaaa agtaggggac tagcggtagc agtgagttcg ttggatggcc gaacccctga    180

gtacagggga gtcgtcaatg gttcgacact ccattagtcg aggagtctcg agatgccatg    240

tggacgaggg catgcccacg gcacatctta acccatgcgg gggttgcatg ggtgaaagcg    300

ctattcgtgg cgttatggac acagcctgat agggtgtagc agagacctgc tattccgcta    360

gtaaaaactc tgctgtacat ggcacatgga gttgttttca aatgaacttt tatacaaaac    420

atataaacaa aaaccagcag gcgtcgtgga acctgtttac gacgtcaacg ggcgcccact    480

gtttggagag agcagtgact tgcacccgca gtcaacacta aaactaccac accaacgagg    540

cagcgccaac atcctgacca atgctaggtc cctaccgcgg aaaggtgact gccggagagg    600

taatgtgtat ggaccggtga gtggcatcta tatcaaacca ggaccgatct actaccagga    660

ttatgtgggc cccgtctatc atagagcccc actggaacta tgtagggagg caagtatgtg    720

cgaaacaact aggagagttg gcagagtgac cggtagtgat gggaaattat atcatatcta    780

catctgcata gatgggtgta tcctcctgaa gagggcgact aggaaccaac cagaagtcct    840

gaaatgggta tacaacagat taaattgtcc tttatgggtc accagctgct ccgatgaagg    900

gagcaagggt gctacaagta agaagcagcc taagccagat aggatagaaa aaggtaagat    960

gaaaatagcc ccaaaagaga cagaaaaaga ttgcaaaacc agaccccccg acgcgactat   1020

agtagtagaa ggggttaagt accaggtgaa gaaaaaagga aaggtaaggg gaaaaaatac   1080

tcaagatggg ttatatcaca acaagaataa gccccctgaa tcaagaaaaa aattggaaaa   1140

ggcactgctg gcttgggcca tcttagcagc ggtcctgctt cagctggtaa caggagagaa   1200

tatcacccag tggaacttga tggacaacgg caccgaggga atacagcaag cgatgttcct   1260

aagaggggtg aacaggagtc tacatggaat ttggccagag aaaatttgca ccggagtacc   1320

aactcactta gcaacagact atgagcttaa agagatagtg gggatgatgg acgcgagtga   1380

gaagaccaac tacacgtgtt gcaggttgca aagacatgag tggaataaac atggttggtg   1440

taactggttt catatagaac cgtggatatg gttgatgaac aaaacccaaa acaacctgac   1500

agaagggcaa ccgcttaggg agtgtgctgt gacttgtagg tatgacaagg aaacagaatt   1560

gaacatcgtg acacaggcta gggacagacc tacaactctg acaggttgca agaaaggcaa   1620

gaatttctct ttcgcaggtg ttatactgga tgggccctgt aactttaaag tatcggttga   1680

agatgtgctg ttcaaggagc acgattgcgg caacatgctg caagagaccg cgatacagct   1740

actcgatggg gcaaccaaca ccattgaggg agcaagggta gggacggcca agttgacaac   1800

ctggttaggg aagcaattag ggatccttgg taagaagttg gagaacaaaa gcaaagcatg   1860

gtttggtgca catgcagcaa gtccatactg cggagtggag aggaagatcg gttacgtatg   1920

gtatacaaaa aactgcactc cagcttgcct tccaagaaac actagaataa taggccccgg   1980

gaaatttgat accaacgccg aagatggaaa aatactccat gagatggggg ggcacctctc   2040
```

-continued

```
agaatttgtc ctattgtcct tggtggttct gtctgacttt gccccggaaa ccgcgagcgt   2100
catctacttg gttctacatt ttgcgatccc gcaaagccac gttgatgtag acacatgcga   2160
caagaaccag ctgaatttaa cggtagcaac cacagtagca gaggtcatac cagggacagt   2220
gtggaaccta gggaagtatg tctgcataag accagactgg tggccatatg agacgacgac   2280
agtcttcgtc atagaggaag cagggcaagt aatcaaattg atgctaaggg ccatcagaga   2340
cttaactagg atatggaatg ctgccactac cacagctttc ttaatctttt tagtaaaagc   2400
actgagggga caactaatcc aagggctatt gtggctgatg ctaataacag gagcacaggg   2460
cttccctgaa tgcaaagagg gcttccaata tgccatatct aaagacagga aaatggggtt   2520
attggggcca gagagcttaa ctacaacatg gcacctcccc accaaaaaaa tagtggattc   2580
catggtgcat gtatggtgtg aaggaaaaga cttgaaaata ttaaaaatgt gcacaaagga   2640
agagaggtat ctagtggctg tgcacgagag agccttatca accagtgccg agtttatgca   2700
gatcagtgat gggacaatag gcccagacgt gatagatatg cctgatgact ttgagtttgg   2760
actctgccct tgtgactcaa aaccagtgat aaagggcaaa tttaatgcca gcttactgaa   2820
tggaccagct ttccagatgg tatgcccaca ggggtggact ggtacaatag aatgcaccct   2880
agcgaaccaa gacaccttgg acacaactgt cattaggaca tatagaagaa ctaccccatt   2940
tcagcggaga aaatggtgta cctatgaaaa aataataggg gaagatatct atgaatgcat   3000
tctaggtgga aactggacat gcataaccgg tgaccatagc aggttgaaag acggacctat   3060
caagaagtgt aagtggtgtg gccatgactt cgtcaactca gaggggctac cacactaccc   3120
aataggcaag tgcatgctca tcaacgagag tgggtacagg tatgtagatg acacctcttg   3180
cgataggggt ggtgtagcca tagttccatc tggcaccgta aagtgtagaa taggtaacgt   3240
cacggtgcaa gttatcgcta ctaacaatga tctgggaccc atgccttgca gcccagctga   3300
agtgatagca agtgaaggac cagtggaaaa gactgcatgc acattcaact attcaaggac   3360
tctacctaat aagtattatg agccaaggga ccggtacttc caacaataca tgttaaaagg   3420
ggagtggcaa tattggttcg acctggattc tgtagaccac cacaaagact acttctcaga   3480
gttcataatc atagcagtgg tcgccttgtt gggtggtaag tacgtactgt ggctcttgat   3540
aacatacaca atactgtctg agcagatggc tatgggtgct ggagtgaata ctgaagagat   3600
agtcatgata ggcaatttgc tgacagacag tgatattgag gttgtggttt atttccttct   3660
tctgtactta atagttaaag aggaactggc gaggaaatgg attatactgg tataccacat   3720
ccttgtagcc aaccctatga aaacaattgg ggtcgtctta ctaatgctag ggggagtggt   3780
gaaggccagc agaatcaatg ctgatgacca aagtgctatg gacccatgct ttcttctcgt   3840
gacaggcgta gtggctgttt tgatgatcgc tagaagagaa cctgccacat taccactgat   3900
tgtagcattg ctagcaataa gaacatcagg attcctactg cccgctagca ttgatgtaac   3960
tgtagcagta gtattaattg tacttttgtt ggctagctac ataacagact actttagata   4020
taaaaagtgg cttcaactct tatttagtct gatagctggt atctttatta taaggagctt   4080
aaaacatatc aaccagatgg aggtaccaga aatatctatg ccaagttgga gacctctagc   4140
tctggtcctt ttctatataa catctacagc aataaccact aattgggaca ttgacttagc   4200
aggcttcctg ctgcaatggg cgccagcagt gatcatgatg gctaccatgt gggcagactt   4260
tttgactctg atcatagtcc tgcccagtta cgagttatct aagctttact tcctaaagaa   4320
cgtcaggaca gacgtggaaa agaactggct cggcaaagtg aaatacagac agatcagttc   4380
```

-continued

```
agtttatgac atctgtgaca gtgaggaagc agtgtaccta tttccatcaa ggcataagag   4440
tggaagcagg ccagatttca tattaccttt tttgaaagcc gtgttaataa gctgcatcag   4500
cagccaatgg caagtggttt acatttctta cctaatactg gaaattacat actatatgca   4560
caggaaaatc atagatgagg tgtcaggagg agcaaatttt ctatcaagac tcatagcagc   4620
catcatagaa ttaaattggg ccatagatga tgaggaatgt aaaggactga agaaactgta   4680
tctcttgtca gggagagcga agaatttgat agttaaacat aaggtaagaa atgaagccgt   4740
ccacagatgg tttggtgagg aggaaatata cggggcaccc aaggtgatca ctatcataaa   4800
agctagtacc ctaagtaaaa acaggcactg cataatctgc acgatctgtg aagggaaaga   4860
atggaatgga gccaactgcc caaagtgtgg aagacaagga aagcccataa catgtggaat   4920
gacactcgca gactttgagg agaaacatta caaaaagata tttataagag aagaatcttc   4980
ttgtcctgtg ccttttgatc cttcttgcca ttgtaattat tttcgccacg atgggccttt   5040
caggaaagag tataagggtt acgtccaata cacagccaga ggacaactct ttctgaggaa   5100
cctaccaatt ctagcgacga agatgaagct attaatggtg ggaaacctcg gcgcagaaat   5160
tggcgacctg gaacatctag gatgggtact gagagggcca gccgtgtgca aaaaaattac   5220
caaccatgag aagtgccacg taaacatcat ggataagcta actgcatttt ttggaatcat   5280
gcctagaggc acgaccccta gggcacctgt gaggttcccc acagcactac taaaagtgag   5340
aaggggggcta gagacgggat gggcttacac gcaccaagga gggatcagct cggtagacca   5400
tgtcacagcc ggaaaggatt tactagtgtg tgacagtatg ggcaggacca gggttgtctg   5460
tcatagtaac aataagatga ctgatgagac tgagtatggc atcaagaccg actcagggtg   5520
tcccgaaggt gcgaggtgtt acgtgctaaa cccagaagct gttaacattt ctggcacaaa   5580
aggagctatg gtacacctcc agaaaacggg gggggagttc acatgtgtca ctgcctcagg   5640
gaccccggct ttcttcgatc tgaaaaatct aaaaggctgg tccgggctac caatttttga   5700
agcatccagt ggcagggtgg ttggtagggt gaaagtcggc aagaatgagg attccaagcc   5760
caccaaacta atgagcggaa tccagacagt gtctaagaac cagacagacc tagcggacat   5820
cgtaaaaaaa ttgactagta tgaacagagg agagttcaaa cagataacat tagccactgg   5880
ggcaggaaaa actacggaac tgccaaggtc cgtcatagag gagataggga ggcacaaaag   5940
ggtcttagtc ctgataccat tgagagcagc agcagagtca gtgtatcagt atatgagagt   6000
gaagtaccca agtatatctt tcaatttgag aataggagat atgaaggaag gtgacatggc   6060
cactggtatc acctacgcct catatgggta cttttgtcag cttcctcagc ccaaactgag   6120
agctgccatg gtagagtact catatatatt cttagatgag taccactgtg ctacacccga   6180
gcaattagca ataattggaa agatacacag gtttgctgaa aatcttagag tggtagcaat   6240
gacagcaacc ccagctggaa cggtcacaac gactggtcag aaacacccta tagaggagtt   6300
catagcccca gaggtgatga aaggtgaaga tctaggtagt gaatacttgg atattgcagg   6360
gttgaagata ccgactgaag agatgaaagg caacatgctc gtgttcgcgc caactaggaa   6420
catggcagta gaaacagcta agaaattgaa ggctaaggga tacaactctg gatactatta   6480
cagtggggaa aacccagaga acttgagggt ggtaacctcg caatccccgt atgtggtagt   6540
agccaccaat gccatagagt caggtgtgac attaccagac ttagacacag ttgtagacac   6600
tggactaaag tgtgagaaga gggtgaggat ttcttcaaaa atgcccttca ttgtaacagg   6660
acttaagaga atggcagtca caatcggaga gcaagcccag cgcaggggta gagtaggaag   6720
agtcaagcca ggtaggtact ataggagtca agaaacagct tcagggtcaa aagattacca   6780
```

```
ttacgaccta ctgcaagccc agaggtacgg aatagaagat ggaattaatg taacaaagtc   6840
attcagggag atgaactatg attggagcct ttacgaagag gacagcttga tgataactca   6900
actcgaggtc cttaacaacc tccttatatc agaagacctg cctgccgcag tgaagaacat   6960
catggcccgg accgatcacc cagaacccat acaactggcc tataacagtt atgaaaacca   7020
aattccagtg ctgttcccaa agatcaaaaa tggtgaggtg acagacagtt atgagaatta   7080
cacatatctc aatgcaagaa aattaggaga ggacgtgccg gcatatgtgt acgccacaga   7140
ggatgaggat ctagcagtgg atcttctggg tatggattgg ccggacccag gcaaccaaca   7200
ggtggtagag acagggaggg cattaaaaca agtaactggc ttatccacag cagaaaacgc   7260
cctcttgata gccctattcg gctacgtcgg gtaccagaca ctttcaaaaa ggcacatacc   7320
catgattact gacatctata cacttgaaga ccacaggctt gaggacacaa cccacctcca   7380
gtttgcccca aacgctataa ggaccgacgg caaggactca gagttgaagg aattagctgt   7440
gggagacctt gataaatatg tggacgcact ggtagactac tccaaacaag ggatgaaatt   7500
catcaaagtc caagctgaaa aggtcagaga ctcccagtct acgaaggaag gcttgcaaac   7560
cattaaggag tatgtggata agtttataca atcactaaca gagaataagg aggagatcat   7620
caggtatgga ctatggggag ttcacacggc actctacaaa agcttggcag cgagactggg   7680
gcatgaaaca gcttttgcaa ctttagtggt aaaatggttg gcttttgggg gcgaaacggt   7740
atctgctcac atcaagcaag tagcagttga tctagtagta tattatatca tcaacaaacc   7800
atcttttcct ggagatacag agacccaaca agaggggagg aagtttgtgg ctagtctttt   7860
tatatctgca ctagcaacat acacatataa aacctggaat tacaacaatc tgcaacgggt   7920
tgtcgaacct gccttagctt acctcccata tgctacaagt gccttgaagt tgttcacacc   7980
cacaagatta gagagtgtgg tcatactcag ttctacaatt tacaagacat acctctctat   8040
aaggaagggt aagagtgacg gcttgttagg tacaggcata agtgcagcca tggagatctt   8100
aaaccaaaac ccaatctcag taggtatatc tgtgatgctg gggtaggtg ccatcgccgc   8160
ccataatgca atagaatcta gtgaacagaa aagaactttg ctgatgaagg tctttgtaaa   8220
aaacttctta gaccaagcag caacagatga gctagtcaaa gagaaccctg aaaaaataat   8280
catggctcta tttgaagcag tccagaccat aggaaacccc ctaagactca tctaccatct   8340
gtacggggtg tactataagg ggtgggaagc aaaagaactc gcagagaaaa ctgctggccg   8400
caacttattc acattgatca tgtttgaggc ctttgagctt ttaggtatgg actcagaagg   8460
aaagataaga aacttgtcag gcaactacat actggactta atcttcaact tgcataataa   8520
attaaacaag ggctcaaaa aactagtcct tgggtgggct cctgcacctt tgagctgtga   8580
ttggacacca agtgatgaga gaataagcct acctcataac aactacttaa gggtagaaac   8640
caggtgtcct tgtggctatg agatgaaggc aataaaaaat gttgctggta aattgacaaa   8700
agttgaagaa aaggggtcct tcctatgcag gaatagatta gggagaggac ctccaaactt   8760
caaagtaaca aagttctatg atgataactt gatagaagtc aagccagtag ctaggctaga   8820
aggccaggtg gacctctatt acaagggagt aacagctaag ttagactaca acaatgggaa   8880
agtactgtta gctaccaaca agtgggaggt ggaccacgct ttcctgacca gactagtaaa   8940
gaagcacaca gggataggtt ttaaaggtgc atatttgggt gaccgaccag accatcaaga   9000
tcttgtcgat agagattgtg caactataac gaagaactca gtacagttcc taaaaatgaa   9060
gaagggttgc gctttcacat atgacctaac aatctctaac cttgtcaggc ttattgaact   9120
```

-continued

```
agtccataag aataatttac aagaaagaga gatccctacc gtgacagtaa ctacttggct   9180
tgcatattct tttgtcaatg aagacctggg gactatcaag cctgtattgg gggagaaagt   9240
catcccagaa ccccccgagg agttgagtct ccaacccacc gtgagactag tcaccactga   9300
aacagcaata accataacag gggaggctga agtgatgacg acagggatca caccagtggt   9360
agagatgaaa gaagaacctc agctggacca ccagtcaact accctaaagg tagggttgaa   9420
ggaaggggaa tatccagggc caggagttaa ccctaaccat ttagcagagg tgatagatga   9480
gaaagatgac aggccttttg tcctaatcat cggtaacaaa ggttctacct cgaacagagc   9540
aagaacggcc aagaatatac ggctgtacaa aggaaacaac ccaagagaga tcagggatct   9600
gatgagccaa ggaagaatat tgacggttgc tctaaaagag ttggacccgg aattaaaaga   9660
attagtagat tacaagggga cctttctcaa tagggaagct ttagaagccc taagcttagg   9720
taagccaatc aagaggaaaa ccacaacagc aatgatcagg aggttaatag agccagaggt   9780
tgaggaggaa ctaccagatt ggttccaagc ggaagaaccc ctatttttgg aagcaaaaat   9840
acagaatgac ttataccacc taattggcag tgtagatagt ataaaaagca aagcaaagga   9900
attaggggcc acagataaca caaagatagt gaaggaagtt ggggctagga cctatacgat   9960
gaaattgagc agctggagca cacaagttac aaaaaaacag atgagtctag cccctctctt  10020
tgaagagctg ttattaaagt gccctccatg tagtaaaatt tcaaagggac atatggtgtc  10080
agcataccaa ctggctcaag gaaactggga accccctcggg tgtggggtct atatgggaac  10140
cataccagct aggcgtctca agatccaccc ttatgaggct taccttaaac tcaaagagct  10200
ggtggaagtt gaatcttcga gggccactgc aaaagaatcc atcataagag aacataacac  10260
ctggatcctg cggaaggtga gacatgaagg gaacctaaga accaaatcaa tgatcaaccc  10320
tgggaaaata tcagatcagc tatgcagaga tggacacaaa agaaacatat ataataagat  10380
cataggctca acaatggcct ctgctggtat taggctggag aaactgccag tagtccgagc  10440
ccaaactgac acaaccagtt tccaccaagc cataagagaa aaaattgata aaacagaaaa  10500
caagcagacc cctgaattgc atgaagaact aatgaaggtc ttcgactgct taaagatccc  10560
agagctgaag gaatcgtatg atgaagtttc atgggaacaa ttagaagccg ggataaaccg  10620
taagggtgca gcaggctatc tagagagcaa gaacataggg gaagtcctag acacagagaa  10680
acacatagta gagcagctga tcaaggatct gaggaagggg aagaagatta ggtactatga  10740
aacagccatc cccaagaatg agaagagaga cgtcagcgac gactgggaag ccggagagtt  10800
cgttgatgaa aagaaaccaa gagtaatcca gtacccggac gccaaggtga gactggccat  10860
tacaaaagtg atgtacaaat gggtaaagca aaaaccagtg gtgatacccg gctatgaagg  10920
taaaacacct ctatttgaca tattcaacaa agtgaagaag gaatgggatt cattccagga  10980
ccccgtagca gtgagctttg acaccaaagc gtgggataca caagtcacca gtagagacct  11040
aatgttgata aaggatatcc agaaatatta tttcaagaga agtatacaca aatttttaga  11100
tacaataaca gaacacatgg tggaggtacc tgtcattaca gcagacggtg aagtttacat  11160
aaggaatggt cagaggggta gtggccaacc cgacacaagt gctggtaata gtatgttgaa  11220
tgtcctaacc atgatatatg ctttctgtaa aagtacaggc ataccttaca ggggattcag  11280
cagagtggca agaatccatg tgtgtggtga tgatggcttt ttgataacag agagaggact  11340
gggactgaaa ttctctgaga agggtatgca gatattacat gaggccggga agccccagaa  11400
aataactgaa ggggacaaaa tgaaagtggc atacagattc gaggacatag agttttgttc  11460
ccatactccc gtgccagtca gatgggcaga taacaccagt agttacatgg cagggaggag  11520
```

-continued

```
cacagccact atactagcta agatggcaac caggctggat tccagcggag agaggggtag  11580

cacagcttat gagaaggccg tagccttcag cttccttttg atgtactcat ggaatcccgt  11640

agttagaagg atctgcttac tggtgttgtc acagtttcca gaaatatccc catccaaaaa  11700

cacaatatac tactaccaag ggatcccat agctgcgtac agagaagtga tagggaaaca  11760

gctgtgtgaa ctgaaaagaa caggatttga gaagctggct ggtctgaatt tgagtatgac  11820

cactctaggc atctggacaa aacatactag taaaagacta atccaagcct gtgtagaaat  11880

aggtaagaga gaaggtacct ggttagttaa tgctgacaga ctgattgcag gaaagactgg  11940

gaagttttac atcccaagca ctggtgtcac tctgttggga aaacactatg aggaaattaa  12000

cttaaagcaa aaggcggcac aaccgccgat agagggggtt gacagatata agttgggccc  12060

catagttaat gttatcttga gaaggctgag ggtgatgctg atgacagttg ccagcggaag  12120

ctggtgaatc cgtccggagc gtcgtgccct cactcaaggt ttttaattgt aaatattgta  12180

aatagacagc taagatattt attgtagttg gatagtaatg cagtgatagt aaataccca  12240

atttaacact acctccaatg cactaagcac tttagctgtg tgaggttaac tcgacgtcca  12300

cggttggact agggaagacc tctaacagcc cc                                12332
```

<210> SEQ ID NO 2
<211> LENGTH: 11840
<212> TYPE: DNA
<213> ORGANISM: Artificial
<220> FEATURE:
<223> OTHER INFORMATION: Mutated BVDV: XIKE- A-NdN

<400> SEQUENCE: 2

```
gtatacgaga ttagctaaag aactcgtata tggattggac gtcaacaaat ttttaattgg    60

caacgtaggg aaccttcccc tcagcgaagg ccgaaaagag gctagccatg cccttagtag   120

gactagcaaa agtaggggac tagcggtagc agtgagttcg ttggatggcc gaacccctga   180

gtacagggga gtcgtcaatg gttcgacact ccattagtcg aggagtctcg agatgccatg   240

tggacgaggg catgcccacg gcacatctta acccatgcgg gggttgcatg ggtgaaagcg   300

ctattcgtgg cgttatggac acagcctgat agggtgtagc agagacctgc tattccgcta   360

gtaaaaactc tgctgtacat ggcacatgga gttgttttcc gatgaaggga gcaagggtgc   420

tacaagtaag aagcagccta agccagatag gatagaaaaa ggtaagatga aaatagcccc   480

aaaagagaca gaaaaagatt gcaaaaccag accccccgac gcgactatag tagtagaagg   540

ggttaagtac caggtgaaga aaaaaggaaa ggtaagggga aaaaatactc aagatgggtt   600

atatcacaac aagaataagc cccctgaatc aagaaaaaaa ttggaaaagg cactgctggc   660

ttgggccatc ttagcagcgg tcctgcttca gctggtaaca ggagagaata tcacccagtg   720

gaacttgatg gacaacggca ccgagggaat acagcaagcg atgttcctaa gaggggtgaa   780

caggagtcta catggaattt ggccagagaa aatttgcacc ggagtaccaa ctcacttagc   840

aacagactat gagcttaaag agatagtggg gatgatggac gcgagtgaga agaccaacta   900

cacgtgttgc aggttgcaaa gacatgagtg gaataaacat ggttggtgta actggtttca   960

tatagaaccg tggatatggt tgatgaacaa aacccaaaac aacctgacag aagggcaacc  1020

gcttagggag tgtgctgtga cttgtaggta tgacaaggaa acagaattga acatcgtgac  1080

acaggctagg gacagaccta caactctgac aggttgcaag aaaggcaaga atttctcttt  1140

cgcaggtgtt atactggatg ggccctgtaa ctttaaagta tcggttgaag atgtgctgtt  1200
```

-continued

```
caaggagcac gattgcggca acatgctgca agagaccgcg atacagctac tcgatggggc   1260
aaccaacacc attgagggag caagggtagg gacggccaag ttgacaacct ggttagggaa   1320
gcaattaggg atccttggta agaagttgga gaacaaaagc aaagcatggt ttggtgcaca   1380
tgcagcaagt ccatactgcg gagtggagag gaagatcggt tacgtatggt atacaaaaaa   1440
ctgcactcca gcttgccttc caagaaacac tagaataata ggccccggga aatttgatac   1500
caacgccgaa gatggaaaaa tactccatga gatggggggg cacctctcag aatttgtcct   1560
attgtccttg gtggttctgt ctgactttgc cccggaaacc gcgagcgtca tctacttggt   1620
tctacatttt gcgatcccgc aaagccacgt tgatgtagac acatgcgaca agaaccagct   1680
gaatttaacg gtagcaacca cagtagcaga ggtcatacca gggacagtgt ggaacctagg   1740
gaagtatgtc tgcataagac cagactggtg gccatatgag acgacgacag tcttcgtcat   1800
agaggaagca gggcaagtaa tcaaattgat gctaagggcc atcagagact taactaggat   1860
atggaatgct gccactacca cagctttctt aatcttttta gtaaaagcac tgaggggaca   1920
actaatccaa gggctattgt ggctgatgct aataacagga gcacagggct tccctgaatg   1980
caaagagggc ttccaatatg ccatatctaa agacaggaaa atggggttat tggggccaga   2040
gagcttaact acaacatggc acctccccac caaaaaaata gtggattcca tggtgcatgt   2100
atggtgtgaa ggaaaagact tgaaaatatt aaaaatgtgc acaaaggaag agaggtatct   2160
agtggctgtg cacgagagag ccttatcaac cagtgccgag tttatgcaga tcagtgatgg   2220
gacaataggc ccagacgtga tagatatgcc tgatgacttt gagtttggac tctgcccttg   2280
tgactcaaaa ccagtgataa agggcaaatt taatgccagc ttactgaatg gaccagcttt   2340
ccagatggta tgcccacagg ggtggactgg tacaatagaa tgcaccctag cgaaccaaga   2400
caccttggac acaactgtca ttaggacata tagaagaact accccatttc agcggagaaa   2460
atggtgtacc tatgaaaaaa taatagggga agatatctat gaatgcattc taggtggaaa   2520
ctggacatgc ataaccggtg accatagcag gttgaaagac ggacctatca agaagtgtaa   2580
gtggtgtggc catgacttcg tcaactcaga ggggctacca cactacccaa taggcaagtg   2640
catgctcatc aacgagagtg ggtacaggta tgtagatgac acctcttgcg ataggggtgg   2700
tgtagccata gttccatctg gcaccgtaaa gtgtagaata ggtaacgtca cggtgcaagt   2760
tatcgctact aacaatgatc tgggacccat gccttgcagc ccagctgaag tgatagcaag   2820
tgaaggacca gtggaaaaga ctgcatgcac attcaactat tcaaggactc tacctaataa   2880
gtattatgag ccaagggacc ggtacttcca acaatacatg ttaaaagggg agtggcaata   2940
ttggttcgac ctggattctg tagaccacca caaagactac ttctcagagt tcataatcat   3000
agcagtggtc gccttgttgg gtggtaagta cgtactgtgg ctcttgataa catacacaat   3060
actgtctgag cagatggcta tgggtgctgg agtgaatact gaagagatag tcatgatagg   3120
caatttgctg acagacagtg atattgaggt tgtggtttat ttccttcttc tgtacttaat   3180
agttaaagag gaactggcga ggaaatggat tatactggta taccacatcc ttgtagccaa   3240
ccctatgaaa acaattgggg tcgtcttact aatgctaggg ggagtggtga aggccagcag   3300
aatcaatgct gatgaccaaa gtgctatgga cccatgcttt cttctcgtga caggcgtagt   3360
ggctgttttg atgatcgcta gaagagaacc tgccacatta ccactgattg tagcattgct   3420
agcaataaga acatcaggat tcctactgcc cgctagcatt gatgtaactg tagcagtagt   3480
attaattgta cttttgttgg ctagctacat aacagactac tttagatata aaaagtggct   3540
tcaactctta tttagtctga tagctggtat ctttattata aggagcttaa aacatatcaa   3600
```

-continued

```
ccagatggag gtaccagaaa tatctatgcc aagttggaga cctctagctc tggtcctttt   3660
ctatataaca tctacagcaa taaccactaa ttgggacatt gacttagcag gcttcctgct   3720
gcaatgggcg ccagcagtga tcatgatggc taccatgtgg gcagactttt tgactctgat   3780
catagtcctg cccagttacg agttatctaa gctttacttc ctaaagaacg tcaggacaga   3840
cgtggaaaag aactggctcg gcaaagtgaa atacagacag atcagttcag tttatgacat   3900
ctgtgacagt gaggaagcag tgtacctatt tccatcaagg cataagagtg gaagcaggcc   3960
agatttcata ttaccttttt tgaaagccgt gttaataagc tgcatcagca gccaatggca   4020
agtggtttac atttcttacc taatactgga aattacatac tatatgcaca ggaaaatcat   4080
agatgaggtg tcaggaggag caaattttct atcaagactc atagcagcca tcatagaatt   4140
aaattgggcc atagatgatg aggaatgtaa aggactgaag aaactgtatc tcttgtcagg   4200
gagagcgaag aatttgatag ttaaacataa ggtaagaaat gaagccgtcc acagatggtt   4260
tggtgaggag gaaatatacg gggcacccaa ggtgatcact atcataaaag ctagtaccct   4320
aagtaaaaac aggcactgca taatctgcac gatctgtgaa gggaaagaat ggaatggagc   4380
caactgccca aagtgtggaa gacaaggaaa gcccataaca tgtggaatga cactcgcaga   4440
ctttgaggag aaacattaca aaaagatatt tataagagaa gaatcttctt gtcctgtgcc   4500
ttttgatcct tcttgccatt gtaattattt tcgccacgat gggcctttca ggaaagagta   4560
taagggttac gtccaataca cagccagagg acaactcttt ctgaggaacc taccaattct   4620
agcgacgaag atgaagctat taatggtggg aaacctcggc gcagaaattg gcgacctgga   4680
acatctagga tgggtactga gagggccagc cgtgtgcaaa aaaattacca accatgagaa   4740
gtgccacgta aacatcatgg ataagctaac tgcatttttt ggaatcatgc ctagaggcac   4800
gacccctagg gcacctgtga ggttccccac agcactacta aaagtgagaa gggggctaga   4860
gacgggatgg gcttacacgc accaaggagg gatcagctcg gtagaccatg tcacagccgg   4920
aaaggattta ctagtgtgtg acagtatggg caggaccagg gttgtctgtc atagtaacaa   4980
taagatgact gatgagactg agtatggcat caagaccgac tcagggtgtc ccgaaggtgc   5040
gaggtgttac gtgctaaacc cagaagctgt taacatttct ggcacaaaag gagctatggt   5100
acacctccag aaaacggggg gggagttcac atgtgtcact gcctcaggga ccccggcttt   5160
cttcgatctg aaaaatctaa aaggctggtc cgggctacca atttttgaag catccagtgg   5220
cagggtggtt ggtagggtga aagtcggcaa gaatgaggat tccaagccca ccaaactaat   5280
gagcggaatc cagacagtgt ctaagaacca gacagaccta gcggacatcg taaaaaaatt   5340
gactagtatg aacagaggag agttcaaaca gataacatta gccactgggg caggaaaaac   5400
tacggaactg ccaaggtccg tcatagagga gatagggagg cacaaaaggg tcttagtcct   5460
gataccattg agagcagcag cagagtcagt gtatcagtat atgagagtga agtacccaag   5520
tatatctttc aatttgagaa taggagatat gaaggaaggt gacatggcca ctggtatcac   5580
ctacgcctca tatgggtact tttgtcagct tcctcagccc aaactgagag ctgccatggt   5640
agagtactca tatatattct tagatgagta ccactgtgct acacccgagc aattagcaat   5700
aattggaaag atacacaggt ttgctgaaaa tcttagagtg gtagcaatga cagcaacccc   5760
agctggaacg gtcacaacga ctggtcagaa acaccctata gaggagttca tagccccaga   5820
ggtgatgaaa ggtgaagatc taggtagtga atacttggat attgcagggt tgaagatacc   5880
gactgaagag atgaaaggca acatgctcgt gttcgcgcca actaggaaca tggcagtaga   5940
```

-continued

```
aacagctaag aaattgaagg ctaagggata caactctgga tactattaca gtggggaaaa   6000
cccagagaac ttgagggtgg taacctcgca atccccgtat gtggtagtag ccaccaatgc   6060
catagagtca ggtgtgacat taccagactt agacacagtt gtagacactg gactaaagtg   6120
tgagaagagg gtgaggattt cttcaaaaat gcccttcatt gtaacaggac ttaagagaat   6180
ggcagtcaca atcggagagc aagcccagcg caggggtaga gtaggaagag tcaagccagg   6240
taggtactat aggagtcaag aaacagcttc agggtcaaaa gattaccatt acgacctact   6300
gcaagcccag aggtacggaa tagaagatgg aattaatgta acaaagtcat tcagggagat   6360
gaactatgat tggagccttt acgaagagga cagcttgatg ataactcaac tcgaggtcct   6420
taacaacctc cttatatcag aagacctgcc tgccgcagtg aagaacatca tggcccggac   6480
cgatcaccca gaacccatac aactggccta taacagttat gaaaaccaaa ttccagtgct   6540
gttcccaaag atcaaaaatg gtgaggtgac agacagttat gagaattaca catatctcaa   6600
tgcaagaaaa ttaggagagg acgtgccggc atatgtgtac gccacagagg atgaggatct   6660
agcagtggat cttctgggta tggattggcc ggacccaggc aaccaacagg tggtagagac   6720
agggagggca ttaaaacaag taactggctt atccacagca gaaaacgccc tcttgatagc   6780
cctattcggc tacgtcgggt accagacact ttcaaaaagg cacataccca tgattactga   6840
catctataca cttgaagacc acaggcttga ggacacaacc cacctccagt ttgccccaaa   6900
cgctataagg accgacggca aggactcaga gttgaaggaa ttagctgtgg gagaccttga   6960
taaatatgtg gacgcactgg tagactactc caaacaaggg atgaaattca tcaaagtcca   7020
agctgaaaag gtcagagact cccagtctac gaaggaaggc ttgcaaacca ttaaggagta   7080
tgtggataag tttatacaat cactaacaga gaataaggag gagatcatca ggtatggact   7140
atggggagtt cacacggcac tctacaaaag cttggcagcg agactggggc atgaaacagc   7200
ttttgcaact ttagtggtaa aatggttggc ttttgggggc gaaacggtat ctgctcacat   7260
caagcaagta gcagttgatc tagtagtata ttatatcatc aacaaaccat cttttcctgg   7320
agatacagag acccaacaag aggggaggaa gtttgtggct agtcttttta tatctgcact   7380
agcaacatac acatataaaa cctggaatta caacaatctg caacgggttg tcgaacctgc   7440
cttagcttac ctcccatatg ctacaagtgc cttgaagttg ttcacaccca caagattaga   7500
gagtgtggtc atactcagtt ctacaattta caagacatac ctctctataa ggaagggtaa   7560
gagtgacggc ttgttaggta caggcataag tgcagccatg gagatcttaa accaaaaccc   7620
aatctcagta ggtatatctg tgatgctggg ggtaggtgcc atcgccgccc ataatgcaat   7680
agaatctagt gaacagaaaa gaactttgct gatgaaggtc tttgtaaaaa acttcttaga   7740
ccaagcagca acagatgagc tagtcaaaga gaaccctgaa aaaataatca tggctctatt   7800
tgaagcagtc cagaccatag gaaaccccct aagactcatc taccatctgt acggggtgta   7860
ctataagggg tgggaagcaa aagaactcgc agagaaaact gctggccgca acttattcac   7920
attgatcatg tttgaggcct ttgagctttt aggtatggac tcagaaggaa agataagaaa   7980
cttgtcaggc aactacatac tggacttaat cttcaacttg cataataaat taaacaaggg   8040
gctcaaaaaa ctagtccttg ggtgggctcc tgcacctttg agctgtgatt ggacaccaag   8100
tgatgagaga ataagcctac ctcataacaa ctacttaagg gtagaaacca ggtgtccttg   8160
tggctatgag atgaaggcaa taaaaaatgt tgctggtaaa ttgacaaaag ttgaagaaaa   8220
ggggtccttc ctatgcagga atagattagg gagaggacct ccaaacttca aagtaacaaa   8280
gttctatgat gataacttga tagaagtcaa gccagtagct aggctagaag gccaggtgga   8340
```

-continued

```
cctctattac aagggagtaa cagctaagtt agactacaac aatgggaaag tactgttagc   8400
taccaacaag tgggaggtgg accacgcttt cctgaccaga ctagtaaaga agcacacagg   8460
gataggtttt aaaggtgcat atttgggtga ccgaccagac catcaagatc ttgtcgatag   8520
agattgtgca actataacga agaactcagt acagttccta aaaatgaaga agggttgcgc   8580
tttcacatat gacctaacaa tctctaacct tgtcaggctt attgaactag tccataagaa   8640
taatttacaa gaaagagaga tccctaccgt gacagtaact acttggcttg catattcttt   8700
tgtcaatgaa gacctgggga ctatcaagcc tgtattgggg gagaaagtca tcccagaacc   8760
ccccgaggag ttgagtctcc aacccaccgt gagactagtc accactgaaa cagcaataac   8820
cataacaggg gaggctgaag tgatgacgac agggatcaca ccagtggtag agatgaaaga   8880
agaacctcag ctggaccacc agtcaactac cctaaaggta gggttgaagg aaggggaata   8940
tccagggcca ggagttaacc ctaaccattt agcagaggtg atagatgaga aagatgacag   9000
gccttttgtc ctaatcatcg gtaacaaagg ttctacctcg aacagagcaa gaacggccaa   9060
gaatatacgg ctgtacaaag gaaacaaccc aagagagatc agggatctga tgagccaagg   9120
aagaatattg acggttgctc taaaagagtt ggacccggaa ttaaaagaat tagtagatta   9180
caaggggacc tttctcaata gggaagcttt agaagcccta agcttaggta agccaatcaa   9240
gaggaaaacc acaacagcaa tgatcaggag gttaatagag ccagaggttg aggaggaact   9300
accagattgg ttccaagcgg aagaacccct atttttggaa gcaaaaatac agaatgactt   9360
ataccaccta attggcagtg tagatagtat aaaaagcaaa gcaaaggaat taggggccac   9420
agataacaca aagatagtga aggaagttgg ggctaggacc tatacgatga aattgagcag   9480
ctggagcaca caagttacaa aaaaacagat gagtctagcc cctctctttg aagagctgtt   9540
attaaagtgc cctccatgta gtaaaatttc aaagggacat atggtgtcag cataccaact   9600
ggctcaagga aactgggaac ccctcgggtg tggggtctat atgggaacca taccagctag   9660
gcgtctcaag atccaccctt atgaggctta ccttaaactc aaagagctgg tggaagttga   9720
atcttcgagg gccactgcaa aagaatccat cataagagaa cataacacct ggatcctgcg   9780
gaaggtgaga catgaaggga acctaagaac caaatcaatg atcaaccctg ggaaaatatc   9840
agatcagcta tgcagagatg gacacaaaag aaacatatat aataagatca taggctcaac   9900
aatggcctct gctggtatta ggctggagaa actgccagta gtccgagccc aaactgacac   9960
aaccagtttc caccaagcca taagagaaaa aattgataaa acagaaaaca agcagacccc  10020
tgaattgcat gaagaactaa tgaaggtctt cgactgctta aagatcccag agctgaagga  10080
atcgtatgat gaagtttcat gggaacaatt agaagccggg ataaaccgta agggtgcagc  10140
aggctatcta gagagcaaga acatagggga agtcctagac acagagaaac acatagtaga  10200
gcagctgatc aaggatctga ggaaggggaa gaagattagg tactatgaaa cagccatccc  10260
caagaatgag aagagagacg tcagcgacga ctgggaagcc ggagagttcg ttgatgaaaa  10320
gaaaccaaga gtaatccagt acccggacgc caaggtgaga ctggccatta caaaagtgat  10380
gtacaaatgg gtaaagcaaa aaccagtggt gatacccggc tatgaaggta aaacacctct  10440
atttgacata ttcaacaaag tgaagaagga atgggattca ttccaggacc ccgtagcagt  10500
gagctttgac accaaagcgt gggatacaca agtcaccagt agagacctaa tgttgataaa  10560
ggatatccag aaatattatt tcaagagaag tatacacaaa tttttagata caataacaga  10620
acacatggtg gaggtacctg tcattacagc agacggtgaa gtttacataa ggaatggtca  10680
```

-continued

```
gaggggtagt ggccaacccg acacaagtgc tggtaatagt atgttgaatg tcctaaccat  10740

gatatatgct ttctgtaaaa gtacaggcat accttacagg ggattcagca gagtggcaag  10800

aatccatgtg tgtggtgatg atggcttttt gataacagag agaggactgg gactgaaatt  10860

ctctgagaag ggtatgcaga tattacatga ggccgggaag ccccagaaaa taactgaagg  10920

ggacaaaatg aaagtggcat acagattcga ggacatagag ttttgttccc atactcccgt  10980

gccagtcaga tgggcagata acaccagtag ttacatggca gggaggagca cagccactat  11040

actagctaag atggcaacca ggctggattc cagcggagag aggggtagca cagcttatga  11100

gaaggccgta gccttcagct tccttttgat gtactcatgg aatcccgtag ttagaaggat  11160

ctgcttactg gtgttgtcac agtttccaga aatatcccca tccaaaaaca caatatacta  11220

ctaccaaggg gatcccatag ctgcgtacag agaagtgata gggaaacagc tgtgtgaact  11280

gaaaagaaca ggatttgaga agctggctgg tctgaatttg agtatgacca ctctaggcat  11340

ctggacaaaa catactagta aaagactaat ccaagcctgt gtagaaatag gtaagagaga  11400

aggtacctgg ttagttaatg ctgacagact gattgcagga aagactggga agttttacat  11460

cccaagcact ggtgtcactc tgttgggaaa acactatgag gaaattaact taaagcaaaa  11520

ggcggcacaa ccgccgatag agggggttga cagatataag ttgggcccca tagttaatgt  11580

tatcttgaga aggctgaggg tgatgctgat gacagttgcc agcggaagct ggtgaatccg  11640

tccggagcgt cgtgccctca ctcaaggttt ttaattgtaa atattgtaaa tagacagcta  11700

agatatttat tgtagttgga tagtaatgca gtgatagtaa ataccccaat ttaacactac  11760

ctccaatgca ctaagcactt tagctgtgtg aggttaactc gacgtccacg gttggactag  11820

ggaagacctc taacagcccc                                                11840
```

```
<210> SEQ ID NO 3
<211> LENGTH: 12329
<212> TYPE: DNA
<213> ORGANISM: Artificial
<220> FEATURE:
<223> OTHER INFORMATION: Mutated BVDV: XIKE-B

<400> SEQUENCE: 3

gtatacgaga ttagctaaag aactcgtata tggattggac gtcaacaaat ttttaattgg     60

caacgtaggg aaccttcccc tcagcgaagg ccgaaaagag gctagccatg cccttagtag    120

gactagcaaa agtaggggac tagcggtagc agtgagttcg ttggatggcc gaacccctga    180

gtacagggga gtcgtcaatg gttcgacact ccattagtcg aggagtctcg agatgccatg    240

tggacgaggg catgcccacg gcacatctta acccatgcgg gggttgcatg ggtgaaagcg    300

ctattcgtgg cgttatggac acagcctgat agggtgtagc agagacctgc tattccgcta    360

gtaaaaactc tgctgtacat ggcacatgga gttgttttca aatgaacttt tatacaaaac    420

atataaacaa aaaccagcag gcgtcgtgga acctgtttac gacgtcaacg ggcgcccact    480

gtttggagag agcagtgact tgcacccgca gtcaacacta aaactaccac accaacgagg    540

cagcgccaac atcctgacca atgctaggtc cctaccgcgg aaaggtgact gccggagagg    600

taatgtgtat ggaccggtga gtggcatcta tatcaaacca ggaccgatct actaccagga    660

ttatgtgggc cccgtctatc atagagcccc actggaacta tgtagggagg caagtatgtg    720

cgaaacaact aggagagttg gcagagtgac cggtagtgat gggaaattat atcatatcta    780

catctgcata gatgggtgta tcctcctgaa gagggcgact aggaaccaac cagaagtcct    840

gaaatgggta tacaacagat taaattgtcc tttatgggtc accagctgct ccgatgaagg    900
```

-continued

```
gagcaagggt gctacaagta agaagcagcc taagccagat aggatagaaa aaggtaagat    960
gaaaatagcc ccaaaagaga cagaaaaaga ttgcaaaacc agaccccccg acgcgactat   1020
agtagtagaa ggggttaagt accaggtgaa gaaaaaagga aaggtaaggg gaaaaaatac   1080
tcaagatggg ttatatcaca acaagaataa gccccctgaa tcaagaaaaa aattggaaaa   1140
ggcactgctg gcttgggcca tcttagcagc ggtcctgctt cagctggtaa caggagagaa   1200
tatcacccag tggaacttga tggacaacgg caccgaggga atacagcaag cgatgttcct   1260
aagaggggtg aacaggagtc tacatggaat ttggccagag aaaatttgca ccggagtacc   1320
aactcactta gcaacagact atgagcttaa agagatagtg ggatgatgg acgcgagtga    1380
gaagaccaac tacacgtgtt gcaggttgca aagacatgag tggaataaag gttggtgtaa   1440
ctggtttcat atagaaccgt ggatatggtt gatgaacaaa acccaaaaca acctgacaga   1500
agggcaaccg cttagggagt gtgctgtgac ttgtaggtat gacaaggaaa cagaattgaa   1560
catcgtgaca caggctaggg acagacctac aactctgaca ggttgcaaga aaggcaagaa   1620
tttctctttc gcaggtgtta tactggatgg gccctgtaac tttaaagtat cggttgaaga   1680
tgtgctgttc aaggagcacg attgcggcaa catgctgcaa gagaccgcga tacagctact   1740
cgatggggca accaacacca ttgagggagc aagggtaggg acggccaagt tgacaacctg   1800
gttagggaag caattaggga tccttggtaa gaagttggag aacaaaagca aagcatggtt   1860
tggtgcacat gcagcaagtc catactgcgg agtggagagg aagatcggtt acgtatggta   1920
tacaaaaaac tgcactccag cttgccttcc aagaaacact agaataatag gccccgggaa   1980
atttgatacc aacgccgaag atggaaaaat actccatgag atgggggggc acctctcaga   2040
atttgtccta ttgtccttgg tggttctgtc tgactttgcc ccggaaaccg cgagcgtcat   2100
ctacttggtt ctacattttg cgatcccgca aagccacgtt gatgtagaca catgcgacaa   2160
gaaccagctg aatttaacgg tagcaaccac agtagcagag gtcataccag ggacagtgtg   2220
gaacctaggg aagtatgtct gcataagacc agactggtgg ccatatgaga cgacgacagt   2280
cttcgtcata gaggaagcag ggcaagtaat caaattgatg ctaagggcca tcagagactt   2340
aactaggata tggaatgctg ccactaccac agctttctta atctttttag taaaagcact   2400
gaggggacaa ctaatccaag ggctattgtg gctgatgcta ataacaggag cacagggctt   2460
ccctgaatgc aaagagggct tccaatatgc catatctaaa gacaggaaaa tggggttatt   2520
ggggccagag agcttaacta caacatggca cctccccacc aaaaaaatag tggattccat   2580
ggtgcatgta tggtgtgaag gaaaagactt gaaaatatta aaatgtgca caaaggaaga    2640
gaggtatcta gtggctgtgc acgagagagc cttatcaacc agtgccgagt ttatgcagat   2700
cagtgatggg acaataggcc cagacgtgat agatatgcct gatgactttg agtttggact   2760
ctgcccttgt gactcaaaac cagtgataaa gggcaaattt aatgccagct tactgaatgg   2820
accagctttc cagatggtat gcccacaggg gtggactggt acaatagaat gcaccctagc   2880
gaaccaagac accttggaca caactgtcat taggacatat agaagaacta ccccatttca   2940
gcggagaaaa tggtgtacct atgaaaaaat aatagggggaa gatatctatg aatgcattct  3000
aggtggaaac tggacatgca taaccggtga ccatagcagg ttgaaagacg gacctatcaa   3060
gaagtgtaag tggtgtggcc atgacttcgt caactcagag ggctaccac actacccaat    3120
aggcaagtgc atgctcatca acgagagtgg gtacaggtat gtagatgaca cctcttgcga   3180
taggggtggt gtagccatag ttccatctgg caccgtaaag tgtagaatag gtaacgtcac   3240
```

-continued

```
ggtgcaagtt atcgctacta acaatgatct gggacccatg ccttgcagcc cagctgaagt   3300
gatagcaagt gaaggaccag tggaaaagac tgcatgcaca ttcaactatt caaggactct   3360
acctaataag tattatgagc caagggaccg gtacttccaa caatacatgt taaaagggga   3420
gtggcaatat tggttcgacc tggattctgt agaccaccac aaagactact tctcagagtt   3480
cataatcata gcagtggtcg ccttgttggg tggtaagtac gtactgtggc tcttgataac   3540
atacacaata ctgtctgagc agatggctat gggtgctgga gtgaatactg aagagatagt   3600
catgataggc aatttgctga cagacagtga tattgaggtt gtggtttatt tccttcttct   3660
gtacttaata gttaaagagg aactggcgag gaaatggatt atactggtat accacatcct   3720
tgtagccaac cctatgaaaa caattggggt cgtcttacta atgctagggg gagtggtgaa   3780
ggccagcaga atcaatgctg atgaccaaag tgctatggac ccatgctttc ttctcgtgac   3840
aggcgtagtg gctgttttga tgatcgctag aagagaacct gccacattac cactgattgt   3900
agcattgcta gcaataagaa catcaggatt cctactgccc gctagcattg atgtaactgt   3960
agcagtagta ttaattgtac ttttgttggc tagctacata acagactact ttagatataa   4020
aaagtggctt caactcttat ttagtctgat agctggtatc tttattataa ggagcttaaa   4080
acatatcaac cagatggagg taccagaaat atctatgcca agttggagac ctctagctct   4140
ggtccttttc tatataacat ctacagcaat aaccactaat tgggacattg acttagcagg   4200
cttcctgctg caatgggcgc cagcagtgat catgatggct accatgtggg cagacttttt   4260
gactctgatc atagtcctgc ccagttacga gttatctaag ctttacttcc taaagaacgt   4320
caggacagac gtggaaaaga actggctcgg caaagtgaaa tacagacaga tcagttcagt   4380
ttatgacatc tgtgacagtg aggaagcagt gtacctattt ccatcaaggc ataagagtgg   4440
aagcaggcca gatttcatat taccttttt gaaagccgtg ttaataagct gcatcagcag   4500
ccaatggcaa gtggtttaca tttcttacct aatactggaa attacatact atatgcacag   4560
gaaaatcata gatgaggtgt caggaggagc aaattttcta tcaagactca tagcagccat   4620
catagaatta aattgggcca tagatgatga ggaatgtaaa ggactgaaga aactgtatct   4680
cttgtcaggg agagcgaaga atttgatagt taaacataag gtaagaaatg aagccgtcca   4740
cagatggttt ggtgaggagg aaatatacgg ggcacccaag gtgatcacta tcataaaagc   4800
tagtacccta agtaaaaaca ggcactgcat aatctgcacg atctgtgaag ggaaagaatg   4860
gaatggagcc aactgcccaa agtgtggaag acaaggaaag cccataacat gtggaatgac   4920
actcgcagac tttgaggaga aacattacaa aaagatattt ataagagaag aatcttcttg   4980
tcctgtgcct tttgatcctt cttgccattg taattatttt cgccacgatg ggcctttcag   5040
gaaagagtat aagggttacg tccaatacac agccagagga caactctttc tgaggaacct   5100
accaattcta gcgacgaaga tgaagctatt aatggtggga aacctcggcg cagaaattgg   5160
cgacctggaa catctaggat gggtactgag agggccagcc gtgtgcaaaa aaattaccaa   5220
ccatgagaag tgccacgtaa acatcatgga taagctaact gcattttttg gaatcatgcc   5280
tagaggcacg acccctaggg cacctgtgag gttccccaca gcactactaa aagtgagaag   5340
gggcctagag acgggatggg cttacacgca ccaaggaggg atcagctcgg tagaccatgt   5400
cacagccgga aaggatttac tagtgtgtga cagtatgggc aggaccaggg ttgtctgtca   5460
tagtaacaat aagatgactg atgagactga gtatggcatc aagaccgact cagggtgtcc   5520
cgaaggtgcg aggtgttacg tgctaaaccc agaagctgtt aacatttctg gcacaaaagg   5580
agctatggta cacctccaga aaacgggggg ggagttcaca tgtgtcactg cctcagggac   5640
```

-continued

```
cccggctttc ttcgatctga aaaatctaaa aggctggtcc gggctaccaa tttttgaagc   5700
atccagtggc agggtggttg gtagggtgaa agtcggcaag aatgaggatt ccaagcccac   5760
caaactaatg agcggaatcc agacagtgtc taagaaccag acagacctag cggacatcgt   5820
aaaaaaattg actagtatga acagaggaga gttcaaacag ataacattag ccactggggc   5880
aggaaaaact acggaactgc caaggtccgt catagaggag atagggaggc acaaaagggt   5940
cttagtcctg ataccattga gagcagcagc agagtcagtg tatcagtata tgagagtgaa   6000
gtacccaagt atatctttca atttgagaat aggagatatg aaggaaggtg acatggccac   6060
tggtatcacc tacgcctcat atgggtactt ttgtcagctt cctcagccca aactgagagc   6120
tgccatggta gagtactcat atatattctt agatgagtac cactgtgcta cacccgagca   6180
attagcaata attggaaaga tacacaggtt tgctgaaaat cttagagtgg tagcaatgac   6240
agcaacccca gctggaacgg tcacaacgac tggtcagaaa caccctatag aggagttcat   6300
agccccagag gtgatgaaag gtgaagatct aggtagtgaa tacttggata ttgcagggtt   6360
gaagataccg actgaagaga tgaaaggcaa catgctcgtg ttcgcgccaa ctaggaacat   6420
ggcagtagaa acagctaaga aattgaaggc taagggatac aactctggat actattacag   6480
tggggaaaac ccagagaact tgagggtggt aacctcgcaa tccccgtatg tggtagtagc   6540
caccaatgcc atagagtcag gtgtgacatt accagactta gacacagttg tagacactgg   6600
actaaagtgt gagaagaggg tgaggatttc ttcaaaaatg cccttcattg taacaggact   6660
taagagaatg gcagtcacaa tcggagagca agcccagcgc aggggtagag taggaagagt   6720
caagccaggt aggtactata ggagtcaaga aacagcttca gggtcaaaag attaccatta   6780
cgacctactg caagcccaga ggtacggaat agaagatgga attaatgtaa caaagtcatt   6840
cagggagatg aactatgatt ggagcottta cgaagaggac agcttgatga taactcaact   6900
cgaggtcctt aacaacctcc ttatatcaga agacctgcct gccgcagtga agaacatcat   6960
ggcccggacc gatcacccag aacccataca actggcctat aacagttatg aaaaccaaat   7020
tccagtgctg ttcccaaaga tcaaaaatgg tgaggtgaca gacagttatg agaattacac   7080
atatctcaat gcaagaaaat taggagagga cgtgccggca tatgtgtacg ccacagagga   7140
tgaggatcta gcagtggatc ttctgggtat ggattggccg gacccaggca accaacaggt   7200
ggtagagaca gggagggcat taaaacaagt aactggctta tccacagcag aaaacgccct   7260
cttgatagcc ctattcggct acgtcgggta ccagacactt tcaaaaaggc acatacccat   7320
gattactgac atctatacac ttgaagacca caggcttgag gacacaaccc acctccagtt   7380
tgccccaaac gctataagga ccgacggcaa ggactcagag ttgaaggaat tagctgtggg   7440
agaccttgat aaatatgtgg acgcactggt agactactcc aaacaaggga tgaaattcat   7500
caaagtccaa gctgaaaagg tcagagactc ccagtctacg aaggaaggct tgcaaaccat   7560
taaggagtat gtggataagt ttatacaatc actaacagag aataaggagg agatcatcag   7620
gtatggacta tggggagttc acacggcact ctacaaaagc ttggcagcga gactggggca   7680
tgaaacagct tttgcaactt tagtggtaaa atggttggct tttgggggcg aaacggtatc   7740
tgctcacatc aagcaagtag cagttgatct agtagtatat tatatcatca acaaaccatc   7800
ttttcctgga gatacagaga cccaacaaga ggggaggaag tttgtggcta gtctttttat   7860
atctgcacta gcaacataca catataaaac ctggaattac aacaatctgc aacgggttgt   7920
cgaacctgcc ttagcttacc tcccatatgc tacaagtgcc ttgaagttgt tcacacccac   7980
```

-continued

```
aagattagag agtgtggtca tactcagttc tacaatttac aagacatacc tctctataag   8040
gaagggtaag agtgacggct tgttaggtac aggcataagt gcagccatgg agatcttaaa   8100
ccaaaaccca atctcagtag gtatatctgt gatgctgggg gtaggtgcca tcgccgccca   8160
taatgcaata gaatctagtg aacagaaaag aactttgctg atgaaggtct ttgtaaaaaa   8220
cttcttagac caagcagcaa cagatgagct agtcaaagag aaccctgaaa aaataatcat   8280
ggctctattt gaagcagtcc agaccatagg aaaccccta agactcatct accatctgta   8340
cggggtgtac tataaggggt gggaagcaaa agaactcgca gagaaaactg ctggccgcaa   8400
cttattcaca ttgatcatgt ttgaggcctt tgagctttta ggtatggact cagaaggaaa   8460
gataagaaac ttgtcaggca actacatact ggacttaatc ttcaacttgc ataataaatt   8520
aaacaagggg ctcaaaaaac tagtccttgg gtgggctcct gcacctttga gctgtgattg   8580
gacaccaagt gatgagagaa taagcctacc tcataacaac tacttaaggg tagaaaccag   8640
gtgtccttgt ggctatgaga tgaaggcaat aaaaaatgtt gctggtaaat tgacaaaagt   8700
tgaagaaaag gggtccttcc tatgcaggaa tagattaggg agaggacctc caaacttcaa   8760
agtaacaaag ttctatgatg ataacttgat agaagtcaag ccagtagcta ggctagaagg   8820
ccaggtggac ctctattaca agggagtaac agctaagtta gactacaaca atgggaaagt   8880
actgttagct accaacaagt gggaggtgga ccacgctttc ctgaccagac tagtaaagaa   8940
gcacacaggg ataggtttta aaggtgcata tttgggtgac cgaccagacc atcaagatct   9000
tgtcgataga gattgtgcaa ctataacgaa gaactcagta cagttcctaa aaatgaagaa   9060
gggttgcgct ttcacatatg acctaacaat ctctaacctt gtcaggctta ttgaactagt   9120
ccataagaat aatttacaag aaagagagat ccctaccgtg acagtaacta cttggcttgc   9180
atattctttt gtcaatgaag acctggggac tatcaagcct gtattggggg agaaagtcat   9240
cccagaaccc cccgaggagt tgagtctcca acccaccgtg agactagtca ccactgaaac   9300
agcaataacc ataacagggg aggctgaagt gatgacgaca gggatcacac cagtggtaga   9360
gatgaaagaa gaacctcagc tggaccacca gtcaactacc ctaaaggtag ggttgaagga   9420
aggggaatat ccagggccag gagttaaccc taaccattta gcagaggtga tagatgagaa   9480
agatgacagg cctttttgtcc taatcatcgg taacaaaggt tctacctcga acagagcaag   9540
aacggccaag aatatacggc tgtacaaagg aaacaaccca agagagatca gggatctgat   9600
gagccaagga agaatattga cggttgctct aaaagagttg gacccggaat taaaagaatt   9660
agtagattac aaggggacct ttctcaatag ggaagcttta gaagccctaa gcttaggtaa   9720
gccaatcaag aggaaaacca caacagcaat gatcaggagg ttaatagagc cagaggttga   9780
ggaggaacta ccagattggt tccaagcgga agaacccta tttttggaag caaaaataca   9840
gaatgactta taccacctaa ttggcagtgt agatagtata aaaagcaaag caaaggaatt   9900
aggggccaca gataacacaa agatagtgaa ggaagttggg gctaggacct atacgatgaa   9960
attgagcagc tggagcacac aagttacaaa aaaacagatg agtctagccc ctctctttga  10020
agagctgtta ttaaagtgcc ctccatgtag taaaatttca aagggacata tggtgtcagc  10080
ataccaactg gctcaaggaa actgggaacc cctcgggtgt ggggtctata tgggaaccat  10140
accagctagg cgtctcaaga tccaccctta tgaggcttac cttaaactca aagagctggt  10200
ggaagttgaa tcttcgaggg ccactgcaaa agaatccatc ataagagaac ataacacctg  10260
gatcctgcgg aaggtgagac atgaagggaa cctaagaacc aaatcaatga tcaaccctgg  10320
gaaaatatca gatcagctat gcagagatgg acacaaaaga aacatatata ataagatcat  10380
```

-continued

```
aggctcaaca atggcctctg ctggtattag gctggagaaa ctgccagtag tccgagccca  10440
aactgacaca accagtttcc accaagccat aagagaaaaa attgataaaa cagaaaacaa  10500
gcagacccct gaattgcatg aagaactaat gaaggtcttc gactgcttaa agatcccaga  10560
gctgaaggaa tcgtatgatg aagtttcatg ggaacaatta gaagccggga taaaccgtaa  10620
gggtgcagca ggctatctag agagcaagaa catagggga gtcctagaca cagagaaaca  10680
catagtagag cagctgatca aggatctgag gaaggggaag aagattaggt actatgaaac  10740
agccatcccc aagaatgaga agagagacgt cagcgacgac tgggaagccg gagagttcgt  10800
tgatgaaaag aaaccaagag taatccagta cccggacgcc aaggtgagac tggccattac  10860
aaaagtgatg tacaaatggg taaagcaaaa accagtggtg atacccggct atgaaggtaa  10920
aacacctcta tttgacatat tcaacaaagt gaagaaggaa tgggattcat tccaggaccc  10980
cgtagcagtg agctttgaca ccaaagcgtg ggatacacaa gtcaccagta gagacctaat  11040
gttgataaag gatatccaga aatattattt caagagaagt atacacaaat ttttagatac  11100
aataacagaa cacatggtgg aggtacctgt cattacagca gacggtgaag tttacataag  11160
gaatggtcag aggggtagtg gccaacccga cacaagtgct ggtaatagta tgttgaatgt  11220
cctaaccatg atatatgctt tctgtaaaag tacaggcata ccttacaggg gattcagcag  11280
agtggcaaga atccatgtgt gtggtgatga tggctttttg ataacagaga gaggactggg  11340
actgaaattc tctgagaagg gtatgcagat attacatgag gccgggaagc cccagaaaat  11400
aactgaaggg gacaaaatga aagtggcata cagattcgag gacatagagt tttgttccca  11460
tactcccgtg ccagtcagat gggcagataa caccagtagt tacatggcag ggaggagcac  11520
agccactata ctagctaaga tggcaaccag gctggattcc agcggagaga ggggtagcac  11580
agcttatgag aaggccgtag ccttcagctt ccttttgatg tactcatgga atcccgtagt  11640
tagaaggatc tgcttactgg tgttgtcaca gtttccagaa atatccccat ccaaaaacac  11700
aatatactac taccaagggg atcccatagc tgcgtacaga gaagtgatag ggaaacagct  11760
gtgtgaactg aaaagaacag gatttgagaa gctggctggt ctgaatttga gtatgaccac  11820
tctaggcatc tggacaaaac atactagtaa aagactaatc caagcctgtg tagaaatagg  11880
taagagagaa ggtacctggt tagttaatgc tgacagactg attgcaggaa agactgggaa  11940
gttttacatc ccaagcactg gtgtcactct gttgggaaaa cactatgagg aaattaactt  12000
aaagcaaaag gcggcacaac cgccgataga gggggttgac agatataagt tgggccccat  12060
agttaatgtt atcttgagaa ggctgagggt gatgctgatg acagttgcca gcggaagctg  12120
gtgaatccgt ccggagcgtc gtgccctcac tcaaggtttt taattgtaaa tattgtaaat  12180
agacagctaa gatatttatt gtagttggat agtaatgcag tgatagtaaa taccccaatt  12240
taacactacc tccaatgcac taagcacttt agctgtgtga ggttaactcg acgtccacgg  12300
ttggactagg gaagacctct aacagcccc                                   12329
```

<210> SEQ ID NO 4
<211> LENGTH: 11837
<212> TYPE: DNA
<213> ORGANISM: Artificial
<220> FEATURE:
<223> OTHER INFORMATION: Mutated BVDV: XIKE-B-NdN

<400> SEQUENCE: 4

```
gtatacgaga ttagctaaag aactcgtata tggattggac gtcaacaaat ttttaattgg     60
```

-continued

```
caacgtaggg aaccttcccc tcagcgaagg ccgaaaagag gctagccatg cccttagtag    120
gactagcaaa agtaggggac tagcggtagc agtgagttcg ttggatggcc gaacccctga    180
gtacagggga gtcgtcaatg gttcgacact ccattagtcg aggagtctcg agatgccatg    240
tggacgaggg catgcccacg gcacatctta acccatgcgg gggttgcatg ggtgaaagcg    300
ctattcgtgg cgttatggac acagcctgat agggtgtagc agagacctgc tattccgcta    360
gtaaaaactc tgctgtacat ggcacatgga gttgttttcc gatgaaggga gcaagggtgc    420
tacaagtaag aagcagccta agccagatag gatagaaaaa ggtaagatga aaatagcccc    480
aaaagagaca gaaaaagatt gcaaaaccag accccccgac gcgactatag tagtagaagg    540
ggttaagtac caggtgaaga aaaaaggaaa ggtaagggga aaaaatactc aagatgggtt    600
atatcacaac aagaataagc cccctgaatc aagaaaaaaa ttggaaaagg cactgctggc    660
ttgggccatc ttagcagcgg tcctgcttca gctggtaaca ggagagaata tcacccagtg    720
gaacttgatg gacaacggca ccgagggaat acagcaagcg atgttcctaa gaggggtgaa    780
caggagtcta catggaattt ggccagagaa aatttgcacc ggagtaccaa ctcacttagc    840
aacagactat gagcttaaag agatagtggg gatgatggac gcgagtgaga agaccaacta    900
cacgtgttgc aggttgcaaa gacatgagtg gaataaaggt tggtgtaact ggtttcatat    960
agaaccgtgg atatggttga tgaacaaaac ccaaaacaac ctgacagaag ggcaaccgct   1020
tagggagtgt gctgtgactt gtaggtatga caaggaaaca gaattgaaca tcgtgacaca   1080
ggctagggac agacctacaa ctctgacagg ttgcaagaaa ggcaagaatt tctctttcgc   1140
aggtgttata ctggatgggc cctgtaactt taaagtatcg gttgaagatg tgctgttcaa   1200
ggagcacgat tgcggcaaca tgctgcaaga gaccgcgata cagctactcg atggggcaac   1260
caacaccatt gagggagcaa gggtagggac ggccaagttg acaacctggt tagggaagca   1320
attagggatc cttggtaaga agttggagaa caaaagcaaa gcatggtttg gtgcacatgc   1380
agcaagtcca tactgcggag tggagaggaa gatcggttac gtatggtata caaaaaactg   1440
cactccagct tgccttccaa gaaacactag aataataggc ccgggaaat ttgataccaa   1500
cgccgaagat ggaaaaatac tccatgagat ggggggcac ctctcagaat ttgtcctatt   1560
gtccttggtg gttctgtctg actttgcccc ggaaaccgcg agcgtcatct acttggttct   1620
acattttgcg atcccgcaaa gccacgttga tgtagacaca tgcgacaaga accagctgaa   1680
tttaacggta gcaaccacag tagcagaggt cataccaggg acagtgtgga acctagggaa   1740
gtatgtctgc ataagaccag actggtggcc atatgagacg acgacagtct tcgtcataga   1800
ggaagcaggg caagtaatca aattgatgct aagggccatc agagacttaa ctaggatatg   1860
gaatgctgcc actaccacag ctttcttaat ctttttagta aaagcactga ggggacaact   1920
aatccaaggg ctattgtggc tgatgctaat aacaggagca cagggcttcc ctgaatgcaa   1980
agagggcttc caatatgcca tatctaaaga caggaaaatg ggttattgg ggccagagag   2040
cttaactaca acatggcacc tccccaccaa aaaaatagtg gattccatgg tgcatgtatg   2100
gtgtgaagga aaagacttga aaatattaaa aatgtgcaca aaggaagaga ggtatctagt   2160
ggctgtgcac gagagagcct tatcaaccag tgccgagttt atgcagatca gtgatgggac   2220
aataggccca gacgtgatag atatgcctga tgactttgag tttggactct gcccttgtga   2280
ctcaaaacca gtgataaagg gcaaatttaa tgccagctta ctgaatggac cagctttcca   2340
gatggtatgc ccacaggggt ggactggtac aatagaatgc accctagcga accaagacac   2400
cttggacaca actgtcatta ggacatatag aagaactacc ccatttcagc ggagaaaatg   2460
```

-continued

```
gtgtacctat gaaaaaataa taggggaaga tatctatgaa tgcattctag gtggaaactg   2520
gacatgcata accggtgacc atagcaggtt gaaagacgga cctatcaaga agtgtaagtg   2580
gtgtggccat gacttcgtca actcagaggg gctaccacac tacccaatag gcaagtgcat   2640
gctcatcaac gagagtgggt acaggtatgt agatgacacc tcttgcgata ggggtggtgt   2700
agccatagtt ccatctggca ccgtaaagtg tagaataggt aacgtcacgg tgcaagttat   2760
cgctactaac aatgatctgg gacccatgcc ttgcagccca gctgaagtga tagcaagtga   2820
aggaccagtg gaaaagactg catgcacatt caactattca aggactctac ctaataagta   2880
ttatgagcca agggaccggt acttccaaca atacatgtta aaaggggagt ggcaatattg   2940
gttcgacctg gattctgtag accaccacaa agactacttc tcagagttca taatcatagc   3000
agtggtcgcc ttgttgggtg gtaagtacgt actgtggctc ttgataacat acacaatact   3060
gtctgagcag atggctatgg gtgctggagt gaatactgaa gagatagtca tgataggcaa   3120
tttgctgaca gacagtgata ttgaggttgt ggtttatttc cttcttctgt acttaatagt   3180
taaagaggaa ctggcgagga aatggattat actggtatac cacatccttg tagccaaccc   3240
tatgaaaaca attggggtcg tcttactaat gctaggggga gtggtgaagg ccagcagaat   3300
caatgctgat gaccaaagtg ctatggaccc atgctttctt ctcgtgacag gcgtagtggc   3360
tgttttgatg atcgctagaa gagaacctgc cacattacca ctgattgtag cattgctagc   3420
aataagaaca tcaggattcc tactgcccgc tagcattgat gtaactgtag cagtagtatt   3480
aattgtactt ttgttggcta gctacataac agactacttt agatataaaa agtggcttca   3540
actcttattt agtctgatag ctggtatctt tattataagg agcttaaaac atatcaacca   3600
gatggaggta ccagaaatat ctatgccaag ttggagacct ctagctctgg tccttttcta   3660
tataacatct acagcaataa ccactaattg ggacattgac ttagcaggct tcctgctgca   3720
atgggcgcca gcagtgatca tgatggctac catgtgggca gactttttga ctctgatcat   3780
agtcctgccc agttacgagt tatctaagct ttacttccta aagaacgtca ggacagacgt   3840
ggaaaagaac tggctcggca aagtgaaata cagacagatc agttcagttt atgacatctg   3900
tgacagtgag gaagcagtgt acctatttcc atcaaggcat aagagtggaa gcaggccaga   3960
tttcatatta cctttttga aagccgtgtt aataagctgc atcagcagcc aatggcaagt   4020
ggtttacatt tcttacctaa tactggaaat tacatactat atgcacagga aaatcataga   4080
tgaggtgtca ggaggagcaa attttctatc aagactcata gcagccatca tagaattaaa   4140
ttgggccata gatgatgagg aatgtaaagg actgaagaaa ctgtatctct tgtcagggag   4200
agcgaagaat ttgatagtta aacataaggt aagaaatgaa gccgtccaca gatggtttgg   4260
tgaggaggaa atatacgggg cacccaaggt gatcactatc ataaaagcta gtaccctaag   4320
taaaaacagg cactgcataa tctgcacgat ctgtgaaggg aaagaatgga atggagccaa   4380
ctgcccaaag tgtggaagac aaggaaagcc cataacatgt ggaatgacac tcgcagactt   4440
tgaggagaaa cattacaaaa agatatttat aagagaagaa tcttcttgtc ctgtgccttt   4500
tgatccttct tgccattgta attattttcg ccacgatggg cctttcagga aagagtataa   4560
gggttacgtc caatacacag ccagaggaca actctttctg aggaacctac caattctagc   4620
gacgaagatg aagctattaa tggtgggaaa cctcggcgca gaaattggcg acctggaaca   4680
tctaggatgg gtactgagag ggccagccgt gtgcaaaaaa attaccaacc atgagaagtg   4740
ccacgtaaac atcatggata agctaactgc atttttgga atcatgccta gaggcacgac   4800
```

-continued

```
ccctagggca cctgtgaggt tccccacagc actactaaaa gtgagaaggg ggctagagac   4860

gggatgggct tacacgcacc aaggagggat cagctcggta gaccatgtca cagccggaaa   4920

ggatttacta gtgtgtgaca gtatgggcag gaccagggtt gtctgtcata gtaacaataa   4980

gatgactgat gagactgagt atggcatcaa gaccgactca gggtgtcccg aaggtgcgag   5040

gtgttacgtg ctaaacccag aagctgttaa catttctggc acaaaaggag ctatggtaca   5100

cctccagaaa acgggggggg agttcacatg tgtcactgcc tcagggaccc cggctttctt   5160

cgatctgaaa aatctaaaag gctggtccgg gctaccaatt tttgaagcat ccagtggcag   5220

ggtggttggt agggtgaaag tcggcaagaa tgaggattcc aagcccacca aactaatgag   5280

cggaatccag acagtgtcta agaaccagac agacctagcg gacatcgtaa aaaaattgac   5340

tagtatgaac agaggagagt tcaaacagat aacattagcc actggggcag gaaaaactac   5400

ggaactgcca aggtccgtca tagaggagat agggaggcac aaaagggtct tagtcctgat   5460

accattgaga gcagcagcag agtcagtgta tcagtatatg agagtgaagt acccaagtat   5520

atctttcaat ttgagaatag gagatatgaa ggaaggtgac atggccactg gtatcaccta   5580

cgcctcatat gggtactttt gtcagcttcc tcagcccaaa ctgagagctg ccatggtaga   5640

gtactcatat atattcttag atgagtacca ctgtgctaca cccgagcaat tagcaataat   5700

tggaaagata cacaggtttg ctgaaaatct tagagtggta gcaatgacag caaccccagc   5760

tggaacggtc acaacgactg gtcagaaaca ccctatagag gagttcatag ccccagaggt   5820

gatgaaaggt gaagatctag gtagtgaata cttggatatt gcagggttga agataccgac   5880

tgaagagatg aaaggcaaca tgctcgtgtt cgcgccaact aggaacatgg cagtagaaac   5940

agctaagaaa ttgaaggcta agggatacaa ctctggatac tattacagtg gggaaaaccc   6000

agagaacttg agggtggtaa cctcgcaatc cccgtatgtg gtagtagcca ccaatgccat   6060

agagtcaggt gtgacattac cagacttaga cacagttgta gacactggac taaagtgtga   6120

gaagagggtg aggatttctt caaaaatgcc cttcattgta acaggactta agagaatggc   6180

agtcacaatc ggagagcaag cccagcgcag ggtagagta ggaagagtca agccaggtag   6240

gtactatagg agtcaagaaa cagcttcagg gtcaaaagat taccattacg acctactgca   6300

agcccagagg tacggaatag aagatggaat taatgtaaca aagtcattca gggagatgaa   6360

ctatgattgg agcctttacg aagaggacag cttgatgata actcaactcg aggtccttaa   6420

caacctcctt atatcagaag acctgcctgc cgcagtgaag aacatcatgg cccggaccga   6480

tcacccagaa cccatacaac tggcctataa cagttatgaa aaccaaattc cagtgctgtt   6540

cccaaagatc aaaaatggtg aggtgacaga cagttatgag aattacacat atctcaatgc   6600

aagaaaatta ggagaggacg tgccggcata tgtgtacgcc acagaggatg aggatctagc   6660

agtggatctt ctgggtatgg attggccgga cccaggcaac caacaggtgg tagagacagg   6720

gagggcatta aaacaagtaa ctggcttatc cacagcagaa aacgccctct tgatagccct   6780

attcggctac gtcgggtacc agacactttc aaaaaggcac atacccatga ttactgacat   6840

ctatacactt gaagaccaca ggcttgagga cacaacccac ctccagtttg ccccaaacgc   6900

tataaggacc gacggcaagg actcagagtt gaaggaatta gctgtgggag accttgataa   6960

atatgtggac gcactggtag actactccaa acaagggatg aaattcatca aagtccaagc   7020

tgaaaaggtc agagactccc agtctacgaa ggaaggcttg caaaccatta aggagtatgt   7080

ggataagttt atacaatcac taacagagaa taaggaggag atcatcaggt atggactatg   7140

gggagttcac acggcactct acaaaagctt ggcagcgaga ctggggcatg aaacagcttt   7200
```

-continued

```
tgcaacttta gtggtaaaat ggttggcttt tgggggcgaa acggtatctg ctcacatcaa   7260
gcaagtagca gttgatctag tagtatatta tatcatcaac aaaccatctt ttcctggaga   7320
tacagagacc caacaagagg ggaggaagtt tgtggctagt ctttttatat ctgcactagc   7380
aacatacaca tataaaacct ggaattacaa caatctgcaa cgggttgtcg aacctgcctt   7440
agcttacctc ccatatgcta caagtgcctt gaagttgttc acacccacaa gattagagag   7500
tgtggtcata ctcagttcta caatttacaa gacatacctc tctataagga agggtaagag   7560
tgacggcttg ttaggtacag gcataagtgc agccatggag atcttaaacc aaaacccaat   7620
ctcagtaggt atatctgtga tgctgggggt aggtgccatc gccgcccata atgcaataga   7680
atctagtgaa cagaaaagaa ctttgctgat gaaggtcttt gtaaaaaact tcttagacca   7740
agcagcaaca gatgagctag tcaaagagaa ccctgaaaaa ataatcatgg ctctatttga   7800
agcagtccag accataggaa acccccctaag actcatctac catctgtacg ggtgtacta   7860
taaggggtgg gaagcaaaag aactcgcaga gaaaactgct ggccgcaact tattcacatt   7920
gatcatgttt gaggcctttg agcttttagg tatggactca gaaggaaaga taagaaactt   7980
gtcaggcaac tacatactgg acttaatctt caacttgcat aataaattaa acaaggggct   8040
caaaaaacta gtccttgggt gggctcctgc acctttgagc tgtgattgga caccaagtga   8100
tgagagaata agcctacctc ataacaacta cttaagggta gaaaccaggt gtccttgtgg   8160
ctatgagatg aaggcaataa aaaatgttgc tggtaaattg acaaaagttg aagaaaaggg   8220
gtccttccta tgcaggaata gattagggag aggacctcca aacttcaaag taacaaagtt   8280
ctatgatgat aacttgatag aagtcaagcc agtagctagg ctagaaggcc aggtggacct   8340
ctattacaag ggagtaacag ctaagttaga ctacaacaat gggaaagtac tgttagctac   8400
caacaagtgg gaggtggacc acgctttcct gaccagacta gtaaagaagc acacagggat   8460
aggttttaaa ggtgcatatt tgggtgaccg accagaccat caagatcttg tcgatagaga   8520
ttgtgcaact ataacgaaga actcagtaca gttcctaaaa atgaagaagg gttgcgcttt   8580
cacatatgac ctaacaatct ctaaccttgt caggcttatt gaactagtcc ataagaataa   8640
tttacaagaa agagagatcc ctaccgtgac agtaactact tggcttgcat attcttttgt   8700
caatgaagac ctggggacta tcaagcctgt attgggggag aaagtcatcc cagaaccccc   8760
cgaggagttg agtctccaac ccaccgtgag actagtcacc actgaaacag caataaccat   8820
aacaggggag gctgaagtga tgacgacagg gatcacacca gtggtagaga tgaaagaaga   8880
acctcagctg gaccaccagt caactaccct aaaggtaggg ttgaaggaag gggaatatcc   8940
agggccagga gttaacccta accatttagc agaggtgata gatgagaaag atgacaggcc   9000
ttttgtccta atcatcggta acaaaggttc tacctcgaac agagcaagaa cggccaagaa   9060
tatacggctg tacaaaggaa acaacccaag agagatcagg gatctgatga gccaaggaag   9120
aatattgacg gttgctctaa aagagttgga cccggaatta aaagaattag tagattacaa   9180
ggggaccttt ctcaataggg aagctttaga agccctaagc ttaggtaagc caatcaagag   9240
gaaaaccaca acagcaatga tcaggaggtt aatagagcca gaggttgagg aggaactacc   9300
agattggttc caagcggaag aacccctatt tttggaagca aaaatacaga atgacttata   9360
ccacctaatt ggcagtgtag atagtataaa aagcaaagca aaggaattag gggccacaga   9420
taacacaaag atagtgaagg aagttggggc taggacctat acgatgaaat tgagcagctg   9480
gagcacacaa gttacaaaaa aacagatgag tctagcccct ctctttgaag agctgttatt   9540
```

-continued

```
aaagtgccct ccatgtagta aaatttcaaa gggacatatg gtgtcagcat accaactggc   9600
tcaaggaaac tgggaacccc tcgggtgtgg ggtctatatg ggaaccatac cagctaggcg   9660
tctcaagatc cacccttatg aggcttacct taaactcaaa gagctggtgg aagttgaatc   9720
ttcgagggcc actgcaaaag aatccatcat aagagaacat aacacctgga tcctgcggaa   9780
ggtgagacat gaagggaacc taagaaccaa atcaatgatc aaccctggga aaatatcaga   9840
tcagctatgc agagatggac acaaaagaaa catatataat aagatcatag gctcaacaat   9900
ggcctctgct ggtattaggc tggagaaact gccagtagtc cgagcccaaa ctgacacaac   9960
cagtttccac caagccataa gagaaaaaat tgataaaaca gaaaacaagc agacccctga  10020
attgcatgaa gaactaatga aggtcttcga ctgcttaaag atcccagagc tgaaggaatc  10080
gtatgatgaa gtttcatggg aacaattaga agccgggata aaccgtaagg gtgcagcagg  10140
ctatctagag agcaagaaca taggggaagt cctagacaca gagaaacaca tagtagagca  10200
gctgatcaag gatctgagga aggggaagaa gattaggtac tatgaaacag ccatccccaa  10260
gaatgagaag agagacgtca gcgacgactg ggaagccgga gagttcgttg atgaaaagaa  10320
accaagagta atccagtacc cggacgccaa ggtgagactg gccattacaa aagtgatgta  10380
caaatgggta aagcaaaaac cagtggtgat acccggctat gaaggtaaaa cacctctatt  10440
tgacatattc aacaaagtga agaaggaatg ggattcattc caggaccccg tagcagtgag  10500
ctttgacacc aaagcgtggg atacacaagt caccagtaga gacctaatgt tgataaagga  10560
tatccagaaa tattatttca agagaagtat acacaaattt ttagatacaa taacagaaca  10620
catggtggag gtacctgtca ttacagcaga cggtgaagtt tacataagga atggtcagag  10680
gggtagtggc caacccgaca caagtgctgg taatagtatg ttgaatgtcc taaccatgat  10740
atatgctttc tgtaaaagta caggcatacc ttacagggga ttcagcagag tggcaagaat  10800
ccatgtgtgt ggtgatgatg gctttttgat aacagagaga ggactgggac tgaaattctc  10860
tgagaagggt atgcagatat tacatgaggc cgggaagccc cagaaaataa ctgaagggga  10920
caaaatgaaa gtggcataca gattcgagga catagagttt tgttcccata ctcccgtgcc  10980
agtcagatgg gcagataaca ccagtagtta catggcaggg aggagcacag ccactatact  11040
agctaagatg gcaaccaggc tggattccag cggagagagg ggtagcacag cttatgagaa  11100
ggccgtagcc ttcagcttcc ttttgatgta ctcatggaat cccgtagtta gaaggatctg  11160
cttactggtg ttgtcacagt ttccagaaat atccccatcc aaaaacacaa tatactacta  11220
ccaaggggat cccatagctg cgtacagaga agtgataggg aaacagctgt gtgaactgaa  11280
aagaacagga tttgagaagc tggctggtct gaatttgagt atgaccactc taggcatctg  11340
gacaaaacat actagtaaaa gactaatcca agcctgtgta gaaataggta agagagaagg  11400
tacctggtta gttaatgctg acagactgat tgcaggaaag actgggaagt tttacatccc  11460
aagcactggt gtcactctgt tgggaaaaca ctatgaggaa attaacttaa agcaaaaggc  11520
ggcacaaccg ccgatagagg gggttgacag atataagttg ggccccatag ttaatgttat  11580
cttgagaagg ctgagggtga tgctgatgac agttgccagc ggaagctggt gaatccgtcc  11640
ggagcgtcgt gccctcactc aaggttttta attgtaaata ttgtaaatag acagctaaga  11700
tatttattgt agttggatag taatgcagtg atagtaaata ccccaattta acactacctc  11760
caatgcacta agcactttag ctgtgtgagg ttaactcgac gtccacggtt ggactaggga  11820
agacctctaa cagcccc                                                 11837
```

-continued

<210> SEQ ID NO 5
<211> LENGTH: 3913
<212> TYPE: PRT
<213> ORGANISM: Wildtyp BVDV: XIKE-A

<400> SEQUENCE: 5

```
Met Glu Leu Phe Ser Asn Glu Leu Leu Tyr Lys Thr Tyr Lys Gln Lys
1               5                   10                  15

Pro Ala Gly Val Val Glu Pro Val Tyr Asp Val Asn Gly Arg Pro Leu
            20                  25                  30

Phe Gly Glu Ser Ser Asp Leu His Pro Gln Ser Thr Leu Lys Leu Pro
        35                  40                  45

His Gln Arg Gly Ser Ala Asn Ile Leu Thr Asn Ala Arg Ser Leu Pro
    50                  55                  60

Arg Lys Gly Asp Cys Arg Arg Gly Asn Val Tyr Gly Pro Val Ser Gly
65                  70                  75                  80

Ile Tyr Ile Lys Pro Gly Pro Ile Tyr Tyr Gln Asp Tyr Val Gly Pro
                85                  90                  95

Val Tyr His Arg Ala Pro Leu Glu Leu Cys Arg Glu Ala Ser Met Cys
            100                 105                 110

Glu Thr Thr Arg Arg Val Gly Arg Val Thr Gly Ser Asp Gly Lys Leu
        115                 120                 125

Tyr His Ile Tyr Ile Cys Ile Asp Gly Cys Ile Leu Leu Lys Arg Ala
    130                 135                 140

Thr Arg Asn Gln Pro Glu Val Leu Lys Trp Val Tyr Asn Arg Leu Asn
145                 150                 155                 160

Cys Pro Leu Trp Val Thr Ser Cys Ser Asp Glu Gly Ser Lys Gly Ala
                165                 170                 175

Thr Ser Lys Lys Gln Pro Lys Pro Asp Arg Ile Glu Lys Gly Lys Met
            180                 185                 190

Lys Ile Ala Pro Lys Glu Thr Glu Lys Asp Cys Lys Thr Arg Pro Pro
        195                 200                 205

Asp Ala Thr Ile Val Val Glu Gly Val Lys Tyr Gln Val Lys Lys Lys
    210                 215                 220

Gly Lys Val Arg Gly Lys Asn Thr Gln Asp Gly Leu Tyr His Asn Lys
225                 230                 235                 240

Asn Lys Pro Pro Glu Ser Arg Lys Lys Leu Glu Lys Ala Leu Leu Ala
                245                 250                 255

Trp Ala Ile Leu Ala Ala Val Leu Leu Gln Leu Val Thr Gly Glu Asn
            260                 265                 270

Ile Thr Gln Trp Asn Leu Met Asp Asn Gly Thr Glu Gly Ile Gln Gln
        275                 280                 285

Ala Met Phe Leu Arg Gly Val Asn Arg Ser Leu His Gly Ile Trp Pro
    290                 295                 300

Glu Lys Ile Cys Thr Gly Val Pro Thr His Leu Ala Thr Asp Tyr Glu
305                 310                 315                 320

Leu Lys Glu Ile Val Gly Met Met Asp Ala Ser Glu Lys Thr Asn Tyr
                325                 330                 335

Thr Cys Cys Arg Leu Gln Arg His Glu Trp Asn Lys His Gly Trp Cys
            340                 345                 350

Asn Trp Phe His Ile Glu Pro Trp Ile Trp Leu Met Asn Lys Thr Gln
        355                 360                 365

Asn Asn Leu Thr Glu Gly Gln Pro Leu Arg Glu Cys Ala Val Thr Cys
    370                 375                 380
```

-continued

```
Arg Tyr Asp Lys Glu Thr Glu Leu Asn Ile Val Thr Gln Ala Arg Asp
385                 390                 395                 400

Arg Pro Thr Thr Leu Thr Gly Cys Lys Lys Gly Lys Asn Phe Ser Phe
                405                 410                 415

Ala Gly Val Ile Leu Asp Gly Pro Cys Asn Phe Lys Val Ser Val Glu
            420                 425                 430

Asp Val Leu Phe Lys Glu His Asp Cys Gly Asn Met Leu Gln Glu Thr
        435                 440                 445

Ala Ile Gln Leu Leu Asp Gly Ala Thr Asn Thr Ile Glu Gly Ala Arg
    450                 455                 460

Val Gly Thr Ala Lys Leu Thr Thr Trp Leu Gly Lys Gln Leu Gly Ile
465                 470                 475                 480

Leu Gly Lys Lys Leu Glu Asn Lys Ser Lys Ala Trp Phe Gly Ala His
                485                 490                 495

Ala Ala Ser Pro Tyr Cys Gly Val Glu Arg Lys Ile Gly Tyr Val Trp
            500                 505                 510

Tyr Thr Lys Asn Cys Thr Pro Ala Cys Leu Pro Arg Asn Thr Arg Ile
        515                 520                 525

Ile Gly Pro Gly Lys Phe Asp Thr Asn Ala Glu Asp Gly Lys Ile Leu
    530                 535                 540

His Glu Met Gly Gly His Leu Ser Glu Phe Val Leu Leu Ser Leu Val
545                 550                 555                 560

Val Leu Ser Asp Phe Ala Pro Glu Thr Ala Ser Val Ile Tyr Leu Val
                565                 570                 575

Leu His Phe Ala Ile Pro Gln Ser His Val Asp Val Asp Thr Cys Asp
            580                 585                 590

Lys Asn Gln Leu Asn Leu Thr Val Ala Thr Thr Val Ala Glu Val Ile
        595                 600                 605

Pro Gly Thr Val Trp Asn Leu Gly Lys Tyr Val Cys Ile Arg Pro Asp
    610                 615                 620

Trp Trp Pro Tyr Glu Thr Thr Thr Val Phe Val Ile Glu Glu Ala Gly
625                 630                 635                 640

Gln Val Ile Lys Leu Met Leu Arg Ala Ile Arg Asp Leu Thr Arg Ile
                645                 650                 655

Trp Asn Ala Ala Thr Thr Thr Ala Phe Leu Ile Phe Leu Val Lys Ala
            660                 665                 670

Leu Arg Gly Gln Leu Ile Gln Gly Leu Leu Trp Leu Met Leu Ile Thr
        675                 680                 685

Gly Ala Gln Gly Phe Pro Glu Cys Lys Glu Gly Phe Gln Tyr Ala Ile
    690                 695                 700

Ser Lys Asp Arg Lys Met Gly Leu Leu Gly Pro Glu Ser Leu Thr Thr
705                 710                 715                 720

Thr Trp His Leu Pro Thr Lys Lys Ile Val Asp Ser Met Val His Val
                725                 730                 735

Trp Cys Glu Gly Lys Asp Leu Lys Ile Leu Lys Met Cys Thr Lys Glu
            740                 745                 750

Glu Arg Tyr Leu Val Ala Val His Glu Arg Ala Leu Ser Thr Ser Ala
        755                 760                 765

Glu Phe Met Gln Ile Ser Asp Gly Thr Ile Gly Pro Asp Val Ile Asp
    770                 775                 780

Met Pro Asp Asp Phe Glu Phe Gly Leu Cys Pro Cys Asp Ser Lys Pro
785                 790                 795                 800

Val Ile Lys Gly Lys Phe Asn Ala Ser Leu Leu Asn Gly Pro Ala Phe
```

-continued

```
                805                 810                 815

Gln Met Val Cys Pro Gln Gly Trp Thr Gly Thr Ile Glu Cys Thr Leu
            820                 825                 830

Ala Asn Gln Asp Thr Leu Asp Thr Thr Val Ile Arg Thr Tyr Arg Arg
        835                 840                 845

Thr Thr Pro Phe Gln Arg Arg Lys Trp Cys Thr Tyr Glu Lys Ile Ile
    850                 855                 860

Gly Glu Asp Ile Tyr Glu Cys Ile Leu Gly Gly Asn Trp Thr Cys Ile
865                 870                 875                 880

Thr Gly Asp His Ser Arg Leu Lys Asp Gly Pro Ile Lys Lys Cys Lys
                885                 890                 895

Trp Cys Gly His Asp Phe Val Asn Ser Glu Gly Leu Pro His Tyr Pro
            900                 905                 910

Ile Gly Lys Cys Met Leu Ile Asn Glu Ser Gly Tyr Arg Tyr Val Asp
        915                 920                 925

Asp Thr Ser Cys Asp Arg Gly Gly Val Ala Ile Val Pro Ser Gly Thr
    930                 935                 940

Val Lys Cys Arg Ile Gly Asn Val Thr Val Gln Val Ile Ala Thr Asn
945                 950                 955                 960

Asn Asp Leu Gly Pro Met Pro Cys Ser Pro Ala Glu Val Ile Ala Ser
                965                 970                 975

Glu Gly Pro Val Glu Lys Thr Ala Cys Thr Phe Asn Tyr Ser Arg Thr
            980                 985                 990

Leu Pro Asn Lys Tyr Tyr Glu Pro  Arg Asp Arg Tyr Phe  Gln Gln Tyr
        995                 1000                1005

Met Leu  Lys Gly Glu Trp Gln  Tyr Trp Phe Asp Leu  Asp Ser Val
    1010                1015                1020

Asp His  His Lys Asp Tyr Phe  Ser Glu Phe Ile Ile  Ile Ala Val
    1025                1030                1035

Val Ala  Leu Leu Gly Gly Lys  Tyr Val Leu Trp Leu  Leu Ile Thr
    1040                1045                1050

Tyr Thr  Ile Leu Ser Glu Gln  Met Ala Met Gly Ala  Gly Val Asn
    1055                1060                1065

Thr Glu  Glu Ile Val Met Ile  Gly Asn Leu Leu Thr  Asp Ser Asp
    1070                1075                1080

Ile Glu  Val Val Val Tyr Phe  Leu Leu Leu Tyr Leu  Ile Val Lys
    1085                1090                1095

Glu Glu  Leu Ala Arg Lys Trp  Ile Ile Leu Val Tyr  His Ile Leu
    1100                1105                1110

Val Ala  Asn Pro Met Lys Thr  Ile Gly Val Val Leu  Leu Met Leu
    1115                1120                1125

Gly Gly  Val Val Lys Ala Ser  Arg Ile Asn Ala Asp  Asp Gln Ser
    1130                1135                1140

Ala Met  Asp Pro Cys Phe Leu  Leu Val Thr Gly Val  Val Ala Val
    1145                1150                1155

Leu Met  Ile Ala Arg Arg Glu  Pro Ala Thr Leu Pro  Leu Ile Val
    1160                1165                1170

Ala Leu  Leu Ala Ile Arg Thr  Ser Gly Phe Leu Leu  Pro Ala Ser
    1175                1180                1185

Ile Asp  Val Thr Val Ala Val  Val Leu Ile Val Leu  Leu Leu Ala
    1190                1195                1200

Ser Tyr  Ile Thr Asp Tyr Phe  Arg Tyr Lys Lys Trp  Leu Gln Leu
    1205                1210                1215
```

-continued

```
Leu Phe  Ser Leu Ile Ala Gly  Ile Phe Ile Ile Arg  Ser Leu Lys
    1220                 1225                 1230

His Ile  Asn Gln Met Glu Val  Pro Glu Ile Ser Met  Pro Ser Trp
    1235                 1240                 1245

Arg Pro  Leu Ala Leu Val Leu  Phe Tyr Ile Thr Ser  Thr Ala Ile
    1250                 1255                 1260

Thr Thr  Asn Trp Asp Ile Asp  Leu Ala Gly Phe Leu  Leu Gln Trp
    1265                 1270                 1275

Ala Pro  Ala Val Ile Met Met  Ala Thr Met Trp Ala  Asp Phe Leu
    1280                 1285                 1290

Thr Leu  Ile Ile Val Leu Pro  Ser Tyr Glu Leu Ser  Lys Leu Tyr
    1295                 1300                 1305

Phe Leu  Lys Asn Val Arg Thr  Asp Val Glu Lys Asn  Trp Leu Gly
    1310                 1315                 1320

Lys Val  Lys Tyr Arg Gln Ile  Ser Ser Val Tyr Asp  Ile Cys Asp
    1325                 1330                 1335

Ser Glu  Glu Ala Val Tyr Leu  Phe Pro Ser Arg His  Lys Ser Gly
    1340                 1345                 1350

Ser Arg  Pro Asp Phe Ile Leu  Pro Phe Leu Lys Ala  Val Leu Ile
    1355                 1360                 1365

Ser Cys  Ile Ser Ser Gln Trp  Gln Val Val Tyr Ile  Ser Tyr Leu
    1370                 1375                 1380

Ile Leu  Glu Ile Thr Tyr Tyr  Met His Arg Lys Ile  Ile Asp Glu
    1385                 1390                 1395

Val Ser  Gly Gly Ala Asn Phe  Leu Ser Arg Leu Ile  Ala Ala Ile
    1400                 1405                 1410

Ile Glu  Leu Asn Trp Ala Ile  Asp Asp Glu Glu Cys  Lys Gly Leu
    1415                 1420                 1425

Lys Lys  Leu Tyr Leu Leu Ser  Gly Arg Ala Lys Asn  Leu Ile Val
    1430                 1435                 1440

Lys His  Lys Val Arg Asn Glu  Ala Val His Arg Trp  Phe Gly Glu
    1445                 1450                 1455

Glu Glu  Ile Tyr Gly Ala Pro  Lys Val Ile Thr Ile  Ile Lys Ala
    1460                 1465                 1470

Ser Thr  Leu Ser Lys Asn Arg  His Cys Ile Ile Cys  Thr Ile Cys
    1475                 1480                 1485

Glu Gly  Lys Glu Trp Asn Gly  Ala Asn Cys Pro Lys  Cys Gly Arg
    1490                 1495                 1500

Gln Gly  Lys Pro Ile Thr Cys  Gly Met Thr Leu Ala  Asp Phe Glu
    1505                 1510                 1515

Glu Lys  His Tyr Lys Lys Ile  Phe Ile Arg Glu Glu  Ser Ser Cys
    1520                 1525                 1530

Pro Val  Pro Phe Asp Pro Ser  Cys His Cys Asn Tyr  Phe Arg His
    1535                 1540                 1545

Asp Gly  Pro Phe Arg Lys Glu  Tyr Lys Gly Tyr Val  Gln Tyr Thr
    1550                 1555                 1560

Ala Arg  Gly Gln Leu Phe Leu  Arg Asn Leu Pro Ile  Leu Ala Thr
    1565                 1570                 1575

Lys Met  Lys Leu Leu Met Val  Gly Asn Leu Gly Ala  Glu Ile Gly
    1580                 1585                 1590

Asp Leu  Glu His Leu Gly Trp  Val Leu Arg Gly Pro  Ala Val Cys
    1595                 1600                 1605
```

-continued

```
Lys Lys  Ile Thr Asn His Glu  Lys Cys His Val Asn  Ile Met Asp
    1610                 1615                 1620

Lys Leu  Thr Ala Phe Phe Gly  Ile Met Pro Arg Gly  Thr Thr Pro
    1625                 1630                 1635

Arg Ala  Pro Val Arg Phe Pro  Thr Ala Leu Leu Lys  Val Arg Arg
    1640                 1645                 1650

Gly Leu  Glu Thr Gly Trp Ala  Tyr Thr His Gln Gly  Gly Ile Ser
    1655                 1660                 1665

Ser Val  Asp His Val Thr Ala  Gly Lys Asp Leu Leu  Val Cys Asp
    1670                 1675                 1680

Ser Met  Gly Arg Thr Arg Val  Val Cys His Ser Asn  Asn Lys Met
    1685                 1690                 1695

Thr Asp  Glu Thr Glu Tyr Gly  Ile Lys Thr Asp Ser  Gly Cys Pro
    1700                 1705                 1710

Glu Gly  Ala Arg Cys Tyr Val  Leu Asn Pro Glu Ala  Val Asn Ile
    1715                 1720                 1725

Ser Gly  Thr Lys Gly Ala Met  Val His Leu Gln Lys  Thr Gly Gly
    1730                 1735                 1740

Glu Phe  Thr Cys Val Thr Ala  Ser Gly Thr Pro Ala  Phe Phe Asp
    1745                 1750                 1755

Leu Lys  Asn Leu Lys Gly Trp  Ser Gly Leu Pro Ile  Phe Glu Ala
    1760                 1765                 1770

Ser Ser  Gly Arg Val Val Gly  Arg Val Lys Val Gly  Lys Asn Glu
    1775                 1780                 1785

Asp Ser  Lys Pro Thr Lys Leu  Met Ser Gly Ile Gln  Thr Val Ser
    1790                 1795                 1800

Lys Asn  Gln Thr Asp Leu Ala  Asp Ile Val Lys Lys  Leu Thr Ser
    1805                 1810                 1815

Met Asn  Arg Gly Glu Phe Lys  Gln Ile Thr Leu Ala  Thr Gly Ala
    1820                 1825                 1830

Gly Lys  Thr Thr Glu Leu Pro  Arg Ser Val Ile Glu  Glu Ile Gly
    1835                 1840                 1845

Arg His  Lys Arg Val Leu Val  Leu Ile Pro Leu Arg  Ala Ala Ala
    1850                 1855                 1860

Glu Ser  Val Tyr Gln Tyr Met  Arg Val Lys Tyr Pro  Ser Ile Ser
    1865                 1870                 1875

Phe Asn  Leu Arg Ile Gly Asp  Met Lys Glu Gly Asp  Met Ala Thr
    1880                 1885                 1890

Gly Ile  Thr Tyr Ala Ser Tyr  Gly Tyr Phe Cys Gln  Leu Pro Gln
    1895                 1900                 1905

Pro Lys  Leu Arg Ala Ala Met  Val Glu Tyr Ser Tyr  Ile Phe Leu
    1910                 1915                 1920

Asp Glu  Tyr His Cys Ala Thr  Pro Glu Gln Leu Ala  Ile Ile Gly
    1925                 1930                 1935

Lys Ile  His Arg Phe Ala Glu  Asn Leu Arg Val Val  Ala Met Thr
    1940                 1945                 1950

Ala Thr  Pro Ala Gly Thr Val  Thr Thr Thr Gly Gln  Lys His Pro
    1955                 1960                 1965

Ile Glu  Glu Phe Ile Ala Pro  Glu Val Met Lys Gly  Glu Asp Leu
    1970                 1975                 1980

Gly Ser  Glu Tyr Leu Asp Ile  Ala Gly Leu Lys Ile  Pro Thr Glu
    1985                 1990                 1995

Glu Met  Lys Gly Asn Met Leu  Val Phe Ala Pro Thr  Arg Asn Met
```

-continued

```
    2000                2005                2010

Ala Val  Glu Thr Ala Lys Lys  Leu Lys Ala Lys Gly  Tyr Asn Ser
    2015                2020                2025

Gly Tyr  Tyr Tyr Ser Gly Glu  Asn Pro Glu Asn Leu  Arg Val Val
    2030                2035                2040

Thr Ser  Gln Ser Pro Tyr Val  Val Val Ala Thr Asn  Ala Ile Glu
    2045                2050                2055

Ser Gly  Val Thr Leu Pro Asp  Leu Asp Thr Val Val  Asp Thr Gly
    2060                2065                2070

Leu Lys  Cys Glu Lys Arg Val  Arg Ile Ser Ser Lys  Met Pro Phe
    2075                2080                2085

Ile Val  Thr Gly Leu Lys Arg  Met Ala Val Thr Ile  Gly Glu Gln
    2090                2095                2100

Ala Gln  Arg Arg Gly Arg Val  Gly Arg Val Lys Pro  Gly Arg Tyr
    2105                2110                2115

Tyr Arg  Ser Gln Glu Thr Ala  Ser Gly Ser Lys Asp  Tyr His Tyr
    2120                2125                2130

Asp Leu  Leu Gln Ala Gln Arg  Tyr Gly Ile Glu Asp  Gly Ile Asn
    2135                2140                2145

Val Thr  Lys Ser Phe Arg Glu  Met Asn Tyr Asp Trp  Ser Leu Tyr
    2150                2155                2160

Glu Glu  Asp Ser Leu Met Ile  Thr Gln Leu Glu Val  Leu Asn Asn
    2165                2170                2175

Leu Leu  Ile Ser Glu Asp Leu  Pro Ala Ala Val Lys  Asn Ile Met
    2180                2185                2190

Ala Arg  Thr Asp His Pro Glu  Pro Ile Gln Leu Ala  Tyr Asn Ser
    2195                2200                2205

Tyr Glu  Asn Gln Ile Pro Val  Leu Phe Pro Lys Ile  Lys Asn Gly
    2210                2215                2220

Glu Val  Thr Asp Ser Tyr Glu  Asn Tyr Thr Tyr Leu  Asn Ala Arg
    2225                2230                2235

Lys Leu  Gly Glu Asp Val Pro  Ala Tyr Val Tyr Ala  Thr Glu Asp
    2240                2245                2250

Glu Asp  Leu Ala Val Asp Leu  Leu Gly Met Asp Trp  Pro Asp Pro
    2255                2260                2265

Gly Asn  Gln Gln Val Val Glu  Thr Gly Arg Ala Leu  Lys Gln Val
    2270                2275                2280

Thr Gly  Leu Ser Thr Ala Glu  Asn Ala Leu Leu Ile  Ala Leu Phe
    2285                2290                2295

Gly Tyr  Val Gly Tyr Gln Thr  Leu Ser Lys Arg His  Ile Pro Met
    2300                2305                2310

Ile Thr  Asp Ile Tyr Thr Leu  Glu Asp His Arg Leu  Glu Asp Thr
    2315                2320                2325

Thr His  Leu Gln Phe Ala Pro  Asn Ala Ile Arg Thr  Asp Gly Lys
    2330                2335                2340

Asp Ser  Glu Leu Lys Glu Leu  Ala Val Gly Asp Leu  Asp Lys Tyr
    2345                2350                2355

Val Asp  Ala Leu Val Asp Tyr  Ser Lys Gln Gly Met  Lys Phe Ile
    2360                2365                2370

Lys Val  Gln Ala Glu Lys Val  Arg Asp Ser Gln Ser  Thr Lys Glu
    2375                2380                2385

Gly Leu  Gln Thr Ile Lys Glu  Tyr Val Asp Lys Phe  Ile Gln Ser
    2390                2395                2400
```

-continued

```
Leu Thr  Glu Asn Lys Glu Glu  Ile Ile Arg Tyr Gly  Leu Trp Gly
    2405                 2410                 2415

Val His  Thr Ala Leu Tyr Lys  Ser Leu Ala Ala Arg  Leu Gly His
    2420                 2425                 2430

Glu Thr  Ala Phe Ala Thr Leu  Val Val Lys Trp Leu  Ala Phe Gly
    2435                 2440                 2445

Gly Glu  Thr Val Ser Ala His  Ile Lys Gln Val Ala  Val Asp Leu
    2450                 2455                 2460

Val Val  Tyr Tyr Ile Ile Asn  Lys Pro Ser Phe Pro  Gly Asp Thr
    2465                 2470                 2475

Glu Thr  Gln Gln Glu Gly Arg  Arg Phe Val Ala Ser  Leu Phe Ile
    2480                 2485                 2490

Ser Ala  Leu Ala Thr Tyr Thr  Tyr Lys Thr Trp Asn  Tyr Asn Asn
    2495                 2500                 2505

Leu Gln  Arg Val Val Glu Pro  Ala Leu Ala Tyr Leu  Pro Tyr Ala
    2510                 2515                 2520

Thr Ser  Ala Leu Lys Leu Phe  Thr Pro Thr Arg Leu  Glu Ser Val
    2525                 2530                 2535

Val Ile  Leu Ser Ser Thr Ile  Tyr Lys Thr Tyr Leu  Ser Ile Arg
    2540                 2545                 2550

Lys Gly  Lys Ser Asp Gly Leu  Leu Gly Thr Gly Ile  Ser Ala Ala
    2555                 2560                 2565

Met Glu  Ile Leu Asn Gln Asn  Pro Ile Ser Val Gly  Ile Ser Val
    2570                 2575                 2580

Met Leu  Gly Val Gly Ala Ile  Ala Ala His Asn Ala  Ile Glu Ser
    2585                 2590                 2595

Ser Glu  Gln Lys Arg Thr Leu  Leu Met Lys Val Phe  Val Lys Asn
    2600                 2605                 2610

Phe Leu  Asp Gln Ala Ala Thr  Asp Glu Leu Val Lys  Glu Asn Pro
    2615                 2620                 2625

Glu Lys  Ile Ile Met Ala Leu  Phe Glu Ala Val Gln  Thr Ile Gly
    2630                 2635                 2640

Asn Pro  Leu Arg Leu Ile Tyr  His Leu Tyr Gly Val  Tyr Tyr Lys
    2645                 2650                 2655

Gly Trp  Glu Ala Lys Glu Leu  Ala Glu Lys Thr Ala  Gly Arg Asn
    2660                 2665                 2670

Leu Phe  Thr Leu Ile Met Phe  Glu Ala Phe Glu Leu  Leu Gly Met
    2675                 2680                 2685

Asp Ser  Glu Gly Lys Ile Arg  Asn Leu Ser Gly Asn  Tyr Ile Leu
    2690                 2695                 2700

Asp Leu  Ile Phe Asn Leu His  Asn Lys Leu Asn Lys  Gly Leu Lys
    2705                 2710                 2715

Lys Leu  Val Leu Gly Trp Ala  Pro Ala Pro Leu Ser  Cys Asp Trp
    2720                 2725                 2730

Thr Pro  Ser Asp Glu Arg Ile  Ser Leu Pro His Asn  Asn Tyr Leu
    2735                 2740                 2745

Arg Val  Glu Thr Arg Cys Pro  Cys Gly Tyr Glu Met  Lys Ala Ile
    2750                 2755                 2760

Lys Asn  Val Ala Gly Lys Leu  Thr Lys Val Glu Glu  Lys Gly Ser
    2765                 2770                 2775

Phe Leu  Cys Arg Asn Arg Leu  Gly Arg Gly Pro Pro  Asn Phe Lys
    2780                 2785                 2790
```

```
Val Thr  Lys Phe Tyr Asp Asp  Asn Leu Ile Glu Val  Lys Pro Val
    2795                 2800                 2805

Ala Arg  Leu Glu Gly Gln Val  Asp Leu Tyr Tyr Lys  Gly Val Thr
    2810                 2815                 2820

Ala Lys  Leu Asp Tyr Asn Asn  Gly Lys Val Leu Leu  Ala Thr Asn
    2825                 2830                 2835

Lys Trp  Glu Val Asp His Ala  Phe Leu Thr Arg Leu  Val Lys Lys
    2840                 2845                 2850

His Thr  Gly Ile Gly Phe Lys  Gly Ala Tyr Leu Gly  Asp Arg Pro
    2855                 2860                 2865

Asp His  Gln Asp Leu Val Asp  Arg Asp Cys Ala Thr  Ile Thr Lys
    2870                 2875                 2880

Asn Ser  Val Gln Phe Leu Lys  Met Lys Lys Gly Cys  Ala Phe Thr
    2885                 2890                 2895

Tyr Asp  Leu Thr Ile Ser Asn  Leu Val Arg Leu Ile  Glu Leu Val
    2900                 2905                 2910

His Lys  Asn Asn Leu Gln Glu  Arg Glu Ile Pro Thr  Val Thr Val
    2915                 2920                 2925

Thr Thr  Trp Leu Ala Tyr Ser  Phe Val Asn Glu Asp  Leu Gly Thr
    2930                 2935                 2940

Ile Lys  Pro Val Leu Gly Glu  Lys Val Ile Pro Glu  Pro Pro Glu
    2945                 2950                 2955

Glu Leu  Ser Leu Gln Pro Thr  Val Arg Leu Val Thr  Thr Glu Thr
    2960                 2965                 2970

Ala Ile  Thr Ile Thr Gly Glu  Ala Glu Val Met Thr  Thr Gly Ile
    2975                 2980                 2985

Thr Pro  Val Val Glu Met Lys  Glu Glu Pro Gln Leu  Asp His Gln
    2990                 2995                 3000

Ser Thr  Thr Leu Lys Val Gly  Leu Lys Glu Gly Glu  Tyr Pro Gly
    3005                 3010                 3015

Pro Gly  Val Asn Pro Asn His  Leu Ala Glu Val Ile  Asp Glu Lys
    3020                 3025                 3030

Asp Asp  Arg Pro Phe Val Leu  Ile Ile Gly Asn Lys  Gly Ser Thr
    3035                 3040                 3045

Ser Asn  Arg Ala Arg Thr Ala  Lys Asn Ile Arg Leu  Tyr Lys Gly
    3050                 3055                 3060

Asn Asn  Pro Arg Glu Ile Arg  Asp Leu Met Ser Gln  Gly Arg Ile
    3065                 3070                 3075

Leu Thr  Val Ala Leu Lys Glu  Leu Asp Pro Glu Leu  Lys Glu Leu
    3080                 3085                 3090

Val Asp  Tyr Lys Gly Thr Phe  Leu Asn Arg Glu Ala  Leu Glu Ala
    3095                 3100                 3105

Leu Ser  Leu Gly Lys Pro Ile  Lys Arg Lys Thr Thr  Thr Ala Met
    3110                 3115                 3120

Ile Arg  Arg Leu Ile Glu Pro  Glu Val Glu Glu Glu  Leu Pro Asp
    3125                 3130                 3135

Trp Phe  Gln Ala Glu Glu Pro  Leu Phe Leu Glu Ala  Lys Ile Gln
    3140                 3145                 3150

Asn Asp  Leu Tyr His Leu Ile  Gly Ser Val Asp Ser  Ile Lys Ser
    3155                 3160                 3165

Lys Ala  Lys Glu Leu Gly Ala  Thr Asp Asn Thr Lys  Ile Val Lys
    3170                 3175                 3180

Glu Val  Gly Ala Arg Thr Tyr  Thr Met Lys Leu Ser  Ser Trp Ser
```

-continued

```
    3185                3190                3195

Thr Gln  Val Thr Lys Lys Gln  Met Ser Leu Ala Pro  Leu Phe Glu
    3200                3205                3210

Glu Leu  Leu Leu Lys Cys Pro  Pro Cys Ser Lys Ile  Ser Lys Gly
    3215                3220                3225

His Met  Val Ser Ala Tyr Gln  Leu Ala Gln Gly Asn  Trp Glu Pro
    3230                3235                3240

Leu Gly  Cys Gly Val Tyr Met  Gly Thr Ile Pro Ala  Arg Arg Leu
    3245                3250                3255

Lys Ile  His Pro Tyr Glu Ala  Tyr Leu Lys Leu Lys  Glu Leu Val
    3260                3265                3270

Glu Val  Glu Ser Ser Arg Ala  Thr Ala Lys Glu Ser  Ile Ile Arg
    3275                3280                3285

Glu His  Asn Thr Trp Ile Leu  Arg Lys Val Arg His  Glu Gly Asn
    3290                3295                3300

Leu Arg  Thr Lys Ser Met Ile  Asn Pro Gly Lys Ile  Ser Asp Gln
    3305                3310                3315

Leu Cys  Arg Asp Gly His Lys  Arg Asn Ile Tyr Asn  Lys Ile Ile
    3320                3325                3330

Gly Ser  Thr Met Ala Ser Ala  Gly Ile Arg Leu Glu  Lys Leu Pro
    3335                3340                3345

Val Val  Arg Ala Gln Thr Asp  Thr Thr Ser Phe His  Gln Ala Ile
    3350                3355                3360

Arg Glu  Lys Ile Asp Lys Thr  Glu Asn Lys Gln Thr  Pro Glu Leu
    3365                3370                3375

His Glu  Glu Leu Met Lys Val  Phe Asp Cys Leu Lys  Ile Pro Glu
    3380                3385                3390

Leu Lys  Glu Ser Tyr Asp Glu  Val Ser Trp Glu Gln  Leu Glu Ala
    3395                3400                3405

Gly Ile  Asn Arg Lys Gly Ala  Ala Gly Tyr Leu Glu  Ser Lys Asn
    3410                3415                3420

Ile Gly  Glu Val Leu Asp Thr  Glu Lys His Ile Val  Glu Gln Leu
    3425                3430                3435

Ile Lys  Asp Leu Arg Lys Gly  Lys Lys Ile Arg Tyr  Tyr Glu Thr
    3440                3445                3450

Ala Ile  Pro Lys Asn Glu Lys  Arg Asp Val Ser Asp  Asp Trp Glu
    3455                3460                3465

Ala Gly  Glu Phe Val Asp Glu  Lys Lys Pro Arg Val  Ile Gln Tyr
    3470                3475                3480

Pro Asp  Ala Lys Val Arg Leu  Ala Ile Thr Lys Val  Met Tyr Lys
    3485                3490                3495

Trp Val  Lys Gln Lys Pro Val  Val Ile Pro Gly Tyr  Glu Gly Lys
    3500                3505                3510

Thr Pro  Leu Phe Asp Ile Phe  Asn Lys Val Lys Lys  Glu Trp Asp
    3515                3520                3525

Ser Phe  Gln Asp Pro Val Ala  Val Ser Phe Asp Thr  Lys Ala Trp
    3530                3535                3540

Asp Thr  Gln Val Thr Ser Arg  Asp Leu Met Leu Ile  Lys Asp Ile
    3545                3550                3555

Gln Lys  Tyr Tyr Phe Lys Arg  Ser Ile His Lys Phe  Leu Asp Thr
    3560                3565                3570

Ile Thr  Glu His Met Val Glu  Val Pro Val Ile Thr  Ala Asp Gly
    3575                3580                3585
```

```
Glu Val Tyr Ile Arg Asn Gly Gln Arg Gly Ser Gly Gln Pro Asp
    3590                3595                3600

Thr Ser Ala Gly Asn Ser Met Leu Asn Val Leu Thr Met Ile Tyr
    3605                3610                3615

Ala Phe Cys Lys Ser Thr Gly Ile Pro Tyr Arg Gly Phe Ser Arg
    3620                3625                3630

Val Ala Arg Ile His Val Cys Gly Asp Asp Gly Phe Leu Ile Thr
    3635                3640                3645

Glu Arg Gly Leu Gly Leu Lys Phe Ser Glu Lys Gly Met Gln Ile
    3650                3655                3660

Leu His Glu Ala Gly Lys Pro Gln Lys Ile Thr Glu Gly Asp Lys
    3665                3670                3675

Met Lys Val Ala Tyr Arg Phe Glu Asp Ile Glu Phe Cys Ser His
    3680                3685                3690

Thr Pro Val Pro Val Arg Trp Ala Asp Asn Thr Ser Ser Tyr Met
    3695                3700                3705

Ala Gly Arg Ser Thr Ala Thr Ile Leu Ala Lys Met Ala Thr Arg
    3710                3715                3720

Leu Asp Ser Ser Gly Glu Arg Gly Ser Thr Ala Tyr Glu Lys Ala
    3725                3730                3735

Val Ala Phe Ser Phe Leu Leu Met Tyr Ser Trp Asn Pro Val Val
    3740                3745                3750

Arg Arg Ile Cys Leu Leu Val Leu Ser Gln Phe Pro Glu Ile Ser
    3755                3760                3765

Pro Ser Lys Asn Thr Ile Tyr Tyr Tyr Gln Gly Asp Pro Ile Ala
    3770                3775                3780

Ala Tyr Arg Glu Val Ile Gly Lys Gln Leu Cys Glu Leu Lys Arg
    3785                3790                3795

Thr Gly Phe Glu Lys Leu Ala Gly Leu Asn Leu Ser Met Thr Thr
    3800                3805                3810

Leu Gly Ile Trp Thr Lys His Thr Ser Lys Arg Leu Ile Gln Ala
    3815                3820                3825

Cys Val Glu Ile Gly Lys Arg Glu Gly Thr Trp Leu Val Asn Ala
    3830                3835                3840

Asp Arg Leu Ile Ala Gly Lys Thr Gly Lys Phe Tyr Ile Pro Ser
    3845                3850                3855

Thr Gly Val Thr Leu Leu Gly Lys His Tyr Glu Glu Ile Asn Leu
    3860                3865                3870

Lys Gln Lys Ala Ala Gln Pro Pro Ile Glu Gly Val Asp Arg Tyr
    3875                3880                3885

Lys Leu Gly Pro Ile Val Asn Val Ile Leu Arg Arg Leu Arg Val
    3890                3895                3900

Met Leu Met Thr Val Ala Ser Gly Ser Trp
    3905                3910
```

<210> SEQ ID NO 6
<211> LENGTH: 3749
<212> TYPE: PRT
<213> ORGANISM: Artificial
<220> FEATURE:
<223> OTHER INFORMATION: Mutated BVDV: XIKE-A-NdN

<400> SEQUENCE: 6

```
Met Glu Leu Phe Ser Asp Glu Gly Ser Lys Gly Ala Thr Ser Lys Lys
1               5                   10                  15
```

-continued

```
Gln Pro Lys Pro Asp Arg Ile Glu Lys Gly Lys Met Lys Ile Ala Pro
            20                  25                  30

Lys Glu Thr Glu Lys Asp Cys Lys Thr Arg Pro Pro Asp Ala Thr Ile
        35                  40                  45

Val Val Glu Gly Val Lys Tyr Gln Val Lys Lys Lys Gly Lys Val Arg
    50                  55                  60

Gly Lys Asn Thr Gln Asp Gly Leu Tyr His Asn Lys Asn Lys Pro Pro
65                  70                  75                  80

Glu Ser Arg Lys Lys Leu Glu Lys Ala Leu Leu Ala Trp Ala Ile Leu
                85                  90                  95

Ala Ala Val Leu Leu Gln Leu Val Thr Gly Glu Asn Ile Thr Gln Trp
            100                 105                 110

Asn Leu Met Asp Asn Gly Thr Glu Gly Ile Gln Gln Ala Met Phe Leu
        115                 120                 125

Arg Gly Val Asn Arg Ser Leu His Gly Ile Trp Pro Glu Lys Ile Cys
    130                 135                 140

Thr Gly Val Pro Thr His Leu Ala Thr Asp Tyr Glu Leu Lys Glu Ile
145                 150                 155                 160

Val Gly Met Met Asp Ala Ser Glu Lys Thr Asn Tyr Thr Cys Cys Arg
                165                 170                 175

Leu Gln Arg His Glu Trp Asn Lys His Gly Trp Cys Asn Trp Phe His
            180                 185                 190

Ile Glu Pro Trp Ile Trp Leu Met Asn Lys Thr Gln Asn Asn Leu Thr
        195                 200                 205

Glu Gly Gln Pro Leu Arg Glu Cys Ala Val Thr Cys Arg Tyr Asp Lys
    210                 215                 220

Glu Thr Glu Leu Asn Ile Val Thr Gln Ala Arg Asp Arg Pro Thr Thr
225                 230                 235                 240

Leu Thr Gly Cys Lys Lys Gly Lys Asn Phe Ser Phe Ala Gly Val Ile
                245                 250                 255

Leu Asp Gly Pro Cys Asn Phe Lys Val Ser Val Glu Asp Val Leu Phe
            260                 265                 270

Lys Glu His Asp Cys Gly Asn Met Leu Gln Glu Thr Ala Ile Gln Leu
        275                 280                 285

Leu Asp Gly Ala Thr Asn Thr Ile Glu Gly Ala Arg Val Gly Thr Ala
    290                 295                 300

Lys Leu Thr Thr Trp Leu Gly Lys Gln Leu Gly Ile Leu Gly Lys Lys
305                 310                 315                 320

Leu Glu Asn Lys Ser Lys Ala Trp Phe Gly Ala His Ala Ala Ser Pro
                325                 330                 335

Tyr Cys Gly Val Glu Arg Lys Ile Gly Tyr Val Trp Tyr Thr Lys Asn
            340                 345                 350

Cys Thr Pro Ala Cys Leu Pro Arg Asn Thr Arg Ile Ile Gly Pro Gly
        355                 360                 365

Lys Phe Asp Thr Asn Ala Glu Asp Gly Lys Ile Leu His Glu Met Gly
    370                 375                 380

Gly His Leu Ser Glu Phe Val Leu Leu Ser Leu Val Val Leu Ser Asp
385                 390                 395                 400

Phe Ala Pro Glu Thr Ala Ser Val Ile Tyr Leu Val Leu His Phe Ala
                405                 410                 415

Ile Pro Gln Ser His Val Asp Val Asp Thr Cys Asp Lys Asn Gln Leu
            420                 425                 430
```

-continued

```
Asn Leu Thr Val Ala Thr Thr Val Ala Glu Val Ile Pro Gly Thr Val
        435                 440                 445

Trp Asn Leu Gly Lys Tyr Val Cys Ile Arg Pro Asp Trp Trp Pro Tyr
    450                 455                 460

Glu Thr Thr Thr Val Phe Val Ile Glu Glu Ala Gly Gln Val Ile Lys
465                 470                 475                 480

Leu Met Leu Arg Ala Ile Arg Asp Leu Thr Arg Ile Trp Asn Ala Ala
                485                 490                 495

Thr Thr Thr Ala Phe Leu Ile Phe Leu Val Lys Ala Leu Arg Gly Gln
            500                 505                 510

Leu Ile Gln Gly Leu Leu Trp Leu Met Leu Ile Thr Gly Ala Gln Gly
        515                 520                 525

Phe Pro Glu Cys Lys Glu Gly Phe Gln Tyr Ala Ile Ser Lys Asp Arg
    530                 535                 540

Lys Met Gly Leu Leu Gly Pro Glu Ser Leu Thr Thr Thr Trp His Leu
545                 550                 555                 560

Pro Thr Lys Lys Ile Val Asp Ser Met Val His Val Trp Cys Glu Gly
                565                 570                 575

Lys Asp Leu Lys Ile Leu Lys Met Cys Thr Lys Glu Glu Arg Tyr Leu
            580                 585                 590

Val Ala Val His Glu Arg Ala Leu Ser Thr Ser Ala Glu Phe Met Gln
        595                 600                 605

Ile Ser Asp Gly Thr Ile Gly Pro Asp Val Ile Asp Met Pro Asp Asp
    610                 615                 620

Phe Glu Phe Gly Leu Cys Pro Cys Asp Ser Lys Pro Val Ile Lys Gly
625                 630                 635                 640

Lys Phe Asn Ala Ser Leu Leu Asn Gly Pro Ala Phe Gln Met Val Cys
                645                 650                 655

Pro Gln Gly Trp Thr Gly Thr Ile Glu Cys Thr Leu Ala Asn Gln Asp
            660                 665                 670

Thr Leu Asp Thr Thr Val Ile Arg Thr Tyr Arg Arg Thr Thr Pro Phe
        675                 680                 685

Gln Arg Arg Lys Trp Cys Thr Tyr Glu Lys Ile Ile Gly Glu Asp Ile
    690                 695                 700

Tyr Glu Cys Ile Leu Gly Gly Asn Trp Thr Cys Ile Thr Gly Asp His
705                 710                 715                 720

Ser Arg Leu Lys Asp Gly Pro Ile Lys Lys Cys Lys Trp Cys Gly His
                725                 730                 735

Asp Phe Val Asn Ser Glu Gly Leu Pro His Tyr Pro Ile Gly Lys Cys
            740                 745                 750

Met Leu Ile Asn Glu Ser Gly Tyr Arg Tyr Val Asp Asp Thr Ser Cys
        755                 760                 765

Asp Arg Gly Gly Val Ala Ile Val Pro Ser Gly Thr Val Lys Cys Arg
    770                 775                 780

Ile Gly Asn Val Thr Val Gln Val Ile Ala Thr Asn Asn Asp Leu Gly
785                 790                 795                 800

Pro Met Pro Cys Ser Pro Ala Glu Val Ile Ala Ser Glu Gly Pro Val
                805                 810                 815

Glu Lys Thr Ala Cys Thr Phe Asn Tyr Ser Arg Thr Leu Pro Asn Lys
            820                 825                 830

Tyr Tyr Glu Pro Arg Asp Arg Tyr Phe Gln Gln Tyr Met Leu Lys Gly
        835                 840                 845

Glu Trp Gln Tyr Trp Phe Asp Leu Asp Ser Val Asp His His Lys Asp
```

-continued

```
    850                 855                 860

Tyr Phe Ser Glu Phe Ile Ile Ile Ala Val Val Ala Leu Leu Gly Gly
865                 870                 875                 880

Lys Tyr Val Leu Trp Leu Leu Ile Thr Tyr Thr Ile Leu Ser Glu Gln
                885                 890                 895

Met Ala Met Gly Ala Gly Val Asn Thr Glu Glu Ile Val Met Ile Gly
            900                 905                 910

Asn Leu Leu Thr Asp Ser Asp Ile Glu Val Val Val Tyr Phe Leu Leu
        915                 920                 925

Leu Tyr Leu Ile Val Lys Glu Glu Leu Ala Arg Lys Trp Ile Ile Leu
    930                 935                 940

Val Tyr His Ile Leu Val Ala Asn Pro Met Lys Thr Ile Gly Val Val
945                 950                 955                 960

Leu Leu Met Leu Gly Gly Val Val Lys Ala Ser Arg Ile Asn Ala Asp
                965                 970                 975

Asp Gln Ser Ala Met Asp Pro Cys Phe Leu Leu Val Thr Gly Val Val
            980                 985                 990

Ala Val Leu Met Ile Ala Arg Arg  Glu Pro Ala Thr Leu  Pro Leu Ile
        995                 1000                1005

Val Ala  Leu Leu Ala Ile Arg  Thr Ser Gly Phe Leu  Leu Pro Ala
    1010                1015                1020

Ser Ile  Asp Val Thr Val Ala  Val Val Leu Ile Val  Leu Leu Leu
    1025                1030                1035

Ala Ser  Tyr Ile Thr Asp Tyr  Phe Arg Tyr Lys Lys  Trp Leu Gln
    1040                1045                1050

Leu Leu  Phe Ser Leu Ile Ala  Gly Ile Phe Ile Ile  Arg Ser Leu
    1055                1060                1065

Lys His  Ile Asn Gln Met Glu  Val Pro Glu Ile Ser  Met Pro Ser
    1070                1075                1080

Trp Arg  Pro Leu Ala Leu Val  Leu Phe Tyr Ile Thr  Ser Thr Ala
    1085                1090                1095

Ile Thr  Thr Asn Trp Asp Ile  Asp Leu Ala Gly Phe  Leu Leu Gln
    1100                1105                1110

Trp Ala  Pro Ala Val Ile Met  Met Ala Thr Met Trp  Ala Asp Phe
    1115                1120                1125

Leu Thr  Leu Ile Ile Val Leu  Pro Ser Tyr Glu Leu  Ser Lys Leu
    1130                1135                1140

Tyr Phe  Leu Lys Asn Val Arg  Thr Asp Val Glu Lys  Asn Trp Leu
    1145                1150                1155

Gly Lys  Val Lys Tyr Arg Gln  Ile Ser Ser Val Tyr  Asp Ile Cys
    1160                1165                1170

Asp Ser  Glu Glu Ala Val Tyr  Leu Phe Pro Ser Arg  His Lys Ser
    1175                1180                1185

Gly Ser  Arg Pro Asp Phe Ile  Leu Pro Phe Leu Lys  Ala Val Leu
    1190                1195                1200

Ile Ser  Cys Ile Ser Ser Gln  Trp Gln Val Val Tyr  Ile Ser Tyr
    1205                1210                1215

Leu Ile  Leu Glu Ile Thr Tyr  Tyr Met His Arg Lys  Ile Ile Asp
    1220                1225                1230

Glu Val  Ser Gly Gly Ala Asn  Phe Leu Ser Arg Leu  Ile Ala Ala
    1235                1240                1245

Ile Ile  Glu Leu Asn Trp Ala  Ile Asp Asp Glu Glu  Cys Lys Gly
    1250                1255                1260
```

-continued

```
Leu Lys Lys Leu Tyr Leu Leu Ser Gly Arg Ala Lys Asn Leu Ile
    1265                1270                1275

Val Lys His Lys Val Arg Asn Glu Ala Val His Arg Trp Phe Gly
    1280                1285                1290

Glu Glu Glu Ile Tyr Gly Ala Pro Lys Val Ile Thr Ile Ile Lys
    1295                1300                1305

Ala Ser Thr Leu Ser Lys Asn Arg His Cys Ile Ile Cys Thr Ile
    1310                1315                1320

Cys Glu Gly Lys Glu Trp Asn Gly Ala Asn Cys Pro Lys Cys Gly
    1325                1330                1335

Arg Gln Gly Lys Pro Ile Thr Cys Gly Met Thr Leu Ala Asp Phe
    1340                1345                1350

Glu Glu Lys His Tyr Lys Lys Ile Phe Ile Arg Glu Glu Ser Ser
    1355                1360                1365

Cys Pro Val Pro Phe Asp Pro Ser Cys His Cys Asn Tyr Phe Arg
    1370                1375                1380

His Asp Gly Pro Phe Arg Lys Glu Tyr Lys Gly Tyr Val Gln Tyr
    1385                1390                1395

Thr Ala Arg Gly Gln Leu Phe Leu Arg Asn Leu Pro Ile Leu Ala
    1400                1405                1410

Thr Lys Met Lys Leu Leu Met Val Gly Asn Leu Gly Ala Glu Ile
    1415                1420                1425

Gly Asp Leu Glu His Leu Gly Trp Val Leu Arg Gly Pro Ala Val
    1430                1435                1440

Cys Lys Lys Ile Thr Asn His Glu Lys Cys His Val Asn Ile Met
    1445                1450                1455

Asp Lys Leu Thr Ala Phe Phe Gly Ile Met Pro Arg Gly Thr Thr
    1460                1465                1470

Pro Arg Ala Pro Val Arg Phe Pro Thr Ala Leu Leu Lys Val Arg
    1475                1480                1485

Arg Gly Leu Glu Thr Gly Trp Ala Tyr Thr His Gln Gly Gly Ile
    1490                1495                1500

Ser Ser Val Asp His Val Thr Ala Gly Lys Asp Leu Leu Val Cys
    1505                1510                1515

Asp Ser Met Gly Arg Thr Arg Val Val Cys His Ser Asn Asn Lys
    1520                1525                1530

Met Thr Asp Glu Thr Glu Tyr Gly Ile Lys Thr Asp Ser Gly Cys
    1535                1540                1545

Pro Glu Gly Ala Arg Cys Tyr Val Leu Asn Pro Glu Ala Val Asn
    1550                1555                1560

Ile Ser Gly Thr Lys Gly Ala Met Val His Leu Gln Lys Thr Gly
    1565                1570                1575

Gly Glu Phe Thr Cys Val Thr Ala Ser Gly Thr Pro Ala Phe Phe
    1580                1585                1590

Asp Leu Lys Asn Leu Lys Gly Trp Ser Gly Leu Pro Ile Phe Glu
    1595                1600                1605

Ala Ser Ser Gly Arg Val Val Gly Arg Val Lys Val Gly Lys Asn
    1610                1615                1620

Glu Asp Ser Lys Pro Thr Lys Leu Met Ser Gly Ile Gln Thr Val
    1625                1630                1635

Ser Lys Asn Gln Thr Asp Leu Ala Asp Ile Val Lys Lys Leu Thr
    1640                1645                1650
```

-continued

```
Ser Met  Asn Arg Gly Glu Phe  Lys Gln Ile Thr Leu  Ala Thr Gly
    1655                 1660                 1665

Ala Gly  Lys Thr Thr Glu Leu  Pro Arg Ser Val Ile  Glu Glu Ile
    1670                 1675                 1680

Gly Arg  His Lys Arg Val Leu  Val Leu Ile Pro Leu  Arg Ala Ala
    1685                 1690                 1695

Ala Glu  Ser Val Tyr Gln Tyr  Met Arg Val Lys Tyr  Pro Ser Ile
    1700                 1705                 1710

Ser Phe  Asn Leu Arg Ile Gly  Asp Met Lys Glu Gly  Asp Met Ala
    1715                 1720                 1725

Thr Gly  Ile Thr Tyr Ala Ser  Tyr Gly Tyr Phe Cys  Gln Leu Pro
    1730                 1735                 1740

Gln Pro  Lys Leu Arg Ala Ala  Met Val Glu Tyr Ser  Tyr Ile Phe
    1745                 1750                 1755

Leu Asp  Glu Tyr His Cys Ala  Thr Pro Glu Gln Leu  Ala Ile Ile
    1760                 1765                 1770

Gly Lys  Ile His Arg Phe Ala  Glu Asn Leu Arg Val  Val Ala Met
    1775                 1780                 1785

Thr Ala  Thr Pro Ala Gly Thr  Val Thr Thr Thr Gly  Gln Lys His
    1790                 1795                 1800

Pro Ile  Glu Glu Phe Ile Ala  Pro Glu Val Met Lys  Gly Glu Asp
    1805                 1810                 1815

Leu Gly  Ser Glu Tyr Leu Asp  Ile Ala Gly Leu Lys  Ile Pro Thr
    1820                 1825                 1830

Glu Glu  Met Lys Gly Asn Met  Leu Val Phe Ala Pro  Thr Arg Asn
    1835                 1840                 1845

Met Ala  Val Glu Thr Ala Lys  Lys Leu Lys Ala Lys  Gly Tyr Asn
    1850                 1855                 1860

Ser Gly  Tyr Tyr Tyr Ser Gly  Glu Asn Pro Glu Asn  Leu Arg Val
    1865                 1870                 1875

Val Thr  Ser Gln Ser Pro Tyr  Val Val Val Ala Thr  Asn Ala Ile
    1880                 1885                 1890

Glu Ser  Gly Val Thr Leu Pro  Asp Leu Asp Thr Val  Val Asp Thr
    1895                 1900                 1905

Gly Leu  Lys Cys Glu Lys Arg  Val Arg Ile Ser Ser  Lys Met Pro
    1910                 1915                 1920

Phe Ile  Val Thr Gly Leu Lys  Arg Met Ala Val Thr  Ile Gly Glu
    1925                 1930                 1935

Gln Ala  Gln Arg Arg Gly Arg  Val Gly Arg Val Lys  Pro Gly Arg
    1940                 1945                 1950

Tyr Tyr  Arg Ser Gln Glu Thr  Ala Ser Gly Ser Lys  Asp Tyr His
    1955                 1960                 1965

Tyr Asp  Leu Leu Gln Ala Gln  Arg Tyr Gly Ile Glu  Asp Gly Ile
    1970                 1975                 1980

Asn Val  Thr Lys Ser Phe Arg  Glu Met Asn Tyr Asp  Trp Ser Leu
    1985                 1990                 1995

Tyr Glu  Glu Asp Ser Leu Met  Ile Thr Gln Leu Glu  Val Leu Asn
    2000                 2005                 2010

Asn Leu  Leu Ile Ser Glu Asp  Leu Pro Ala Ala Val  Lys Asn Ile
    2015                 2020                 2025

Met Ala  Arg Thr Asp His Pro  Glu Pro Ile Gln Leu  Ala Tyr Asn
    2030                 2035                 2040

Ser Tyr  Glu Asn Gln Ile Pro  Val Leu Phe Pro Lys  Ile Lys Asn
```

```
    2045                2050                2055

Gly Glu  Val Thr Asp Ser Tyr  Glu Asn Tyr Thr Tyr  Leu Asn Ala
    2060                2065                2070

Arg Lys  Leu Gly Glu Asp Val  Pro Ala Tyr Val Tyr  Ala Thr Glu
    2075                2080                2085

Asp Glu  Asp Leu Ala Val Asp  Leu Leu Gly Met Asp  Trp Pro Asp
    2090                2095                2100

Pro Gly  Asn Gln Gln Val Val  Glu Thr Gly Arg Ala  Leu Lys Gln
    2105                2110                2115

Val Thr  Gly Leu Ser Thr Ala  Glu Asn Ala Leu Leu  Ile Ala Leu
    2120                2125                2130

Phe Gly  Tyr Val Gly Tyr Gln  Thr Leu Ser Lys Arg  His Ile Pro
    2135                2140                2145

Met Ile  Thr Asp Ile Tyr Thr  Leu Glu Asp His Arg  Leu Glu Asp
    2150                2155                2160

Thr Thr  His Leu Gln Phe Ala  Pro Asn Ala Ile Arg  Thr Asp Gly
    2165                2170                2175

Lys Asp  Ser Glu Leu Lys Glu  Leu Ala Val Gly Asp  Leu Asp Lys
    2180                2185                2190

Tyr Val  Asp Ala Leu Val Asp  Tyr Ser Lys Gln Gly  Met Lys Phe
    2195                2200                2205

Ile Lys  Val Gln Ala Glu Lys  Val Arg Asp Ser Gln  Ser Thr Lys
    2210                2215                2220

Glu Gly  Leu Gln Thr Ile Lys  Glu Tyr Val Asp Lys  Phe Ile Gln
    2225                2230                2235

Ser Leu  Thr Glu Asn Lys Glu  Glu Ile Ile Arg Tyr  Gly Leu Trp
    2240                2245                2250

Gly Val  His Thr Ala Leu Tyr  Lys Ser Leu Ala Ala  Arg Leu Gly
    2255                2260                2265

His Glu  Thr Ala Phe Ala Thr  Leu Val Val Lys Trp  Leu Ala Phe
    2270                2275                2280

Gly Gly  Glu Thr Val Ser Ala  His Ile Lys Gln Val  Ala Val Asp
    2285                2290                2295

Leu Val  Val Tyr Tyr Ile Ile  Asn Lys Pro Ser Phe  Pro Gly Asp
    2300                2305                2310

Thr Glu  Thr Gln Gln Glu Gly  Arg Arg Phe Val Ala  Ser Leu Phe
    2315                2320                2325

Ile Ser  Ala Leu Ala Thr Tyr  Thr Tyr Lys Thr Trp  Asn Tyr Asn
    2330                2335                2340

Asn Leu  Gln Arg Val Val Glu  Pro Ala Leu Ala Tyr  Leu Pro Tyr
    2345                2350                2355

Ala Thr  Ser Ala Leu Lys Leu  Phe Thr Pro Thr Arg  Leu Glu Ser
    2360                2365                2370

Val Val  Ile Leu Ser Ser Thr  Ile Tyr Lys Thr Tyr  Leu Ser Ile
    2375                2380                2385

Arg Lys  Gly Lys Ser Asp Gly  Leu Leu Gly Thr Gly  Ile Ser Ala
    2390                2395                2400

Ala Met  Glu Ile Leu Asn Gln  Asn Pro Ile Ser Val  Gly Ile Ser
    2405                2410                2415

Val Met  Leu Gly Val Gly Ala  Ile Ala Ala His Asn  Ala Ile Glu
    2420                2425                2430

Ser Ser  Glu Gln Lys Arg Thr  Leu Leu Met Lys Val  Phe Val Lys
    2435                2440                2445
```

-continued

```
Asn Phe  Leu Asp Gln Ala Ala  Thr Asp Glu Leu Val  Lys Glu Asn
    2450                 2455                 2460

Pro Glu  Lys Ile Ile Met Ala  Leu Phe Glu Ala Val  Gln Thr Ile
    2465                 2470                 2475

Gly Asn  Pro Leu Arg Leu Ile  Tyr His Leu Tyr Gly  Val Tyr Tyr
    2480                 2485                 2490

Lys Gly  Trp Glu Ala Lys Glu  Leu Ala Glu Lys Thr  Ala Gly Arg
    2495                 2500                 2505

Asn Leu  Phe Thr Leu Ile Met  Phe Glu Ala Phe Glu  Leu Leu Gly
    2510                 2515                 2520

Met Asp  Ser Glu Gly Lys Ile  Arg Asn Leu Ser Gly  Asn Tyr Ile
    2525                 2530                 2535

Leu Asp  Leu Ile Phe Asn Leu  His Asn Lys Leu Asn  Lys Gly Leu
    2540                 2545                 2550

Lys Lys  Leu Val Leu Gly Trp  Ala Pro Ala Pro Leu  Ser Cys Asp
    2555                 2560                 2565

Trp Thr  Pro Ser Asp Glu Arg  Ile Ser Leu Pro His  Asn Asn Tyr
    2570                 2575                 2580

Leu Arg  Val Glu Thr Arg Cys  Pro Cys Gly Tyr Glu  Met Lys Ala
    2585                 2590                 2595

Ile Lys  Asn Val Ala Gly Lys  Leu Thr Lys Val Glu  Glu Lys Gly
    2600                 2605                 2610

Ser Phe  Leu Cys Arg Asn Arg  Leu Gly Arg Gly Pro  Pro Asn Phe
    2615                 2620                 2625

Lys Val  Thr Lys Phe Tyr Asp  Asp Asn Leu Ile Glu  Val Lys Pro
    2630                 2635                 2640

Val Ala  Arg Leu Glu Gly Gln  Val Asp Leu Tyr Tyr  Lys Gly Val
    2645                 2650                 2655

Thr Ala  Lys Leu Asp Tyr Asn  Asn Gly Lys Val Leu  Leu Ala Thr
    2660                 2665                 2670

Asn Lys  Trp Glu Val Asp His  Ala Phe Leu Thr Arg  Leu Val Lys
    2675                 2680                 2685

Lys His  Thr Gly Ile Gly Phe  Lys Gly Ala Tyr Leu  Gly Asp Arg
    2690                 2695                 2700

Pro Asp  His Gln Asp Leu Val  Asp Arg Asp Cys Ala  Thr Ile Thr
    2705                 2710                 2715

Lys Asn  Ser Val Gln Phe Leu  Lys Met Lys Lys Gly  Cys Ala Phe
    2720                 2725                 2730

Thr Tyr  Asp Leu Thr Ile Ser  Asn Leu Val Arg Leu  Ile Glu Leu
    2735                 2740                 2745

Val His  Lys Asn Asn Leu Gln  Glu Arg Glu Ile Pro  Thr Val Thr
    2750                 2755                 2760

Val Thr  Thr Trp Leu Ala Tyr  Ser Phe Val Asn Glu  Asp Leu Gly
    2765                 2770                 2775

Thr Ile  Lys Pro Val Leu Gly  Glu Lys Val Ile Pro  Glu Pro Pro
    2780                 2785                 2790

Glu Glu  Leu Ser Leu Gln Pro  Thr Val Arg Leu Val  Thr Thr Glu
    2795                 2800                 2805

Thr Ala  Ile Thr Ile Thr Gly  Glu Ala Glu Val Met  Thr Thr Gly
    2810                 2815                 2820

Ile Thr  Pro Val Val Glu Met  Lys Glu Glu Pro Gln  Leu Asp His
    2825                 2830                 2835
```

-continued

```
Gln Ser Thr Thr Leu Lys Val Gly Leu Lys Glu Gly Glu Tyr Pro
    2840                2845                2850

Gly Pro Gly Val Asn Pro Asn His Leu Ala Glu Val Ile Asp Glu
    2855                2860                2865

Lys Asp Asp Arg Pro Phe Val Leu Ile Ile Gly Asn Lys Gly Ser
    2870                2875                2880

Thr Ser Asn Arg Ala Arg Thr Ala Lys Asn Ile Arg Leu Tyr Lys
    2885                2890                2895

Gly Asn Asn Pro Arg Glu Ile Arg Asp Leu Met Ser Gln Gly Arg
    2900                2905                2910

Ile Leu Thr Val Ala Leu Lys Glu Leu Asp Pro Glu Leu Lys Glu
    2915                2920                2925

Leu Val Asp Tyr Lys Gly Thr Phe Leu Asn Arg Glu Ala Leu Glu
    2930                2935                2940

Ala Leu Ser Leu Gly Lys Pro Ile Lys Arg Lys Thr Thr Thr Ala
    2945                2950                2955

Met Ile Arg Arg Leu Ile Glu Pro Glu Val Glu Glu Glu Leu Pro
    2960                2965                2970

Asp Trp Phe Gln Ala Glu Glu Pro Leu Phe Leu Glu Ala Lys Ile
    2975                2980                2985

Gln Asn Asp Leu Tyr His Leu Ile Gly Ser Val Asp Ser Ile Lys
    2990                2995                3000

Ser Lys Ala Lys Glu Leu Gly Ala Thr Asp Asn Thr Lys Ile Val
    3005                3010                3015

Lys Glu Val Gly Ala Arg Thr Tyr Thr Met Lys Leu Ser Ser Trp
    3020                3025                3030

Ser Thr Gln Val Thr Lys Lys Gln Met Ser Leu Ala Pro Leu Phe
    3035                3040                3045

Glu Glu Leu Leu Leu Lys Cys Pro Pro Cys Ser Lys Ile Ser Lys
    3050                3055                3060

Gly His Met Val Ser Ala Tyr Gln Leu Ala Gln Gly Asn Trp Glu
    3065                3070                3075

Pro Leu Gly Cys Gly Val Tyr Met Gly Thr Ile Pro Ala Arg Arg
    3080                3085                3090

Leu Lys Ile His Pro Tyr Glu Ala Tyr Leu Lys Leu Lys Glu Leu
    3095                3100                3105

Val Glu Val Glu Ser Ser Arg Ala Thr Ala Lys Glu Ser Ile Ile
    3110                3115                3120

Arg Glu His Asn Thr Trp Ile Leu Arg Lys Val Arg His Glu Gly
    3125                3130                3135

Asn Leu Arg Thr Lys Ser Met Ile Asn Pro Gly Lys Ile Ser Asp
    3140                3145                3150

Gln Leu Cys Arg Asp Gly His Lys Arg Asn Ile Tyr Asn Lys Ile
    3155                3160                3165

Ile Gly Ser Thr Met Ala Ser Ala Gly Ile Arg Leu Glu Lys Leu
    3170                3175                3180

Pro Val Val Arg Ala Gln Thr Asp Thr Thr Ser Phe His Gln Ala
    3185                3190                3195

Ile Arg Glu Lys Ile Asp Lys Thr Glu Asn Lys Gln Thr Pro Glu
    3200                3205                3210

Leu His Glu Glu Leu Met Lys Val Phe Asp Cys Leu Lys Ile Pro
    3215                3220                3225

Glu Leu Lys Glu Ser Tyr Asp Glu Val Ser Trp Glu Gln Leu Glu
```

-continued

```
    3230                3235                3240

Ala Gly  Ile Asn Arg Lys Gly  Ala Ala Gly Tyr Leu  Glu Ser Lys
    3245                3250                3255

Asn Ile  Gly Glu Val Leu Asp  Thr Glu Lys His Ile  Val Glu Gln
    3260                3265                3270

Leu Ile  Lys Asp Leu Arg Lys  Gly Lys Lys Ile Arg  Tyr Tyr Glu
    3275                3280                3285

Thr Ala  Ile Pro Lys Asn Glu  Lys Arg Asp Val Ser  Asp Asp Trp
    3290                3295                3300

Glu Ala  Gly Glu Phe Val Asp  Glu Lys Lys Pro Arg  Val Ile Gln
    3305                3310                3315

Tyr Pro  Asp Ala Lys Val Arg  Leu Ala Ile Thr Lys  Val Met Tyr
    3320                3325                3330

Lys Trp  Val Lys Gln Lys Pro  Val Val Ile Pro Gly  Tyr Glu Gly
    3335                3340                3345

Lys Thr  Pro Leu Phe Asp Ile  Phe Asn Lys Val Lys  Lys Glu Trp
    3350                3355                3360

Asp Ser  Phe Gln Asp Pro Val  Ala Val Ser Phe Asp  Thr Lys Ala
    3365                3370                3375

Trp Asp  Thr Gln Val Thr Ser  Arg Asp Leu Met Leu  Ile Lys Asp
    3380                3385                3390

Ile Gln  Lys Tyr Tyr Phe Lys  Arg Ser Ile His Lys  Phe Leu Asp
    3395                3400                3405

Thr Ile  Thr Glu His Met Val  Glu Val Pro Val Ile  Thr Ala Asp
    3410                3415                3420

Gly Glu  Val Tyr Ile Arg Asn  Gly Gln Arg Gly Ser  Gly Gln Pro
    3425                3430                3435

Asp Thr  Ser Ala Gly Asn Ser  Met Leu Asn Val Leu  Thr Met Ile
    3440                3445                3450

Tyr Ala  Phe Cys Lys Ser Thr  Gly Ile Pro Tyr Arg  Gly Phe Ser
    3455                3460                3465

Arg Val  Ala Arg Ile His Val  Cys Gly Asp Asp Gly  Phe Leu Ile
    3470                3475                3480

Thr Glu  Arg Gly Leu Gly Leu  Lys Phe Ser Glu Lys  Gly Met Gln
    3485                3490                3495

Ile Leu  His Glu Ala Gly Lys  Pro Gln Lys Ile Thr  Glu Gly Asp
    3500                3505                3510

Lys Met  Lys Val Ala Tyr Arg  Phe Glu Asp Ile Glu  Phe Cys Ser
    3515                3520                3525

His Thr  Pro Val Pro Val Arg  Trp Ala Asp Asn Thr  Ser Ser Tyr
    3530                3535                3540

Met Ala  Gly Arg Ser Thr Ala  Thr Ile Leu Ala Lys  Met Ala Thr
    3545                3550                3555

Arg Leu  Asp Ser Ser Gly Glu  Arg Gly Ser Thr Ala  Tyr Glu Lys
    3560                3565                3570

Ala Val  Ala Phe Ser Phe Leu  Leu Met Tyr Ser Trp  Asn Pro Val
    3575                3580                3585

Val Arg  Arg Ile Cys Leu Leu  Val Leu Ser Gln Phe  Pro Glu Ile
    3590                3595                3600

Ser Pro  Ser Lys Asn Thr Ile  Tyr Tyr Tyr Gln Gly  Asp Pro Ile
    3605                3610                3615

Ala Ala  Tyr Arg Glu Val Ile  Gly Lys Gln Leu Cys  Glu Leu Lys
    3620                3625                3630
```

-continued

```
Arg Thr  Gly Phe Glu Lys Leu  Ala Gly Leu Asn Leu  Ser Met Thr
    3635                 3640                 3645

Thr Leu  Gly Ile Trp Thr Lys  His Thr Ser Lys Arg  Leu Ile Gln
    3650                 3655                 3660

Ala Cys  Val Glu Ile Gly Lys  Arg Glu Gly Thr Trp  Leu Val Asn
    3665                 3670                 3675

Ala Asp  Arg Leu Ile Ala Gly  Lys Thr Gly Lys Phe  Tyr Ile Pro
    3680                 3685                 3690

Ser Thr  Gly Val Thr Leu Leu  Gly Lys His Tyr Glu  Glu Ile Asn
    3695                 3700                 3705

Leu Lys  Gln Lys Ala Ala Gln  Pro Pro Ile Glu Gly  Val Asp Arg
    3710                 3715                 3720

Tyr Lys  Leu Gly Pro Ile Val  Asn Val Ile Leu Arg  Arg Leu Arg
    3725                 3730                 3735

Val Met  Leu Met Thr Val Ala  Ser Gly Ser Trp
    3740                 3745
```

<210> SEQ ID NO 7
<211> LENGTH: 3912
<212> TYPE: PRT
<213> ORGANISM: Artificial
<220> FEATURE:
<223> OTHER INFORMATION: Mutated BVDV: XIKE-B

<400> SEQUENCE: 7

```
Met Glu Leu Phe Ser Asn Glu Leu Leu Tyr Lys Thr Tyr Lys Gln Lys
1               5                   10                  15

Pro Ala Gly Val Val Glu Pro Val Tyr Asp Val Asn Gly Arg Pro Leu
            20                  25                  30

Phe Gly Glu Ser Ser Asp Leu His Pro Gln Ser Thr Leu Lys Leu Pro
        35                  40                  45

His Gln Arg Gly Ser Ala Asn Ile Leu Thr Asn Ala Arg Ser Leu Pro
    50                  55                  60

Arg Lys Gly Asp Cys Arg Arg Gly Asn Val Tyr Gly Pro Val Ser Gly
65                  70                  75                  80

Ile Tyr Ile Lys Pro Gly Pro Ile Tyr Tyr Gln Asp Tyr Val Gly Pro
                85                  90                  95

Val Tyr His Arg Ala Pro Leu Glu Leu Cys Arg Glu Ala Ser Met Cys
            100                 105                 110

Glu Thr Thr Arg Arg Val Gly Arg Val Thr Gly Ser Asp Gly Lys Leu
        115                 120                 125

Tyr His Ile Tyr Ile Cys Ile Asp Gly Cys Ile Leu Leu Lys Arg Ala
    130                 135                 140

Thr Arg Asn Gln Pro Glu Val Leu Lys Trp Val Tyr Asn Arg Leu Asn
145                 150                 155                 160

Cys Pro Leu Trp Val Thr Ser Cys Ser Asp Glu Gly Ser Lys Gly Ala
                165                 170                 175

Thr Ser Lys Lys Gln Pro Lys Pro Asp Arg Ile Glu Lys Gly Lys Met
            180                 185                 190

Lys Ile Ala Pro Lys Glu Thr Glu Lys Asp Cys Lys Thr Arg Pro Pro
        195                 200                 205

Asp Ala Thr Ile Val Val Glu Gly Val Lys Tyr Gln Val Lys Lys Lys
    210                 215                 220

Gly Lys Val Arg Gly Lys Asn Thr Gln Asp Gly Leu Tyr His Asn Lys
225                 230                 235                 240
```

-continued

```
Asn Lys Pro Pro Glu Ser Arg Lys Lys Leu Glu Lys Ala Leu Leu Ala
                245                 250                 255

Trp Ala Ile Leu Ala Ala Val Leu Leu Gln Leu Val Thr Gly Glu Asn
            260                 265                 270

Ile Thr Gln Trp Asn Leu Met Asp Asn Gly Thr Glu Gly Ile Gln Gln
        275                 280                 285

Ala Met Phe Leu Arg Gly Val Asn Arg Ser Leu His Gly Ile Trp Pro
    290                 295                 300

Glu Lys Ile Cys Thr Gly Val Pro Thr His Leu Ala Thr Asp Tyr Glu
305                 310                 315                 320

Leu Lys Glu Ile Val Gly Met Met Asp Ala Ser Glu Lys Thr Asn Tyr
                325                 330                 335

Thr Cys Cys Arg Leu Gln Arg His Glu Trp Asn Lys Gly Trp Cys Asn
            340                 345                 350

Trp Phe His Ile Glu Pro Trp Ile Trp Leu Met Asn Lys Thr Gln Asn
        355                 360                 365

Asn Leu Thr Glu Gly Gln Pro Leu Arg Glu Cys Ala Val Thr Cys Arg
    370                 375                 380

Tyr Asp Lys Glu Thr Glu Leu Asn Ile Val Thr Gln Ala Arg Asp Arg
385                 390                 395                 400

Pro Thr Thr Leu Thr Gly Cys Lys Lys Gly Lys Asn Phe Ser Phe Ala
                405                 410                 415

Gly Val Ile Leu Asp Gly Pro Cys Asn Phe Lys Val Ser Val Glu Asp
            420                 425                 430

Val Leu Phe Lys Glu His Asp Cys Gly Asn Met Leu Gln Glu Thr Ala
        435                 440                 445

Ile Gln Leu Leu Asp Gly Ala Thr Asn Thr Ile Glu Gly Ala Arg Val
    450                 455                 460

Gly Thr Ala Lys Leu Thr Thr Trp Leu Gly Lys Gln Leu Gly Ile Leu
465                 470                 475                 480

Gly Lys Lys Leu Glu Asn Lys Ser Lys Ala Trp Phe Gly Ala His Ala
                485                 490                 495

Ala Ser Pro Tyr Cys Gly Val Glu Arg Lys Ile Gly Tyr Val Trp Tyr
            500                 505                 510

Thr Lys Asn Cys Thr Pro Ala Cys Leu Pro Arg Asn Thr Arg Ile Ile
        515                 520                 525

Gly Pro Gly Lys Phe Asp Thr Asn Ala Glu Asp Gly Lys Ile Leu His
    530                 535                 540

Glu Met Gly Gly His Leu Ser Glu Phe Val Leu Leu Ser Leu Val Val
545                 550                 555                 560

Leu Ser Asp Phe Ala Pro Glu Thr Ala Ser Val Ile Tyr Leu Val Leu
                565                 570                 575

His Phe Ala Ile Pro Gln Ser His Val Asp Val Asp Thr Cys Asp Lys
            580                 585                 590

Asn Gln Leu Asn Leu Thr Val Ala Thr Thr Val Ala Glu Val Ile Pro
        595                 600                 605

Gly Thr Val Trp Asn Leu Gly Lys Tyr Val Cys Ile Arg Pro Asp Trp
    610                 615                 620

Trp Pro Tyr Glu Thr Thr Thr Val Phe Val Ile Glu Glu Ala Gly Gln
625                 630                 635                 640

Val Ile Lys Leu Met Leu Arg Ala Ile Arg Asp Leu Thr Arg Ile Trp
                645                 650                 655
```

-continued

```
Asn Ala Ala Thr Thr Thr Ala Phe Leu Ile Phe Leu Val Lys Ala Leu
            660                 665                 670

Arg Gly Gln Leu Ile Gln Gly Leu Leu Trp Leu Met Leu Ile Thr Gly
        675                 680                 685

Ala Gln Gly Phe Pro Glu Cys Lys Glu Gly Phe Gln Tyr Ala Ile Ser
    690                 695                 700

Lys Asp Arg Lys Met Gly Leu Leu Gly Pro Glu Ser Leu Thr Thr Thr
705                 710                 715                 720

Trp His Leu Pro Thr Lys Lys Ile Val Asp Ser Met Val His Val Trp
                725                 730                 735

Cys Glu Gly Lys Asp Leu Lys Ile Leu Lys Met Cys Thr Lys Glu Glu
            740                 745                 750

Arg Tyr Leu Val Ala Val His Glu Arg Ala Leu Ser Thr Ser Ala Glu
        755                 760                 765

Phe Met Gln Ile Ser Asp Gly Thr Ile Gly Pro Asp Val Ile Asp Met
    770                 775                 780

Pro Asp Asp Phe Glu Phe Gly Leu Cys Pro Cys Asp Ser Lys Pro Val
785                 790                 795                 800

Ile Lys Gly Lys Phe Asn Ala Ser Leu Leu Asn Gly Pro Ala Phe Gln
                805                 810                 815

Met Val Cys Pro Gln Gly Trp Thr Gly Thr Ile Glu Cys Thr Leu Ala
            820                 825                 830

Asn Gln Asp Thr Leu Asp Thr Thr Val Ile Arg Thr Tyr Arg Arg Thr
        835                 840                 845

Thr Pro Phe Gln Arg Arg Lys Trp Cys Thr Tyr Glu Lys Ile Ile Gly
    850                 855                 860

Glu Asp Ile Tyr Glu Cys Ile Leu Gly Gly Asn Trp Thr Cys Ile Thr
865                 870                 875                 880

Gly Asp His Ser Arg Leu Lys Asp Gly Pro Ile Lys Lys Cys Lys Trp
                885                 890                 895

Cys Gly His Asp Phe Val Asn Ser Glu Gly Leu Pro His Tyr Pro Ile
            900                 905                 910

Gly Lys Cys Met Leu Ile Asn Glu Ser Gly Tyr Arg Tyr Val Asp Asp
        915                 920                 925

Thr Ser Cys Asp Arg Gly Gly Val Ala Ile Val Pro Ser Gly Thr Val
    930                 935                 940

Lys Cys Arg Ile Gly Asn Val Thr Val Gln Val Ile Ala Thr Asn Asn
945                 950                 955                 960

Asp Leu Gly Pro Met Pro Cys Ser Pro Ala Glu Val Ile Ala Ser Glu
                965                 970                 975

Gly Pro Val Glu Lys Thr Ala Cys Thr Phe Asn Tyr Ser Arg Thr Leu
            980                 985                 990

Pro Asn Lys Tyr Tyr Glu Pro Arg  Asp Arg Tyr Phe Gln  Gln Tyr Met
        995                 1000                1005

Leu Lys  Gly Glu Trp Gln Tyr  Trp Phe Asp Leu Asp  Ser Val Asp
    1010                1015                1020

His His  Lys Asp Tyr Phe Ser  Glu Phe Ile Ile Ile  Ala Val Val
    1025                1030                1035

Ala Leu  Leu Gly Gly Lys Tyr  Val Leu Trp Leu Leu  Ile Thr Tyr
    1040                1045                1050

Thr Ile  Leu Ser Glu Gln Met  Ala Met Gly Ala Gly  Val Asn Thr
    1055                1060                1065

Glu Glu  Ile Val Met Ile Gly  Asn Leu Leu Thr Asp  Ser Asp Ile
```

```
    1070                1075                1080

Glu Val  Val Val Tyr Phe Leu  Leu Leu Tyr Leu Ile  Val Lys Glu
    1085                1090                1095

Glu Leu  Ala Arg Lys Trp Ile  Ile Leu Val Tyr His  Ile Leu Val
    1100                1105                1110

Ala Asn  Pro Met Lys Thr Ile  Gly Val Val Leu Leu  Met Leu Gly
    1115                1120                1125

Gly Val  Val Lys Ala Ser Arg  Ile Asn Ala Asp Asp  Gln Ser Ala
    1130                1135                1140

Met Asp  Pro Cys Phe Leu Leu  Val Thr Gly Val Val  Ala Val Leu
    1145                1150                1155

Met Ile  Ala Arg Arg Glu Pro  Ala Thr Leu Pro Leu  Ile Val Ala
    1160                1165                1170

Leu Leu  Ala Ile Arg Thr Ser  Gly Phe Leu Leu Pro  Ala Ser Ile
    1175                1180                1185

Asp Val  Thr Val Ala Val Val  Leu Ile Val Leu Leu  Leu Ala Ser
    1190                1195                1200

Tyr Ile  Thr Asp Tyr Phe Arg  Tyr Lys Lys Trp Leu  Gln Leu Leu
    1205                1210                1215

Phe Ser  Leu Ile Ala Gly Ile  Phe Ile Ile Arg Ser  Leu Lys His
    1220                1225                1230

Ile Asn  Gln Met Glu Val Pro  Glu Ile Ser Met Pro  Ser Trp Arg
    1235                1240                1245

Pro Leu  Ala Leu Val Leu Phe  Tyr Ile Thr Ser Thr  Ala Ile Thr
    1250                1255                1260

Thr Asn  Trp Asp Ile Asp Leu  Ala Gly Phe Leu Leu  Gln Trp Ala
    1265                1270                1275

Pro Ala  Val Ile Met Met Ala  Thr Met Trp Ala Asp  Phe Leu Thr
    1280                1285                1290

Leu Ile  Ile Val Leu Pro Ser  Tyr Glu Leu Ser Lys  Leu Tyr Phe
    1295                1300                1305

Leu Lys  Asn Val Arg Thr Asp  Val Glu Lys Asn Trp  Leu Gly Lys
    1310                1315                1320

Val Lys  Tyr Arg Gln Ile Ser  Ser Val Tyr Asp Ile  Cys Asp Ser
    1325                1330                1335

Glu Glu  Ala Val Tyr Leu Phe  Pro Ser Arg His Lys  Ser Gly Ser
    1340                1345                1350

Arg Pro  Asp Phe Ile Leu Pro  Phe Leu Lys Ala Val  Leu Ile Ser
    1355                1360                1365

Cys Ile  Ser Ser Gln Trp Gln  Val Val Tyr Ile Ser  Tyr Leu Ile
    1370                1375                1380

Leu Glu  Ile Thr Tyr Tyr Met  His Arg Lys Ile Ile  Asp Glu Val
    1385                1390                1395

Ser Gly  Gly Ala Asn Phe Leu  Ser Arg Leu Ile Ala  Ala Ile Ile
    1400                1405                1410

Glu Leu  Asn Trp Ala Ile Asp  Asp Glu Glu Cys Lys  Gly Leu Lys
    1415                1420                1425

Lys Leu  Tyr Leu Leu Ser Gly  Arg Ala Lys Asn Leu  Ile Val Lys
    1430                1435                1440

His Lys  Val Arg Asn Glu Ala  Val His Arg Trp Phe  Gly Glu Glu
    1445                1450                1455

Glu Ile  Tyr Gly Ala Pro Lys  Val Ile Thr Ile Ile  Lys Ala Ser
    1460                1465                1470
```

-continued

```
Thr Leu Ser Lys Asn Arg His Cys Ile Ile Cys Thr Ile Cys Glu
    1475                1480                1485

Gly Lys Glu Trp Asn Gly Ala Asn Cys Pro Lys Cys Gly Arg Gln
    1490                1495                1500

Gly Lys Pro Ile Thr Cys Gly Met Thr Leu Ala Asp Phe Glu Glu
    1505                1510                1515

Lys His Tyr Lys Lys Ile Phe Ile Arg Glu Glu Ser Ser Cys Pro
    1520                1525                1530

Val Pro Phe Asp Pro Ser Cys His Cys Asn Tyr Phe Arg His Asp
    1535                1540                1545

Gly Pro Phe Arg Lys Glu Tyr Lys Gly Tyr Val Gln Tyr Thr Ala
    1550                1555                1560

Arg Gly Gln Leu Phe Leu Arg Asn Leu Pro Ile Leu Ala Thr Lys
    1565                1570                1575

Met Lys Leu Leu Met Val Gly Asn Leu Gly Ala Glu Ile Gly Asp
    1580                1585                1590

Leu Glu His Leu Gly Trp Val Leu Arg Gly Pro Ala Val Cys Lys
    1595                1600                1605

Lys Ile Thr Asn His Glu Lys Cys His Val Asn Ile Met Asp Lys
    1610                1615                1620

Leu Thr Ala Phe Phe Gly Ile Met Pro Arg Gly Thr Thr Pro Arg
    1625                1630                1635

Ala Pro Val Arg Phe Pro Thr Ala Leu Leu Lys Val Arg Arg Gly
    1640                1645                1650

Leu Glu Thr Gly Trp Ala Tyr Thr His Gln Gly Gly Ile Ser Ser
    1655                1660                1665

Val Asp His Val Thr Ala Gly Lys Asp Leu Leu Val Cys Asp Ser
    1670                1675                1680

Met Gly Arg Thr Arg Val Val Cys His Ser Asn Asn Lys Met Thr
    1685                1690                1695

Asp Glu Thr Glu Tyr Gly Ile Lys Thr Asp Ser Gly Cys Pro Glu
    1700                1705                1710

Gly Ala Arg Cys Tyr Val Leu Asn Pro Glu Ala Val Asn Ile Ser
    1715                1720                1725

Gly Thr Lys Gly Ala Met Val His Leu Gln Lys Thr Gly Gly Glu
    1730                1735                1740

Phe Thr Cys Val Thr Ala Ser Gly Thr Pro Ala Phe Phe Asp Leu
    1745                1750                1755

Lys Asn Leu Lys Gly Trp Ser Gly Leu Pro Ile Phe Glu Ala Ser
    1760                1765                1770

Ser Gly Arg Val Val Gly Arg Val Lys Val Gly Lys Asn Glu Asp
    1775                1780                1785

Ser Lys Pro Thr Lys Leu Met Ser Gly Ile Gln Thr Val Ser Lys
    1790                1795                1800

Asn Gln Thr Asp Leu Ala Asp Ile Val Lys Lys Leu Thr Ser Met
    1805                1810                1815

Asn Arg Gly Glu Phe Lys Gln Ile Thr Leu Ala Thr Gly Ala Gly
    1820                1825                1830

Lys Thr Thr Glu Leu Pro Arg Ser Val Ile Glu Glu Ile Gly Arg
    1835                1840                1845

His Lys Arg Val Leu Val Leu Ile Pro Leu Arg Ala Ala Ala Glu
    1850                1855                1860
```

-continued

```
Ser Val  Tyr Gln Tyr Met Arg  Val Lys Tyr Pro Ser  Ile Ser Phe
    1865                 1870                 1875

Asn Leu  Arg Ile Gly Asp Met  Lys Glu Gly Asp Met  Ala Thr Gly
    1880                 1885                 1890

Ile Thr  Tyr Ala Ser Tyr Gly  Tyr Phe Cys Gln Leu  Pro Gln Pro
    1895                 1900                 1905

Lys Leu  Arg Ala Ala Met Val  Glu Tyr Ser Tyr Ile  Phe Leu Asp
    1910                 1915                 1920

Glu Tyr  His Cys Ala Thr Pro  Glu Gln Leu Ala Ile  Ile Gly Lys
    1925                 1930                 1935

Ile His  Arg Phe Ala Glu Asn  Leu Arg Val Val Ala  Met Thr Ala
    1940                 1945                 1950

Thr Pro  Ala Gly Thr Val Thr  Thr Thr Gly Gln Lys  His Pro Ile
    1955                 1960                 1965

Glu Glu  Phe Ile Ala Pro Glu  Val Met Lys Gly Glu  Asp Leu Gly
    1970                 1975                 1980

Ser Glu  Tyr Leu Asp Ile Ala  Gly Leu Lys Ile Pro  Thr Glu Glu
    1985                 1990                 1995

Met Lys  Gly Asn Met Leu Val  Phe Ala Pro Thr Arg  Asn Met Ala
    2000                 2005                 2010

Val Glu  Thr Ala Lys Lys Leu  Lys Ala Lys Gly Tyr  Asn Ser Gly
    2015                 2020                 2025

Tyr Tyr  Tyr Ser Gly Glu Asn  Pro Glu Asn Leu Arg  Val Val Thr
    2030                 2035                 2040

Ser Gln  Ser Pro Tyr Val Val  Val Ala Thr Asn Ala  Ile Glu Ser
    2045                 2050                 2055

Gly Val  Thr Leu Pro Asp Leu  Asp Thr Val Val Asp  Thr Gly Leu
    2060                 2065                 2070

Lys Cys  Glu Lys Arg Val Arg  Ile Ser Ser Lys Met  Pro Phe Ile
    2075                 2080                 2085

Val Thr  Gly Leu Lys Arg Met  Ala Val Thr Ile Gly  Glu Gln Ala
    2090                 2095                 2100

Gln Arg  Arg Gly Arg Val Gly  Arg Val Lys Pro Gly  Arg Tyr Tyr
    2105                 2110                 2115

Arg Ser  Gln Glu Thr Ala Ser  Gly Ser Lys Asp Tyr  His Tyr Asp
    2120                 2125                 2130

Leu Leu  Gln Ala Gln Arg Tyr  Gly Ile Glu Asp Gly  Ile Asn Val
    2135                 2140                 2145

Thr Lys  Ser Phe Arg Glu Met  Asn Tyr Asp Trp Ser  Leu Tyr Glu
    2150                 2155                 2160

Glu Asp  Ser Leu Met Ile Thr  Gln Leu Glu Val Leu  Asn Asn Leu
    2165                 2170                 2175

Leu Ile  Ser Glu Asp Leu Pro  Ala Ala Val Lys Asn  Ile Met Ala
    2180                 2185                 2190

Arg Thr  Asp His Pro Glu Pro  Ile Gln Leu Ala Tyr  Asn Ser Tyr
    2195                 2200                 2205

Glu Asn  Gln Ile Pro Val Leu  Phe Pro Lys Ile Lys  Asn Gly Glu
    2210                 2215                 2220

Val Thr  Asp Ser Tyr Glu Asn  Tyr Thr Tyr Leu Asn  Ala Arg Lys
    2225                 2230                 2235

Leu Gly  Glu Asp Val Pro Ala  Tyr Val Tyr Ala Thr  Glu Asp Glu
    2240                 2245                 2250

Asp Leu  Ala Val Asp Leu Leu  Gly Met Asp Trp Pro  Asp Pro Gly
```

```
    2255                2260                2265

Asn Gln  Gln Val Val Glu Thr  Gly Arg Ala Leu Lys  Gln Val Thr
    2270                2275                2280

Gly Leu  Ser Thr Ala Glu Asn  Ala Leu Leu Ile Ala  Leu Phe Gly
    2285                2290                2295

Tyr Val  Gly Tyr Gln Thr Leu  Ser Lys Arg His Ile  Pro Met Ile
    2300                2305                2310

Thr Asp  Ile Tyr Thr Leu Glu  Asp His Arg Leu Glu  Asp Thr Thr
    2315                2320                2325

His Leu  Gln Phe Ala Pro Asn  Ala Ile Arg Thr Asp  Gly Lys Asp
    2330                2335                2340

Ser Glu  Leu Lys Glu Leu Ala  Val Gly Asp Leu Asp  Lys Tyr Val
    2345                2350                2355

Asp Ala  Leu Val Asp Tyr Ser  Lys Gln Gly Met Lys  Phe Ile Lys
    2360                2365                2370

Val Gln  Ala Glu Lys Val Arg  Asp Ser Gln Ser Thr  Lys Glu Gly
    2375                2380                2385

Leu Gln  Thr Ile Lys Glu Tyr  Val Asp Lys Phe Ile  Gln Ser Leu
    2390                2395                2400

Thr Glu  Asn Lys Glu Glu Ile  Ile Arg Tyr Gly Leu  Trp Gly Val
    2405                2410                2415

His Thr  Ala Leu Tyr Lys Ser  Leu Ala Ala Arg Leu  Gly His Glu
    2420                2425                2430

Thr Ala  Phe Ala Thr Leu Val  Val Lys Trp Leu Ala  Phe Gly Gly
    2435                2440                2445

Glu Thr  Val Ser Ala His Ile  Lys Gln Val Ala Val  Asp Leu Val
    2450                2455                2460

Val Tyr  Tyr Ile Ile Asn Lys  Pro Ser Phe Pro Gly  Asp Thr Glu
    2465                2470                2475

Thr Gln  Gln Glu Gly Arg Arg  Phe Val Ala Ser Leu  Phe Ile Ser
    2480                2485                2490

Ala Leu  Ala Thr Tyr Thr Tyr  Lys Thr Trp Asn Tyr  Asn Asn Leu
    2495                2500                2505

Gln Arg  Val Val Glu Pro Ala  Leu Ala Tyr Leu Pro  Tyr Ala Thr
    2510                2515                2520

Ser Ala  Leu Lys Leu Phe Thr  Pro Thr Arg Leu Glu  Ser Val Val
    2525                2530                2535

Ile Leu  Ser Ser Thr Ile Tyr  Lys Thr Tyr Leu Ser  Ile Arg Lys
    2540                2545                2550

Gly Lys  Ser Asp Gly Leu Leu  Gly Thr Gly Ile Ser  Ala Ala Met
    2555                2560                2565

Glu Ile  Leu Asn Gln Asn Pro  Ile Ser Val Gly Ile  Ser Val Met
    2570                2575                2580

Leu Gly  Val Gly Ala Ile Ala  Ala His Asn Ala Ile  Glu Ser Ser
    2585                2590                2595

Glu Gln  Lys Arg Thr Leu Leu  Met Lys Val Phe Val  Lys Asn Phe
    2600                2605                2610

Leu Asp  Gln Ala Ala Thr Asp  Glu Leu Val Lys Glu  Asn Pro Glu
    2615                2620                2625

Lys Ile  Ile Met Ala Leu Phe  Glu Ala Val Gln Thr  Ile Gly Asn
    2630                2635                2640

Pro Leu  Arg Leu Ile Tyr His  Leu Tyr Gly Val Tyr  Tyr Lys Gly
    2645                2650                2655
```

-continued

```
Trp Glu Ala Lys Glu Leu Ala Glu Lys Thr Ala Gly Arg Asn Leu
    2660                2665                2670

Phe Thr Leu Ile Met Phe Glu Ala Phe Glu Leu Leu Gly Met Asp
    2675                2680                2685

Ser Glu Gly Lys Ile Arg Asn Leu Ser Gly Asn Tyr Ile Leu Asp
    2690                2695                2700

Leu Ile Phe Asn Leu His Asn Lys Leu Asn Lys Gly Leu Lys Lys
    2705                2710                2715

Leu Val Leu Gly Trp Ala Pro Ala Pro Leu Ser Cys Asp Trp Thr
    2720                2725                2730

Pro Ser Asp Glu Arg Ile Ser Leu Pro His Asn Asn Tyr Leu Arg
    2735                2740                2745

Val Glu Thr Arg Cys Pro Cys Gly Tyr Glu Met Lys Ala Ile Lys
    2750                2755                2760

Asn Val Ala Gly Lys Leu Thr Lys Val Glu Glu Lys Gly Ser Phe
    2765                2770                2775

Leu Cys Arg Asn Arg Leu Gly Arg Gly Pro Pro Asn Phe Lys Val
    2780                2785                2790

Thr Lys Phe Tyr Asp Asp Asn Leu Ile Glu Val Lys Pro Val Ala
    2795                2800                2805

Arg Leu Glu Gly Gln Val Asp Leu Tyr Tyr Lys Gly Val Thr Ala
    2810                2815                2820

Lys Leu Asp Tyr Asn Asn Gly Lys Val Leu Leu Ala Thr Asn Lys
    2825                2830                2835

Trp Glu Val Asp His Ala Phe Leu Thr Arg Leu Val Lys Lys His
    2840                2845                2850

Thr Gly Ile Gly Phe Lys Gly Ala Tyr Leu Gly Asp Arg Pro Asp
    2855                2860                2865

His Gln Asp Leu Val Asp Arg Asp Cys Ala Thr Ile Thr Lys Asn
    2870                2875                2880

Ser Val Gln Phe Leu Lys Met Lys Lys Gly Cys Ala Phe Thr Tyr
    2885                2890                2895

Asp Leu Thr Ile Ser Asn Leu Val Arg Leu Ile Glu Leu Val His
    2900                2905                2910

Lys Asn Asn Leu Gln Glu Arg Glu Ile Pro Thr Val Thr Val Thr
    2915                2920                2925

Thr Trp Leu Ala Tyr Ser Phe Val Asn Glu Asp Leu Gly Thr Ile
    2930                2935                2940

Lys Pro Val Leu Gly Glu Lys Val Ile Pro Glu Pro Pro Glu Glu
    2945                2950                2955

Leu Ser Leu Gln Pro Thr Val Arg Leu Val Thr Thr Glu Thr Ala
    2960                2965                2970

Ile Thr Ile Thr Gly Glu Ala Glu Val Met Thr Thr Gly Ile Thr
    2975                2980                2985

Pro Val Val Glu Met Lys Glu Glu Pro Gln Leu Asp His Gln Ser
    2990                2995                3000

Thr Thr Leu Lys Val Gly Leu Lys Glu Gly Glu Tyr Pro Gly Pro
    3005                3010                3015

Gly Val Asn Pro Asn His Leu Ala Glu Val Ile Asp Glu Lys Asp
    3020                3025                3030

Asp Arg Pro Phe Val Leu Ile Ile Gly Asn Lys Gly Ser Thr Ser
    3035                3040                3045
```

-continued

```
Asn Arg  Ala Arg Thr Ala Lys  Asn Ile Arg Leu Tyr  Lys Gly Asn
    3050                 3055                 3060

Asn Pro  Arg Glu Ile Arg Asp  Leu Met Ser Gln Gly  Arg Ile Leu
    3065                 3070                 3075

Thr Val  Ala Leu Lys Glu Leu  Asp Pro Glu Leu Lys  Glu Leu Val
    3080                 3085                 3090

Asp Tyr  Lys Gly Thr Phe Leu  Asn Arg Glu Ala Leu  Glu Ala Leu
    3095                 3100                 3105

Ser Leu  Gly Lys Pro Ile Lys  Arg Lys Thr Thr Thr  Ala Met Ile
    3110                 3115                 3120

Arg Arg  Leu Ile Glu Pro Glu  Val Glu Glu Glu Leu  Pro Asp Trp
    3125                 3130                 3135

Phe Gln  Ala Glu Glu Pro Leu  Phe Leu Glu Ala Lys  Ile Gln Asn
    3140                 3145                 3150

Asp Leu  Tyr His Leu Ile Gly  Ser Val Asp Ser Ile  Lys Ser Lys
    3155                 3160                 3165

Ala Lys  Glu Leu Gly Ala Thr  Asp Asn Thr Lys Ile  Val Lys Glu
    3170                 3175                 3180

Val Gly  Ala Arg Thr Tyr Thr  Met Lys Leu Ser Ser  Trp Ser Thr
    3185                 3190                 3195

Gln Val  Thr Lys Lys Gln Met  Ser Leu Ala Pro Leu  Phe Glu Glu
    3200                 3205                 3210

Leu Leu  Leu Lys Cys Pro Pro  Cys Ser Lys Ile Ser  Lys Gly His
    3215                 3220                 3225

Met Val  Ser Ala Tyr Gln Leu  Ala Gln Gly Asn Trp  Glu Pro Leu
    3230                 3235                 3240

Gly Cys  Gly Val Tyr Met Gly  Thr Ile Pro Ala Arg  Arg Leu Lys
    3245                 3250                 3255

Ile His  Pro Tyr Glu Ala Tyr  Leu Lys Leu Lys Glu  Leu Val Glu
    3260                 3265                 3270

Val Glu  Ser Ser Arg Ala Thr  Ala Lys Glu Ser Ile  Ile Arg Glu
    3275                 3280                 3285

His Asn  Thr Trp Ile Leu Arg  Lys Val Arg His Glu  Gly Asn Leu
    3290                 3295                 3300

Arg Thr  Lys Ser Met Ile Asn  Pro Gly Lys Ile Ser  Asp Gln Leu
    3305                 3310                 3315

Cys Arg  Asp Gly His Lys Arg  Asn Ile Tyr Asn Lys  Ile Ile Gly
    3320                 3325                 3330

Ser Thr  Met Ala Ser Ala Gly  Ile Arg Leu Glu Lys  Leu Pro Val
    3335                 3340                 3345

Val Arg  Ala Gln Thr Asp Thr  Thr Ser Phe His Gln  Ala Ile Arg
    3350                 3355                 3360

Glu Lys  Ile Asp Lys Thr Glu  Asn Lys Gln Thr Pro  Glu Leu His
    3365                 3370                 3375

Glu Glu  Leu Met Lys Val Phe  Asp Cys Leu Lys Ile  Pro Glu Leu
    3380                 3385                 3390

Lys Glu  Ser Tyr Asp Glu Val  Ser Trp Glu Gln Leu  Glu Ala Gly
    3395                 3400                 3405

Ile Asn  Arg Lys Gly Ala Ala  Gly Tyr Leu Glu Ser  Lys Asn Ile
    3410                 3415                 3420

Gly Glu  Val Leu Asp Thr Glu  Lys His Ile Val Glu  Gln Leu Ile
    3425                 3430                 3435

Lys Asp  Leu Arg Lys Gly Lys  Lys Ile Arg Tyr Tyr  Glu Thr Ala
```

-continued

```
    3440                3445                3450

Ile Pro  Lys Asn Glu Lys Arg  Asp Val Ser Asp Asp  Trp Glu Ala
    3455                3460                3465

Gly Glu  Phe Val Asp Glu Lys  Lys Pro Arg Val Ile  Gln Tyr Pro
    3470                3475                3480

Asp Ala  Lys Val Arg Leu Ala  Ile Thr Lys Val Met  Tyr Lys Trp
    3485                3490                3495

Val Lys  Gln Lys Pro Val Val  Ile Pro Gly Tyr Glu  Gly Lys Thr
    3500                3505                3510

Pro Leu  Phe Asp Ile Phe Asn  Lys Val Lys Lys Glu  Trp Asp Ser
    3515                3520                3525

Phe Gln  Asp Pro Val Ala Val  Ser Phe Asp Thr Lys  Ala Trp Asp
    3530                3535                3540

Thr Gln  Val Thr Ser Arg Asp  Leu Met Leu Ile Lys  Asp Ile Gln
    3545                3550                3555

Lys Tyr  Tyr Phe Lys Arg Ser  Ile His Lys Phe Leu  Asp Thr Ile
    3560                3565                3570

Thr Glu  His Met Val Glu Val  Pro Val Ile Thr Ala  Asp Gly Glu
    3575                3580                3585

Val Tyr  Ile Arg Asn Gly Gln  Arg Gly Ser Gly Gln  Pro Asp Thr
    3590                3595                3600

Ser Ala  Gly Asn Ser Met Leu  Asn Val Leu Thr Met  Ile Tyr Ala
    3605                3610                3615

Phe Cys  Lys Ser Thr Gly Ile  Pro Tyr Arg Gly Phe  Ser Arg Val
    3620                3625                3630

Ala Arg  Ile His Val Cys Gly  Asp Asp Gly Phe Leu  Ile Thr Glu
    3635                3640                3645

Arg Gly  Leu Gly Leu Lys Phe  Ser Glu Lys Gly Met  Gln Ile Leu
    3650                3655                3660

His Glu  Ala Gly Lys Pro Gln  Lys Ile Thr Glu Gly  Asp Lys Met
    3665                3670                3675

Lys Val  Ala Tyr Arg Phe Glu  Asp Ile Glu Phe Cys  Ser His Thr
    3680                3685                3690

Pro Val  Pro Val Arg Trp Ala  Asp Asn Thr Ser Ser  Tyr Met Ala
    3695                3700                3705

Gly Arg  Ser Thr Ala Thr Ile  Leu Ala Lys Met Ala  Thr Arg Leu
    3710                3715                3720

Asp Ser  Ser Gly Glu Arg Gly  Ser Thr Ala Tyr Glu  Lys Ala Val
    3725                3730                3735

Ala Phe  Ser Phe Leu Leu Met  Tyr Ser Trp Asn Pro  Val Val Arg
    3740                3745                3750

Arg Ile  Cys Leu Leu Val Leu  Ser Gln Phe Pro Glu  Ile Ser Pro
    3755                3760                3765

Ser Lys  Asn Thr Ile Tyr Tyr  Tyr Gln Gly Asp Pro  Ile Ala Ala
    3770                3775                3780

Tyr Arg  Glu Val Ile Gly Lys  Gln Leu Cys Glu Leu  Lys Arg Thr
    3785                3790                3795

Gly Phe  Glu Lys Leu Ala Gly  Leu Asn Leu Ser Met  Thr Thr Leu
    3800                3805                3810

Gly Ile  Trp Thr Lys His Thr  Ser Lys Arg Leu Ile  Gln Ala Cys
    3815                3820                3825

Val Glu  Ile Gly Lys Arg Glu  Gly Thr Trp Leu Val  Asn Ala Asp
    3830                3835                3840
```

```
Arg Leu Ile Ala Gly Lys Thr Gly Lys Phe Tyr Ile Pro Ser Thr
    3845                3850                3855

Gly Val Thr Leu Leu Gly Lys His Tyr Glu Glu Ile Asn Leu Lys
    3860                3865                3870

Gln Lys Ala Ala Gln Pro Pro Ile Glu Gly Val Asp Arg Tyr Lys
    3875                3880                3885

Leu Gly Pro Ile Val Asn Val Ile Leu Arg Arg Leu Arg Val Met
    3890                3895                3900

Leu Met Thr Val Ala Ser Gly Ser Trp
    3905                3910


<210> SEQ ID NO 8
<211> LENGTH: 3748
<212> TYPE: PRT
<213> ORGANISM: Artificial
<220> FEATURE:
<223> OTHER INFORMATION: Mutated BVDV: XIKE-B-NdN

<400> SEQUENCE: 8

Met Glu Leu Phe Ser Asp Glu Gly Ser Lys Gly Ala Thr Ser Lys Lys
1               5                   10                  15

Gln Pro Lys Pro Asp Arg Ile Glu Lys Gly Lys Met Lys Ile Ala Pro
            20                  25                  30

Lys Glu Thr Glu Lys Asp Cys Lys Thr Arg Pro Pro Asp Ala Thr Ile
        35                  40                  45

Val Val Glu Gly Val Lys Tyr Gln Val Lys Lys Lys Gly Lys Val Arg
    50                  55                  60

Gly Lys Asn Thr Gln Asp Gly Leu Tyr His Asn Lys Asn Lys Pro Pro
65                  70                  75                  80

Glu Ser Arg Lys Lys Leu Glu Lys Ala Leu Leu Ala Trp Ala Ile Leu
                85                  90                  95

Ala Ala Val Leu Leu Gln Leu Val Thr Gly Glu Asn Ile Thr Gln Trp
            100                 105                 110

Asn Leu Met Asp Asn Gly Thr Glu Gly Ile Gln Gln Ala Met Phe Leu
        115                 120                 125

Arg Gly Val Asn Arg Ser Leu His Gly Ile Trp Pro Glu Lys Ile Cys
    130                 135                 140

Thr Gly Val Pro Thr His Leu Ala Thr Asp Tyr Glu Leu Lys Glu Ile
145                 150                 155                 160

Val Gly Met Met Asp Ala Ser Glu Lys Thr Asn Tyr Thr Cys Cys Arg
                165                 170                 175

Leu Gln Arg His Glu Trp Asn Lys Gly Trp Cys Asn Trp Phe His Ile
            180                 185                 190

Glu Pro Trp Ile Trp Leu Met Asn Lys Thr Gln Asn Asn Leu Thr Glu
        195                 200                 205

Gly Gln Pro Leu Arg Glu Cys Ala Val Thr Cys Arg Tyr Asp Lys Glu
    210                 215                 220

Thr Glu Leu Asn Ile Val Thr Gln Ala Arg Asp Arg Pro Thr Thr Leu
225                 230                 235                 240

Thr Gly Cys Lys Lys Gly Lys Asn Phe Ser Phe Ala Gly Val Ile Leu
                245                 250                 255

Asp Gly Pro Cys Asn Phe Lys Val Ser Val Glu Asp Val Leu Phe Lys
            260                 265                 270

Glu His Asp Cys Gly Asn Met Leu Gln Glu Thr Ala Ile Gln Leu Leu
        275                 280                 285
```

-continued

```
Asp Gly Ala Thr Asn Thr Ile Glu Gly Ala Arg Val Gly Thr Ala Lys
    290                 295                 300

Leu Thr Thr Trp Leu Gly Lys Gln Leu Gly Ile Leu Gly Lys Lys Leu
305                 310                 315                 320

Glu Asn Lys Ser Lys Ala Trp Phe Gly Ala His Ala Ala Ser Pro Tyr
                325                 330                 335

Cys Gly Val Glu Arg Lys Ile Gly Tyr Val Trp Tyr Thr Lys Asn Cys
            340                 345                 350

Thr Pro Ala Cys Leu Pro Arg Asn Thr Arg Ile Ile Gly Pro Gly Lys
        355                 360                 365

Phe Asp Thr Asn Ala Glu Asp Gly Lys Ile Leu His Glu Met Gly Gly
    370                 375                 380

His Leu Ser Glu Phe Val Leu Leu Ser Leu Val Val Leu Ser Asp Phe
385                 390                 395                 400

Ala Pro Glu Thr Ala Ser Val Ile Tyr Leu Val Leu His Phe Ala Ile
                405                 410                 415

Pro Gln Ser His Val Asp Val Asp Thr Cys Asp Lys Asn Gln Leu Asn
            420                 425                 430

Leu Thr Val Ala Thr Thr Val Ala Glu Val Ile Pro Gly Thr Val Trp
        435                 440                 445

Asn Leu Gly Lys Tyr Val Cys Ile Arg Pro Asp Trp Trp Pro Tyr Glu
    450                 455                 460

Thr Thr Thr Val Phe Val Ile Glu Glu Ala Gly Gln Val Ile Lys Leu
465                 470                 475                 480

Met Leu Arg Ala Ile Arg Asp Leu Thr Arg Ile Trp Asn Ala Ala Thr
                485                 490                 495

Thr Thr Ala Phe Leu Ile Phe Leu Val Lys Ala Leu Arg Gly Gln Leu
            500                 505                 510

Ile Gln Gly Leu Leu Trp Leu Met Leu Ile Thr Gly Ala Gln Gly Phe
        515                 520                 525

Pro Glu Cys Lys Glu Gly Phe Gln Tyr Ala Ile Ser Lys Asp Arg Lys
    530                 535                 540

Met Gly Leu Leu Gly Pro Glu Ser Leu Thr Thr Thr Trp His Leu Pro
545                 550                 555                 560

Thr Lys Lys Ile Val Asp Ser Met Val His Val Trp Cys Glu Gly Lys
                565                 570                 575

Asp Leu Lys Ile Leu Lys Met Cys Thr Lys Glu Glu Arg Tyr Leu Val
            580                 585                 590

Ala Val His Glu Arg Ala Leu Ser Thr Ser Ala Glu Phe Met Gln Ile
        595                 600                 605

Ser Asp Gly Thr Ile Gly Pro Asp Val Ile Asp Met Pro Asp Asp Phe
    610                 615                 620

Glu Phe Gly Leu Cys Pro Cys Asp Ser Lys Pro Val Ile Lys Gly Lys
625                 630                 635                 640

Phe Asn Ala Ser Leu Leu Asn Gly Pro Ala Phe Gln Met Val Cys Pro
                645                 650                 655

Gln Gly Trp Thr Gly Thr Ile Glu Cys Thr Leu Ala Asn Gln Asp Thr
            660                 665                 670

Leu Asp Thr Thr Val Ile Arg Thr Tyr Arg Arg Thr Thr Pro Phe Gln
        675                 680                 685

Arg Arg Lys Trp Cys Thr Tyr Glu Lys Ile Ile Gly Glu Asp Ile Tyr
    690                 695                 700
```

-continued

```
Glu Cys Ile Leu Gly Gly Asn Trp Thr Cys Ile Thr Gly Asp His Ser
705                 710                 715                 720

Arg Leu Lys Asp Gly Pro Ile Lys Lys Cys Lys Trp Cys Gly His Asp
                725                 730                 735

Phe Val Asn Ser Glu Gly Leu Pro His Tyr Pro Ile Gly Lys Cys Met
            740                 745                 750

Leu Ile Asn Glu Ser Gly Tyr Arg Tyr Val Asp Asp Thr Ser Cys Asp
        755                 760                 765

Arg Gly Gly Val Ala Ile Val Pro Ser Gly Thr Val Lys Cys Arg Ile
    770                 775                 780

Gly Asn Val Thr Val Gln Val Ile Ala Thr Asn Asn Asp Leu Gly Pro
785                 790                 795                 800

Met Pro Cys Ser Pro Ala Glu Val Ile Ala Ser Glu Gly Pro Val Glu
                805                 810                 815

Lys Thr Ala Cys Thr Phe Asn Tyr Ser Arg Thr Leu Pro Asn Lys Tyr
            820                 825                 830

Tyr Glu Pro Arg Asp Arg Tyr Phe Gln Gln Tyr Met Leu Lys Gly Glu
        835                 840                 845

Trp Gln Tyr Trp Phe Asp Leu Asp Ser Val Asp His His Lys Asp Tyr
    850                 855                 860

Phe Ser Glu Phe Ile Ile Ile Ala Val Val Ala Leu Leu Gly Gly Lys
865                 870                 875                 880

Tyr Val Leu Trp Leu Leu Ile Thr Tyr Thr Ile Leu Ser Glu Gln Met
                885                 890                 895

Ala Met Gly Ala Gly Val Asn Thr Glu Glu Ile Val Met Ile Gly Asn
            900                 905                 910

Leu Leu Thr Asp Ser Asp Ile Glu Val Val Val Tyr Phe Leu Leu Leu
        915                 920                 925

Tyr Leu Ile Val Lys Glu Glu Leu Ala Arg Lys Trp Ile Ile Leu Val
    930                 935                 940

Tyr His Ile Leu Val Ala Asn Pro Met Lys Thr Ile Gly Val Val Leu
945                 950                 955                 960

Leu Met Leu Gly Gly Val Val Lys Ala Ser Arg Ile Asn Ala Asp Asp
                965                 970                 975

Gln Ser Ala Met Asp Pro Cys Phe Leu Leu Val Thr Gly Val Val Ala
            980                 985                 990

Val Leu Met Ile Ala Arg Arg Glu  Pro Ala Thr Leu Pro  Leu Ile Val
        995                 1000                1005

Ala Leu  Leu Ala Ile Arg Thr  Ser Gly Phe Leu Leu  Pro Ala Ser
    1010                1015                1020

Ile Asp  Val Thr Val Ala Val  Val Leu Ile Val Leu  Leu Leu Ala
    1025                1030                1035

Ser Tyr  Ile Thr Asp Tyr Phe  Arg Tyr Lys Lys Trp  Leu Gln Leu
    1040                1045                1050

Leu Phe  Ser Leu Ile Ala Gly  Ile Phe Ile Ile Arg  Ser Leu Lys
    1055                1060                1065

His Ile  Asn Gln Met Glu Val  Pro Glu Ile Ser Met  Pro Ser Trp
    1070                1075                1080

Arg Pro  Leu Ala Leu Val Leu  Phe Tyr Ile Thr Ser  Thr Ala Ile
    1085                1090                1095

Thr Thr  Asn Trp Asp Ile Asp  Leu Ala Gly Phe Leu  Leu Gln Trp
    1100                1105                1110

Ala Pro  Ala Val Ile Met Met  Ala Thr Met Trp Ala  Asp Phe Leu
```

-continued

```
    1115                1120                1125

Thr Leu  Ile Ile Val Leu Pro  Ser Tyr Glu Leu Ser  Lys Leu Tyr
    1130                1135                1140

Phe Leu  Lys Asn Val Arg Thr  Asp Val Glu Lys Asn  Trp Leu Gly
    1145                1150                1155

Lys Val  Lys Tyr Arg Gln Ile  Ser Ser Val Tyr Asp  Ile Cys Asp
    1160                1165                1170

Ser Glu  Glu Ala Val Tyr Leu  Phe Pro Ser Arg His  Lys Ser Gly
    1175                1180                1185

Ser Arg  Pro Asp Phe Ile Leu  Pro Phe Leu Lys Ala  Val Leu Ile
    1190                1195                1200

Ser Cys  Ile Ser Ser Gln Trp  Gln Val Val Tyr Ile  Ser Tyr Leu
    1205                1210                1215

Ile Leu  Glu Ile Thr Tyr Tyr  Met His Arg Lys Ile  Ile Asp Glu
    1220                1225                1230

Val Ser  Gly Gly Ala Asn Phe  Leu Ser Arg Leu Ile  Ala Ala Ile
    1235                1240                1245

Ile Glu  Leu Asn Trp Ala Ile  Asp Asp Glu Glu Cys  Lys Gly Leu
    1250                1255                1260

Lys Lys  Leu Tyr Leu Leu Ser  Gly Arg Ala Lys Asn  Leu Ile Val
    1265                1270                1275

Lys His  Lys Val Arg Asn Glu  Ala Val His Arg Trp  Phe Gly Glu
    1280                1285                1290

Glu Glu  Ile Tyr Gly Ala Pro  Lys Val Ile Thr Ile  Ile Lys Ala
    1295                1300                1305

Ser Thr  Leu Ser Lys Asn Arg  His Cys Ile Ile Cys  Thr Ile Cys
    1310                1315                1320

Glu Gly  Lys Glu Trp Asn Gly  Ala Asn Cys Pro Lys  Cys Gly Arg
    1325                1330                1335

Gln Gly  Lys Pro Ile Thr Cys  Gly Met Thr Leu Ala  Asp Phe Glu
    1340                1345                1350

Glu Lys  His Tyr Lys Lys Ile  Phe Ile Arg Glu Glu  Ser Ser Cys
    1355                1360                1365

Pro Val  Pro Phe Asp Pro Ser  Cys His Cys Asn Tyr  Phe Arg His
    1370                1375                1380

Asp Gly  Pro Phe Arg Lys Glu  Tyr Lys Gly Tyr Val  Gln Tyr Thr
    1385                1390                1395

Ala Arg  Gly Gln Leu Phe Leu  Arg Asn Leu Pro Ile  Leu Ala Thr
    1400                1405                1410

Lys Met  Lys Leu Leu Met Val  Gly Asn Leu Gly Ala  Glu Ile Gly
    1415                1420                1425

Asp Leu  Glu His Leu Gly Trp  Val Leu Arg Gly Pro  Ala Val Cys
    1430                1435                1440

Lys Lys  Ile Thr Asn His Glu  Lys Cys His Val Asn  Ile Met Asp
    1445                1450                1455

Lys Leu  Thr Ala Phe Phe Gly  Ile Met Pro Arg Gly  Thr Thr Pro
    1460                1465                1470

Arg Ala  Pro Val Arg Phe Pro  Thr Ala Leu Leu Lys  Val Arg Arg
    1475                1480                1485

Gly Leu  Glu Thr Gly Trp Ala  Tyr Thr His Gln Gly  Gly Ile Ser
    1490                1495                1500

Ser Val  Asp His Val Thr Ala  Gly Lys Asp Leu Leu  Val Cys Asp
    1505                1510                1515
```

-continued

```
Ser Met Gly Arg Thr Arg Val Val Cys His Ser Asn Asn Lys Met
    1520                1525                1530

Thr Asp Glu Thr Glu Tyr Gly Ile Lys Thr Asp Ser Gly Cys Pro
    1535                1540                1545

Glu Gly Ala Arg Cys Tyr Val Leu Asn Pro Glu Ala Val Asn Ile
    1550                1555                1560

Ser Gly Thr Lys Gly Ala Met Val His Leu Gln Lys Thr Gly Gly
    1565                1570                1575

Glu Phe Thr Cys Val Thr Ala Ser Gly Thr Pro Ala Phe Phe Asp
    1580                1585                1590

Leu Lys Asn Leu Lys Gly Trp Ser Gly Leu Pro Ile Phe Glu Ala
    1595                1600                1605

Ser Ser Gly Arg Val Val Gly Arg Val Lys Val Gly Lys Asn Glu
    1610                1615                1620

Asp Ser Lys Pro Thr Lys Leu Met Ser Gly Ile Gln Thr Val Ser
    1625                1630                1635

Lys Asn Gln Thr Asp Leu Ala Asp Ile Val Lys Lys Leu Thr Ser
    1640                1645                1650

Met Asn Arg Gly Glu Phe Lys Gln Ile Thr Leu Ala Thr Gly Ala
    1655                1660                1665

Gly Lys Thr Thr Glu Leu Pro Arg Ser Val Ile Glu Glu Ile Gly
    1670                1675                1680

Arg His Lys Arg Val Leu Val Leu Ile Pro Leu Arg Ala Ala Ala
    1685                1690                1695

Glu Ser Val Tyr Gln Tyr Met Arg Val Lys Tyr Pro Ser Ile Ser
    1700                1705                1710

Phe Asn Leu Arg Ile Gly Asp Met Lys Glu Gly Asp Met Ala Thr
    1715                1720                1725

Gly Ile Thr Tyr Ala Ser Tyr Gly Tyr Phe Cys Gln Leu Pro Gln
    1730                1735                1740

Pro Lys Leu Arg Ala Ala Met Val Glu Tyr Ser Tyr Ile Phe Leu
    1745                1750                1755

Asp Glu Tyr His Cys Ala Thr Pro Glu Gln Leu Ala Ile Ile Gly
    1760                1765                1770

Lys Ile His Arg Phe Ala Glu Asn Leu Arg Val Val Ala Met Thr
    1775                1780                1785

Ala Thr Pro Ala Gly Thr Val Thr Thr Thr Gly Gln Lys His Pro
    1790                1795                1800

Ile Glu Glu Phe Ile Ala Pro Glu Val Met Lys Gly Glu Asp Leu
    1805                1810                1815

Gly Ser Glu Tyr Leu Asp Ile Ala Gly Leu Lys Ile Pro Thr Glu
    1820                1825                1830

Glu Met Lys Gly Asn Met Leu Val Phe Ala Pro Thr Arg Asn Met
    1835                1840                1845

Ala Val Glu Thr Ala Lys Lys Leu Lys Ala Lys Gly Tyr Asn Ser
    1850                1855                1860

Gly Tyr Tyr Tyr Ser Gly Glu Asn Pro Glu Asn Leu Arg Val Val
    1865                1870                1875

Thr Ser Gln Ser Pro Tyr Val Val Val Ala Thr Asn Ala Ile Glu
    1880                1885                1890

Ser Gly Val Thr Leu Pro Asp Leu Asp Thr Val Val Asp Thr Gly
    1895                1900                1905
```

-continued

```
Leu Lys  Cys Glu Lys Arg Val  Arg Ile Ser Ser Lys  Met Pro Phe
    1910                 1915                 1920

Ile Val  Thr Gly Leu Lys Arg  Met Ala Val Thr Ile  Gly Glu Gln
    1925                 1930                 1935

Ala Gln  Arg Arg Gly Arg Val  Gly Arg Val Lys Pro  Gly Arg Tyr
    1940                 1945                 1950

Tyr Arg  Ser Gln Glu Thr Ala  Ser Gly Ser Lys Asp  Tyr His Tyr
    1955                 1960                 1965

Asp Leu  Leu Gln Ala Gln Arg  Tyr Gly Ile Glu Asp  Gly Ile Asn
    1970                 1975                 1980

Val Thr  Lys Ser Phe Arg Glu  Met Asn Tyr Asp Trp  Ser Leu Tyr
    1985                 1990                 1995

Glu Glu  Asp Ser Leu Met Ile  Thr Gln Leu Glu Val  Leu Asn Asn
    2000                 2005                 2010

Leu Leu  Ile Ser Glu Asp Leu  Pro Ala Ala Val Lys  Asn Ile Met
    2015                 2020                 2025

Ala Arg  Thr Asp His Pro Glu  Pro Ile Gln Leu Ala  Tyr Asn Ser
    2030                 2035                 2040

Tyr Glu  Asn Gln Ile Pro Val  Leu Phe Pro Lys Ile  Lys Asn Gly
    2045                 2050                 2055

Glu Val  Thr Asp Ser Tyr Glu  Asn Tyr Thr Tyr Leu  Asn Ala Arg
    2060                 2065                 2070

Lys Leu  Gly Glu Asp Val Pro  Ala Tyr Val Tyr Ala  Thr Glu Asp
    2075                 2080                 2085

Glu Asp  Leu Ala Val Asp Leu  Leu Gly Met Asp Trp  Pro Asp Pro
    2090                 2095                 2100

Gly Asn  Gln Gln Val Val Glu  Thr Gly Arg Ala Leu  Lys Gln Val
    2105                 2110                 2115

Thr Gly  Leu Ser Thr Ala Glu  Asn Ala Leu Leu Ile  Ala Leu Phe
    2120                 2125                 2130

Gly Tyr  Val Gly Tyr Gln Thr  Leu Ser Lys Arg His  Ile Pro Met
    2135                 2140                 2145

Ile Thr  Asp Ile Tyr Thr Leu  Glu Asp His Arg Leu  Glu Asp Thr
    2150                 2155                 2160

Thr His  Leu Gln Phe Ala Pro  Asn Ala Ile Arg Thr  Asp Gly Lys
    2165                 2170                 2175

Asp Ser  Glu Leu Lys Glu Leu  Ala Val Gly Asp Leu  Asp Lys Tyr
    2180                 2185                 2190

Val Asp  Ala Leu Val Asp Tyr  Ser Lys Gln Gly Met  Lys Phe Ile
    2195                 2200                 2205

Lys Val  Gln Ala Glu Lys Val  Arg Asp Ser Gln Ser  Thr Lys Glu
    2210                 2215                 2220

Gly Leu  Gln Thr Ile Lys Glu  Tyr Val Asp Lys Phe  Ile Gln Ser
    2225                 2230                 2235

Leu Thr  Glu Asn Lys Glu Glu  Ile Ile Arg Tyr Gly  Leu Trp Gly
    2240                 2245                 2250

Val His  Thr Ala Leu Tyr Lys  Ser Leu Ala Ala Arg  Leu Gly His
    2255                 2260                 2265

Glu Thr  Ala Phe Ala Thr Leu  Val Val Lys Trp Leu  Ala Phe Gly
    2270                 2275                 2280

Gly Glu  Thr Val Ser Ala His  Ile Lys Gln Val Ala  Val Asp Leu
    2285                 2290                 2295

Val Val  Tyr Tyr Ile Ile Asn  Lys Pro Ser Phe Pro  Gly Asp Thr
```

```
    2300                2305                2310

Glu Thr  Gln Gln Glu Gly Arg  Arg Phe Val Ala Ser  Leu Phe Ile
    2315                2320                2325

Ser Ala  Leu Ala Thr Tyr Thr  Tyr Lys Thr Trp Asn  Tyr Asn Asn
    2330                2335                2340

Leu Gln  Arg Val Val Glu Pro  Ala Leu Ala Tyr Leu  Pro Tyr Ala
    2345                2350                2355

Thr Ser  Ala Leu Lys Leu Phe  Thr Pro Thr Arg Leu  Glu Ser Val
    2360                2365                2370

Val Ile  Leu Ser Ser Thr Ile  Tyr Lys Thr Tyr Leu  Ser Ile Arg
    2375                2380                2385

Lys Gly  Lys Ser Asp Gly Leu  Leu Gly Thr Gly Ile  Ser Ala Ala
    2390                2395                2400

Met Glu  Ile Leu Asn Gln Asn  Pro Ile Ser Val Gly  Ile Ser Val
    2405                2410                2415

Met Leu  Gly Val Gly Ala Ile  Ala Ala His Asn Ala  Ile Glu Ser
    2420                2425                2430

Ser Glu  Gln Lys Arg Thr Leu  Leu Met Lys Val Phe  Val Lys Asn
    2435                2440                2445

Phe Leu  Asp Gln Ala Ala Thr  Asp Glu Leu Val Lys  Glu Asn Pro
    2450                2455                2460

Glu Lys  Ile Ile Met Ala Leu  Phe Glu Ala Val Gln  Thr Ile Gly
    2465                2470                2475

Asn Pro  Leu Arg Leu Ile Tyr  His Leu Tyr Gly Val  Tyr Tyr Lys
    2480                2485                2490

Gly Trp  Glu Ala Lys Glu Leu  Ala Glu Lys Thr Ala  Gly Arg Asn
    2495                2500                2505

Leu Phe  Thr Leu Ile Met Phe  Glu Ala Phe Glu Leu  Leu Gly Met
    2510                2515                2520

Asp Ser  Glu Gly Lys Ile Arg  Asn Leu Ser Gly Asn  Tyr Ile Leu
    2525                2530                2535

Asp Leu  Ile Phe Asn Leu His  Asn Lys Leu Asn Lys  Gly Leu Lys
    2540                2545                2550

Lys Leu  Val Leu Gly Trp Ala  Pro Ala Pro Leu Ser  Cys Asp Trp
    2555                2560                2565

Thr Pro  Ser Asp Glu Arg Ile  Ser Leu Pro His Asn  Asn Tyr Leu
    2570                2575                2580

Arg Val  Glu Thr Arg Cys Pro  Cys Gly Tyr Glu Met  Lys Ala Ile
    2585                2590                2595

Lys Asn  Val Ala Gly Lys Leu  Thr Lys Val Glu Glu  Lys Gly Ser
    2600                2605                2610

Phe Leu  Cys Arg Asn Arg Leu  Gly Arg Gly Pro Pro  Asn Phe Lys
    2615                2620                2625

Val Thr  Lys Phe Tyr Asp Asp  Asn Leu Ile Glu Val  Lys Pro Val
    2630                2635                2640

Ala Arg  Leu Glu Gly Gln Val  Asp Leu Tyr Tyr Lys  Gly Val Thr
    2645                2650                2655

Ala Lys  Leu Asp Tyr Asn Asn  Gly Lys Val Leu Leu  Ala Thr Asn
    2660                2665                2670

Lys Trp  Glu Val Asp His Ala  Phe Leu Thr Arg Leu  Val Lys Lys
    2675                2680                2685

His Thr  Gly Ile Gly Phe Lys  Gly Ala Tyr Leu Gly  Asp Arg Pro
    2690                2695                2700
```

```
Asp His  Gln Asp Leu Val Asp  Arg Asp Cys Ala Thr  Ile Thr Lys
    2705                 2710                 2715

Asn Ser  Val Gln Phe Leu Lys  Met Lys Lys Gly Cys  Ala Phe Thr
    2720                 2725                 2730

Tyr Asp  Leu Thr Ile Ser Asn  Leu Val Arg Leu Ile  Glu Leu Val
    2735                 2740                 2745

His Lys  Asn Asn Leu Gln Glu  Arg Glu Ile Pro Thr  Val Thr Val
    2750                 2755                 2760

Thr Thr  Trp Leu Ala Tyr Ser  Phe Val Asn Glu Asp  Leu Gly Thr
    2765                 2770                 2775

Ile Lys  Pro Val Leu Gly Glu  Lys Val Ile Pro Glu  Pro Pro Glu
    2780                 2785                 2790

Glu Leu  Ser Leu Gln Pro Thr  Val Arg Leu Val Thr  Thr Glu Thr
    2795                 2800                 2805

Ala Ile  Thr Ile Thr Gly Glu  Ala Glu Val Met Thr  Thr Gly Ile
    2810                 2815                 2820

Thr Pro  Val Val Glu Met Lys  Glu Glu Pro Gln Leu  Asp His Gln
    2825                 2830                 2835

Ser Thr  Thr Leu Lys Val Gly  Leu Lys Glu Gly Glu  Tyr Pro Gly
    2840                 2845                 2850

Pro Gly  Val Asn Pro Asn His  Leu Ala Glu Val Ile  Asp Glu Lys
    2855                 2860                 2865

Asp Asp  Arg Pro Phe Val Leu  Ile Ile Gly Asn Lys  Gly Ser Thr
    2870                 2875                 2880

Ser Asn  Arg Ala Arg Thr Ala  Lys Asn Ile Arg Leu  Tyr Lys Gly
    2885                 2890                 2895

Asn Asn  Pro Arg Glu Ile Arg  Asp Leu Met Ser Gln  Gly Arg Ile
    2900                 2905                 2910

Leu Thr  Val Ala Leu Lys Glu  Leu Asp Pro Glu Leu  Lys Glu Leu
    2915                 2920                 2925

Val Asp  Tyr Lys Gly Thr Phe  Leu Asn Arg Glu Ala  Leu Glu Ala
    2930                 2935                 2940

Leu Ser  Leu Gly Lys Pro Ile  Lys Arg Lys Thr Thr  Thr Ala Met
    2945                 2950                 2955

Ile Arg  Arg Leu Ile Glu Pro  Glu Val Glu Glu Glu  Leu Pro Asp
    2960                 2965                 2970

Trp Phe  Gln Ala Glu Glu Pro  Leu Phe Leu Glu Ala  Lys Ile Gln
    2975                 2980                 2985

Asn Asp  Leu Tyr His Leu Ile  Gly Ser Val Asp Ser  Ile Lys Ser
    2990                 2995                 3000

Lys Ala  Lys Glu Leu Gly Ala  Thr Asp Asn Thr Lys  Ile Val Lys
    3005                 3010                 3015

Glu Val  Gly Ala Arg Thr Tyr  Thr Met Lys Leu Ser  Ser Trp Ser
    3020                 3025                 3030

Thr Gln  Val Thr Lys Lys Gln  Met Ser Leu Ala Pro  Leu Phe Glu
    3035                 3040                 3045

Glu Leu  Leu Leu Lys Cys Pro  Pro Cys Ser Lys Ile  Ser Lys Gly
    3050                 3055                 3060

His Met  Val Ser Ala Tyr Gln  Leu Ala Gln Gly Asn  Trp Glu Pro
    3065                 3070                 3075

Leu Gly  Cys Gly Val Tyr Met  Gly Thr Ile Pro Ala  Arg Arg Leu
    3080                 3085                 3090
```

-continued

```
Lys Ile  His Pro Tyr Glu Ala  Tyr Leu Lys Leu Lys  Glu Leu Val
    3095                 3100                 3105

Glu Val  Glu Ser Ser Arg Ala  Thr Ala Lys Glu Ser  Ile Ile Arg
    3110                 3115                 3120

Glu His  Asn Thr Trp Ile Leu  Arg Lys Val Arg His  Glu Gly Asn
    3125                 3130                 3135

Leu Arg  Thr Lys Ser Met Ile  Asn Pro Gly Lys Ile  Ser Asp Gln
    3140                 3145                 3150

Leu Cys  Arg Asp Gly His Lys  Arg Asn Ile Tyr Asn  Lys Ile Ile
    3155                 3160                 3165

Gly Ser  Thr Met Ala Ser Ala  Gly Ile Arg Leu Glu  Lys Leu Pro
    3170                 3175                 3180

Val Val  Arg Ala Gln Thr Asp  Thr Thr Ser Phe His  Gln Ala Ile
    3185                 3190                 3195

Arg Glu  Lys Ile Asp Lys Thr  Glu Asn Lys Gln Thr  Pro Glu Leu
    3200                 3205                 3210

His Glu  Glu Leu Met Lys Val  Phe Asp Cys Leu Lys  Ile Pro Glu
    3215                 3220                 3225

Leu Lys  Glu Ser Tyr Asp Glu  Val Ser Trp Glu Gln  Leu Glu Ala
    3230                 3235                 3240

Gly Ile  Asn Arg Lys Gly Ala  Ala Gly Tyr Leu Glu  Ser Lys Asn
    3245                 3250                 3255

Ile Gly  Glu Val Leu Asp Thr  Glu Lys His Ile Val  Glu Gln Leu
    3260                 3265                 3270

Ile Lys  Asp Leu Arg Lys Gly  Lys Lys Ile Arg Tyr  Tyr Glu Thr
    3275                 3280                 3285

Ala Ile  Pro Lys Asn Glu Lys  Arg Asp Val Ser Asp  Asp Trp Glu
    3290                 3295                 3300

Ala Gly  Glu Phe Val Asp Glu  Lys Lys Pro Arg Val  Ile Gln Tyr
    3305                 3310                 3315

Pro Asp  Ala Lys Val Arg Leu  Ala Ile Thr Lys Val  Met Tyr Lys
    3320                 3325                 3330

Trp Val  Lys Gln Lys Pro Val  Val Ile Pro Gly Tyr  Glu Gly Lys
    3335                 3340                 3345

Thr Pro  Leu Phe Asp Ile Phe  Asn Lys Val Lys Lys  Glu Trp Asp
    3350                 3355                 3360

Ser Phe  Gln Asp Pro Val Ala  Val Ser Phe Asp Thr  Lys Ala Trp
    3365                 3370                 3375

Asp Thr  Gln Val Thr Ser Arg  Asp Leu Met Leu Ile  Lys Asp Ile
    3380                 3385                 3390

Gln Lys  Tyr Tyr Phe Lys Arg  Ser Ile His Lys Phe  Leu Asp Thr
    3395                 3400                 3405

Ile Thr  Glu His Met Val Glu  Val Pro Val Ile Thr  Ala Asp Gly
    3410                 3415                 3420

Glu Val  Tyr Ile Arg Asn Gly  Gln Arg Gly Ser Gly  Gln Pro Asp
    3425                 3430                 3435

Thr Ser  Ala Gly Asn Ser Met  Leu Asn Val Leu Thr  Met Ile Tyr
    3440                 3445                 3450

Ala Phe  Cys Lys Ser Thr Gly  Ile Pro Tyr Arg Gly  Phe Ser Arg
    3455                 3460                 3465

Val Ala  Arg Ile His Val Cys  Gly Asp Asp Gly Phe  Leu Ile Thr
    3470                 3475                 3480

Glu Arg  Gly Leu Gly Leu Lys  Phe Ser Glu Lys Gly  Met Gln Ile
```

-continued

```
    3485                3490                3495

Leu His  Glu Ala Gly Lys Pro  Gln Lys Ile Thr Glu  Gly Asp Lys
    3500                3505                3510

Met Lys  Val Ala Tyr Arg Phe  Glu Asp Ile Glu Phe  Cys Ser His
    3515                3520                3525

Thr Pro  Val Pro Val Arg Trp  Ala Asp Asn Thr Ser  Ser Tyr Met
    3530                3535                3540

Ala Gly  Arg Ser Thr Ala Thr  Ile Leu Ala Lys Met  Ala Thr Arg
    3545                3550                3555

Leu Asp  Ser Ser Gly Glu Arg  Gly Ser Thr Ala Tyr  Glu Lys Ala
    3560                3565                3570

Val Ala  Phe Ser Phe Leu Leu  Met Tyr Ser Trp Asn  Pro Val Val
    3575                3580                3585

Arg Arg  Ile Cys Leu Leu Val  Leu Ser Gln Phe Pro  Glu Ile Ser
    3590                3595                3600

Pro Ser  Lys Asn Thr Ile Tyr  Tyr Tyr Gln Gly Asp  Pro Ile Ala
    3605                3610                3615

Ala Tyr  Arg Glu Val Ile Gly  Lys Gln Leu Cys Glu  Leu Lys Arg
    3620                3625                3630

Thr Gly  Phe Glu Lys Leu Ala  Gly Leu Asn Leu Ser  Met Thr Thr
    3635                3640                3645

Leu Gly  Ile Trp Thr Lys His  Thr Ser Lys Arg Leu  Ile Gln Ala
    3650                3655                3660

Cys Val  Glu Ile Gly Lys Arg  Glu Gly Thr Trp Leu  Val Asn Ala
    3665                3670                3675

Asp Arg  Leu Ile Ala Gly Lys  Thr Gly Lys Phe Tyr  Ile Pro Ser
    3680                3685                3690

Thr Gly  Val Thr Leu Leu Gly  Lys His Tyr Glu Glu  Ile Asn Leu
    3695                3700                3705

Lys Gln  Lys Ala Ala Gln Pro  Pro Ile Glu Gly Val  Asp Arg Tyr
    3710                3715                3720

Lys Leu  Gly Pro Ile Val Asn  Val Ile Leu Arg Arg  Leu Arg Val
    3725                3730                3735

Met Leu  Met Thr Val Ala Ser  Gly Ser Trp
    3740                3745


<210> SEQ ID NO 9
<211> LENGTH: 3913
<212> TYPE: PRT
<213> ORGANISM: Artificial
<220> FEATURE:
<223> OTHER INFORMATION: XIKE-C BVDV-Sequence

<400> SEQUENCE: 9

Met Glu Leu Phe Ser Asn Glu Leu Leu Tyr Lys Thr Tyr Lys Gln Lys
1               5                   10                  15

Pro Ala Gly Val Val Glu Pro Val Tyr Asp Val Asn Gly Arg Pro Leu
            20                  25                  30

Phe Gly Glu Ser Ser Asp Leu His Pro Gln Ser Thr Leu Lys Leu Pro
        35                  40                  45

His Gln Arg Gly Ser Ala Asn Ile Leu Thr Asn Ala Arg Ser Leu Pro
    50                  55                  60

Arg Lys Gly Asp Cys Arg Arg Gly Asn Val Tyr Gly Pro Val Ser Gly
65                  70                  75                  80

Ile Tyr Ile Lys Pro Gly Pro Ile Tyr Tyr Gln Asp Tyr Val Gly Pro
```

-continued

```
                85                  90                  95

Val Tyr His Arg Ala Pro Leu Glu Leu Cys Arg Glu Ala Ser Met Cys
            100                 105                 110

Glu Thr Thr Arg Arg Val Gly Arg Val Thr Gly Ser Asp Gly Lys Leu
        115                 120                 125

Tyr His Ile Tyr Ile Cys Ile Asp Gly Cys Ile Leu Leu Lys Arg Ala
    130                 135                 140

Thr Arg Asn Gln Pro Glu Val Leu Lys Trp Val Tyr Asn Arg Leu Asn
145                 150                 155                 160

Cys Pro Leu Trp Val Thr Ser Cys Ser Asp Glu Gly Ser Lys Gly Ala
                165                 170                 175

Thr Ser Lys Lys Gln Pro Lys Pro Asp Arg Ile Glu Lys Gly Lys Met
            180                 185                 190

Lys Ile Ala Pro Lys Glu Thr Glu Lys Asp Cys Lys Thr Arg Pro Pro
        195                 200                 205

Asp Ala Thr Ile Val Val Glu Gly Val Lys Tyr Gln Val Lys Lys Lys
    210                 215                 220

Gly Lys Val Arg Gly Lys Asn Thr Gln Asp Gly Leu Tyr His Asn Lys
225                 230                 235                 240

Asn Lys Pro Pro Glu Ser Arg Lys Lys Leu Glu Lys Ala Leu Leu Ala
                245                 250                 255

Trp Ala Ile Leu Ala Ala Val Leu Leu Gln Leu Val Thr Gly Glu Asn
            260                 265                 270

Ile Thr Gln Trp Asn Leu Met Asp Asn Gly Thr Glu Gly Ile Gln Gln
        275                 280                 285

Ala Met Phe Leu Arg Gly Val Asn Arg Ser Leu Leu Gly Ile Trp Pro
    290                 295                 300

Glu Lys Ile Cys Thr Gly Val Pro Thr His Leu Ala Thr Asp Tyr Glu
305                 310                 315                 320

Leu Lys Glu Ile Val Gly Met Met Asp Ala Ser Glu Lys Thr Asn Tyr
                325                 330                 335

Thr Cys Cys Arg Leu Gln Arg His Glu Trp Asn Lys His Gly Trp Cys
            340                 345                 350

Asn Trp Phe His Ile Glu Pro Trp Ile Trp Leu Met Asn Lys Thr Gln
        355                 360                 365

Asn Asn Leu Thr Glu Gly Gln Pro Leu Arg Glu Cys Ala Val Thr Cys
    370                 375                 380

Arg Tyr Asp Lys Glu Thr Glu Leu Asn Ile Val Thr Gln Ala Arg Asp
385                 390                 395                 400

Arg Pro Thr Thr Leu Thr Gly Cys Lys Lys Gly Lys Asn Phe Ser Phe
                405                 410                 415

Ala Gly Val Ile Leu Asp Gly Pro Cys Asn Phe Lys Val Ser Val Glu
            420                 425                 430

Asp Val Leu Phe Lys Glu His Asp Cys Gly Asn Met Leu Gln Glu Thr
        435                 440                 445

Ala Ile Gln Leu Leu Asp Gly Ala Thr Asn Thr Ile Glu Gly Ala Arg
    450                 455                 460

Val Gly Thr Ala Lys Leu Thr Thr Trp Leu Gly Lys Gln Leu Gly Ile
465                 470                 475                 480

Leu Gly Lys Lys Leu Glu Asn Lys Ser Lys Ala Trp Phe Gly Ala His
                485                 490                 495

Ala Ala Ser Pro Tyr Cys Gly Val Glu Arg Lys Ile Gly Tyr Val Trp
            500                 505                 510
```

```
Tyr Thr Lys Asn Cys Thr Pro Ala Cys Leu Pro Arg Asn Thr Arg Ile
        515                 520                 525

Ile Gly Pro Gly Lys Phe Asp Thr Asn Ala Glu Asp Gly Lys Ile Leu
    530                 535                 540

His Glu Met Gly Gly His Leu Ser Glu Phe Val Leu Leu Ser Leu Val
545                 550                 555                 560

Val Leu Ser Asp Phe Ala Pro Glu Thr Ala Ser Val Ile Tyr Leu Val
                565                 570                 575

Leu His Phe Ala Ile Pro Gln Ser His Val Asp Val Asp Thr Cys Asp
            580                 585                 590

Lys Asn Gln Leu Asn Leu Thr Val Ala Thr Thr Val Ala Glu Val Ile
        595                 600                 605

Pro Gly Thr Val Trp Asn Leu Gly Lys Tyr Val Cys Ile Arg Pro Asp
    610                 615                 620

Trp Trp Pro Tyr Glu Thr Thr Thr Val Phe Val Ile Glu Glu Ala Gly
625                 630                 635                 640

Gln Val Ile Lys Leu Met Leu Arg Ala Ile Arg Asp Leu Thr Arg Ile
                645                 650                 655

Trp Asn Ala Ala Thr Thr Thr Ala Phe Leu Ile Phe Leu Val Lys Ala
            660                 665                 670

Leu Arg Gly Gln Leu Ile Gln Gly Leu Leu Trp Leu Met Leu Ile Thr
        675                 680                 685

Gly Ala Gln Gly Phe Pro Glu Cys Lys Glu Gly Phe Gln Tyr Ala Ile
    690                 695                 700

Ser Lys Asp Arg Lys Met Gly Leu Leu Gly Pro Glu Ser Leu Thr Thr
705                 710                 715                 720

Thr Trp His Leu Pro Thr Lys Lys Ile Val Asp Ser Met Val His Val
                725                 730                 735

Trp Cys Glu Gly Lys Asp Leu Lys Ile Leu Lys Met Cys Thr Lys Glu
            740                 745                 750

Glu Arg Tyr Leu Val Ala Val His Glu Arg Ala Leu Ser Thr Ser Ala
        755                 760                 765

Glu Phe Met Gln Ile Ser Asp Gly Thr Ile Gly Pro Asp Val Ile Asp
    770                 775                 780

Met Pro Asp Asp Phe Glu Phe Gly Leu Cys Pro Cys Asp Ser Lys Pro
785                 790                 795                 800

Val Ile Lys Gly Lys Phe Asn Ala Ser Leu Leu Asn Gly Pro Ala Phe
                805                 810                 815

Gln Met Val Cys Pro Gln Gly Trp Thr Gly Thr Ile Glu Cys Thr Leu
            820                 825                 830

Ala Asn Gln Asp Thr Leu Asp Thr Thr Val Ile Arg Thr Tyr Arg Arg
        835                 840                 845

Thr Thr Pro Phe Gln Arg Arg Lys Trp Cys Thr Tyr Glu Lys Ile Ile
    850                 855                 860

Gly Glu Asp Ile Tyr Glu Cys Ile Leu Gly Gly Asn Trp Thr Cys Ile
865                 870                 875                 880

Thr Gly Asp His Ser Arg Leu Lys Asp Gly Pro Ile Lys Lys Cys Lys
                885                 890                 895

Trp Cys Gly His Asp Phe Val Asn Ser Glu Gly Leu Pro His Tyr Pro
            900                 905                 910

Ile Gly Lys Cys Met Leu Ile Asn Glu Ser Gly Tyr Arg Tyr Val Asp
        915                 920                 925
```

-continued

```
Asp Thr Ser Cys Asp Arg Gly Gly Val Ala Ile Val Pro Ser Gly Thr
    930                 935                 940

Val Lys Cys Arg Ile Gly Asn Val Thr Val Gln Val Ile Ala Thr Asn
945                 950                 955                 960

Asn Asp Leu Gly Pro Met Pro Cys Ser Pro Ala Glu Val Ile Ala Ser
                965                 970                 975

Glu Gly Pro Val Glu Lys Thr Ala Cys Thr Phe Asn Tyr Ser Arg Thr
            980                 985                 990

Leu Pro Asn Lys Tyr Tyr Glu Pro  Arg Asp Arg Tyr Phe  Gln Gln Tyr
        995                 1000                 1005

Met Leu  Lys Gly Glu Trp Gln  Tyr Trp Phe Asp Leu  Asp Ser Val
    1010                 1015                 1020

Asp His  His Lys Asp Tyr Phe  Ser Glu Phe Ile Ile  Ile Ala Val
    1025                 1030                 1035

Val Ala  Leu Leu Gly Gly Lys  Tyr Val Leu Trp Leu  Leu Ile Thr
    1040                 1045                 1050

Tyr Thr  Ile Leu Ser Glu Gln  Met Ala Met Gly Ala  Gly Val Asn
    1055                 1060                 1065

Thr Glu  Glu Ile Val Met Ile  Gly Asn Leu Leu Thr  Asp Ser Asp
    1070                 1075                 1080

Ile Glu  Val Val Val Tyr Phe  Leu Leu Leu Tyr Leu  Ile Val Lys
    1085                 1090                 1095

Glu Glu  Leu Ala Arg Lys Trp  Ile Ile Leu Val Tyr  His Ile Leu
    1100                 1105                 1110

Val Ala  Asn Pro Met Lys Thr  Ile Gly Val Val Leu  Leu Met Leu
    1115                 1120                 1125

Gly Gly  Val Val Lys Ala Ser  Arg Ile Asn Ala Asp  Asp Gln Ser
    1130                 1135                 1140

Ala Met  Asp Pro Cys Phe Leu  Leu Val Thr Gly Val  Val Ala Val
    1145                 1150                 1155

Leu Met  Ile Ala Arg Arg Glu  Pro Ala Thr Leu Pro  Leu Ile Val
    1160                 1165                 1170

Ala Leu  Leu Ala Ile Arg Thr  Ser Gly Phe Leu Leu  Pro Ala Ser
    1175                 1180                 1185

Ile Asp  Val Thr Val Ala Val  Val Leu Ile Val Leu  Leu Leu Ala
    1190                 1195                 1200

Ser Tyr  Ile Thr Asp Tyr Phe  Arg Tyr Lys Lys Trp  Leu Gln Leu
    1205                 1210                 1215

Leu Phe  Ser Leu Ile Ala Gly  Ile Phe Ile Ile Arg  Ser Leu Lys
    1220                 1225                 1230

His Ile  Asn Gln Met Glu Val  Pro Glu Ile Ser Met  Pro Ser Trp
    1235                 1240                 1245

Arg Pro  Leu Ala Leu Val Leu  Phe Tyr Ile Thr Ser  Thr Ala Ile
    1250                 1255                 1260

Thr Thr  Asn Trp Asp Ile Asp  Leu Ala Gly Phe Leu  Leu Gln Trp
    1265                 1270                 1275

Ala Pro  Ala Val Ile Met Met  Ala Thr Met Trp Ala  Asp Phe Leu
    1280                 1285                 1290

Thr Leu  Ile Ile Val Leu Pro  Ser Tyr Glu Leu Ser  Lys Leu Tyr
    1295                 1300                 1305

Phe Leu  Lys Asn Val Arg Thr  Asp Val Glu Lys Asn  Trp Leu Gly
    1310                 1315                 1320

Lys Val  Lys Tyr Arg Gln Ile  Ser Ser Val Tyr Asp  Ile Cys Asp
```

-continued

```
    1325                1330                1335

Ser Glu  Glu Ala Val Tyr Leu  Phe Pro Ser Arg His  Lys Ser Gly
    1340                1345                1350

Ser Arg  Pro Asp Phe Ile Leu  Pro Phe Leu Lys Ala  Val Leu Ile
    1355                1360                1365

Ser Cys  Ile Ser Ser Gln Trp  Gln Val Val Tyr Ile  Ser Tyr Leu
    1370                1375                1380

Ile Leu  Glu Ile Thr Tyr Tyr  Met His Arg Lys Ile  Ile Asp Glu
    1385                1390                1395

Val Ser  Gly Gly Ala Asn Phe  Leu Ser Arg Leu Ile  Ala Ala Ile
    1400                1405                1410

Ile Glu  Leu Asn Trp Ala Ile  Asp Asp Glu Glu Cys  Lys Gly Leu
    1415                1420                1425

Lys Lys  Leu Tyr Leu Leu Ser  Gly Arg Ala Lys Asn  Leu Ile Val
    1430                1435                1440

Lys His  Lys Val Arg Asn Glu  Ala Val His Arg Trp  Phe Gly Glu
    1445                1450                1455

Glu Glu  Ile Tyr Gly Ala Pro  Lys Val Ile Thr Ile  Ile Lys Ala
    1460                1465                1470

Ser Thr  Leu Ser Lys Asn Arg  His Cys Ile Ile Cys  Thr Ile Cys
    1475                1480                1485

Glu Gly  Lys Glu Trp Asn Gly  Ala Asn Cys Pro Lys  Cys Gly Arg
    1490                1495                1500

Gln Gly  Lys Pro Ile Thr Cys  Gly Met Thr Leu Ala  Asp Phe Glu
    1505                1510                1515

Glu Lys  His Tyr Lys Lys Ile  Phe Ile Arg Glu Glu  Ser Ser Cys
    1520                1525                1530

Pro Val  Pro Phe Asp Pro Ser  Cys His Cys Asn Tyr  Phe Arg His
    1535                1540                1545

Asp Gly  Pro Phe Arg Lys Glu  Tyr Lys Gly Tyr Val  Gln Tyr Thr
    1550                1555                1560

Ala Arg  Gly Gln Leu Phe Leu  Arg Asn Leu Pro Ile  Leu Ala Thr
    1565                1570                1575

Lys Met  Lys Leu Leu Met Val  Gly Asn Leu Gly Ala  Glu Ile Gly
    1580                1585                1590

Asp Leu  Glu His Leu Gly Trp  Val Leu Arg Gly Pro  Ala Val Cys
    1595                1600                1605

Lys Lys  Ile Thr Asn His Glu  Lys Cys His Val Asn  Ile Met Asp
    1610                1615                1620

Lys Leu  Thr Ala Phe Phe Gly  Ile Met Pro Arg Gly  Thr Thr Pro
    1625                1630                1635

Arg Ala  Pro Val Arg Phe Pro  Thr Ala Leu Leu Lys  Val Arg Arg
    1640                1645                1650

Gly Leu  Glu Thr Gly Trp Ala  Tyr Thr His Gln Gly  Gly Ile Ser
    1655                1660                1665

Ser Val  Asp His Val Thr Ala  Gly Lys Asp Leu Leu  Val Cys Asp
    1670                1675                1680

Ser Met  Gly Arg Thr Arg Val  Val Cys His Ser Asn  Asn Lys Met
    1685                1690                1695

Thr Asp  Glu Thr Glu Tyr Gly  Ile Lys Thr Asp Ser  Gly Cys Pro
    1700                1705                1710

Glu Gly  Ala Arg Cys Tyr Val  Leu Asn Pro Glu Ala  Val Asn Ile
    1715                1720                1725
```

```
Ser Gly  Thr Lys Gly Ala Met  Val His Leu Gln Lys  Thr Gly Gly
    1730                 1735                 1740

Glu Phe  Thr Cys Val Thr Ala  Ser Gly Thr Pro Ala  Phe Phe Asp
    1745                 1750                 1755

Leu Lys  Asn Leu Lys Gly Trp  Ser Gly Leu Pro Ile  Phe Glu Ala
    1760                 1765                 1770

Ser Ser  Gly Arg Val Val Gly  Arg Val Lys Val Gly  Lys Asn Glu
    1775                 1780                 1785

Asp Ser  Lys Pro Thr Lys Leu  Met Ser Gly Ile Gln  Thr Val Ser
    1790                 1795                 1800

Lys Asn  Gln Thr Asp Leu Ala  Asp Ile Val Lys Lys  Leu Thr Ser
    1805                 1810                 1815

Met Asn  Arg Gly Glu Phe Lys  Gln Ile Thr Leu Ala  Thr Gly Ala
    1820                 1825                 1830

Gly Lys  Thr Thr Glu Leu Pro  Arg Ser Val Ile Glu  Glu Ile Gly
    1835                 1840                 1845

Arg His  Lys Arg Val Leu Val  Leu Ile Pro Leu Arg  Ala Ala Ala
    1850                 1855                 1860

Glu Ser  Val Tyr Gln Tyr Met  Arg Val Lys Tyr Pro  Ser Ile Ser
    1865                 1870                 1875

Phe Asn  Leu Arg Ile Gly Asp  Met Lys Glu Gly Asp  Met Ala Thr
    1880                 1885                 1890

Gly Ile  Thr Tyr Ala Ser Tyr  Gly Tyr Phe Cys Gln  Leu Pro Gln
    1895                 1900                 1905

Pro Lys  Leu Arg Ala Ala Met  Val Glu Tyr Ser Tyr  Ile Phe Leu
    1910                 1915                 1920

Asp Glu  Tyr His Cys Ala Thr  Pro Glu Gln Leu Ala  Ile Ile Gly
    1925                 1930                 1935

Lys Ile  His Arg Phe Ala Glu  Asn Leu Arg Val Val  Ala Met Thr
    1940                 1945                 1950

Ala Thr  Pro Ala Gly Thr Val  Thr Thr Thr Gly Gln  Lys His Pro
    1955                 1960                 1965

Ile Glu  Glu Phe Ile Ala Pro  Glu Val Met Lys Gly  Glu Asp Leu
    1970                 1975                 1980

Gly Ser  Glu Tyr Leu Asp Ile  Ala Gly Leu Lys Ile  Pro Thr Glu
    1985                 1990                 1995

Glu Met  Lys Gly Asn Met Leu  Val Phe Ala Pro Thr  Arg Asn Met
    2000                 2005                 2010

Ala Val  Glu Thr Ala Lys Lys  Leu Lys Ala Lys Gly  Tyr Asn Ser
    2015                 2020                 2025

Gly Tyr  Tyr Tyr Ser Gly Glu  Asn Pro Glu Asn Leu  Arg Val Val
    2030                 2035                 2040

Thr Ser  Gln Ser Pro Tyr Val  Val Val Ala Thr Asn  Ala Ile Glu
    2045                 2050                 2055

Ser Gly  Val Thr Leu Pro Asp  Leu Asp Thr Val Val  Asp Thr Gly
    2060                 2065                 2070

Leu Lys  Cys Glu Lys Arg Val  Arg Ile Ser Ser Lys  Met Pro Phe
    2075                 2080                 2085

Ile Val  Thr Gly Leu Lys Arg  Met Ala Val Thr Ile  Gly Glu Gln
    2090                 2095                 2100

Ala Gln  Arg Arg Gly Arg Val  Gly Arg Val Lys Pro  Gly Arg Tyr
    2105                 2110                 2115
```

-continued

```
Tyr Arg  Ser Gln Glu Thr Ala  Ser Gly Ser Lys Asp  Tyr His Tyr
    2120                 2125                 2130

Asp Leu  Leu Gln Ala Gln Arg  Tyr Gly Ile Glu Asp  Gly Ile Asn
    2135                 2140                 2145

Val Thr  Lys Ser Phe Arg Glu  Met Asn Tyr Asp Trp  Ser Leu Tyr
    2150                 2155                 2160

Glu Glu  Asp Ser Leu Met Ile  Thr Gln Leu Glu Val  Leu Asn Asn
    2165                 2170                 2175

Leu Leu  Ile Ser Glu Asp Leu  Pro Ala Ala Val Lys  Asn Ile Met
    2180                 2185                 2190

Ala Arg  Thr Asp His Pro Glu  Pro Ile Gln Leu Ala  Tyr Asn Ser
    2195                 2200                 2205

Tyr Glu  Asn Gln Ile Pro Val  Leu Phe Pro Lys Ile  Lys Asn Gly
    2210                 2215                 2220

Glu Val  Thr Asp Ser Tyr Glu  Asn Tyr Thr Tyr Leu  Asn Ala Arg
    2225                 2230                 2235

Lys Leu  Gly Glu Asp Val Pro  Ala Tyr Val Tyr Ala  Thr Glu Asp
    2240                 2245                 2250

Glu Asp  Leu Ala Val Asp Leu  Leu Gly Met Asp Trp  Pro Asp Pro
    2255                 2260                 2265

Gly Asn  Gln Gln Val Val Glu  Thr Gly Arg Ala Leu  Lys Gln Val
    2270                 2275                 2280

Thr Gly  Leu Ser Thr Ala Glu  Asn Ala Leu Leu Ile  Ala Leu Phe
    2285                 2290                 2295

Gly Tyr  Val Gly Tyr Gln Thr  Leu Ser Lys Arg His  Ile Pro Met
    2300                 2305                 2310

Ile Thr  Asp Ile Tyr Thr Leu  Glu Asp His Arg Leu  Glu Asp Thr
    2315                 2320                 2325

Thr His  Leu Gln Phe Ala Pro  Asn Ala Ile Arg Thr  Asp Gly Lys
    2330                 2335                 2340

Asp Ser  Glu Leu Lys Glu Leu  Ala Val Gly Asp Leu  Asp Lys Tyr
    2345                 2350                 2355

Val Asp  Ala Leu Val Asp Tyr  Ser Lys Gln Gly Met  Lys Phe Ile
    2360                 2365                 2370

Lys Val  Gln Ala Glu Lys Val  Arg Asp Ser Gln Ser  Thr Lys Glu
    2375                 2380                 2385

Gly Leu  Gln Thr Ile Lys Glu  Tyr Val Asp Lys Phe  Ile Gln Ser
    2390                 2395                 2400

Leu Thr  Glu Asn Lys Glu Glu  Ile Ile Arg Tyr Gly  Leu Trp Gly
    2405                 2410                 2415

Val His  Thr Ala Leu Tyr Lys  Ser Leu Ala Ala Arg  Leu Gly His
    2420                 2425                 2430

Glu Thr  Ala Phe Ala Thr Leu  Val Val Lys Trp Leu  Ala Phe Gly
    2435                 2440                 2445

Gly Glu  Thr Val Ser Ala His  Ile Lys Gln Val Ala  Val Asp Leu
    2450                 2455                 2460

Val Val  Tyr Tyr Ile Ile Asn  Lys Pro Ser Phe Pro  Gly Asp Thr
    2465                 2470                 2475

Glu Thr  Gln Gln Glu Gly Arg  Arg Phe Val Ala Ser  Leu Phe Ile
    2480                 2485                 2490

Ser Ala  Leu Ala Thr Tyr Thr  Tyr Lys Thr Trp Asn  Tyr Asn Asn
    2495                 2500                 2505

Leu Gln  Arg Val Val Glu Pro  Ala Leu Ala Tyr Leu  Pro Tyr Ala
```

-continued

```
    2510                2515                2520

Thr Ser  Ala Leu Lys Leu Phe  Thr Pro Thr Arg Leu  Glu Ser Val
    2525                2530                2535

Val Ile  Leu Ser Ser Thr Ile  Tyr Lys Thr Tyr Leu  Ser Ile Arg
    2540                2545                2550

Lys Gly  Lys Ser Asp Gly Leu  Leu Gly Thr Gly Ile  Ser Ala Ala
    2555                2560                2565

Met Glu  Ile Leu Asn Gln Asn  Pro Ile Ser Val Gly  Ile Ser Val
    2570                2575                2580

Met Leu  Gly Val Gly Ala Ile  Ala Ala His Asn Ala  Ile Glu Ser
    2585                2590                2595

Ser Glu  Gln Lys Arg Thr Leu  Leu Met Lys Val Phe  Val Lys Asn
    2600                2605                2610

Phe Leu  Asp Gln Ala Ala Thr  Asp Glu Leu Val Lys  Glu Asn Pro
    2615                2620                2625

Glu Lys  Ile Ile Met Ala Leu  Phe Glu Ala Val Gln  Thr Ile Gly
    2630                2635                2640

Asn Pro  Leu Arg Leu Ile Tyr  His Leu Tyr Gly Val  Tyr Tyr Lys
    2645                2650                2655

Gly Trp  Glu Ala Lys Glu Leu  Ala Glu Lys Thr Ala  Gly Arg Asn
    2660                2665                2670

Leu Phe  Thr Leu Ile Met Phe  Glu Ala Phe Glu Leu  Leu Gly Met
    2675                2680                2685

Asp Ser  Glu Gly Lys Ile Arg  Asn Leu Ser Gly Asn  Tyr Ile Leu
    2690                2695                2700

Asp Leu  Ile Phe Asn Leu His  Asn Lys Leu Asn Lys  Gly Leu Lys
    2705                2710                2715

Lys Leu  Val Leu Gly Trp Ala  Pro Ala Pro Leu Ser  Cys Asp Trp
    2720                2725                2730

Thr Pro  Ser Asp Glu Arg Ile  Ser Leu Pro His Asn  Asn Tyr Leu
    2735                2740                2745

Arg Val  Glu Thr Arg Cys Pro  Cys Gly Tyr Glu Met  Lys Ala Ile
    2750                2755                2760

Lys Asn  Val Ala Gly Lys Leu  Thr Lys Val Glu Glu  Lys Gly Ser
    2765                2770                2775

Phe Leu  Cys Arg Asn Arg Leu  Gly Arg Gly Pro Pro  Asn Phe Lys
    2780                2785                2790

Val Thr  Lys Phe Tyr Asp Asp  Asn Leu Ile Glu Val  Lys Pro Val
    2795                2800                2805

Ala Arg  Leu Glu Gly Gln Val  Asp Leu Tyr Tyr Lys  Gly Val Thr
    2810                2815                2820

Ala Lys  Leu Asp Tyr Asn Asn  Gly Lys Val Leu Leu  Ala Thr Asn
    2825                2830                2835

Lys Trp  Glu Val Asp His Ala  Phe Leu Thr Arg Leu  Val Lys Lys
    2840                2845                2850

His Thr  Gly Ile Gly Phe Lys  Gly Ala Tyr Leu Gly  Asp Arg Pro
    2855                2860                2865

Asp His  Gln Asp Leu Val Asp  Arg Asp Cys Ala Thr  Ile Thr Lys
    2870                2875                2880

Asn Ser  Val Gln Phe Leu Lys  Met Lys Lys Gly Cys  Ala Phe Thr
    2885                2890                2895

Tyr Asp  Leu Thr Ile Ser Asn  Leu Val Arg Leu Ile  Glu Leu Val
    2900                2905                2910
```

-continued

```
His Lys  Asn Asn Leu Gln Glu  Arg Glu Ile Pro Thr  Val Thr Val
    2915                 2920                 2925

Thr Thr  Trp Leu Ala Tyr Ser  Phe Val Asn Glu Asp  Leu Gly Thr
    2930                 2935                 2940

Ile Lys  Pro Val Leu Gly Glu  Lys Val Ile Pro Glu  Pro Pro Glu
    2945                 2950                 2955

Glu Leu  Ser Leu Gln Pro Thr  Val Arg Leu Val Thr  Thr Glu Thr
    2960                 2965                 2970

Ala Ile  Thr Ile Thr Gly Glu  Ala Glu Val Met Thr  Thr Gly Ile
    2975                 2980                 2985

Thr Pro  Val Val Glu Met Lys  Glu Glu Pro Gln Leu  Asp His Gln
    2990                 2995                 3000

Ser Thr  Thr Leu Lys Val Gly  Leu Lys Glu Gly Glu  Tyr Pro Gly
    3005                 3010                 3015

Pro Gly  Val Asn Pro Asn His  Leu Ala Glu Val Ile  Asp Glu Lys
    3020                 3025                 3030

Asp Asp  Arg Pro Phe Val Leu  Ile Ile Gly Asn Lys  Gly Ser Thr
    3035                 3040                 3045

Ser Asn  Arg Ala Arg Thr Ala  Lys Asn Ile Arg Leu  Tyr Lys Gly
    3050                 3055                 3060

Asn Asn  Pro Arg Glu Ile Arg  Asp Leu Met Ser Gln  Gly Arg Ile
    3065                 3070                 3075

Leu Thr  Val Ala Leu Lys Glu  Leu Asp Pro Glu Leu  Lys Glu Leu
    3080                 3085                 3090

Val Asp  Tyr Lys Gly Thr Phe  Leu Asn Arg Glu Ala  Leu Glu Ala
    3095                 3100                 3105

Leu Ser  Leu Gly Lys Pro Ile  Lys Arg Lys Thr Thr  Thr Ala Met
    3110                 3115                 3120

Ile Arg  Arg Leu Ile Glu Pro  Glu Val Glu Glu Glu  Leu Pro Asp
    3125                 3130                 3135

Trp Phe  Gln Ala Glu Glu Pro  Leu Phe Leu Glu Ala  Lys Ile Gln
    3140                 3145                 3150

Asn Asp  Leu Tyr His Leu Ile  Gly Ser Val Asp Ser  Ile Lys Ser
    3155                 3160                 3165

Lys Ala  Lys Glu Leu Gly Ala  Thr Asp Asn Thr Lys  Ile Val Lys
    3170                 3175                 3180

Glu Val  Gly Ala Arg Thr Tyr  Thr Met Lys Leu Ser  Ser Trp Ser
    3185                 3190                 3195

Thr Gln  Val Thr Lys Lys Gln  Met Ser Leu Ala Pro  Leu Phe Glu
    3200                 3205                 3210

Glu Leu  Leu Leu Lys Cys Pro  Pro Cys Ser Lys Ile  Ser Lys Gly
    3215                 3220                 3225

His Met  Val Ser Ala Tyr Gln  Leu Ala Gln Gly Asn  Trp Glu Pro
    3230                 3235                 3240

Leu Gly  Cys Gly Val Tyr Met  Gly Thr Ile Pro Ala  Arg Arg Leu
    3245                 3250                 3255

Lys Ile  His Pro Tyr Glu Ala  Tyr Leu Lys Leu Lys  Glu Leu Val
    3260                 3265                 3270

Glu Val  Glu Ser Ser Arg Ala  Thr Ala Lys Glu Ser  Ile Ile Arg
    3275                 3280                 3285

Glu His  Asn Thr Trp Ile Leu  Arg Lys Val Arg His  Glu Gly Asn
    3290                 3295                 3300
```

-continued

```
Leu Arg  Thr Lys Ser Met Ile  Asn Pro Gly Lys Ile  Ser Asp Gln
    3305                 3310                 3315

Leu Cys  Arg Asp Gly His Lys  Arg Asn Ile Tyr Asn  Lys Ile Ile
    3320                 3325                 3330

Gly Ser  Thr Met Ala Ser Ala  Gly Ile Arg Leu Glu  Lys Leu Pro
    3335                 3340                 3345

Val Val  Arg Ala Gln Thr Asp  Thr Thr Ser Phe His  Gln Ala Ile
    3350                 3355                 3360

Arg Glu  Lys Ile Asp Lys Thr  Glu Asn Lys Gln Thr  Pro Glu Leu
    3365                 3370                 3375

His Glu  Glu Leu Met Lys Val  Phe Asp Cys Leu Lys  Ile Pro Glu
    3380                 3385                 3390

Leu Lys  Glu Ser Tyr Asp Glu  Val Ser Trp Glu Gln  Leu Glu Ala
    3395                 3400                 3405

Gly Ile  Asn Arg Lys Gly Ala  Ala Gly Tyr Leu Glu  Ser Lys Asn
    3410                 3415                 3420

Ile Gly  Glu Val Leu Asp Thr  Glu Lys His Ile Val  Glu Gln Leu
    3425                 3430                 3435

Ile Lys  Asp Leu Arg Lys Gly  Lys Lys Ile Arg Tyr  Tyr Glu Thr
    3440                 3445                 3450

Ala Ile  Pro Lys Asn Glu Lys  Arg Asp Val Ser Asp  Asp Trp Glu
    3455                 3460                 3465

Ala Gly  Glu Phe Val Asp Glu  Lys Lys Pro Arg Val  Ile Gln Tyr
    3470                 3475                 3480

Pro Asp  Ala Lys Val Arg Leu  Ala Ile Thr Lys Val  Met Tyr Lys
    3485                 3490                 3495

Trp Val  Lys Gln Lys Pro Val  Val Ile Pro Gly Tyr  Glu Gly Lys
    3500                 3505                 3510

Thr Pro  Leu Phe Asp Ile Phe  Asn Lys Val Lys Lys  Glu Trp Asp
    3515                 3520                 3525

Ser Phe  Gln Asp Pro Val Ala  Val Ser Phe Asp Thr  Lys Ala Trp
    3530                 3535                 3540

Asp Thr  Gln Val Thr Ser Arg  Asp Leu Met Leu Ile  Lys Asp Ile
    3545                 3550                 3555

Gln Lys  Tyr Tyr Phe Lys Arg  Ser Ile His Lys Phe  Leu Asp Thr
    3560                 3565                 3570

Ile Thr  Glu His Met Val Glu  Val Pro Val Ile Thr  Ala Asp Gly
    3575                 3580                 3585

Glu Val  Tyr Ile Arg Asn Gly  Gln Arg Gly Ser Gly  Gln Pro Asp
    3590                 3595                 3600

Thr Ser  Ala Gly Asn Ser Met  Leu Asn Val Leu Thr  Met Ile Tyr
    3605                 3610                 3615

Ala Phe  Cys Lys Ser Thr Gly  Ile Pro Tyr Arg Gly  Phe Ser Arg
    3620                 3625                 3630

Val Ala  Arg Ile His Val Cys  Gly Asp Asp Gly Phe  Leu Ile Thr
    3635                 3640                 3645

Glu Arg  Gly Leu Gly Leu Lys  Phe Ser Glu Lys Gly  Met Gln Ile
    3650                 3655                 3660

Leu His  Glu Ala Gly Lys Pro  Gln Lys Ile Thr Glu  Gly Asp Lys
    3665                 3670                 3675

Met Lys  Val Ala Tyr Arg Phe  Glu Asp Ile Glu Phe  Cys Ser His
    3680                 3685                 3690

Thr Pro  Val Pro Val Arg Trp  Ala Asp Asn Thr Ser  Ser Tyr Met
```

```
    3695                3700                3705

Ala Gly Arg Ser Thr Ala Thr Ile Leu Ala Lys Met Ala Thr Arg
    3710                3715                3720

Leu Asp Ser Ser Gly Glu Arg Gly Ser Thr Ala Tyr Glu Lys Ala
    3725                3730                3735

Val Ala Phe Ser Phe Leu Leu Met Tyr Ser Trp Asn Pro Val Val
    3740                3745                3750

Arg Arg Ile Cys Leu Leu Val Leu Ser Gln Phe Pro Glu Ile Ser
    3755                3760                3765

Pro Ser Lys Asn Thr Ile Tyr Tyr Tyr Gln Gly Asp Pro Ile Ala
    3770                3775                3780

Ala Tyr Arg Glu Val Ile Gly Lys Gln Leu Cys Glu Leu Lys Arg
    3785                3790                3795

Thr Gly Phe Glu Lys Leu Ala Gly Leu Asn Leu Ser Met Thr Thr
    3800                3805                3810

Leu Gly Ile Trp Thr Lys His Thr Ser Lys Arg Leu Ile Gln Ala
    3815                3820                3825

Cys Val Glu Ile Gly Lys Arg Glu Gly Thr Trp Leu Val Asn Ala
    3830                3835                3840

Asp Arg Leu Ile Ala Gly Lys Thr Gly Lys Phe Tyr Ile Pro Ser
    3845                3850                3855

Thr Gly Val Thr Leu Leu Gly Lys His Tyr Glu Glu Ile Asn Leu
    3860                3865                3870

Lys Gln Lys Ala Ala Gln Pro Pro Ile Glu Gly Val Asp Arg Tyr
    3875                3880                3885

Lys Leu Gly Pro Ile Val Asn Val Ile Leu Arg Arg Leu Arg Val
    3890                3895                3900

Met Leu Met Thr Val Ala Ser Gly Ser Trp
    3905                3910
```

<210> SEQ ID NO 10
<211> LENGTH: 12332
<212> TYPE: DNA
<213> ORGANISM: Artificial
<220> FEATURE:
<223> OTHER INFORMATION: XIKE-C BVDV-Sequence

<400> SEQUENCE: 10

```
gtatacgaga ttagctaaag aactcgtata tggattggac gtcaacaaat ttttaattgg     60

caacgtaggg aaccttcccc tcagcgaagg ccgaaaagag gctagccatg cccttagtag    120

gactagcaaa agtaggggac tagcggtagc agtgagttcg ttggatggcc gaacccctga    180

gtacagggga gtcgtcaatg gttcgacact ccattagtcg aggagtctcg agatgccatg    240

tggacgaggg catgcccacg gcacatctta acccatgcgg gggttgcatg ggtgaaagcg    300

ctattcgtgg cgttatggac acagcctgat agggtgtagc agagacctgc tattccgcta    360

gtaaaaactc tgctgtacat ggcacatgga gttgttttca aatgaacttt tatacaaaac    420

atataaacaa aaaccagcag gcgtcgtgga acctgtttac gacgtcaacg ggcgcccact    480

gtttggagag agcagtgact tgcacccgca gtcaacacta aaactaccac accaacgagg    540

cagcgccaac atcctgacca atgctaggtc cctaccgcgg aaaggtgact gccggagagg    600

taatgtgtat ggaccggtga gtggcatcta tatcaaacca ggaccgatct actaccagga    660

ttatgtgggc cccgtctatc atagagcccc actggaacta tgtagggagg caagtatgtg    720

cgaaacaact aggagagttg gcagagtgac cggtagtgat gggaaattat atcatatcta    780
```

-continued

```
catctgcata gatgggtgta tcctcctgaa gagggcgact aggaaccaac cagaagtcct    840
gaaatgggta tacaacagat taaattgtcc tttatgggtc accagctgct ccgatgaagg    900
gagcaagggt gctacaagta agaagcagcc taagccagat aggatagaaa aaggtaagat    960
gaaaatagcc ccaaaagaga cagaaaaaga ttgcaaaacc agaccccccg acgcgactat   1020
agtagtagaa ggggttaagt accaggtgaa gaaaaaagga aaggtaaggg gaaaaaatac   1080
tcaagatggg ttatatcaca acaagaataa gccccctgaa tcaagaaaaa aattggaaaa   1140
ggcactgctg gcttgggcca tcttagcagc ggtcctgctt cagctggtaa caggagagaa   1200
tatcacccag tggaacttga tggacaacgg caccgaggga atacagcaag cgatgttcct   1260
aagaggggtg aacaggagtc tattaggaat ttggccagag aaaatttgca ccggagtacc   1320
aactcactta gcaacagact atgagcttaa agagatagtg gggatgatgg acgcgagtga   1380
gaagaccaac tacacgtgtt gcaggttgca aagacatgag tggaataaac atggttggtg   1440
taactggttt catatagaac cgtggatatg gttgatgaac aaaacccaaa acaacctgac   1500
agaagggcaa ccgcttaggg agtgtgctgt gacttgtagg tatgacaagg aaacagaatt   1560
gaacatcgtg acacaggcta gggacagacc tacaactctg acaggttgca agaaaggcaa   1620
gaatttctct ttcgcaggtg ttatactgga tgggccctgt aactttaaag tatcggttga   1680
agatgtgctg ttcaaggagc acgattgcgg caacatgctg caagagaccg cgatacagct   1740
actcgatggg gcaaccaaca ccattgaggg agcaagggta gggacggcca agttgacaac   1800
ctggttaggg aagcaattag ggatccttgg taagaagttg gagaacaaaa gcaaagcatg   1860
gtttggtgca catgcagcaa gtccatactg cggagtggag aggaagatcg gttacgtatg   1920
gtatacaaaa aactgcactc cagcttgcct tccaagaaac actagaataa taggccccgg   1980
gaaatttgat accaacgccg aagatggaaa aatactccat gagatggggg ggcacctctc   2040
agaatttgtc ctattgtcct tggtggttct gtctgacttt gccccggaaa ccgcgagcgt   2100
catctacttg gttctacatt ttgcgatccc gcaaagccac gttgatgtag acacatgcga   2160
caagaaccag ctgaatttaa cggtagcaac cacagtagca gaggtcatac cagggacagt   2220
gtggaaccta gggaagtatg tctgcataag accagactgg tggccatatg agacgacgac   2280
agtcttcgtc atagaggaag cagggcaagt aatcaaattg atgctaaggg ccatcagaga   2340
cttaactagg atatggaatg ctgccactac cacagctttc ttaatctttt tagtaaaagc   2400
actgagggga caactaatcc aagggctatt gtggctgatg ctaataacag gagcacaggg   2460
cttccctgaa tgcaaagagg gcttccaata tgccatatct aaagacagga aaatggggtt   2520
attggggcca gagagcttaa ctacaacatg gcacctcccc accaaaaaaa tagtggattc   2580
catggtgcat gtatggtgtg aaggaaaaga cttgaaaata ttaaaaatgt gcacaaagga   2640
agagaggtat ctagtggctg tgcacgagag agccttatca accagtgccg agtttatgca   2700
gatcagtgat gggacaatag gcccagacgt gatagatatg cctgatgact ttgagtttgg   2760
actctgccct tgtgactcaa aaccagtgat aaagggcaaa tttaatgcca gcttactgaa   2820
tggaccagct ttccagatgg tatgcccaca ggggtggact ggtacaatag aatgcaccct   2880
agcgaaccaa gacaccttgg acacaactgt cattaggaca tatagaagaa ctaccccatt   2940
tcagcggaga aaatggtgta cctatgaaaa aataataggg gaagatatct atgaatgcat   3000
tctaggtgga aactggacat gcataaccgg tgaccatagc aggttgaaag acggacctat   3060
caagaagtgt aagtggtgtg gccatgactt cgtcaactca gaggggctac cacactaccc   3120
```

-continued

```
aataggcaag tgcatgctca tcaacgagag tgggtacagg tatgtagatg acacctcttg   3180
cgataggggt ggtgtagcca tagttccatc tggcaccgta aagtgtagaa taggtaacgt   3240
cacggtgcaa gttatcgcta ctaacaatga tctgggaccc atgccttgca gcccagctga   3300
agtgatagca agtgaaggac cagtggaaaa gactgcatgc acattcaact attcaaggac   3360
tctacctaat aagtattatg agccaaggga ccggtacttc caacaataca tgttaaaagg   3420
ggagtggcaa tattggttcg acctggattc tgtagaccac cacaaagact acttctcaga   3480
gttcataatc atagcagtgg tcgccttgtt gggtggtaag tacgtactgt ggctcttgat   3540
aacatacaca atactgtctg agcagatggc tatgggtgct ggagtgaata ctgaagagat   3600
agtcatgata ggcaatttgc tgacagacag tgatattgag gttgtggttt atttccttct   3660
tctgtactta atagttaaag aggaactggc gaggaaatgg attatactgg tataccacat   3720
ccttgtagcc aaccctatga aaacaattgg ggtcgtctta ctaatgctag ggggagtggt   3780
gaaggccagc agaatcaatg ctgatgacca aagtgctatg gacccatgct ttcttctcgt   3840
gacaggcgta gtggctgttt tgatgatcgc tagaagagaa cctgccacat taccactgat   3900
tgtagcattg ctagcaataa gaacatcagg attcctactg cccgctagca ttgatgtaac   3960
tgtagcagta gtattaattg tacttttgtt ggctagctac ataacagact actttagata   4020
taaaaagtgg cttcaactct tatttagtct gatagctggt atctttatta taaggagctt   4080
aaaacatatc aaccagatgg aggtaccaga aatatctatg ccaagttgga gacctctagc   4140
tctggtcctt ttctatataa catctacagc aataaccact aattgggaca ttgacttagc   4200
aggcttcctg ctgcaatggg cgccagcagt gatcatgatg gctaccatgt gggcagactt   4260
tttgactctg atcatagtcc tgcccagtta cgagttatct aagctttact tcctaaagaa   4320
cgtcaggaca gacgtggaaa agaactggct cggcaaagtg aaatacagac agatcagttc   4380
agtttatgac atctgtgaca gtgaggaagc agtgtaccta tttccatcaa ggcataagag   4440
tggaagcagg ccagatttca tattaccttt tttgaaagcc gtgttaataa gctgcatcag   4500
cagccaatgg caagtggttt acatttctta cctaatactg gaaattacat actatatgca   4560
caggaaaatc atagatgagg tgtcaggagg agcaaatttt ctatcaagac tcatagcagc   4620
catcatagaa ttaaattggg ccatagatga tgaggaatgt aaaggactga agaaactgta   4680
tctcttgtca gggagagcga agaatttgat agttaaacat aaggtaagaa atgaagccgt   4740
ccacagatgg tttggtgagg aggaaatata cggggcaccc aaggtgatca ctatcataaa   4800
agctagtacc ctaagtaaaa acaggcactg cataatctgc acgatctgtg aagggaaaga   4860
atggaatgga gccaactgcc caaagtgtgg aagacaagga aagcccataa catgtggaat   4920
gacactcgca gactttgagg agaaacatta caaaaagata tttataagag aagaatcttc   4980
ttgtcctgtg ccttttgatc cttcttgcca ttgtaattat tttcgccacg atgggccttt   5040
caggaaagag tataagggtt acgtccaata cacagccaga ggacaactct ttctgaggaa   5100
cctaccaatt ctagcgacga agatgaagct attaatggtg ggaaacctcg gcgcagaaat   5160
tggcgacctg gaacatctag gatgggtact gagagggcca gccgtgtgca aaaaaattac   5220
caaccatgag aagtgccacg taaacatcat ggataagcta actgcatttt ttggaatcat   5280
gcctagaggc acgaccccta gggcacctgt gaggttcccc acagcactac taaaagtgag   5340
aagggggcta gagacgggat gggcttacac gcaccaagga gggatcagct cggtagacca   5400
tgtcacagcc ggaaaggatt tactagtgtg tgacagtatg ggcaggacca gggttgtctg   5460
tcatagtaac aataagatga ctgatgagac tgagtatggc atcaagaccg actcagggtg   5520
```

-continued

```
tcccgaaggt gcgaggtgtt acgtgctaaa cccagaagct gttaacattt ctggcacaaa   5580
aggagctatg gtacacctcc agaaaacggg gggggagttc acatgtgtca ctgcctcagg   5640
gaccccggct ttcttcgatc tgaaaaatct aaaaggctgg tccgggctac caatttttga   5700
agcatccagt ggcagggtgg ttggtagggt gaaagtcggc aagaatgagg attccaagcc   5760
caccaaacta atgagcggaa tccagacagt gtctaagaac cagacagacc tagcggacat   5820
cgtaaaaaaa ttgactagta tgaacagagg agagttcaaa cagataacat tagccactgg   5880
ggcaggaaaa actacggaac tgccaaggtc cgtcatagag gagataggga ggcacaaaag   5940
ggtcttagtc ctgataccat tgagagcagc agcagagtca gtgtatcagt atatgagagt   6000
gaagtaccca agtatatctt tcaatttgag aataggagat atgaaggaag gtgacatggc   6060
cactggtatc acctacgcct catatgggta cttttgtcag cttcctcagc ccaaactgag   6120
agctgccatg gtagagtact catatatatt cttagatgag taccactgtg ctacacccga   6180
gcaattagca ataattggaa agatacacag gtttgctgaa aatcttagag tggtagcaat   6240
gacagcaacc ccagctggaa cggtcacaac gactggtcag aaacacccta tagaggagtt   6300
catagcccca gaggtgatga aaggtgaaga tctaggtagt gaatacttgg atattgcagg   6360
gttgaagata ccgactgaag agatgaaagg caacatgctc gtgttcgcgc caactaggaa   6420
catggcagta gaaacagcta agaaattgaa ggctaaggga tacaactctg gatactatta   6480
cagtggggaa aacccagaga acttgagggt ggtaacctcg caatccccgt atgtggtagt   6540
agccaccaat gccatagagt caggtgtgac attaccagac ttagacacag ttgtagacac   6600
tggactaaag tgtgagaaga gggtgaggat ttcttcaaaa atgcccttca ttgtaacagg   6660
acttaagaga atggcagtca caatcggaga gcaagcccag cgcaggggta gagtaggaag   6720
agtcaagcca ggtaggtact ataggagtca agaaacagct tcagggtcaa aagattacca   6780
ttacgaccta ctgcaagccc agaggtacgg aatagaagat ggaattaatg taacaaagtc   6840
attcagggag atgaactatg attggagcct ttacgaagag gacagcttga tgataactca   6900
actcgaggtc cttaacaacc tccttatatc agaagacctg cctgccgcag tgaagaacat   6960
catggcccgg accgatcacc cagaacccat acaactggcc tataacagtt atgaaaacca   7020
aattccagtg ctgttcccaa agatcaaaaa tggtgaggtg acagacagtt atgagaatta   7080
cacatatctc aatgcaagaa aattaggaga ggacgtgccg gcatatgtgt acgccacaga   7140
ggatgaggat ctagcagtgg atcttctggg tatggattgg ccggacccag gcaaccaaca   7200
ggtggtagag acagggaggg cattaaaaca agtaactggc ttatccacag cagaaaacgc   7260
cctcttgata gccctattcg gctacgtcgg gtaccagaca ctttcaaaaa ggcacatacc   7320
catgattact gacatctata cacttgaaga ccacaggctt gaggacacaa cccacctcca   7380
gtttgcccca aacgctataa ggaccgacgg caaggactca gagttgaagg aattagctgt   7440
gggagacctt gataaatatg tggacgcact ggtagactac tccaaacaag ggatgaaatt   7500
catcaaagtc caagctgaaa aggtcagaga ctcccagtct acgaaggaag gcttgcaaac   7560
cattaaggag tatgtggata agtttataca atcactaaca gagaataagg aggagatcat   7620
caggtatgga ctatggggag ttcacacggc actctacaaa agcttggcag cgagactggg   7680
gcatgaaaca gcttttgcaa ctttagtggt aaaatggttg gcttttgggg gcgaaacggt   7740
atctgctcac atcaagcaag tagcagttga tctagtagta tattatatca tcaacaaacc   7800
atcttttcct ggagatacag agacccaaca agaggggagg aagtttgtgg ctagtctttt   7860
```

-continued

```
tatatctgca ctagcaacat acacatataa aacctggaat tacaacaatc tgcaacgggt   7920
tgtcgaacct gccttagctt acctcccata tgctacaagt gccttgaagt tgttcacacc   7980
cacaagatta gagagtgtgg tcatactcag ttctacaatt tacaagacat acctctctat   8040
aaggaagggt aagagtgacg gcttgttagg tacaggcata agtgcagcca tggagatctt   8100
aaaccaaaac ccaatctcag taggtatatc tgtgatgctg gggtaggtg ccatcgccgc   8160
ccataatgca atagaatcta gtgaacagaa aagaactttg ctgatgaagg tctttgtaaa   8220
aaacttctta gaccaagcag caacagatga gctagtcaaa gagaaccctg aaaaaataat   8280
catggctcta tttgaagcag tccagaccat aggaaacccc ctaagactca tctaccatct   8340
gtacggggtg tactataagg ggtgggaagc aaaagaactc gcagagaaaa ctgctggccg   8400
caacttattc acattgatca tgtttgaggc ctttgagctt ttaggtatgg actcagaagg   8460
aaagataaga aacttgtcag gcaactacat actggactta atcttcaact tgcataataa   8520
attaaacaag gggctcaaaa aactagtcct tgggtgggct cctgcacctt tgagctgtga   8580
ttggacacca agtgatgaga gaataagcct acctcataac aactacttaa gggtagaaac   8640
caggtgtcct tgtggctatg agatgaaggc aataaaaaat gttgctggta aattgacaaa   8700
agttgaagaa aaggggtcct tcctatgcag gaatagatta gggagaggac ctccaaactt   8760
caaagtaaca aagttctatg atgataactt gatagaagtc aagccagtag ctaggctaga   8820
aggccaggtg gacctctatt acaagggagt aacagctaag ttagactaca acaatgggaa   8880
agtactgtta gctaccaaca agtgggaggt ggaccacgct ttcctgacca gactagtaaa   8940
gaagcacaca gggataggtt ttaaaggtgc atatttgggt gaccgaccag accatcaaga   9000
tcttgtcgat agagattgtg caactataac gaagaactca gtacagttcc taaaaatgaa   9060
gaagggttgc gctttcacat atgacctaac aatctctaac cttgtcaggc ttattgaact   9120
agtccataag aataatttac aagaaagaga gatccctacc gtgacagtaa ctacttggct   9180
tgcatattct tttgtcaatg aagacctggg gactatcaag cctgtattgg gggagaaagt   9240
catcccagaa ccccccgagg agttgagtct ccaacccacc gtgagactag tcaccactga   9300
aacagcaata accataacag gggaggctga agtgatgacg acagggatca caccagtggt   9360
agagatgaaa gaagaacctc agctggacca ccagtcaact accctaaagg tagggttgaa   9420
ggaaggggaa tatccagggc caggagttaa ccctaaccat ttagcagagg tgatagatga   9480
gaaagatgac aggcctttg tcctaatcat cggtaacaaa ggttctacct cgaacagagc   9540
aagaacggcc aagaatatac ggctgtacaa aggaaacaac ccaagagaga tcagggatct   9600
gatgagccaa ggaagaatat tgacggttgc tctaaaagag ttggacccgg aattaaaaga   9660
attagtagat tacaagggga cctttctcaa tagggaagct ttagaagccc taagcttagg   9720
taagccaatc aagaggaaaa ccacaacagc aatgatcagg aggttaatag agccagaggt   9780
tgaggaggaa ctaccagatt ggttccaagc ggaagaaccc ctatttttgg aagcaaaaat   9840
acagaatgac ttataccacc taattggcag tgtagatagt ataaaaagca aagcaaagga   9900
attaggggcc acagataaca caaagatagt gaaggaagtt ggggctagga cctatacgat   9960
gaaattgagc agctggagca cacaagttac aaaaaaacag atgagtctag cccctctctt  10020
tgaagagctg ttattaaagt gccctccatg tagtaaaatt tcaaagggac atatggtgtc  10080
agcataccaa ctggctcaag gaaactggga acccctcggg tgtggggtct atatgggaac  10140
cataccagct aggcgtctca agatccaccc ttatgaggct taccttaaac tcaaagagct  10200
ggtggaagtt gaatcttcga gggccactgc aaaagaatcc atcataagag aacataacac  10260
```

```
ctggatcctg cggaaggtga gacatgaagg gaacctaaga accaaatcaa tgatcaaccc  10320
tgggaaaata tcagatcagc tatgcagaga tggacacaaa agaaacatat ataataagat  10380
cataggctca acaatggcct ctgctggtat taggctggag aaactgccag tagtccgagc  10440
ccaaactgac acaaccagtt tccaccaagc cataagagaa aaaattgata aaacagaaaa  10500
caagcagacc cctgaattgc atgaagaact aatgaaggtc ttcgactgct taaagatccc  10560
agagctgaag gaatcgtatg atgaagtttc atgggaacaa ttagaagccg ggataaaccg  10620
taagggtgca gcaggctatc tagagagcaa gaacataggg gaagtcctag acacagagaa  10680
acacatagta gagcagctga tcaaggatct gaggaagggg aagaagatta ggtactatga  10740
aacagccatc cccaagaatg agaagagaga cgtcagcgac gactgggaag ccggagagtt  10800
cgttgatgaa aagaaaccaa gagtaatcca gtacccggac gccaaggtga gactggccat  10860
tacaaaagtg atgtacaaat gggtaaagca aaaaccagtg gtgatacccg gctatgaagg  10920
taaaacacct ctatttgaca tattcaacaa agtgaagaag gaatgggatt cattccagga  10980
ccccgtagca gtgagctttg acaccaaagc gtgggataca caagtcacca gtagagacct  11040
aatgttgata aaggatatcc agaaatatta tttcaagaga agtatacaca aatttttaga  11100
tacaataaca gaacacatgg tggaggtacc tgtcattaca gcagacggtg aagtttacat  11160
aaggaatggt cagaggggta gtggccaacc cgacacaagt gctggtaata gtatgttgaa  11220
tgtcctaacc atgatatatg ctttctgtaa aagtacaggc ataccttaca ggggattcag  11280
cagagtggca agaatccatg tgtgtggtga tgatggcttt ttgataacag agagaggact  11340
gggactgaaa ttctctgaga agggtatgca gatattacat gaggccggga agccccagaa  11400
aataactgaa ggggacaaaa tgaaagtggc atacagattc gaggacatag agttttgttc  11460
ccatactccc gtgccagtca gatgggcaga taacaccagt agttacatgg cagggaggag  11520
cacagccact atactagcta agatggcaac caggctggat tccagcggag agaggggtag  11580
cacagcttat gagaaggccg tagccttcag cttccttttg atgtactcat ggaatcccgt  11640
agttagaagg atctgcttac tggtgttgtc acagtttcca gaaatatccc catccaaaaa  11700
cacaatatac tactaccaag gggatcccat agctgcgtac agagaagtga tagggaaaca  11760
gctgtgtgaa ctgaaaagaa caggatttga gaagctggct ggtctgaatt tgagtatgac  11820
cactctaggc atctggacaa aacatactag taaaagacta atccaagcct gtgtagaaat  11880
aggtaagaga gaaggtacct ggttagttaa tgctgacaga ctgattgcag gaaagactgg  11940
gaagttttac atcccaagca ctggtgtcac tctgttggga aaacactatg aggaaattaa  12000
cttaaagcaa aaggcggcac aaccgccgat agagggggtt gacagatata agttgggccc  12060
catagttaat gttatcttga gaaggctgag ggtgatgctg atgacagttg ccagcggaag  12120
ctggtgaatc cgtccggagc gtcgtgccct cactcaaggt tttaattgt aaatattgta  12180
aatagacagc taagatattt attgtagttg gatagtaatg cagtgatagt aaatacccca  12240
atttaacact acctccaatg cactaagcac tttagctgtg tgaggttaac tcgacgtcca  12300
cggttggact agggaagacc tctaacagcc cc                                12332
```

```
<210> SEQ ID NO 11
<211> LENGTH: 11840
<212> TYPE: DNA
<213> ORGANISM: Artificial
<220> FEATURE:
<223> OTHER INFORMATION: XIKE-C-NdN BVDV-Sequence
```

-continued

<400> SEQUENCE: 11

```
gtatacgaga ttagctaaag aactcgtata tggattggac gtcaacaaat ttttaattgg     60
caacgtaggg aaccttcccc tcagcgaagg ccgaaaagag gctagccatg cccttagtag    120
gactagcaaa agtaggggac tagcggtagc agtgagttcg ttggatggcc gaacccctga    180
gtacagggga gtcgtcaatg gttcgacact ccattagtcg aggagtctcg agatgccatg    240
tggacgaggg catgcccacg gcacatctta acccatgcgg gggttgcatg ggtgaaagcg    300
ctattcgtgg cgttatggac acagcctgat agggtgtagc agagacctgc tattccgcta    360
gtaaaaactc tgctgtacat ggcacatgga gttgttttcc gatgaaggga gcaagggtgc    420
tacaagtaag aagcagccta agccagatag gatagaaaaa ggtaagatga aaatagcccc    480
aaaagagaca gaaaaagatt gcaaaaccag accccccgac gcgactatag tagtagaagg    540
ggttaagtac caggtgaaga aaaaaggaaa ggtaagggga aaaaatactc aagatgggtt    600
atatcacaac aagaataagc cccctgaatc aagaaaaaaa ttggaaaagg cactgctggc    660
ttgggccatc ttagcagcgg tcctgcttca gctggtaaca ggagagaata tcacccagtg    720
gaacttgatg gacaacggca ccgagggaat acagcaagcg atgttcctaa gaggggtgaa    780
caggagtcta ttaggaattt ggccagagaa aatttgcacc ggagtaccaa ctcacttagc    840
aacagactat gagcttaaag agatagtggg gatgatggac gcgagtgaga agaccaacta    900
cacgtgttgc aggttgcaaa gacatgagtg gaataaacat ggttggtgta actggtttca    960
tatagaaccg tggatatggt tgatgaacaa aacccaaaac aacctgacag aagggcaacc   1020
gcttagggag tgtgctgtga cttgtaggta tgacaaggaa acagaattga acatcgtgac   1080
acaggctagg gacagaccta caactctgac aggttgcaag aaaggcaaga atttctcttt   1140
cgcaggtgtt atactggatg ggccctgtaa ctttaaagta tcggttgaag atgtgctgtt   1200
caaggagcac gattgcggca acatgctgca agagaccgcg atacagctac tcgatggggc   1260
aaccaacacc attgagggag caagggtagg gacggccaag ttgacaacct ggttagggaa   1320
gcaattaggg atccttggta agaagttgga gaacaaaagc aaagcatggt ttggtgcaca   1380
tgcagcaagt ccatactgcg gagtggagag gaagatcggt tacgtatggt atacaaaaaa   1440
ctgcactcca gcttgccttc caagaaacac tagaataata ggccccggga aatttgatac   1500
caacgccgaa gatggaaaaa tactccatga gatggggggg cacctctcag aatttgtcct   1560
attgtccttg gtggttctgt ctgactttgc cccggaaacc gcgagcgtca tctacttggt   1620
tctacatttt gcgatcccgc aaagccacgt tgatgtagac acatgcgaca agaaccagct   1680
gaatttaacg gtagcaacca cagtagcaga ggtcatacca gggacagtgt ggaacctagg   1740
gaagtatgtc tgcataagac cagactggtg gccatatgag acgacgacag tcttcgtcat   1800
agaggaagca gggcaagtaa tcaaattgat gctaagggcc atcagagact taactaggat   1860
atggaatgct gccactacca cagctttctt aatcttttta gtaaaagcac tgaggggaca   1920
actaatccaa gggctattgt ggctgatgct aataacagga gcacagggct tccctgaatg   1980
caaagagggc ttccaatatg ccatatctaa agacaggaaa atggggttat tggggccaga   2040
gagcttaact acaacatggc acctccccac caaaaaaata gtggattcca tggtgcatgt   2100
atggtgtgaa ggaaaagact tgaaaatatt aaaaatgtgc acaaaggaag agaggtatct   2160
agtggctgtg cacgagagag ccttatcaac cagtgccgag tttatgcaga tcagtgatgg   2220
gacaataggc ccagacgtga tagatatgcc tgatgacttt gagtttggac tctgcccttg   2280
tgactcaaaa ccagtgataa agggcaaatt taatgccagc ttactgaatg gaccagcttt   2340
```

-continued

```
ccagatggta tgcccacagg ggtggactgg tacaatagaa tgcaccctag cgaaccaaga   2400
caccttggac acaactgtca ttaggacata tagaagaact accccatttc agcggagaaa   2460
atggtgtacc tatgaaaaaa taatagggga agatatctat gaatgcattc taggtggaaa   2520
ctggacatgc ataaccggtg accatagcag gttgaaagac ggacctatca agaagtgtaa   2580
gtggtgtggc catgacttcg tcaactcaga ggggctacca cactacccaa taggcaagtg   2640
catgctcatc aacgagagtg ggtacaggta tgtagatgac acctcttgcg ataggggtgg   2700
tgtagccata gttccatctg gcaccgtaaa gtgtagaata ggtaacgtca cggtgcaagt   2760
tatcgctact aacaatgatc tgggacccat gccttgcagc ccagctgaag tgatagcaag   2820
tgaaggacca gtggaaaaga ctgcatgcac attcaactat tcaaggactc tacctaataa   2880
gtattatgag ccaagggacc ggtacttcca acaatacatg ttaaaagggg agtggcaata   2940
ttggttcgac ctggattctg tagaccacca caaagactac ttctcagagt tcataatcat   3000
agcagtggtc gccttgttgg gtggtaagta cgtactgtgg ctcttgataa catacacaat   3060
actgtctgag cagatggcta tgggtgctgg agtgaatact gaagagatag tcatgatagg   3120
caatttgctg acagacagtg atattgaggt tgtggtttat ttccttcttc tgtacttaat   3180
agttaaagag gaactggcga ggaaatggat tatactggta taccacatcc ttgtagccaa   3240
ccctatgaaa acaattgggg tcgtcttact aatgctaggg ggagtggtga aggccagcag   3300
aatcaatgct gatgaccaaa gtgctatgga cccatgcttt cttctcgtga caggcgtagt   3360
ggctgttttg atgatcgcta gaagagaacc tgccacatta ccactgattg tagcattgct   3420
agcaataaga acatcaggat tcctactgcc cgctagcatt gatgtaactg tagcagtagt   3480
attaattgta cttttgttgg ctagctacat aacagactac tttagatata aaaagtggct   3540
tcaactctta tttagtctga tagctggtat ctttattata aggagcttaa aacatatcaa   3600
ccagatggag gtaccagaaa tatctatgcc aagttggaga cctctagctc tggtcctttt   3660
ctatataaca tctacagcaa taaccactaa ttgggacatt gacttagcag gcttcctgct   3720
gcaatgggcg ccagcagtga tcatgatggc taccatgtgg gcagactttt tgactctgat   3780
catagtcctg cccagttacg agttatctaa gctttacttc ctaaagaacg tcaggacaga   3840
cgtggaaaag aactggctcg gcaaagtgaa atacagacag atcagttcag tttatgacat   3900
ctgtgacagt gaggaagcag tgtacctatt tccatcaagg cataagagtg gaagcaggcc   3960
agatttcata ttaccttttt tgaaagccgt gttaataagc tgcatcagca gccaatggca   4020
agtggtttac atttcttacc taatactgga aattacatac tatatgcaca ggaaaatcat   4080
agatgaggtg tcaggaggag caaattttct atcaagactc atagcagcca tcatagaatt   4140
aaattgggcc atagatgatg aggaatgtaa aggactgaag aaactgtatc tcttgtcagg   4200
gagagcgaag aatttgatag ttaaacataa ggtaagaaat gaagccgtcc acagatggtt   4260
tggtgaggag gaaatatacg gggcacccaa ggtgatcact atcataaaag ctagtaccct   4320
aagtaaaaac aggcactgca taatctgcac gatctgtgaa gggaaagaat ggaatggagc   4380
caactgccca aagtgtggaa gacaaggaaa gcccataaca tgtggaatga cactcgcaga   4440
ctttgaggag aaacattaca aaaagatatt tataagagaa gaatcttctt gtcctgtgcc   4500
ttttgatcct tcttgccatt gtaattattt tcgccacgat gggcctttca ggaaagagta   4560
taagggttac gtccaataca cagccagagg acaactcttt ctgaggaacc taccaattct   4620
agcgacgaag atgaagctat taatggtggg aaacctcggc gcagaaattg gcgacctgga   4680
```

-continued

```
acatctagga tgggtactga gagggccagc cgtgtgcaaa aaaattacca accatgagaa   4740
gtgccacgta aacatcatgg ataagctaac tgcatttttt ggaatcatgc ctagaggcac   4800
gacccctagg gcacctgtga ggttccccac agcactacta aaagtgagaa gggggctaga   4860
gacgggatgg gcttacacgc accaaggagg gatcagctcg gtagaccatg tcacagccgg   4920
aaaggattta ctagtgtgtg acagtatggg caggaccagg gttgtctgtc atagtaacaa   4980
taagatgact gatgagactg agtatggcat caagaccgac tcagggtgtc ccgaaggtgc   5040
gaggtgttac gtgctaaacc cagaagctgt taacatttct ggcacaaaag gagctatggt   5100
acacctccag aaaacggggg gggagttcac atgtgtcact gcctcaggga ccccggcttt   5160
cttcgatctg aaaaatctaa aaggctggtc cgggctacca atttttgaag catccagtgg   5220
cagggtggtt ggtagggtga aagtcggcaa gaatgaggat tccaagccca ccaaactaat   5280
gagcggaatc cagacagtgt ctaagaacca gacagaccta gcggacatcg taaaaaaatt   5340
gactagtatg aacagaggag agttcaaaca gataacatta gccactgggg caggaaaaac   5400
tacggaactg ccaaggtccg tcatagagga gatagggagg cacaaaaggg tcttagtcct   5460
gataccattg agagcagcag cagagtcagt gtatcagtat atgagagtga agtacccaag   5520
tatatctttc aatttgagaa taggagatat gaaggaaggt gacatggcca ctggtatcac   5580
ctacgcctca tatgggtact tttgtcagct tcctcagccc aaactgagag ctgccatggt   5640
agagtactca tatatattct tagatgagta ccactgtgct acacccgagc aattagcaat   5700
aattggaaag atacacaggt ttgctgaaaa tcttagagtg gtagcaatga cagcaacccc   5760
agctggaacg gtcacaacga ctggtcagaa acaccctata gaggagttca tagccccaga   5820
ggtgatgaaa ggtgaagatc taggtagtga atacttggat attgcagggt tgaagatacc   5880
gactgaagag atgaaaggca acatgctcgt gttcgcgcca actaggaaca tggcagtaga   5940
aacagctaag aaattgaagg ctaagggata caactctgga tactattaca gtggggaaaa   6000
cccagagaac ttgagggtgg taacctcgca atccccgtat gtggtagtag ccaccaatgc   6060
catagagtca ggtgtgacat taccagactt agacacagtt gtagacactg gactaaagtg   6120
tgagaagagg gtgaggattt cttcaaaaat gcccttcatt gtaacaggac ttaagagaat   6180
ggcagtcaca atcggagagc aagcccagcg caggggtaga gtaggaagag tcaagccagg   6240
taggtactat aggagtcaag aaacagcttc agggtcaaaa gattaccatt acgacctact   6300
gcaagcccag aggtacggaa tagaagatgg aattaatgta acaaagtcat tcagggagat   6360
gaactatgat tggagccttt acgaagagga cagcttgatg ataactcaac tcgaggtcct   6420
taacaacctc cttatatcag aagacctgcc tgccgcagtg aagaacatca tggcccggac   6480
cgatcaccca gaacccatac aactggccta taacagttat gaaaaccaaa ttccagtgct   6540
gttcccaaag atcaaaaatg gtgaggtgac agacagttat gagaattaca catatctcaa   6600
tgcaagaaaa ttaggagagg acgtgccggc atatgtgtac gccacagagg atgaggatct   6660
agcagtggat cttctgggta tggattggcc ggacccaggc aaccaacagg tggtagagac   6720
agggagggca ttaaaacaag taactggctt atccacagca gaaaacgccc tcttgatagc   6780
cctattcggc tacgtcgggt accagacact ttcaaaaagg cacataccca tgattactga   6840
catctataca cttgaagacc acaggcttga ggacacaacc cacctccagt ttgccccaaa   6900
cgctataagg accgacggca aggactcaga gttgaaggaa ttagctgtgg gagaccttga   6960
taaatatgtg gacgcactgg tagactactc caaacaaggg atgaaattca tcaaagtcca   7020
agctgaaaag gtcagagact cccagtctac gaaggaaggc ttgcaaacca ttaaggagta   7080
```

-continued

```
tgtggataag tttatacaat cactaacaga gaataaggag gagatcatca ggtatggact   7140
atggggagtt cacacggcac tctacaaaag cttggcagcg agactggggc atgaaacagc   7200
ttttgcaact ttagtggtaa aatggttggc ttttgggggc gaaacggtat ctgctcacat   7260
caagcaagta gcagttgatc tagtagtata ttatatcatc aacaaaccat cttttcctgg   7320
agatacagag acccaacaag aggggaggaa gtttgtggct agtcttttta tatctgcact   7380
agcaacatac acatataaaa cctggaatta caacaatctg caacgggttg tcgaacctgc   7440
cttagcttac ctcccatatg ctacaagtgc cttgaagttg ttcacaccca caagattaga   7500
gagtgtggtc atactcagtt ctacaattta caagacatac ctctctataa ggaagggtaa   7560
gagtgacggc ttgttaggta caggcataag tgcagccatg gagatcttaa accaaaaccc   7620
aatctcagta ggtatatctg tgatgctggg ggtaggtgcc atcgccgccc ataatgcaat   7680
agaatctagt gaacagaaaa gaactttgct gatgaaggtc tttgtaaaaa acttcttaga   7740
ccaagcagca acagatgagc tagtcaaaga gaaccctgaa aaaataatca tggctctatt   7800
tgaagcagtc cagaccatag gaaacccccct aagactcatc taccatctgt acggggtgta   7860
ctataagggg tgggaagcaa aagaactcgc agagaaaact gctggccgca acttattcac   7920
attgatcatg tttgaggcct ttgagctttt aggtatggac tcagaaggaa agataagaaa   7980
cttgtcaggc aactacatac tggacttaat cttcaacttg cataataaat taaacaaggg   8040
gctcaaaaaa ctagtccttg ggtgggctcc tgcacctttg agctgtgatt ggacaccaag   8100
tgatgagaga ataagcctac ctcataacaa ctacttaagg gtagaaacca ggtgtccttg   8160
tggctatgag atgaaggcaa taaaaaatgt tgctggtaaa ttgacaaaag ttgaagaaaa   8220
ggggtccttc ctatgcagga atagattagg gagaggacct ccaaacttca aagtaacaaa   8280
gttctatgat gataacttga tagaagtcaa gccagtagct aggctagaag gccaggtgga   8340
cctctattac aagggagtaa cagctaagtt agactacaac aatgggaaag tactgttagc   8400
taccaacaag tgggaggtgg accacgcttt cctgaccaga ctagtaaaga agcacacagg   8460
gataggtttt aaaggtgcat atttgggtga ccgaccagac catcaagatc ttgtcgatag   8520
agattgtgca actataacga agaactcagt acagttccta aaaatgaaga agggttgcgc   8580
tttcacatat gacctaacaa tctctaacct tgtcaggctt attgaactag tccataagaa   8640
taatttacaa gaaagagaga tccctaccgt gacagtaact acttggcttg catattcttt   8700
tgtcaatgaa gacctgggga ctatcaagcc tgtattgggg gagaaagtca tcccagaacc   8760
ccccgaggag ttgagtctcc aacccaccgt gagactagtc accactgaaa cagcaataac   8820
cataacaggg gaggctgaag tgatgacgac agggatcaca ccagtggtag agatgaaaga   8880
agaacctcag ctggaccacc agtcaactac cctaaaggta gggttgaagg aaggggaata   8940
tccagggcca ggagttaacc ctaaccattt agcagaggtg atagatgaga aagatgacag   9000
gccttttgtc ctaatcatcg gtaacaaagg ttctacctcg aacagagcaa gaacggccaa   9060
gaatatacgg ctgtacaaag gaaacaaccc aagagagatc agggatctga tgagccaagg   9120
aagaatattg acggttgctc taaaagagtt ggacccggaa ttaaaagaat tagtagatta   9180
caaggggacc tttctcaata gggaagcttt agaagcccta agcttaggta agccaatcaa   9240
gaggaaaacc acaacagcaa tgatcaggag gttaatagag ccagaggttg aggaggaact   9300
accagattgg ttccaagcgg aagaacccct atttttggaa gcaaaaatac agaatgactt   9360
ataccaccta attggcagtg tagatagtat aaaaagcaaa gcaaaggaat taggggccac   9420
```

-continued

```
agataacaca aagatagtga aggaagttgg ggctaggacc tatacgatga aattgagcag   9480
ctggagcaca caagttacaa aaaaacagat gagtctagcc cctctctttg aagagctgtt   9540
attaaagtgc cctccatgta gtaaaatttc aaagggacat atggtgtcag cataccaact   9600
ggctcaagga aactgggaac ccctcgggtg tggggtctat atgggaacca taccagctag   9660
gcgtctcaag atccaccctt atgaggctta ccttaaactc aaagagctgg tggaagttga   9720
atcttcgagg gccactgcaa aagaatccat cataagagaa cataacacct ggatcctgcg   9780
gaaggtgaga catgaaggga acctaagaac caaatcaatg atcaaccctg ggaaaatatc   9840
agatcagcta tgcagagatg gacacaaaag aaacatatat aataagatca taggctcaac   9900
aatggcctct gctggtatta ggctggagaa actgccagta gtccgagccc aaactgacac   9960
aaccagtttc caccaagcca taagagaaaa aattgataaa acagaaaaca agcagacccc  10020
tgaattgcat gaagaactaa tgaaggtctt cgactgctta aagatcccag agctgaagga  10080
atcgtatgat gaagtttcat gggaacaatt agaagccggg ataaaccgta agggtgcagc  10140
aggctatcta gagagcaaga acatagggga agtcctagac acagagaaac acatagtaga  10200
gcagctgatc aaggatctga ggaaggggaa gaagattagg tactatgaaa cagccatccc  10260
caagaatgag aagagagacg tcagcgacga ctgggaagcc ggagagttcg ttgatgaaaa  10320
gaaaccaaga gtaatccagt acccggacgc caaggtgaga ctggccatta caaaagtgat  10380
gtacaaatgg gtaaagcaaa aaccagtggt gatacccggc tatgaaggta aaacacctct  10440
atttgacata ttcaacaaag tgaagaagga atgggattca ttccaggacc ccgtagcagt  10500
gagctttgac accaaagcgt gggatacaca agtcaccagt agagacctaa tgttgataaa  10560
ggatatccag aaatattatt tcaagagaag tatacacaaa tttttagata caataacaga  10620
acacatggtg gaggtacctg tcattacagc agacggtgaa gtttacataa ggaatggtca  10680
gaggggtagt ggccaacccg acacaagtgc tggtaatagt atgttgaatg tcctaaccat  10740
gatatatgct ttctgtaaaa gtacaggcat accttacagg ggattcagca gagtggcaag  10800
aatccatgtg tgtggtgatg atggcttttt gataacagag agaggactgg gactgaaatt  10860
ctctgagaag ggtatgcaga tattacatga ggccgggaag ccccagaaaa taactgaagg  10920
ggacaaaatg aaagtggcat acagattcga ggacatagag ttttgttccc atactcccgt  10980
gccagtcaga tgggcagata acaccagtag ttacatggca gggaggagca cagccactat  11040
actagctaag atggcaacca ggctggattc cagcggagag aggggtagca cagcttatga  11100
gaaggccgta gccttcagct tccttttgat gtactcatgg aatcccgtag ttagaaggat  11160
ctgcttactg gtgttgtcac agtttccaga aatatcccca tccaaaaaca caatatacta  11220
ctaccaaggg gatcccatag ctgcgtacag agaagtgata gggaaacagc tgtgtgaact  11280
gaaaagaaca ggatttgaga agctggctgg tctgaatttg agtatgacca ctctaggcat  11340
ctggacaaaa catactagta aaagactaat ccaagcctgt gtagaaatag gtaagagaga  11400
aggtacctgg ttagttaatg ctgacagact gattgcagga aagactggga agttttacat  11460
cccaagcact ggtgtcactc tgttgggaaa acactatgag gaaattaact taaagcaaaa  11520
ggcggcacaa ccgccgatag agggggttga cagatataag ttgggcccca tagttaatgt  11580
tatcttgaga aggctgaggg tgatgctgat gacagttgcc agcggaagct ggtgaatccg  11640
tccggagcgt cgtgccctca ctcaaggttt ttaattgtaa atattgtaaa tagacagcta  11700
agatatttat tgtagttgga tagtaatgca gtgatagtaa ataccccaat ttaacactac  11760
ctccaatgca ctaagcactt tagctgtgtg aggttaactc gacgtccacg gttggactag  11820
```

```
ggaagacctc taacagcccc                                             11840

<210> SEQ ID NO 12
<211> LENGTH: 3749
<212> TYPE: PRT
<213> ORGANISM: Artificial
<220> FEATURE:
<223> OTHER INFORMATION: XIKE-C-NdN

<400> SEQUENCE: 12

Met Glu Leu Phe Ser Asp Glu Gly Ser Lys Gly Ala Thr Ser Lys Lys
1               5                   10                  15

Gln Pro Lys Pro Asp Arg Ile Glu Lys Gly Lys Met Lys Ile Ala Pro
            20                  25                  30

Lys Glu Thr Glu Lys Asp Cys Lys Thr Arg Pro Pro Asp Ala Thr Ile
        35                  40                  45

Val Val Glu Gly Val Lys Tyr Gln Val Lys Lys Lys Gly Lys Val Arg
    50                  55                  60

Gly Lys Asn Thr Gln Asp Gly Leu Tyr His Asn Lys Asn Lys Pro Pro
65                  70                  75                  80

Glu Ser Arg Lys Lys Leu Glu Lys Ala Leu Leu Ala Trp Ala Ile Leu
                85                  90                  95

Ala Ala Val Leu Leu Gln Leu Val Thr Gly Glu Asn Ile Thr Gln Trp
            100                 105                 110

Asn Leu Met Asp Asn Gly Thr Glu Gly Ile Gln Gln Ala Met Phe Leu
        115                 120                 125

Arg Gly Val Asn Arg Ser Leu Leu Gly Ile Trp Pro Glu Lys Ile Cys
    130                 135                 140

Thr Gly Val Pro Thr His Leu Ala Thr Asp Tyr Glu Leu Lys Glu Ile
145                 150                 155                 160

Val Gly Met Met Asp Ala Ser Glu Lys Thr Asn Tyr Thr Cys Cys Arg
                165                 170                 175

Leu Gln Arg His Glu Trp Asn Lys His Gly Trp Cys Asn Trp Phe His
            180                 185                 190

Ile Glu Pro Trp Ile Trp Leu Met Asn Lys Thr Gln Asn Asn Leu Thr
        195                 200                 205

Glu Gly Gln Pro Leu Arg Glu Cys Ala Val Thr Cys Arg Tyr Asp Lys
    210                 215                 220

Glu Thr Glu Leu Asn Ile Val Thr Gln Ala Arg Asp Arg Pro Thr Thr
225                 230                 235                 240

Leu Thr Gly Cys Lys Lys Gly Lys Asn Phe Ser Phe Ala Gly Val Ile
                245                 250                 255

Leu Asp Gly Pro Cys Asn Phe Lys Val Ser Val Glu Asp Val Leu Phe
            260                 265                 270

Lys Glu His Asp Cys Gly Asn Met Leu Gln Glu Thr Ala Ile Gln Leu
        275                 280                 285

Leu Asp Gly Ala Thr Asn Thr Ile Glu Gly Ala Arg Val Gly Thr Ala
    290                 295                 300

Lys Leu Thr Thr Trp Leu Gly Lys Gln Leu Gly Ile Leu Gly Lys Lys
305                 310                 315                 320

Leu Glu Asn Lys Ser Lys Ala Trp Phe Gly Ala His Ala Ala Ser Pro
                325                 330                 335

Tyr Cys Gly Val Glu Arg Lys Ile Gly Tyr Val Trp Tyr Thr Lys Asn
            340                 345                 350
```

```
Cys Thr Pro Ala Cys Leu Pro Arg Asn Thr Arg Ile Ile Gly Pro Gly
        355                 360                 365

Lys Phe Asp Thr Asn Ala Glu Asp Gly Lys Ile Leu His Glu Met Gly
    370                 375                 380

Gly His Leu Ser Glu Phe Val Leu Leu Ser Leu Val Val Leu Ser Asp
385                 390                 395                 400

Phe Ala Pro Glu Thr Ala Ser Val Ile Tyr Leu Val Leu His Phe Ala
                405                 410                 415

Ile Pro Gln Ser His Val Asp Val Asp Thr Cys Asp Lys Asn Gln Leu
            420                 425                 430

Asn Leu Thr Val Ala Thr Thr Val Ala Glu Val Ile Pro Gly Thr Val
        435                 440                 445

Trp Asn Leu Gly Lys Tyr Val Cys Ile Arg Pro Asp Trp Trp Pro Tyr
    450                 455                 460

Glu Thr Thr Thr Val Phe Val Ile Glu Glu Ala Gly Gln Val Ile Lys
465                 470                 475                 480

Leu Met Leu Arg Ala Ile Arg Asp Leu Thr Arg Ile Trp Asn Ala Ala
                485                 490                 495

Thr Thr Thr Ala Phe Leu Ile Phe Leu Val Lys Ala Leu Arg Gly Gln
            500                 505                 510

Leu Ile Gln Gly Leu Leu Trp Leu Met Leu Ile Thr Gly Ala Gln Gly
        515                 520                 525

Phe Pro Glu Cys Lys Glu Gly Phe Gln Tyr Ala Ile Ser Lys Asp Arg
    530                 535                 540

Lys Met Gly Leu Leu Gly Pro Glu Ser Leu Thr Thr Thr Trp His Leu
545                 550                 555                 560

Pro Thr Lys Lys Ile Val Asp Ser Met Val His Val Trp Cys Glu Gly
                565                 570                 575

Lys Asp Leu Lys Ile Leu Lys Met Cys Thr Lys Glu Glu Arg Tyr Leu
            580                 585                 590

Val Ala Val His Glu Arg Ala Leu Ser Thr Ser Ala Glu Phe Met Gln
        595                 600                 605

Ile Ser Asp Gly Thr Ile Gly Pro Asp Val Ile Asp Met Pro Asp Asp
    610                 615                 620

Phe Glu Phe Gly Leu Cys Pro Cys Asp Ser Lys Pro Val Ile Lys Gly
625                 630                 635                 640

Lys Phe Asn Ala Ser Leu Leu Asn Gly Pro Ala Phe Gln Met Val Cys
                645                 650                 655

Pro Gln Gly Trp Thr Gly Thr Ile Glu Cys Thr Leu Ala Asn Gln Asp
            660                 665                 670

Thr Leu Asp Thr Thr Val Ile Arg Thr Tyr Arg Arg Thr Thr Pro Phe
        675                 680                 685

Gln Arg Arg Lys Trp Cys Thr Tyr Glu Lys Ile Ile Gly Glu Asp Ile
    690                 695                 700

Tyr Glu Cys Ile Leu Gly Gly Asn Trp Thr Cys Ile Thr Gly Asp His
705                 710                 715                 720

Ser Arg Leu Lys Asp Gly Pro Ile Lys Lys Cys Lys Trp Cys Gly His
                725                 730                 735

Asp Phe Val Asn Ser Glu Gly Leu Pro His Tyr Pro Ile Gly Lys Cys
            740                 745                 750

Met Leu Ile Asn Glu Ser Gly Tyr Arg Tyr Val Asp Asp Thr Ser Cys
        755                 760                 765

Asp Arg Gly Gly Val Ala Ile Val Pro Ser Gly Thr Val Lys Cys Arg
```

-continued

```
    770                 775                 780

Ile Gly Asn Val Thr Val Gln Val Ile Ala Thr Asn Asn Asp Leu Gly
785                 790                 795                 800

Pro Met Pro Cys Ser Pro Ala Glu Val Ile Ala Ser Glu Gly Pro Val
                805                 810                 815

Glu Lys Thr Ala Cys Thr Phe Asn Tyr Ser Arg Thr Leu Pro Asn Lys
            820                 825                 830

Tyr Tyr Glu Pro Arg Asp Arg Tyr Phe Gln Gln Tyr Met Leu Lys Gly
        835                 840                 845

Glu Trp Gln Tyr Trp Phe Asp Leu Asp Ser Val Asp His His Lys Asp
    850                 855                 860

Tyr Phe Ser Glu Phe Ile Ile Ile Ala Val Val Ala Leu Leu Gly Gly
865                 870                 875                 880

Lys Tyr Val Leu Trp Leu Leu Ile Thr Tyr Thr Ile Leu Ser Glu Gln
                885                 890                 895

Met Ala Met Gly Ala Gly Val Asn Thr Glu Glu Ile Val Met Ile Gly
            900                 905                 910

Asn Leu Leu Thr Asp Ser Asp Ile Glu Val Val Val Tyr Phe Leu Leu
        915                 920                 925

Leu Tyr Leu Ile Val Lys Glu Glu Leu Ala Arg Lys Trp Ile Ile Leu
    930                 935                 940

Val Tyr His Ile Leu Val Ala Asn Pro Met Lys Thr Ile Gly Val Val
945                 950                 955                 960

Leu Leu Met Leu Gly Gly Val Val Lys Ala Ser Arg Ile Asn Ala Asp
                965                 970                 975

Asp Gln Ser Ala Met Asp Pro Cys Phe Leu Leu Val Thr Gly Val Val
            980                 985                 990

Ala Val Leu Met Ile Ala Arg Arg  Glu Pro Ala Thr Leu  Pro Leu Ile
        995                 1000                1005

Val Ala  Leu Leu Ala Ile Arg  Thr Ser Gly Phe Leu  Leu Pro Ala
    1010                1015                1020

Ser Ile  Asp Val Thr Val Ala  Val Val Leu Ile Val  Leu Leu Leu
    1025                1030                1035

Ala Ser  Tyr Ile Thr Asp Tyr  Phe Arg Tyr Lys Lys  Trp Leu Gln
    1040                1045                1050

Leu Leu  Phe Ser Leu Ile Ala  Gly Ile Phe Ile Ile  Arg Ser Leu
    1055                1060                1065

Lys His  Ile Asn Gln Met Glu  Val Pro Glu Ile Ser  Met Pro Ser
    1070                1075                1080

Trp Arg  Pro Leu Ala Leu Val  Leu Phe Tyr Ile Thr  Ser Thr Ala
    1085                1090                1095

Ile Thr  Thr Asn Trp Asp Ile  Asp Leu Ala Gly Phe  Leu Leu Gln
    1100                1105                1110

Trp Ala  Pro Ala Val Ile Met  Met Ala Thr Met Trp  Ala Asp Phe
    1115                1120                1125

Leu Thr  Leu Ile Ile Val Leu  Pro Ser Tyr Glu Leu  Ser Lys Leu
    1130                1135                1140

Tyr Phe  Leu Lys Asn Val Arg  Thr Asp Val Glu Lys  Asn Trp Leu
    1145                1150                1155

Gly Lys  Val Lys Tyr Arg Gln  Ile Ser Ser Val Tyr  Asp Ile Cys
    1160                1165                1170

Asp Ser  Glu Glu Ala Val Tyr  Leu Phe Pro Ser Arg  His Lys Ser
    1175                1180                1185
```

```
Gly Ser  Arg Pro Asp Phe Ile  Leu Pro Phe Leu Lys  Ala Val Leu
    1190                 1195                 1200

Ile Ser  Cys Ile Ser Ser Gln  Trp Gln Val Val Tyr  Ile Ser Tyr
    1205                 1210                 1215

Leu Ile  Leu Glu Ile Thr Tyr  Tyr Met His Arg Lys  Ile Ile Asp
    1220                 1225                 1230

Glu Val  Ser Gly Gly Ala Asn  Phe Leu Ser Arg Leu  Ile Ala Ala
    1235                 1240                 1245

Ile Ile  Glu Leu Asn Trp Ala  Ile Asp Asp Glu Glu  Cys Lys Gly
    1250                 1255                 1260

Leu Lys  Lys Leu Tyr Leu Leu  Ser Gly Arg Ala Lys  Asn Leu Ile
    1265                 1270                 1275

Val Lys  His Lys Val Arg Asn  Glu Ala Val His Arg  Trp Phe Gly
    1280                 1285                 1290

Glu Glu  Glu Ile Tyr Gly Ala  Pro Lys Val Ile Thr  Ile Ile Lys
    1295                 1300                 1305

Ala Ser  Thr Leu Ser Lys Asn  Arg His Cys Ile Ile  Cys Thr Ile
    1310                 1315                 1320

Cys Glu  Gly Lys Glu Trp Asn  Gly Ala Asn Cys Pro  Lys Cys Gly
    1325                 1330                 1335

Arg Gln  Gly Lys Pro Ile Thr  Cys Gly Met Thr Leu  Ala Asp Phe
    1340                 1345                 1350

Glu Glu  Lys His Tyr Lys Lys  Ile Phe Ile Arg Glu  Glu Ser Ser
    1355                 1360                 1365

Cys Pro  Val Pro Phe Asp Pro  Ser Cys His Cys Asn  Tyr Phe Arg
    1370                 1375                 1380

His Asp  Gly Pro Phe Arg Lys  Glu Tyr Lys Gly Tyr  Val Gln Tyr
    1385                 1390                 1395

Thr Ala  Arg Gly Gln Leu Phe  Leu Arg Asn Leu Pro  Ile Leu Ala
    1400                 1405                 1410

Thr Lys  Met Lys Leu Leu Met  Val Gly Asn Leu Gly  Ala Glu Ile
    1415                 1420                 1425

Gly Asp  Leu Glu His Leu Gly  Trp Val Leu Arg Gly  Pro Ala Val
    1430                 1435                 1440

Cys Lys  Lys Ile Thr Asn His  Glu Lys Cys His Val  Asn Ile Met
    1445                 1450                 1455

Asp Lys  Leu Thr Ala Phe Phe  Gly Ile Met Pro Arg  Gly Thr Thr
    1460                 1465                 1470

Pro Arg  Ala Pro Val Arg Phe  Pro Thr Ala Leu Leu  Lys Val Arg
    1475                 1480                 1485

Arg Gly  Leu Glu Thr Gly Trp  Ala Tyr Thr His Gln  Gly Gly Ile
    1490                 1495                 1500

Ser Ser  Val Asp His Val Thr  Ala Gly Lys Asp Leu  Leu Val Cys
    1505                 1510                 1515

Asp Ser  Met Gly Arg Thr Arg  Val Val Cys His Ser  Asn Asn Lys
    1520                 1525                 1530

Met Thr  Asp Glu Thr Glu Tyr  Gly Ile Lys Thr Asp  Ser Gly Cys
    1535                 1540                 1545

Pro Glu  Gly Ala Arg Cys Tyr  Val Leu Asn Pro Glu  Ala Val Asn
    1550                 1555                 1560

Ile Ser  Gly Thr Lys Gly Ala  Met Val His Leu Gln  Lys Thr Gly
    1565                 1570                 1575
```

-continued

```
Gly Glu  Phe Thr Cys Val Thr  Ala Ser Gly Thr Pro  Ala Phe Phe
    1580                 1585                 1590

Asp Leu  Lys Asn Leu Lys Gly  Trp Ser Gly Leu Pro  Ile Phe Glu
    1595                 1600                 1605

Ala Ser  Ser Gly Arg Val Val  Gly Arg Val Lys Val  Gly Lys Asn
    1610                 1615                 1620

Glu Asp  Ser Lys Pro Thr Lys  Leu Met Ser Gly Ile  Gln Thr Val
    1625                 1630                 1635

Ser Lys  Asn Gln Thr Asp Leu  Ala Asp Ile Val Lys  Lys Leu Thr
    1640                 1645                 1650

Ser Met  Asn Arg Gly Glu Phe  Lys Gln Ile Thr Leu  Ala Thr Gly
    1655                 1660                 1665

Ala Gly  Lys Thr Thr Glu Leu  Pro Arg Ser Val Ile  Glu Glu Ile
    1670                 1675                 1680

Gly Arg  His Lys Arg Val Leu  Val Leu Ile Pro Leu  Arg Ala Ala
    1685                 1690                 1695

Ala Glu  Ser Val Tyr Gln Tyr  Met Arg Val Lys Tyr  Pro Ser Ile
    1700                 1705                 1710

Ser Phe  Asn Leu Arg Ile Gly  Asp Met Lys Glu Gly  Asp Met Ala
    1715                 1720                 1725

Thr Gly  Ile Thr Tyr Ala Ser  Tyr Gly Tyr Phe Cys  Gln Leu Pro
    1730                 1735                 1740

Gln Pro  Lys Leu Arg Ala Ala  Met Val Glu Tyr Ser  Tyr Ile Phe
    1745                 1750                 1755

Leu Asp  Glu Tyr His Cys Ala  Thr Pro Glu Gln Leu  Ala Ile Ile
    1760                 1765                 1770

Gly Lys  Ile His Arg Phe Ala  Glu Asn Leu Arg Val  Val Ala Met
    1775                 1780                 1785

Thr Ala  Thr Pro Ala Gly Thr  Val Thr Thr Thr Gly  Gln Lys His
    1790                 1795                 1800

Pro Ile  Glu Glu Phe Ile Ala  Pro Glu Val Met Lys  Gly Glu Asp
    1805                 1810                 1815

Leu Gly  Ser Glu Tyr Leu Asp  Ile Ala Gly Leu Lys  Ile Pro Thr
    1820                 1825                 1830

Glu Glu  Met Lys Gly Asn Met  Leu Val Phe Ala Pro  Thr Arg Asn
    1835                 1840                 1845

Met Ala  Val Glu Thr Ala Lys  Lys Leu Lys Ala Lys  Gly Tyr Asn
    1850                 1855                 1860

Ser Gly  Tyr Tyr Tyr Ser Gly  Glu Asn Pro Glu Asn  Leu Arg Val
    1865                 1870                 1875

Val Thr  Ser Gln Ser Pro Tyr  Val Val Val Ala Thr  Asn Ala Ile
    1880                 1885                 1890

Glu Ser  Gly Val Thr Leu Pro  Asp Leu Asp Thr Val  Val Asp Thr
    1895                 1900                 1905

Gly Leu  Lys Cys Glu Lys Arg  Val Arg Ile Ser Ser  Lys Met Pro
    1910                 1915                 1920

Phe Ile  Val Thr Gly Leu Lys  Arg Met Ala Val Thr  Ile Gly Glu
    1925                 1930                 1935

Gln Ala  Gln Arg Arg Gly Arg  Val Gly Arg Val Lys  Pro Gly Arg
    1940                 1945                 1950

Tyr Tyr  Arg Ser Gln Glu Thr  Ala Ser Gly Ser Lys  Asp Tyr His
    1955                 1960                 1965

Tyr Asp  Leu Leu Gln Ala Gln  Arg Tyr Gly Ile Glu  Asp Gly Ile
```

-continued

```
    1970                1975                1980

Asn Val  Thr Lys Ser Phe Arg  Glu Met Asn Tyr Asp  Trp Ser Leu
    1985                1990                1995

Tyr Glu  Glu Asp Ser Leu Met  Ile Thr Gln Leu Glu  Val Leu Asn
    2000                2005                2010

Asn Leu  Leu Ile Ser Glu Asp  Leu Pro Ala Ala Val  Lys Asn Ile
    2015                2020                2025

Met Ala  Arg Thr Asp His Pro  Glu Pro Ile Gln Leu  Ala Tyr Asn
    2030                2035                2040

Ser Tyr  Glu Asn Gln Ile Pro  Val Leu Phe Pro Lys  Ile Lys Asn
    2045                2050                2055

Gly Glu  Val Thr Asp Ser Tyr  Glu Asn Tyr Thr Tyr  Leu Asn Ala
    2060                2065                2070

Arg Lys  Leu Gly Glu Asp Val  Pro Ala Tyr Val Tyr  Ala Thr Glu
    2075                2080                2085

Asp Glu  Asp Leu Ala Val Asp  Leu Leu Gly Met Asp  Trp Pro Asp
    2090                2095                2100

Pro Gly  Asn Gln Gln Val Val  Glu Thr Gly Arg Ala  Leu Lys Gln
    2105                2110                2115

Val Thr  Gly Leu Ser Thr Ala  Glu Asn Ala Leu Leu  Ile Ala Leu
    2120                2125                2130

Phe Gly  Tyr Val Gly Tyr Gln  Thr Leu Ser Lys Arg  His Ile Pro
    2135                2140                2145

Met Ile  Thr Asp Ile Tyr Thr  Leu Glu Asp His Arg  Leu Glu Asp
    2150                2155                2160

Thr Thr  His Leu Gln Phe Ala  Pro Asn Ala Ile Arg  Thr Asp Gly
    2165                2170                2175

Lys Asp  Ser Glu Leu Lys Glu  Leu Ala Val Gly Asp  Leu Asp Lys
    2180                2185                2190

Tyr Val  Asp Ala Leu Val Asp  Tyr Ser Lys Gln Gly  Met Lys Phe
    2195                2200                2205

Ile Lys  Val Gln Ala Glu Lys  Val Arg Asp Ser Gln  Ser Thr Lys
    2210                2215                2220

Glu Gly  Leu Gln Thr Ile Lys  Glu Tyr Val Asp Lys  Phe Ile Gln
    2225                2230                2235

Ser Leu  Thr Glu Asn Lys Glu  Glu Ile Ile Arg Tyr  Gly Leu Trp
    2240                2245                2250

Gly Val  His Thr Ala Leu Tyr  Lys Ser Leu Ala Ala  Arg Leu Gly
    2255                2260                2265

His Glu  Thr Ala Phe Ala Thr  Leu Val Val Lys Trp  Leu Ala Phe
    2270                2275                2280

Gly Gly  Glu Thr Val Ser Ala  His Ile Lys Gln Val  Ala Val Asp
    2285                2290                2295

Leu Val  Val Tyr Tyr Ile Ile  Asn Lys Pro Ser Phe  Pro Gly Asp
    2300                2305                2310

Thr Glu  Thr Gln Gln Glu Gly  Arg Arg Phe Val Ala  Ser Leu Phe
    2315                2320                2325

Ile Ser  Ala Leu Ala Thr Tyr  Thr Tyr Lys Thr Trp  Asn Tyr Asn
    2330                2335                2340

Asn Leu  Gln Arg Val Val Glu  Pro Ala Leu Ala Tyr  Leu Pro Tyr
    2345                2350                2355

Ala Thr  Ser Ala Leu Lys Leu  Phe Thr Pro Thr Arg  Leu Glu Ser
    2360                2365                2370
```

-continued

```
Val Val  Ile Leu Ser Ser Thr  Ile Tyr Lys Thr Tyr  Leu Ser Ile
    2375                 2380                 2385

Arg Lys  Gly Lys Ser Asp Gly  Leu Leu Gly Thr Gly  Ile Ser Ala
    2390                 2395                 2400

Ala Met  Glu Ile Leu Asn Gln  Asn Pro Ile Ser Val  Gly Ile Ser
    2405                 2410                 2415

Val Met  Leu Gly Val Gly Ala  Ile Ala Ala His Asn  Ala Ile Glu
    2420                 2425                 2430

Ser Ser  Glu Gln Lys Arg Thr  Leu Leu Met Lys Val  Phe Val Lys
    2435                 2440                 2445

Asn Phe  Leu Asp Gln Ala Ala  Thr Asp Glu Leu Val  Lys Glu Asn
    2450                 2455                 2460

Pro Glu  Lys Ile Ile Met Ala  Leu Phe Glu Ala Val  Gln Thr Ile
    2465                 2470                 2475

Gly Asn  Pro Leu Arg Leu Ile  Tyr His Leu Tyr Gly  Val Tyr Tyr
    2480                 2485                 2490

Lys Gly  Trp Glu Ala Lys Glu  Leu Ala Glu Lys Thr  Ala Gly Arg
    2495                 2500                 2505

Asn Leu  Phe Thr Leu Ile Met  Phe Glu Ala Phe Glu  Leu Leu Gly
    2510                 2515                 2520

Met Asp  Ser Glu Gly Lys Ile  Arg Asn Leu Ser Gly  Asn Tyr Ile
    2525                 2530                 2535

Leu Asp  Leu Ile Phe Asn Leu  His Asn Lys Leu Asn  Lys Gly Leu
    2540                 2545                 2550

Lys Lys  Leu Val Leu Gly Trp  Ala Pro Ala Pro Leu  Ser Cys Asp
    2555                 2560                 2565

Trp Thr  Pro Ser Asp Glu Arg  Ile Ser Leu Pro His  Asn Asn Tyr
    2570                 2575                 2580

Leu Arg  Val Glu Thr Arg Cys  Pro Cys Gly Tyr Glu  Met Lys Ala
    2585                 2590                 2595

Ile Lys  Asn Val Ala Gly Lys  Leu Thr Lys Val Glu  Glu Lys Gly
    2600                 2605                 2610

Ser Phe  Leu Cys Arg Asn Arg  Leu Gly Arg Gly Pro  Pro Asn Phe
    2615                 2620                 2625

Lys Val  Thr Lys Phe Tyr Asp  Asp Asn Leu Ile Glu  Val Lys Pro
    2630                 2635                 2640

Val Ala  Arg Leu Glu Gly Gln  Val Asp Leu Tyr Tyr  Lys Gly Val
    2645                 2650                 2655

Thr Ala  Lys Leu Asp Tyr Asn  Asn Gly Lys Val Leu  Leu Ala Thr
    2660                 2665                 2670

Asn Lys  Trp Glu Val Asp His  Ala Phe Leu Thr Arg  Leu Val Lys
    2675                 2680                 2685

Lys His  Thr Gly Ile Gly Phe  Lys Gly Ala Tyr Leu  Gly Asp Arg
    2690                 2695                 2700

Pro Asp  His Gln Asp Leu Val  Asp Arg Asp Cys Ala  Thr Ile Thr
    2705                 2710                 2715

Lys Asn  Ser Val Gln Phe Leu  Lys Met Lys Lys Gly  Cys Ala Phe
    2720                 2725                 2730

Thr Tyr  Asp Leu Thr Ile Ser  Asn Leu Val Arg Leu  Ile Glu Leu
    2735                 2740                 2745

Val His  Lys Asn Asn Leu Gln  Glu Arg Glu Ile Pro  Thr Val Thr
    2750                 2755                 2760
```

-continued

```
Val Thr  Thr Trp Leu Ala Tyr  Ser Phe Val Asn Glu  Asp Leu Gly
    2765                 2770                 2775

Thr Ile  Lys Pro Val Leu Gly  Glu Lys Val Ile Pro  Glu Pro Pro
    2780                 2785                 2790

Glu Glu  Leu Ser Leu Gln Pro  Thr Val Arg Leu Val  Thr Thr Glu
    2795                 2800                 2805

Thr Ala  Ile Thr Ile Thr Gly  Glu Ala Glu Val Met  Thr Thr Gly
    2810                 2815                 2820

Ile Thr  Pro Val Val Glu Met  Lys Glu Glu Pro Gln  Leu Asp His
    2825                 2830                 2835

Gln Ser  Thr Thr Leu Lys Val  Gly Leu Lys Glu Gly  Glu Tyr Pro
    2840                 2845                 2850

Gly Pro  Gly Val Asn Pro Asn  His Leu Ala Glu Val  Ile Asp Glu
    2855                 2860                 2865

Lys Asp  Asp Arg Pro Phe Val  Leu Ile Ile Gly Asn  Lys Gly Ser
    2870                 2875                 2880

Thr Ser  Asn Arg Ala Arg Thr  Ala Lys Asn Ile Arg  Leu Tyr Lys
    2885                 2890                 2895

Gly Asn  Asn Pro Arg Glu Ile  Arg Asp Leu Met Ser  Gln Gly Arg
    2900                 2905                 2910

Ile Leu  Thr Val Ala Leu Lys  Glu Leu Asp Pro Glu  Leu Lys Glu
    2915                 2920                 2925

Leu Val  Asp Tyr Lys Gly Thr  Phe Leu Asn Arg Glu  Ala Leu Glu
    2930                 2935                 2940

Ala Leu  Ser Leu Gly Lys Pro  Ile Lys Arg Lys Thr  Thr Thr Ala
    2945                 2950                 2955

Met Ile  Arg Arg Leu Ile Glu  Pro Glu Val Glu Glu  Glu Leu Pro
    2960                 2965                 2970

Asp Trp  Phe Gln Ala Glu Glu  Pro Leu Phe Leu Glu  Ala Lys Ile
    2975                 2980                 2985

Gln Asn  Asp Leu Tyr His Leu  Ile Gly Ser Val Asp  Ser Ile Lys
    2990                 2995                 3000

Ser Lys  Ala Lys Glu Leu Gly  Ala Thr Asp Asn Thr  Lys Ile Val
    3005                 3010                 3015

Lys Glu  Val Gly Ala Arg Thr  Tyr Thr Met Lys Leu  Ser Ser Trp
    3020                 3025                 3030

Ser Thr  Gln Val Thr Lys Lys  Gln Met Ser Leu Ala  Pro Leu Phe
    3035                 3040                 3045

Glu Glu  Leu Leu Leu Lys Cys  Pro Pro Cys Ser Lys  Ile Ser Lys
    3050                 3055                 3060

Gly His  Met Val Ser Ala Tyr  Gln Leu Ala Gln Gly  Asn Trp Glu
    3065                 3070                 3075

Pro Leu  Gly Cys Gly Val Tyr  Met Gly Thr Ile Pro  Ala Arg Arg
    3080                 3085                 3090

Leu Lys  Ile His Pro Tyr Glu  Ala Tyr Leu Lys Leu  Lys Glu Leu
    3095                 3100                 3105

Val Glu  Val Glu Ser Ser Arg  Ala Thr Ala Lys Glu  Ser Ile Ile
    3110                 3115                 3120

Arg Glu  His Asn Thr Trp Ile  Leu Arg Lys Val Arg  His Glu Gly
    3125                 3130                 3135

Asn Leu  Arg Thr Lys Ser Met  Ile Asn Pro Gly Lys  Ile Ser Asp
    3140                 3145                 3150

Gln Leu  Cys Arg Asp Gly His  Lys Arg Asn Ile Tyr  Asn Lys Ile
```

-continued

```
    3155                3160                3165

Ile Gly  Ser Thr Met Ala Ser  Ala Gly Ile Arg Leu  Glu Lys Leu
    3170                3175                3180

Pro Val  Val Arg Ala Gln Thr  Asp Thr Thr Ser Phe  His Gln Ala
    3185                3190                3195

Ile Arg  Glu Lys Ile Asp Lys  Thr Glu Asn Lys Gln  Thr Pro Glu
    3200                3205                3210

Leu His  Glu Glu Leu Met Lys  Val Phe Asp Cys Leu  Lys Ile Pro
    3215                3220                3225

Glu Leu  Lys Glu Ser Tyr Asp  Glu Val Ser Trp Glu  Gln Leu Glu
    3230                3235                3240

Ala Gly  Ile Asn Arg Lys Gly  Ala Ala Gly Tyr Leu  Glu Ser Lys
    3245                3250                3255

Asn Ile  Gly Glu Val Leu Asp  Thr Glu Lys His Ile  Val Glu Gln
    3260                3265                3270

Leu Ile  Lys Asp Leu Arg Lys  Gly Lys Lys Ile Arg  Tyr Tyr Glu
    3275                3280                3285

Thr Ala  Ile Pro Lys Asn Glu  Lys Arg Asp Val Ser  Asp Asp Trp
    3290                3295                3300

Glu Ala  Gly Glu Phe Val Asp  Glu Lys Lys Pro Arg  Val Ile Gln
    3305                3310                3315

Tyr Pro  Asp Ala Lys Val Arg  Leu Ala Ile Thr Lys  Val Met Tyr
    3320                3325                3330

Lys Trp  Val Lys Gln Lys Pro  Val Val Ile Pro Gly  Tyr Glu Gly
    3335                3340                3345

Lys Thr  Pro Leu Phe Asp Ile  Phe Asn Lys Val Lys  Lys Glu Trp
    3350                3355                3360

Asp Ser  Phe Gln Asp Pro Val  Ala Val Ser Phe Asp  Thr Lys Ala
    3365                3370                3375

Trp Asp  Thr Gln Val Thr Ser  Arg Asp Leu Met Leu  Ile Lys Asp
    3380                3385                3390

Ile Gln  Lys Tyr Tyr Phe Lys  Arg Ser Ile His Lys  Phe Leu Asp
    3395                3400                3405

Thr Ile  Thr Glu His Met Val  Glu Val Pro Val Ile  Thr Ala Asp
    3410                3415                3420

Gly Glu  Val Tyr Ile Arg Asn  Gly Gln Arg Gly Ser  Gly Gln Pro
    3425                3430                3435

Asp Thr  Ser Ala Gly Asn Ser  Met Leu Asn Val Leu  Thr Met Ile
    3440                3445                3450

Tyr Ala  Phe Cys Lys Ser Thr  Gly Ile Pro Tyr Arg  Gly Phe Ser
    3455                3460                3465

Arg Val  Ala Arg Ile His Val  Cys Gly Asp Asp Gly  Phe Leu Ile
    3470                3475                3480

Thr Glu  Arg Gly Leu Gly Leu  Lys Phe Ser Glu Lys  Gly Met Gln
    3485                3490                3495

Ile Leu  His Glu Ala Gly Lys  Pro Gln Lys Ile Thr  Glu Gly Asp
    3500                3505                3510

Lys Met  Lys Val Ala Tyr Arg  Phe Glu Asp Ile Glu  Phe Cys Ser
    3515                3520                3525

His Thr  Pro Val Pro Val Arg  Trp Ala Asp Asn Thr  Ser Ser Tyr
    3530                3535                3540

Met Ala  Gly Arg Ser Thr Ala  Thr Ile Leu Ala Lys  Met Ala Thr
    3545                3550                3555
```

-continued

```
Arg Leu  Asp Ser Ser Gly Glu  Arg Gly Ser Thr Ala  Tyr Glu Lys
    3560                3565                3570

Ala Val  Ala Phe Ser Phe Leu  Leu Met Tyr Ser Trp  Asn Pro Val
    3575                3580                3585

Val Arg  Arg Ile Cys Leu Leu  Val Leu Ser Gln Phe  Pro Glu Ile
    3590                3595                3600

Ser Pro  Ser Lys Asn Thr Ile  Tyr Tyr Tyr Gln Gly  Asp Pro Ile
    3605                3610                3615

Ala Ala  Tyr Arg Glu Val Ile  Gly Lys Gln Leu Cys  Glu Leu Lys
    3620                3625                3630

Arg Thr  Gly Phe Glu Lys Leu  Ala Gly Leu Asn Leu  Ser Met Thr
    3635                3640                3645

Thr Leu  Gly Ile Trp Thr Lys  His Thr Ser Lys Arg  Leu Ile Gln
    3650                3655                3660

Ala Cys  Val Glu Ile Gly Lys  Arg Glu Gly Thr Trp  Leu Val Asn
    3665                3670                3675

Ala Asp  Arg Leu Ile Ala Gly  Lys Thr Gly Lys Phe  Tyr Ile Pro
    3680                3685                3690

Ser Thr  Gly Val Thr Leu Leu  Gly Lys His Tyr Glu  Glu Ile Asn
    3695                3700                3705

Leu Lys  Gln Lys Ala Ala Gln  Pro Pro Ile Glu Gly  Val Asp Arg
    3710                3715                3720

Tyr Lys  Leu Gly Pro Ile Val  Asn Val Ile Leu Arg  Arg Leu Arg
    3725                3730                3735

Val Met  Leu Met Thr Val Ala  Ser Gly Ser Trp
    3740                3745
```